(12) United States Patent
Frendewey et al.

(10) Patent No.: US 11,820,997 B2
(45) Date of Patent: *Nov. 21, 2023

(54) METHODS AND COMPOSITIONS FOR THE TARGETED MODIFICATION OF A GENOME

(71) Applicant: Regeneron Pharmaceuticals, Inc., Tarrytown, NY (US)

(72) Inventors: David Frendewey, New York, NY (US); Wojtek Auerbach, Ridgewood, NJ (US); Ka-Man Venus Lai, Seattle, WA (US); David M. Valenzuela, Yorktown Heights, NY (US); George D. Yancopoulos, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 697 days.

This patent is subject to a terminal disclaimer.

(21) Appl. No.: 16/891,978

(22) Filed: Jun. 3, 2020

(65) Prior Publication Data
US 2020/0291425 A1 Sep. 17, 2020

Related U.S. Application Data

(60) Continuation of application No. 16/224,413, filed on Dec. 18, 2018, now Pat. No. 10,711,280, which is a
(Continued)

(51) Int. Cl.
*C12N 15/85* (2006.01)
*C12N 15/90* (2006.01)
(Continued)

(52) U.S. Cl.
CPC ...... *C12N 15/8509* (2013.01); *A01K 67/0276* (2013.01); *A01K 67/0278* (2013.01);
(Continued)

(58) Field of Classification Search
None
See application file for complete search history.

(56) References Cited

U.S. PATENT DOCUMENTS

| 5,981,175 A | 11/1999 | Loring |
| 6,136,566 A | 10/2000 | Sands et al. |

(Continued)

FOREIGN PATENT DOCUMENTS

| EP | 1 726 640 A1 | 11/2005 |
| EP | 2336329 A1 | 6/2011 |

(Continued)

OTHER PUBLICATIONS

EP 3080279 Communication in Reply to Rule 116 EPC submission mailed Apr. 12, 2021 including appendix A, B.
(Continued)

*Primary Examiner* — Christopher M Babic
*Assistant Examiner* — Kimberly A Aron
(74) *Attorney, Agent, or Firm* — Yongjin Choi; Alston & Bird LLP

(57) ABSTRACT

Compositions and methods are provided for modifying a genomic locus of interest in a eukaryotic cell, a mammalian cell, a human cell or a non-human mammalian cell using a large targeting vector (LTVEC) comprising various endogenous or exogenous nucleic acid sequences as described herein. Further methods combine the use of the LTVEC with a CRISPR/Cas system. Compositions and methods for generating a genetically modified non-human animal comprising one or more targeted genetic modifications in their germline are also provided.

73 Claims, 63 Drawing Sheets
(39 of 63 Drawing Sheet(s) Filed in Color)
Specification includes a Sequence Listing.

Related U.S. Application Data continuation of application No. 15/354,270, filed on Nov. 17, 2016, now Pat. No. 10,208,317, which is a division of application No. 14/515,503, filed on Oct. 15, 2014, now Pat. No. 9,546,384.

(60) Provisional application No. 61/914,768, filed on Dec. 11, 2013, provisional application No. 62/017,416, filed on Jun. 26, 2014, provisional application No. 62/029,261, filed on Jul. 25, 2014, provisional application No. 62/052,906, filed on Sep. 19, 2014, provisional application No. 62/059,527, filed on Oct. 3, 2014, provisional application No. 62/064,384, filed on Oct. 15, 2014.

(51) Int. Cl.
*C12N 9/22* (2006.01)
*A01K 67/027* (2006.01)
*C12N 5/10* (2006.01)
*C12N 15/10* (2006.01)

(52) U.S. Cl.
CPC ............ *C12N 9/22* (2013.01); *C12N 15/1024* (2013.01); *C12N 15/85* (2013.01); *C12N 15/907* (2013.01); *A01K 2217/072* (2013.01); *A01K 2217/075* (2013.01); *A01K 2227/105* (2013.01); *A01K 2267/0362* (2013.01); *A01K 2267/0387* (2013.01); *C12N 2015/8527* (2013.01); *C12N 2800/40* (2013.01); *C12N 2810/00* (2013.01); *C12N 2810/10* (2013.01); *C12N 2810/40* (2013.01); *C12N 2999/007* (2013.01)

(56) References Cited

U.S. PATENT DOCUMENTS

| | | |
|---|---|---|
| 6,372,956 B1 | 4/2002 | Goldsmith et al. |
| 6,566,579 B1 | 5/2003 | Jaisser et al. |
| 7,294,754 B2 | 11/2007 | Poueymirou et al. |
| 7,771,967 B2 | 8/2010 | Huang et al. |
| 8,338,179 B2 | 12/2012 | Enenkel et al. |
| 8,502,018 B2 | 8/2013 | Murphy et al. |
| 8,628,957 B2 | 1/2014 | Teratani et al. |
| 8,697,359 B1 | 4/2014 | Zhang |
| 8,703,485 B2 | 4/2014 | Buelow |
| 8,907,157 B2 | 12/2014 | Buelow |
| 8,921,332 B2 | 12/2014 | Choulika et al. |
| 9,228,208 B2 | 1/2016 | Frendewey et al. |
| 9,528,124 B2 | 12/2016 | Fahrenkrug et al. |
| 9,546,384 B2 | 1/2017 | Frendewey et al. |
| 10,208,317 B2 | 2/2019 | Frendewey et al. |
| 10,711,280 B2 | 7/2020 | Frendewey et al. |
| 2003/0134318 A1 | 7/2003 | Case et al. |
| 2003/0175968 A1 | 9/2003 | Golic et al. |
| 2004/0018626 A1 | 1/2004 | Murphy et al. |
| 2004/0197317 A1 | 10/2004 | Rao et al. |
| 2005/0144655 A1 | 6/2005 | Economides et al. |
| 2007/0186293 A1 | 8/2007 | Teratani et al. |
| 2008/0014638 A1 | 1/2008 | Smith et al. |
| 2008/0066197 A1 | 3/2008 | Ying et al. |
| 2008/0113437 A1 | 5/2008 | Joly et al. |
| 2008/0299580 A1 | 12/2008 | DeKelver et al. |
| 2009/0055943 A1 | 2/2009 | Economides et al. |
| 2010/0041137 A1 | 2/2010 | Smith et al. |
| 2010/0047805 A1 | 2/2010 | Wang |
| 2010/0076057 A1 | 3/2010 | Sontheimer et al. |
| 2010/0218264 A1 | 8/2010 | Cui et al. |
| 2011/0041197 A1 | 2/2011 | Frendewey et al. |
| 2011/0119779 A1 | 5/2011 | Shizuya et al. |
| 2011/0207221 A1 | 8/2011 | Cost et al. |
| 2011/0263028 A1 | 10/2011 | Cabaniols et al. |
| 2011/0307968 A1 | 12/2011 | Auerbach et al. |
| 2012/0142092 A1 | 6/2012 | Terantani et al. |
| 2012/0167237 A1 | 6/2012 | Bradley et al. |
| 2012/0204278 A1 | 8/2012 | Bradley et al. |
| 2012/0272349 A1 | 10/2012 | Ochiya et al. |
| 2012/0315670 A1 | 12/2012 | Jacobson et al. |
| 2013/0309670 A1 | 11/2013 | Frendewey et al. |
| 2014/0065142 A1 | 3/2014 | Roschke et al. |
| 2014/0068797 A1 | 3/2014 | Doudna et al. |
| 2014/0154701 A1 | 6/2014 | MacDonald et al. |
| 2014/0179770 A1 | 6/2014 | Zhang et al. |
| 2014/0186843 A1 | 7/2014 | Zhang et al. |
| 2014/0186958 A1 | 7/2014 | Zhang et al. |
| 2014/0235933 A1 | 8/2014 | Lee et al. |
| 2014/0242702 A1 | 8/2014 | Chen et al. |
| 2014/0248702 A1 | 9/2014 | Zhang et al. |
| 2014/0256046 A1 | 9/2014 | Zhang et al. |
| 2014/0273037 A1 | 9/2014 | Wu |
| 2014/0273226 A1 | 9/2014 | Wu |
| 2014/0273231 A1 | 9/2014 | Zhang et al. |
| 2014/0273232 A1 | 9/2014 | Zhang et al. |
| 2014/0273233 A1 | 9/2014 | Chen et al. |
| 2014/0273234 A1 | 9/2014 | Zhang et al. |
| 2014/0301990 A1 | 10/2014 | Gregory et al. |
| 2014/0309487 A1 | 10/2014 | Lee et al. |
| 2014/0310828 A1 | 10/2014 | Lee et al. |
| 2014/0315301 A1 | 10/2014 | Hanna et al. |
| 2014/0315985 A1 | 10/2014 | May et al. |
| 2014/0335063 A1 | 11/2014 | Cannon et al. |
| 2014/0342456 A1 | 11/2014 | Mali et al. |
| 2014/0342458 A1 | 11/2014 | Mali et al. |
| 2014/0349400 A1 | 11/2014 | Jakimo et al. |
| 2014/0359795 A1 | 12/2014 | Fahrenkrug et al. |
| 2015/0024500 A1 | 1/2015 | Yu et al. |
| 2015/0031132 A1 | 1/2015 | Church et al. |
| 2015/0031133 A1 | 1/2015 | Church et al. |
| 2015/0059009 A1 | 2/2015 | McWhirter et al. |
| 2015/0071889 A1 | 3/2015 | Musunuru et al. |
| 2015/0079680 A1 | 3/2015 | Bradley et al. |
| 2015/0110762 A1 | 4/2015 | Holmes et al. |
| 2015/0140664 A1 | 5/2015 | Byrne et al. |
| 2015/0152436 A1 | 6/2015 | Musunuru et al. |
| 2015/0159174 A1 | 6/2015 | Frendewey et al. |
| 2015/0159175 A1 | 6/2015 | Frendewey et al. |
| 2015/0176013 A1 | 6/2015 | Musunuru et al. |
| 2015/0184199 A1 | 7/2015 | Horwitz et al. |
| 2015/0232881 A1 | 8/2015 | Glucksmann et al. |
| 2015/0232883 A1 | 8/2015 | Dahlman et al. |
| 2015/0240263 A1 | 8/2015 | Holmes et al. |
| 2015/0252358 A1 | 9/2015 | Maeder et al. |
| 2015/0267205 A1 | 9/2015 | Froelich et al. |
| 2015/0283265 A1 | 10/2015 | Peyman |
| 2015/0291965 A1 | 10/2015 | Zhang et al. |
| 2015/0291966 A1 | 10/2015 | Zhang et al. |
| 2015/0291969 A1 | 10/2015 | Nair et al. |
| 2015/0368670 A1 | 12/2015 | Quake et al. |
| 2015/0376583 A1 | 12/2015 | Quake et al. |
| 2015/0376650 A1 | 12/2015 | Auerbach et al. |
| 2015/0376651 A1 | 12/2015 | Frendewey et al. |
| 2016/0017301 A1 | 1/2016 | Khalili et al. |
| 2016/0024529 A1 | 1/2016 | Carstens |
| 2016/0032292 A1 | 2/2016 | Storici et al. |
| 2016/0040155 A1 | 2/2016 | Maizels et al. |
| 2016/0046960 A1 | 2/2016 | Frendewey et al. |
| 2016/0060637 A1 | 3/2016 | Hommelsheim et al. |
| 2016/0060655 A1 | 3/2016 | Quake et al. |
| 2016/0060657 A1 | 3/2016 | Frendewey et al. |
| 2016/0074535 A1 | 3/2016 | Ranganathan et al. |
| 2016/0090607 A1 | 3/2016 | Conway et al. |
| 2016/0108360 A1 | 4/2016 | Lee et al. |
| 2016/0108369 A1 | 4/2016 | Kuno et al. |
| 2016/0122774 A1 | 5/2016 | Duchateau et al. |
| 2016/0138045 A1 | 5/2016 | Koshland et al. |
| 2016/0138046 A1 | 5/2016 | Wu |
| 2016/0145646 A1 | 5/2016 | Frendewey et al. |
| 2016/0151491 A1 | 6/2016 | Rabinovich et al. |
| 2016/0153003 A1 | 6/2016 | Joung et al. |
| 2016/0153004 A1 | 6/2016 | Zhang et al. |
| 2016/0153005 A1 | 6/2016 | Zhang et al. |
| 2016/0153006 A1 | 6/2016 | Zhang et al. |

(56) References Cited

U.S. PATENT DOCUMENTS

| | | |
|---|---|---|
| 2016/0160210 A1 | 6/2016 | Mali et al. |
| 2016/0175462 A1 | 6/2016 | Zhang et al. |
| 2016/0177278 A1 | 6/2016 | Wolfe et al. |
| 2016/0177339 A1 | 6/2016 | Voronina et al. |
| 2016/0177340 A1 | 6/2016 | Bradley et al. |
| 2016/0184362 A1 | 6/2016 | Duchateau et al. |
| 2016/0186213 A1 | 6/2016 | Zhang et al. |
| 2016/0201072 A1 | 7/2016 | Cigan et al. |
| 2016/0207983 A1 | 7/2016 | Bradley et al. |
| 2016/0208243 A1 | 7/2016 | Zhang et al. |
| 2016/0208288 A1 | 7/2016 | Liu et al. |
| 2016/0208319 A1 | 7/2016 | Berman et al. |
| 2016/0215276 A1 | 7/2016 | Liu et al. |
| 2016/0215300 A1 | 7/2016 | May et al. |
| 2016/0250300 A1 | 9/2016 | Khalili et al. |
| 2016/0257948 A1 | 9/2016 | Bradley et al. |
| 2016/0257967 A1 | 9/2016 | Russell et al. |
| 2016/0257974 A1 | 9/2016 | Bradley et al. |
| 2016/0264995 A1 | 9/2016 | Yamamoto et al. |
| 2016/0281111 A1 | 9/2016 | Cotta-Ramusino et al. |
| 2017/0275611 A1 | 9/2017 | Bradley et al. |
| 2019/0112619 A1 | 4/2019 | Frendewey et al. |
| 2019/0338274 A1 | 11/2019 | Bradley et al. |

FOREIGN PATENT DOCUMENTS

| | | | |
|---|---|---|---|
| EP | 2152880 B1 | 8/2011 | |
| EP | 1360287 B1 | 9/2012 | |
| EP | 2508595 A1 | 10/2012 | |
| EP | 2602323 A1 | 6/2013 | |
| EP | 3009511 A2 | 4/2016 | |
| EP | 3064585 A1 | 9/2016 | |
| EP | 3418379 A2 | 12/2018 | |
| EP | 3418379 B1 | 12/2020 | |
| GB | 2 436 737 A | 10/2007 | |
| GB | 1316560.0 | 3/2015 | |
| GB | 1321210.5 | 3/2015 | |
| WO | WO 1997/030151 A1 | 8/1997 | |
| WO | WO 2002/066630 A1 | 8/2002 | |
| WO | WO 2003/087341 A2 | 10/2003 | |
| WO | WO 2006/028723 A1 | 3/2006 | |
| WO | WO 2006/044962 A1 | 4/2006 | |
| WO | WO 2007/113505 A2 | 10/2007 | |
| WO | WO 2007/117410 A2 | 10/2007 | |
| WO | WO 2008/015418 A2 | 2/2008 | |
| WO | WO 2008/151081 A1 | 12/2008 | |
| WO | WO 2011/044684 A1 | 4/2011 | |
| WO | WO 2011/051390 A1 | 5/2011 | |
| WO | WO 2011/078665 A1 | 6/2011 | |
| WO | WO 2011/146121 A1 | 11/2011 | |
| WO | WO 2011/154927 A2 | 12/2011 | |
| WO | WO 2012/012667 A2 | 1/2012 | |
| WO | WO 2012/018726 A1 | 9/2012 | |
| WO | WO 2012/129198 A1 | 9/2012 | |
| WO | WO 2012/168307 A2 | 12/2012 | |
| WO | WO 2013/061078 A1 | 5/2013 | |
| WO | WO 2013/063361 A1 | 5/2013 | |
| WO | WO 2013/141680 A1 | 9/2013 | |
| WO | WO 2013/142578 A1 | 9/2013 | |
| WO | WO 2013/163394 A1 | 10/2013 | |
| WO | WO 2013/169802 A1 | 11/2013 | |
| WO | WO 2013/176772 A1 | 11/2013 | |
| WO | WO 2013/188522 A2 | 12/2013 | |
| WO | WO 2014/018423 A2 | 1/2014 | |
| WO | WO 2014/065596 A1 | 5/2014 | |
| WO | WO 2014/089290 A1 | 6/2014 | |
| WO | WO 2014/093479 A1 | 6/2014 | |
| WO | WO 2014/093595 A1 | 6/2014 | |
| WO | WO 2014/093622 A2 | 6/2014 | |
| WO | WO 2014/093635 A1 | 6/2014 | |
| WO | WO 2014/093655 A2 | 6/2014 | |
| WO | WO 2014/093661 A2 | 6/2014 | |
| WO | WO 2014/093694 A1 | 6/2014 | |
| WO | WO 2014/093701 A1 | 6/2014 | |
| WO | WO 2014/093709 A1 | 6/2014 | |
| WO | WO 2014/093712 A1 | 6/2014 | |
| WO | WO 2014/093718 A1 | 6/2014 | |
| WO | WO 2014/099744 A1 | 6/2014 | |
| WO | WO 2014/099750 A2 | 6/2014 | |
| WO | WO 2014/104878 A1 | 7/2014 | |
| WO | WO 2014/127287 A1 | 8/2014 | |
| WO | WO 2014/130706 A1 | 8/2014 | |
| WO | WO 2014/130955 A1 | 8/2014 | |
| WO | WO 2014/131833 A1 | 9/2014 | |
| WO | WO 2014/143381 A1 | 9/2014 | |
| WO | WO 2014/150624 A1 | 9/2014 | |
| WO | WO 2014/165825 A2 | 10/2014 | |
| WO | WO 2014/172458 A1 | 10/2014 | |
| WO | WO 2014/172470 A2 | 10/2014 | |
| WO | WO 2014/172489 A2 | 10/2014 | |
| WO | WO 2014/173955 A1 | 10/2014 | |
| WO | WO 2014/182700 A1 | 11/2014 | |
| WO | WO 2014/186585 A2 | 11/2014 | |
| WO | WO 2014/191128 A1 | 12/2014 | |
| WO | WO 2014/191518 A1 | 12/2014 | |
| WO | WO 2014/201015 A2 | 12/2014 | |
| WO | WO 2014/204723 A1 | 12/2014 | |
| WO | WO 2014/204724 A1 | 12/2014 | |
| WO | WO 2014/204725 A1 | 12/2014 | |
| WO | WO 2014/204726 A1 | 12/2014 | |
| WO | WO 2014/204728 A1 | 12/2014 | |
| WO | WO 2014/204729 A1 | 12/2014 | |
| WO | WO 2014/205192 A2 | 12/2014 | |
| WO | WO 2015/006290 A1 | 1/2015 | |
| WO | WO 2015/006294 A1 | 1/2015 | |
| WO | WO 2015/006498 A2 | 1/2015 | |
| WO | WO 2015/010114 A1 | 1/2015 | |
| WO | WO 2015/013583 A2 | 1/2015 | |
| WO | WO 2015/026885 A1 | 2/2015 | |
| WO | WO 2015/035139 A2 | 3/2015 | |
| WO | WO 2015/035162 A2 | 3/2015 | |
| WO | WO 2015/040402 A1 | 3/2015 | |
| WO | WO 2015/048690 A1 | 4/2015 | |
| WO | WO 2015/052231 A2 | 4/2015 | |
| WO | WO 2015/057980 A1 | 4/2015 | |
| WO | WO 2015/070083 A1 | 5/2015 | |
| WO | WO 2015/077290 A2 | 5/2015 | |
| WO | WO 2015/079057 A2 | 6/2015 | |
| WO | WO 2015/086798 A2 | 6/2015 | |
| WO | WO 2015/088643 A1 | 6/2015 | |
| WO | WO 2015/089351 A1 | 6/2015 | |
| WO | WO 2015/089427 A1 | 6/2015 | |
| WO | WO 2015/089462 A1 | 6/2015 | |
| WO | WO 2015/089465 A | 6/2015 | |
| WO | WO 2015/089473 A1 | 6/2015 | |
| WO | WO 2015/095804 A1 | 6/2015 | |
| WO | WO 2015/105928 A1 | 7/2015 | |
| WO | WO 2015/112790 A2 | 7/2015 | |
| WO | WO 2015/116969 A2 | 8/2015 | |
| WO | WO 2015/117041 A1 | 8/2015 | |
| WO | WO 2015/123339 A1 | 8/2015 | |
| WO | WO 2015/127439 A1 | 8/2015 | |
| WO | WO 2015/134812 A1 | 9/2015 | |
| WO | WO 2015/138510 A1 | 9/2015 | |
| WO | WO 2015/138739 A2 | 9/2015 | |
| WO | WO 2015/139008 A1 | 9/2015 | |
| WO | WO 2015/143046 A2 | 9/2015 | |
| WO | WO 2015/148761 A1 | 10/2015 | |
| WO | WO 2015/159086 A1 | 10/2015 | |
| WO | WO 2015/163733 A1 | 10/2015 | |
| WO | WO 2015/166272 A2 | 11/2015 | |
| WO | WO 2015/173436 A1 | 11/2015 | |
| WO | WO 2015/184259 A1 | 12/2015 | |
| WO | WO 2015/184262 A1 | 12/2015 | |
| WO | WO 2015/184268 A1 | 12/2015 | |
| WO | WO 2015/188109 A1 | 12/2015 | |
| WO | WO 2015/200805 A2 | 12/2015 | |
| WO | WO 2016/011210 A2 | 1/2016 | |
| WO | WO 2016/011428 A1 | 1/2016 | |
| WO | WO 2016/033246 A1 | 3/2016 | |
| WO | WO 2016/033315 A2 | 3/2016 | |
| WO | WO 2016/036754 A1 | 3/2016 | |
| WO | WO 2016/037161 A2 | 3/2016 | |
| WO | WO 2016/037162 A1 | 3/2016 | |

(56) References Cited

FOREIGN PATENT DOCUMENTS

| | | | |
|---|---|---|---|
| WO | WO 2016/049024 A2 | 3/2016 |
| WO | WO 2016/049163 A2 | 3/2016 |
| WO | WO 2016/049258 A2 | 3/2016 |
| WO | WO 2016/054032 A1 | 4/2016 |
| WO | WO 2016/054326 A1 | 4/2016 |
| WO | WO 2016/057821 A2 | 4/2016 |
| WO | WO 2016/057961 A1 | 4/2016 |
| WO | WO 2016/061073 A1 | 4/2016 |
| WO | WO 2016/061374 A1 | 4/2016 |
| WO | WO 2016/061481 A1 | 4/2016 |
| WO | WO 2016/061523 A1 | 4/2016 |
| WO | WO 2016/065364 A1 | 4/2016 |
| WO | WO 2016/073955 A2 | 5/2016 |
| WO | WO 2016/073990 A1 | 5/2016 |
| WO | WO 2016/081923 A2 | 5/2016 |
| WO | WO 2016/084084 A1 | 6/2016 |
| WO | WO 2016/089866 A1 | 6/2016 |
| WO | WO 2016/094872 A1 | 6/2016 |
| WO | WO 2016/094874 A1 | 6/2016 |
| WO | WO 2016/094880 A1 | 6/2016 |
| WO | WO 2016/097751 A1 | 6/2016 |
| WO | WO 2016/100819 A1 | 6/2016 |
| WO | WO 2016/106338 A2 | 6/2016 |
| WO | WO 2016/108926 A1 | 7/2016 |
| WO | WO 2016/112242 A1 | 7/2016 |
| WO | WO 2016/112351 A1 | 7/2016 |
| WO | WO 2016/114972 A1 | 7/2016 |
| WO | WO 2016/115326 A1 | 7/2016 |
| WO | WO 2016/130697 A1 | 8/2016 |
| WO | WO 2016/135557 A2 | 9/2016 |
| WO | WO 2016/135558 A2 | 9/2016 |
| WO | WO 2016/135559 A2 | 9/2016 |
| WO | WO 2016/142719 A1 | 9/2016 |
| WO | WO 2016/154579 A2 | 9/2016 |
| WO | WO 2016/138574 A1 | 8/2020 |

OTHER PUBLICATIONS

EP 3080279 Communication in Reply to Rule 116 EPC submission mailed Apr. 12, 2021.
EP 3080279 Communication in Reply to the opponent submission of proprietor mailed Mar. 15, 2021.
EP 3080279 Communication in Reply to the preliminary opinion dated Mar. 2, 2021.
EP 3080279 Summons to appear at Oral Preceedings mailed Oct. 13, 2020.
Thomas, et al., "High-fidelity gene targeting in embryonic stem cells by using sequence replacement vectors," Mol. Cell. Biol. 12(7):2919-2923, (1992).
Zhang et al., "The CRISPR/Cas9 system produces specific and homozygous targeted gene editing in rice in one generation," Plant Biotechnol. J., vol. 12(6), pp. 797-807, May 23, 2014.
"Stem Cells: Scientific Progress and Future Research Directions," National Institute of Health, Department of Health and Human Services, (2001).
Abudayyeh et al., "C2c2 is a single-component programmable RNA-guided RNA-targeting CRISPR effector," Science, vol. 353(6299), Jun. 2, 2016.
Aitman et al., "Progress and prospects in rat genetics: a community view," Nature Genetics, vol. 40(5), pp. 516-522, May 2008.
Auerbach et al., "Establishment and chimera analysis of 129/SvEv- and C57BL/6-derived mouse embryonic stem cell lines," Biotechniques, vol. 29(5), pp. 1024-1028, 1030, 1032, Nov. 2000.
Baker, M., "Gene editing at CRISPR speed," Nature Biotechnology (2014), vol. 32(4), p. 309-312.
Barrangou, "RNA-mediated programmable DNA cleavage," Nature Biotechnology, 2012, vol. 30(9), pp. 836-838.
Bassett, A.R., et al., "CRISPR/Cas9 and Genome Editing in *Drosophila*," Journal of Genetics and Genomics (2014), vol. 41, pp. 7-19.
Benders et al., "Cloning whole bacterial genomes in yeast," Nucleic Acids Res., vol. 38(8), pp. 2558-2569, Mar. 7, 2010.

Berdien, et al., "Talen-mediated editing of endogenous T-cell receptors facilitates efficient reprogramming of T lymphocytes by lentiviral gene transfer," Gene Therapy, 21, 539-548 (2014).
Bernardini et al., "Site-specific genetic engineering of the Anopheles gambiae Y chromosome," Proc. Natl. Acad. Sci. USA, vol. 111(21), pp. 7600-7605, May 12, 2014.
Beumer et al., "Donor DNA Utilization During Gene Targeting with Zinc-Finger Nucleases," Genes Genomes Genetics, vol. 3, pp. 657-664, Apr. 2013.
Blair et al., "Culture parameters for stable expansion, genetic modification and germline transmission of rat pluripotent stem cells," Biol. Open, vol. 1(1): pp. 58-65, Nov. 1, 2011.
Brouns, S.J.J., "A Swiss Army Knife of Immunity," Science (2012), vol. 337, pp. 808-809.
Buehr et al., "Capture of Authentic Embryonic Stem Cells from Rat Blastocysts," Cell, vol. 135, pp. 1287-1298, 2008.
Byrne et al., "Multi-kilobase homozygous targeted gene replacement in human induced pluripotent stem cells," Nucleic Acids Research, Vo. 43(3), p. e21, 2014 (epub Nov. 20, 2014).
Carlson, et al., "Targeting DNA with Fingers and TALENs," Molecular Therapy-Nucleic Acids, 2012, 1:e3.
Carroll, "Staying on target with CRISPR-Cas," Nature Biotechnology, 2013, vol. 31(9), pp. 807-809.
Carroll, "Zinc-Finger Nucleases as Gene Therapy Agents", Gene Ther., Nov. 15, 2008:(22):1463-1468.
Cartwright et al., "LIF/STAT3 controls ES cell self-renewal and pluripotency by a Myc- dependent mechanism," Development, vol. 132(5), pp. 885-896, 2005.
Casanova et al., "Cross-Species Genome Wide Expression Analysis during Pluripotent Cell Determination in Mouse and Rat Preimplantation Embryos," PLoS One, vol. 7(10), e47107, 2012.
Cathomen, et al., "Zinc-finger nucleases: the next generation emerges," Molecular Therapy, 208, vol. 16(7), pp. 1200-1207 (Jul. 2008).
Certificate of Analysis for KNOCKOUT™ DMEM, Life Technologies, Catalog No. 10829, Lot No. 1677060, May 21, 2015.
Chang et al., "Genome editing with RNA-guided Cas9 nuclease in Zebrafish embryos," Cell Research, vol. 23, pp. 465-472, 2013. (published Mar. 2013).
Chari et al., "Unraveling CRISPR-Cas9 genome engineering parameters via a library-on- library approach," Nature Methods, vol. 12(9): 823-826 plus Supplementary Figures, Jul. 13, 2015.
Chen et al., "Chemically defined conditions for human iPSC derivation and culture," Nature Methods, vol. 8(5), pp. 424-429 plus supplementary materials, 2011 (epub Apr. 20, 2011).
Chen et al., "High-frequency genome editing using ssDNA oligonucleotides with zinc-finger nucleases," Nature Methods, vol. 8(9), pp. 753-755, 2011. (Jul. 17, 2011).
Chen et al., "Highly Efficient Mouse Genome Editing by CRISPR Ribonucleoprotein Electroporation of Zygoes," J. Biol. Chem., May 5, 2016.
Chen, "iPSC derivation from fibroblast in chemically defined medium," Stembook, Jun. 13, 2012.
Cho, et al., "Targeting genome engineering in human cells with the Cas9 RNA-guided endonuclease," Nature Biotechnology, 2013, vol. 31(3):230-232.
Choulika et al., "Induction of Homologous Recombination in Mammalian Chromosomes by Using the I-SceI System of *Saccharomyces cerevisiae*," Mol. Cell. Biol., vol. 15(4), pp. 1968-1973, 1995.
Christian M., et al., "Targeting DNA Double-Strand Breaks with TAL Effector Nucleases," Genetics (2010), vol. 186, pp. 757-761.
Chu et al., "Increasing the efficiency of homology-directed repair for CRISPR-Cas9-induced precise gene editing in mammalian cells," Nature Biotech., vol. 33(5), pp. 543-548, 2015. (published Mar. 2015).
Cobb and Zhao, "Direct cloning of large genomic sequences," Nature Biotechnology, 2012, vol. 30(5), pp. 405-406.
Cong et al., "Multiplex Genome Engineering Using CRISPR/Cas Systems," Science, vol. 339(6121), pp. 819-823 plus Supplemental Materials, Jan. 3, 2013.
Cui, et al., "Targeted integration in rat and mouse embryos with zinc-finger nucleases," Nature Biotechnology, vol. 29, No. 1, 64-68 (Dec. 12, 2010).

(56) References Cited

OTHER PUBLICATIONS

D'Aiuto et al., "Large-scale generation of human iPSC-derived neural stem cells/early neural progenitor cells and their neuronal differentiation," Organogenesis, vol. 10(4), pp. 365-377, Oct. 2, 2014.
Dechiara, T.M., et al., "VelociMouse: Fully ES Cell-Derived F0-Generation Mice Obtained from the Injection of ES Cells into Eight-Cell-Stage Embryos," Jan. 1, 2009, Methods in Molecular Biology, 530(16): 311-324.
Dickinson, et al., "Engineering the Caenorhabditis elegans Genome Using Cas9-Triggered Homologous Recombination," Nat Methods, 10(10): 1028-1034, (2013).
Ding et al., "Enhanced Efficiency of Human Pluripotent Stem Cell Genome Editing through Replacing TALENs with CRISPRs," Cell Stem Cell, vol. 12, pp. 393-394 plus supplemental materials, 2013 (Apr. 4, 2013).
Ding, et al., "A Talen genome-editing system for generating human stem cell-based disease models," Cell Stem Cell, 2013, vol. 12, pp. 238-251.
Donoho et al., "Analysis of Gene Targeting and Intrachromosomal Homologous Recombination Stimulated by Genomic Double-Strand Breaks in Mouse Embryonic Stem Cells," Mol. Cell. Biol., vol. 18(7), pp. 4070-4078, 1998.
Doudna et al., "The new frontier of genome engineering with CRISPR-Cas9," Science, vol. 346(6213), pp. 1258096-1-1258096-9, Nov. 28, 2014.
EMD-Millipore, Certificate of Analysis for Recombinant Human Leukemia Inhibitory Factor, retrieved from internet on Apr. 25, 2015 at http://www.emdmillipore.com/US/en/product/Leukemia-Inhibitory-Factor-Protein%2C- Recombinant-human, MM_NF-LIF1010#documentation.
EMD-Millipore, "Product Information sheet for Rat ESGRO," retrieved from internet on Apr. 25, 2015 at < http://www.emdmillipore.com/US/en/product/Rat-ESGRO%C2%AE%2C-1-million-units1-mL,MM_NF-ESG2206#anchor_COA.
EP 3080279 Communication of Notice of Opposition mailed Oct. 8, 2018.
EP 3080279 Communication of Response to Patentee's Submission in Opposition Proceedings mailed Feb. 25, 2020.
EP 3080279 Submission in Opposition Proceedings mailed Jul. 1, 2019.
EP 3080279 Summons to Attend Oral Proceedings mailed Mar. 6, 2020.
EP Application No. 14754746.7, Extended European Search Report dated Jun. 13, 2016.
EP Application No. 14784879.0, Extended European Search Report dated Sep. 19, 2016.
EP Application No. 18188401.6 Extended European Search Report dated Jan. 23, 2019.
Evers et al., "CRISPR knockout screening outperforms shRNA and CRISPRi in identifying essential genes," Nature Biotechnology, vol. 24(6), pp. 631-633, Apr. 25, 2016.
Fan et al., "107 Genetic Inactivation of the Sry Gene in Argali Wild and Romney Domestic Sheep with CRISPR/Cas Systems for Producing Sex-Reversed Female Animals," Reproduction Fertility and Development, vol. 26(1), p. 167, Dec. 5, 2013.
Flisikowska, et al., "Efficient Immunoglobulin Gene Disruption and Targeted Replacement in Rabbit Using Zinc Finger Nucleases," Plos one, vol. 6 Issue 6 (Jun. 2011).
Frendewey ,"VelociGene: Large-scale Modification of Rodent Genomes," Wellcome Trust Advanced Course: Genetic Engineering of Mammalian Stem Cells, Mar. 13, 2014.
Frendewey, "VelociGene: Large-scale Modification of Rodent Genomes," Wellcome Trust Advanced Course: Genetic Engineering of Mammalian Stem Cells, Feb. 20, 2015.
Frokjaer-Jensen C., "Exciting Prospects for Precise Engineering of Caenorhabditis elegans Genomes with CRISPR/Cas9," Genetics (2013), vol. 195, pp. 635-642.

Fu, et al., "High-frequency off-target mutagenesis induced by CRISPR-Cas nucleases in human cells," Nature Biotechnology, 2013, vol. 31(9), pp. 822-826.
Fujii et al., "Efficient generation of genome-modified mice via offset-nicking by CRISPR/Cas system," Biochemical and Biophysical Research Communications, vol. 445(4), pp. 791-794 plus Supplementary Information, Jan. 31, 2014.
Fujii W., et al., "Efficient generation of large-scale genome-modified mice using gRNA and CAS9 endonuclease," Nucleic Acids Research (2013), vol. 41(20), p. e187.
Gafni et al., "Derivation of novel human ground state naïve pluripotent stem cells," Nature, vol. 504(7479), p. 282-286 plus supplementary materials, 2013 (epub Oct. 30, 2013).
Gaj et al., "ZFN, Talen, and CRISPR/Cas-based methods for genome engineering," Trends Biotech., vol. 31(7), pp. 397-405, 2013.
Gao et al., "DNA-guided genome editing using the Natronobacterium gregoryi Argonaute," Nature Biotechnology, vol. 34(7), pp. 768-773, May 2, 2016.
Garg, A., et al., "Engineering synthetic TAL effectors with orthogonal target sites," Nucleic Acids Research (2012), vol. 40(15), p. 7584-7595.
Gasiunas, G., et al., "Cas9-crRNA ribonucleoprotein complex mediates specific DNA cleavage for adaptive immunity in bacteria," PNAS, 2012, vol. 108, pp. 10098-10103.
Gennequin, et al., "CRISPR/Cas-induced double-strand breaks boost the frequency of gene replacements for humanizing the mouse Cnr2 gene," Biochem. Biophys. Res. Commun., 441:815-819, (2013).
Gibco Data Sheet for "Recombinant Mouse Leukemia Inhibitory Factor (LIF), PMC4054,"pp. 1-2, 2011.
Gibson, D., et al., "Enzymatic assembly of DNA molecules up to several hundred kilobases," Nature Methods, 2009, vol. 6(5), pp. 343-345.
Gibson, Daniel G., "Enzymatic Assembly Of Overlapping DNA Fragments," Methods in Enzymology, 2011, vol. 498, pp. 349-361.
Graf et al., "The Role of the Leukemia Inhibitory Factor (LIF)—Pathway in Derivation and Maintenance of Murine Pluripotent Stem Cells," Genes, vol. 2, pp. 280-297, 2011.
Gratz et al., "Genome Engineering of Drosophila with the CRISPR RNA-Guided Cas9 Nuclease," Genetics, vol. 194, pp. 1029-1035, 2013, (published May 2013).
Gratz et al., "Highly Specific and Efficient CRISPR/Cas9-Catalyzed Homology-Directed Repair in Drosophila," Genetics, vol. 196(4), pp. 961-971 plus Supporting Information, Jan. 29, 2014.
Hanna et al., "Human embryonic stem cells with biological and epigenetic characteristics similar to those of mouse ESCs," Proc. Natl. Acad. Sci. U.S.A., vol. 107(20), pp. 9222-9227 plus supplementary materials, 2010 (epub May 4, 2010).
Harrison, M.M., et al., "A CRISPR view of development," Genes & Development (2014), vol. 28(17), pp. 1859-1872.
Hirabayashi et al., "Establishment of Rat Embryonic Stem Cell Lines That Can Participate in Germline Chimerae at High Efficiency," Mol. Reprod. Dev., vol. 77, p. 94, 2010.
Hirano et al., "Human and Mouse Induced Pluripotent Stem Cells Are Differentially Reprogrammed in Response to Kinase Inhibitors," Stem Cells and Development, vol. 21(8), pp. 1287-1298, May 20, 2012.
Horvath, P., et al., "CRISPR/Cas, the Immune System of Bacteria and Archaea," Science, 2010, vol. 327, pp. 167-170.
Hsu, et al., "DNA targeting specificity of RNA-guided Cas9 nucleases," Nature Biotechnology, 2013, vol. 31(9), pp. 827-832.
Hsu, P.D., et al., "Development and Applications of CRISPR-Cas9 for Genome Engineering," Cell (2014), vol. 157, pp. 1262-1278.
Hwang et al., "Efficient In Vivo Genome Editing Using RNA-Guided Nucleases," Nat. Biotechnol., vol. 31(3), pp. 227-229 (plus supplemental materials), 2013.
Iannaccone, P., et al., "Pluripotent Embryonic Stem Cells from the Rat Are Capable of Producing Chimeras," Developmental Biology, 1994, vol. 163, pp. 288-292.
Jallepalli et al., "Securin is required for chromosomal stability in human cells," Cell, vol. 105(4), pp. 445-457, May 18, 2001.

(56) References Cited

OTHER PUBLICATIONS

Jao et al., "Efficient multiplex biallelic zebrafish genome editing using a CRISPR nuclease system," Proc. Natl. Acad. Sci. U.S.A., vol. 110(34), pp. 13904-13909 plus Supporting Information, Aug. 5, 2013.
Jasin, et al., "Repair of Strand Breaks by Homologous Recombination," Cold Spring Harb. Perspect. Biol., vol. 5(11), p. a012740, Nov. 1, 2013.
Jiang, et al., "RNA-guided editing of bacterial genomes using CRISPR-Cas systems," Nature Biotechnology, 2013, vol. 31(3), pp. 233-239.
Jinek et al., "A Programmable Dual-RNA-Guided DNA Endonuclease in Adaptive Bacterial Immunity," Science, vol. 337, pp. 816-821 plus Supplemental Materials, Jun. 28, 2012.
Johnson, et al., "A rapid assay to quantify the cleavage efficiency of custom-designed nucleases in planta," Plant Mol Biol, 82:207-221 (2013).
Kashimada et al., "Sry: the master switch in mammalian sex determination," Development, vol. 137(23), pp. 3921-3930, Dec. 2, 2010.
Kato et al., "Production of Sry knockout mouse using Talen via oocyte injection," Scientific Reports, vol. 3, p. 3136, 2013 (published Nov. 5, 2013).
Kawamata et al., "Two distinct knockout approaches highlight a critical role for p53 in rat development," Sci. Rep., vol. 2, p. 945, 2012.
Kawamata, et al., "Generation of genetically modified rats from embryonic stem cells," Proc. Natl. Acad. Sci. U.S.A., vol. 107(32), pp. 14223-14228, Aug. 10, 2010.
Kawamata, M., et al., "Establishment of Embryonic Stem Cells from Rat Blastocysts," Methods Mol. Biol., 2010, vol. 597, pp. 169-177.
Kim et al., "Targeted genome editing in human cells with zinc finger nucleases constructed via modular assembly," Genome Res., vol. 19(7), pp. 1279-1288, 2009.
Kobayashi et al., "Identification of Rat Rosa26 Locus Enables Generation of Knock-In Rat Lines Ubiquitously Expressing tdTomato," Stem Cells and Development, vol. 21(16), pp. 2981-2986, May 7, 2012.
Komor et al, "Programmable editing of a target base in genomic DNA without double- stranded cleavage," Nature, vol. 533(7603), pp. 420-424, Apr. 20, 2016.
Kondo et al., "Protein kinase A-mediated enhancement of miniature IPSC frequency by noradrenaline in rat cerebellar stellate cells," The Journal of Physiology, vol. 498(1), pp. 165-176, Jan. 1, 1997.
Kondo, et al., "Highly Improved Gene Targeting by Germline-Specific Cas9 Expression in *Drosophila*," Genetics, vol. 195, pp. 715-721, Sep. 3, 2013.
Konermann et al., "Genome-scale transcriptional activation by an engineered CRISPR-Cas9 complex," Nature, vol. 517(7536), pp. 583-588, published online Dec. 10, 2014.
Kosicki et al., "Repair of double-strand breaks induced by CRISPR-Cas9 leads to large deletions and complex rearrangements," Nat. Biotechnol., 36(8): 765-771, (Jul. 16, 2018).
Krivokharchenko, A., et al., "In Vitro Formation of Tetraploid Rat Blastocysts After Fusion of Two-Cell Embryos," Molecular Reproduction And Development, 2002, vol. 61, pp. 460-465.
Kuijpers et al., "One-step assembly and targeted integration of multigene constructs assisted by the I-SceI meganuclease in *Saccharomyces cerevisiae*," FEMS Yeast Res., vol. 13(8), pp. 769-781, Oct. 7, 2013.
Kuno et al., "Generation of fertile and fecund F0 XY female mice from XY ES cells," Transgenic Research, vol. 24(1), pp. 19-29, 2014 (epub Aug. 3, 2014).
Kuroiwa, et al., "Sequential targeting of the genes encoding immunoglobulin-μ and prion protein in cattle," Nature Genetics, vol. 36, No. 7, (Jul. 2004).
Kushi et al., "Generation of mutant mice with large chromosomal deletion by use of irradiated ES cells—analysis of large deletion around hprt locus of ES cell," Mamm. Genome 9(4):269-273, (1998).
Li et al., "Derivation of Germline Competent Rat Embryonic Stem Cells from DA Rats," J. Genet. Genomics, vol. 39, pp. 603-606, 2012.
Li et al., "Germline Competent Embryonic Stem Cells Derived from Rat Blastocysts," Cell, vol. 135, pp. 1299-1310, 2008.
Li et al., "Genetic modification and screening in rat using haploid embryonic stem cells," Cell Stem Cell, vol. 14(3); pp. 404-414, 2013 (epub Dec. 19, 2013).
Li et al., "Optimization of Genome Engineering Approaches with the CRISPR/Cas9 System," PLoS One, vol. 9(8), p. e105779, Aug. 28, 2014.
Li, D., et al., "Heritable gene targeting in the mouse and rat using a CRISPR-Cas system," Nature Biotechnology, 2013, vol. 31(8), pp. 681-683.
Li, et al., "Modularly assembled designer TAL effector nucleases for targeted gene knockout and gene replacement in eukaryotes," Nucleic Acids Research, 2011, vol. 39(14), pp. 6315-6325.
Li, M., et al., "A Cut above the Rest: Targeted Genome Editing Technologies in Human Pluripotent Stem Cells," Journal of Biological Chemistry (2014), vol. 289(8), pp. 4594-4599.
Lin et al., "Enhanced homology-directed human genome engineering by controlled timing of CRISPR/Cas9 delivery," eLife, vol. 3, e04766, 2014. (published Dec. 15, 2014).
Lin, S.-C., et al., "Strategies for gene disruption in *Drosophila*," Cell & Bioscience (2014), vol. 4(1), p. 63.
Liu et al., "A one-step cloning method for the construction of somatic cell gene targeting vectors: application to production of human knockout cell lines," BMC Biotechnol., vol. 12, p. 71, Oct. 9, 2012.
Liu, L., et al., "CRISPR-Cas system: a powerful tool for genome engineering," Plant Molecular Biology (2014), vol. 85, pp. 209-218.
Lombardo, et al., "Gene editing in human stem cells using zinc finger nucleases and integrase-defective lentiviral vector delivery," Nature Biotechnology, 2007, vol. 25(11), pp. 1298-1306.
Ma et al., "Heritable multiplex genetic engineering in rats using CRISPR/Cas9," PLoS One, vol. 9(3), p. e89413, Mar. 5, 2014.
Macdonald, et al., "Precise and in situ genetic humanization of 6 Mb of mouse immunoglobulin genes," PNAS, vol. 111, No. 14: 5147-5152, (Apr. 8, 2014).
Mali et al., "RNA-Guided Human Genome Engineering via Cas9," Science, vol. 339(6121), pp. 823-826 plus Supplemental Materials, Jan. 3, 2013.
Mali et al., "CAS9 transcriptional activators for target specificity screening and paired nickases for cooperative genome engineering," Nature Biotechnology, vol. 31(9), pp. 833-838 plus Supplementary Information, Aug. 1, 2013.
Mali, et al., "Cas9 as a versatile tool for engineering biology," Nature Methods, vol. 10(10), pp. 957-963, 2013.
Manjunath., et al., "Newer Gene Editing Technologies toward HIV Gene Therapy," Viruses (2013), vol. 5, pp. 2748-2766.
Maruyama et al., "Increasing the efficiency of precise genome editing with CRISPR-Cas9 by inhibition of nonhomologous end joining," Nature Biotech., vol. 33(5), pp. 538-542, 2015. (published Mar. 2015).
Mashiko et al., "Generation of mutant mice by pronuclear injection of circular plasmid expressing Cas9 and single guided RNA," Sci. Rep., vol. 3, p. 3355, Nov. 27, 2013.
Mashimo et al., "Generation of knockout rats with X-linked severe combined immunodeficiency (X-SCID) using zinc finger nucleases," PLoS One, vol. 5(1), p. e8870, 2010.
Matsuda et al., "STAT3 activation is sufficient to maintain an undifferentiated state of mouse embryonic stem cells," The EMBO Journal, vol. 18(15), pp. 4261-4269, 1999.
Meek et al., "Efficient Gene Targeting by Homologous Recombination in Rat Embryonic Stem Cells," PLoS One, vol. 5(12), p. e14225, 2010.
Men et al., "Germline Transmission of a Novel Rat Embryonic Stem Cell Line Derived from Transgenic Rats," Stem Cells Dev., vol. 21(14), pp. 2606-2612, 2012.

(56) References Cited

OTHER PUBLICATIONS

Miller, et al., "A Tale nuclease architecture for efficient genome editing," Nature Biotechnology, 2011, vol. 29(2), pp. 143-148.
Moehle et al., "Targeted gene addition into a specified location in the human genome using designed zinc finger nucleases," Proc. Natl. Acad. Sci. U.S.A., vol. 104(9), pp. 3055-3060, 2007 (epub Feb. 20, 2007).
Morgens et al., "Systematic comparison of CRISPR/Cas9 and RNAi screens for essential genes," Nature Biotechnology, vol. 34(6), pp. 634-636, May 9, 2016.
Moscou and Bogdanove, "A simple cipher governs DNA recognition by TAL effectors," Science, 2009, vol. 326, p. 1501.
Musser, "Rodent," Brittanica. Retrieved from the Internet May 31, 2016: http://www.brittanica.com/animal/rodent.
Mussolino, et al., "Tale nucleases: tailored genome engineering made easy," Curr. Opin. Biotechnol., vol. 23(5), pp. 644-650, 2012, (epub Feb. 17, 2012).
Narsinh, et al., "Gene Correction in Human Embryonic and Induced Pluripotent Stem Cells: Promise and Challenges Ahead", Molecular Therapy, vol. 18, No. 6, pp. 1061-1063, (Jun. (2010).
News Feature "Move over ZFNs," Nature Biotechnology, 2011, vol. 29(8), pp. 681-684.
Ota, S., et al., "Zebrafish: A model vertebrate suitable for the analysis of human genetic disorders," Congenital Anomalies (2014), vol. 54, pp. 8-11.
Parikh et al., "Detailed Phenotypic and Molecular Analyses of Genetically Modified Mice Generated by CRISPR-Cas9-Mediated Editing," PLoS One, vol. 10(1), p. e0116484, Jan. 14, 2015.
Pattanayak, et al., "High-throughput profiling of off-target DNA cleavage reveals RNA- programmed Cas9 nuclease specificity," Nature Biotechnology, 2013, vol. 31(9), pp. 839-843.
PCT International Preliminary Report on Patentability for application PCT/US2013/038165 dated Oct. 28, 2014.
PCT International Preliminary Report on Patentability for application PCT/US2014/017452 dated Aug. 25, 2015.
PCT International Preliminary Report on Patentability for application PCT/US2014/034412 dated Oct. 30, 2015.
PCT International Preliminary Report on Patentability for application PCT/US2014/060788 dated Jun. 23, 2016.
PCT International Search Report and Written Opinion of the International Searching Authority for application PCT/US2014/060788 dated Jan. 26, 2015.
PCT International Search Report and Written Opinion of the International Searching Authority for application PCT/US2015/038001 dated Feb. 25, 2016.
PCT International Search Report and Written Opinion of the International Searching Authority for application PCT/US2015/055776 dated Jan. 29, 2016.
PCT International Search Report and Written Opinion of the International Searching Authority for application PCT/US2015/062023 dated May 13, 2016.
PCT International Search Report and Written Opinion of the International Searching Authority for application PCT/US2015/066681 dated Mar. 29, 2016.
PCT International Search Report for application PCT/US2015/034503 dated Sep. 8, 2015.
PCT Written Opinion of the International Searching Authority for application PCT/US2015/034503 dated Sep. 8, 2015.
PCT/US2013/038165 International Search Report and Written Opinion dated Jul. 12, 2013.
PCT/US2014/017452 International Search Report and Written Opinion of the Searching Authority dated May 14, 2014.
PCT/US2014/034412 International Search Report and Written Opinion of the Searching Authority dated Oct. 9, 2014.
PCT/US2015/038001 Invitation of Pay Additional Fees mailed Nov. 13, 2015.
PCT/US2015/062023 Invitation of Pay Additional Fees mailed Feb. 8, 2016.
Peng, Y., et al., "Making designer mutants in model organisms," Development (2014), vol. 141, pp. 4042-4054.

Pennisi, E., "Beyond TALENs," Science (2012), vol. 338, p. 1411.
Perez et al., "Establishment of HIV-1 resistance in CD4+ T cells by genome editing using zinc finger nucleases," Nature Biotech., vol. 26(7), pp. 808-816, 2008.
Piatkevich et al., "Guide to Red Fluorescent Proteins and Biosensors for Flow Cytometry," Methods Cell Biol., vol. 102, pp. 431-461, 2011.
Platt et al., "CRISPR-Cas9 Knockin Mice for Genome Editing and Cancer Modeling," Cell, vol. 159, pp. 1-16, Sep. 25, 2014.
Port et al., "Optimized CRISPR/Cas tools for efficient germline and somatic genome engineering in *Drosophila*," Proc. Natl. Acad. Sci. U.S.A., vol. 111(29), pp. E2967-E2976 plus Supporting Information, Jul. 7, 2014.
Porteus, et al,, "Gene targeting using zinc finger nucleases," Nature Biotechnology, vol. 23(8), pp. 967-973, 2005.
Poueymirou et al., "F0 generation mice fully derived from gene-targeted embryonic stem cells allowing immediate analysis," Nature Biotechnology, Epub Dec. 24, 2006, vol. 25(1):91-99.
Qi, et al., "Repurposing CRISPR as an RNA-guided platform for sequence-specific control of gene expression," Cell, 2013, vol. 152, pp. 1173-1183.
Quinn et al., "A Site-Specific, Single-Copy Transgenesis Strategy to Identify 5' Regulatory Sequences of the Mouse Testis-Determining Gene Sry," PLoS One, vol. 9(4), p. e94813, Apr. 2014.
Ramirez et al., "Engineered zinc finger nickases induce homology-directed repair with reduced mutagenic effects," Nucleic Acids Research, vol. 40(12), pp. 5560-5568, 2012. (published Feb. 2012).
Ran et al., "Double nicking by RNA-guided CRISPR Cas9 for enhanced genome editing specificity," Cell, vol. 154, pp. 1380-1389, 2013.
Ran et al., "Genome engineering using the CRISPR-Cas9 system," Nature Protocols, vol. 8(11), pp. 2281-2308, Oct. 24, 2013.
Ran et al., "In vivo genome editing using *Staphylococcus aureus* Cas9," Nature, vol. 520(7546), pp. 186-191, Apr. 1, 2015.
Rathjen et al., "Differentiation Inhibiting Activity Is Produced in Matrix-Associated and Diffusible Forms That Are Generated by Alternate Promoter Usage," Cell, vol. 62, pp. 1105-1114, 1990.
Richter, et al., "Exploiting CRISPR/Cas: Interference Mechanisms and Applications," Int. J. Mol. Sci., 14(7):14518-14531, (2013).
Ruhnke, M., et al., "Long-Term Culture and Differentiation of Rat Embryonic Stem Cell-Like Cells into Neuronal, Glial, Endothelial, and Hepatic Lineages," Stem Cells, 2003, vol. 21, pp. 428-436.
Sadhu et al., "CRISPR-directed mitotic recombination enables genetic mapping without crosses," Science, vol. 352(6289): 1113-1116, May 5, 2016.
Scharenberg, A.M., et al., "Genome Engineering with TAL-Effector Nucleases and Alternative Modular Nuclease Technologies," Current Gene Therapy (2013), vol. 13, pp. 291-303.
Schwank, G., et al., "Functional Repair of CFTR by CRISPR/Cas9 in Intestinal Stem Cell Organoids of Cystic Fibrosis Patients," Cell Stem Cell (2013), vol. 13, pp. 653-658.
Shan et al., "Targeted genome modification of crop plants using a CRISPR-Cas system," Nature Biotechnology, vol. 31(8), pp. 686-688, Aug. 1, 2013.
Shao et al., "CRISPR/Cas-mediated genome editing in the rat via direct injection of one-cell embryos," Nature Protocols, vol. 9(10), pp. 2493-2512, 2014 (epub Sep. 25, 2014).
Shen, H, et al., "The heterogeneity and dynamic equilibrium of rat embryonic stem cells," Cell Research (2011), vol. 21, pp. 1143-1147.
Siao et al., "Single-step homozygous humanization induced by dual CRISPR/Cas9 cleavage," Oct. 28, 2015.
Sigma-Aldrich, "Product Information sheet for Leukemia Inhibitory Factor human," retrieved from internet on Apr. 25, 2015 at http://www.sigmaaldrich.com/content/dam/sigma-aldrich/docs/Sigma/Datasheet/4/15283dat.pdf.
Singh et al., "A Mouse Geneticist's Practical Guide to CRISPR Applications," Genetics, vol. 199, pp. 1-15, (2015).
Stemgent Product Specification Sheet, PD0325901, pp. 1-2 (2012).
Straub A., et al., "Zinc Fingers, TAL Effectors, or Cas9-Based DNA Binding Proteins: What's Best for Targeting Desired Genome Loci?," Molecular Plant (2013), vol. 6(5), pp. 1384-1387.

(56) References Cited

OTHER PUBLICATIONS

Technical Manual, Maintenance of Human Pluripotent Stem Cells in mTeSRtn, Version 4.1.0, Document 29106, Copyright by Stemcell Technologies, Inc. 2015.
Tong et al., "Production of p53 gene knockout rats by homologous recombination in embryonic stem cells," Nature, vol. 467(7312), pp. 211-213, 2010.
Tong et al., "Generating gene knockout rats by homologous recombination in embryonic stem cells," Nature Protocols, vol. 6(6), pp. 827-844, 2011 (epub May 26, 2011).
U.S. Appl. No. 13/870,280 Final Rejection dated Oct. 15, 2015.
U.S. Appl. No. 13/870,280, Requirement for Restriction/Election dated Jul. 22, 2014.
U.S. Appl. No. 14/185,703 Non-Final Office Action dated Dec. 3, 2015.
U.S. Appl. No. 14/185,703, Requirement for Restriction/Election dated Sep. 4, 2015.
U.S. Appl. No. 14/254,715 Final Office Action dated Nov. 30, 2015.
U.S. Appl. No. 14/254,715, Final Office Action dated Sep. 19, 2016.
U.S. Appl. No. 14/254,715, Non-Final Office Action dated Apr. 21, 2016.
U.S. Appl. No. 14/254,715, Non-Final Office Action dated Aug. 12, 2015.
U.S. Appl. No. 14/314,866, Advisory Action dated Aug. 12, 2015.
U.S. Appl. No. 14/314,866, Advisory Action dated Aug. 15, 2016.
U.S. Appl. No. 14/314,866, Final Office Action dated Apr. 26, 2016.
U.S. Appl. No. 14/314,866, Non-Final Office Action dated Sep. 19, 2016.
U.S. Appl. No. 14/314,866, Non-Final Office Action dated Dec. 26, 2014.
U.S. Appl. No. 14/314,866, Non-Final Office Action dated Nov. 27, 2015.
U.S. Appl. No. 14/314,866, Requirement for Restriction/Election dated Sep. 22, 2014.
U.S. Appl. No. 14/314,866, Final Office Action dated Jun. 4, 2015.
U.S. Appl. No. 14/515,503, Non-Final Office Action dated May 20, 2016.
U.S. Appl. No. 14/515,503, Notice of Allowance dated Sep. 23, 2016.
U.S. Appl. No. 14/515,503, Requirement for Restriction/Election dated Mar. 4, 2016.
U.S. Appl. No. 14/578,291, Non-Final Office Action dated Mar. 10, 2015.
U.S. Appl. No. 14/578,291, Notice of Allowance dated Aug. 26, 2015.
U.S. Appl. No. 14/731,914 , Requirement for Restriction/Election dated Dec. 31, 2015.
U.S. Appl. No. 14/731,914, Non-Final Office Action dated Jun. 17, 2016.
U.S. Appl. No. 14/751,807, Requirement for Restriction/Election dated Aug. 26, 2016.
U.S. Appl. No. 14/926,773, Non-Final Office Action dated May 6, 2016.
U.S. Appl. No. 14/926,773, Requirement for Restriction/Election dated Feb. 16, 2016.
U.S. Appl. No. 14/928,134, Advisory Action dated Jul. 15, 2016.
U.S. Appl. No. 14/928,134, Final Office Action dated Apr. 14, 2016.
U.S. Appl. No. 14/928,180, Advisory Action dated Aug. 22, 2016.
U.S. Appl. No. 14/928,180, Final Office Action dated Jun. 6, 2016.
U.S. Appl. No. 15/354,270, Notice of Allowance dated Oct. 2, 2018.
U.S. Appl. No. 15/354,270, Notice of Allowance dated Nov. 29, 2018.
U.S. Appl. No. 16/224,413, Corrected Notice of Allowance dated Apr. 23, 2020.
U.S. Appl. No. 16/224,413, Non-Final Office Action dated Nov. 15, 2019.
U.S. Appl. No. 16/224,413, Notice of Allowance dated Mar. 5, 2020.
U.S. Appl. No. 13/870,280 , Advisory Action dated Jan. 5, 2016.
U.S. Appl. No. 13/870,280, Non-Final Office Action dated Mar. 13, 2015.
U.S. Appl. No. 14/185,703, Final Office Action dated Apr. 20, 2016.
U.S. Appl. No. 14/254,715, Requirement for Restriction/Election dated Jun. 4, 2015.
U.S. Appl. No. 14/928,180, Non-Final Office Action dated Jan. 5, 2016.
Ueda et al., "Establishment of Rat Embryonic Stem Cells and Making of Chimera Rats," PLoS One, vol. 3(7), p. e2800, 2008.
U.S. Appl. No. 62/008,832, filed Jun. 6, 2014; Priority Document of WO 2015/188109 A1 Published Dec. 10, 2015.
U.S. Appl. No. 14/928,134 Non-Final Office Action dated Feb. 1, 2016.
Valenzuela et al., "High-throughput engineering of the mouse genome coupled with high- resolution expression analysis," Nature Biotech. 21(6):652-659, (2003).
Van Der Oost, "New tool for genome surgery," Science, 2013, vol. 339(6121), pp. 768-770.
Varlakhanova et al., "Myc Maintains Embryonic Stem Cell Pluripotency and Self-Renewal," Differentiation, vol. 80(1), pp. 9-19, 2010.
Wang et al., "One-Step Generation of Mice Carrying Mutations in Multiple Genes by CRISPR/Cas-Mediated Genome Engineering," Cell, vol. 153, pp. 910-918 plus supplemental materials, 2013. (published May 2013).
Wang et al., "Talen-mediated editing of the mouse Y chromosome," Nature Biotechnology, vol. 31 (6), p. 530-532, 2013 (epub May 12, 2013).
Watanabe et al., "A Rock inhibitor permits survival of dissociated human embryonic stem cells," Nature Biotechnology, vol. 25(6), pp. 681-686, 2007 (epub May 27, 2007).
Wen et al., "Completely ES Cell-Derived Mice Produced by Tetraploid Complementation Using Inner Cell Mass (ICM) Deficient Blastocysts," PLoS One, vol. 9(4), e94730, Apr. 14, 2014.
Whitworth et al., "Use of the CRISPR/Cas9 System to Produce Genetically Engineered Pigs from In Vitro-Derived Oocytes and Embryos," Biology of Reproduction, vol. 91(3), p. 78, Aug. 6, 2014.
Wu, Y., et al., "Correction of a Genetic Disease in Mouse via Use of CRISPR-Cas9," Cell Stem Cell (2013), vol. 13, pp. 659-662.
Xu, T., et al., "Cas9-Based Tools for Targeted Genome Editing and Transcriptional Control," Applied and Environmental Microbiology (2014), vol. 80(5), pp. 1544-1552.
Yamamoto et al., "Derivation of rat embryonic stem cells and generation of protease- activated receptor-2 knockout rats," Transgenic Res., vol. 21, pp. 743-755, 2012.
Yang et al., "One-step generation of mice carrying reporter and conditional alleles by CRISPR/Cas-mediated genome engineering," Cell, vol. 154(6), pp. 1370-1379, Aug. 29, 2013.
Yang et al., "Optimization of scarless human stem cell genome editing," Nucleic Acids Res., vol. 41(19), pp. 9049-9061, 2013 (epub Jul. 31, 2013).
Yang et al., "Targeted and genome-wide sequencing reveal single nucleotide variations impacting specificity of Cas9 in human stem cells," Nat. Commun., vol. 5, p. 5507, (2014).
Yang, S., et al., "Derivation and Genetic Modification of Embryonic Stem Cells from Disease- Model Inbred Rat Strains," Stem Cells And Development., 2013, vol. 22(20), Abstract only.
Yang, S., et al., Retraction of "Derivation and Genetic Modification of Embryonic Stem Cells from Disease-Model Inbred Rat Strains," Stem Cells And Development, 2013, vol. 22(20), 2813.
Yen et al., "Somatic mosaicism and allele complexity induced by CRISPR/Cas9 RNA injections in mouse zygotes," Dev. Biol., vol. 393(1), pp. 3-9, Jun. 28, 2014.
Yoshimi et al., "Allele-specific genome editing and correction of disease-associated phenotypes in rats using the CRISPR-Cas platform," Nature Communications, vol. 5, p. 4240 plus Supplementary Information, Jun. 26, 2014.
Yoshimi et al., "ssODN-mediated knock-in with CRISPR-Cas for large genomic regions in zygotes," Nat. Commun., vol. 7, p. 10431, Jan. 20, 2016.
Yu et al., "Highly Efficient Genome Modifications Mediated by CRISPR/Cas9 in *Drosophila*," Genetics, vol. 195, pp. 289-291 plus supporting information, Sep. 2013.

(56) References Cited

OTHER PUBLICATIONS

Zetsche et al., "Cpf1 Is a Single RNA-Guided Endonuclease of a Class 2 CRISPR-Cas System," Cell, vol. 163, pp. 1-13, 2015 (available online Sep. 25, 2015).
Zhang et al., "Biallelic targeting of expressed genes in mouse embryonic stem cells using the Cas9 system," Methods, vol. 69(2), pp. 171-178, Jun. 12, 2014.
Zhao et al., "Derivation of embryonic stem cells from Brown Norway rats blastocysts," J. Genet. Genomics, vol. 37, pp. 467-473, 2010.
Zhao et al., "iPS cells produce viable mice through tetraploid complementation," Nature 461(7260):86-90, (2009).
Zhou et al., "Dual sgRNAs facilitate CRISPR/Cas9-mediated mouse genome targeting," FEBS J., vol. 281 (7), pp. 1717-1725, Feb. 26, 2014.
Zhou, H., et al., "Large chromosomal deletions and heritable small genetic changes induced by CRISPR/Cas9 in rice," Nucleic Acids Research (2014), vol. 42(17), pp. 10903-10914.
EP 3080279 Grounds for Appeal filed Oct. 18, 2021.
EP 3080279 Grounds for Appeal filed Oct. 19, 2021.
EP 3080279 Interlocutory decision in Opposition proceedings mailed Jun. 9, 2021.
EP 3080279 Reply to Grounds for Appeal filed Feb. 21, 2022.
EP 3080279 Reply to Grounds for Appeal filed Feb. 25, 2022.
EP 3080279 Communication of Board of Appeal dated Jun. 27, 2023.
EP 3080279 Decision of Technical Board of Appeal T1294/21-3.3.08 dated Aug. 17, 2023.

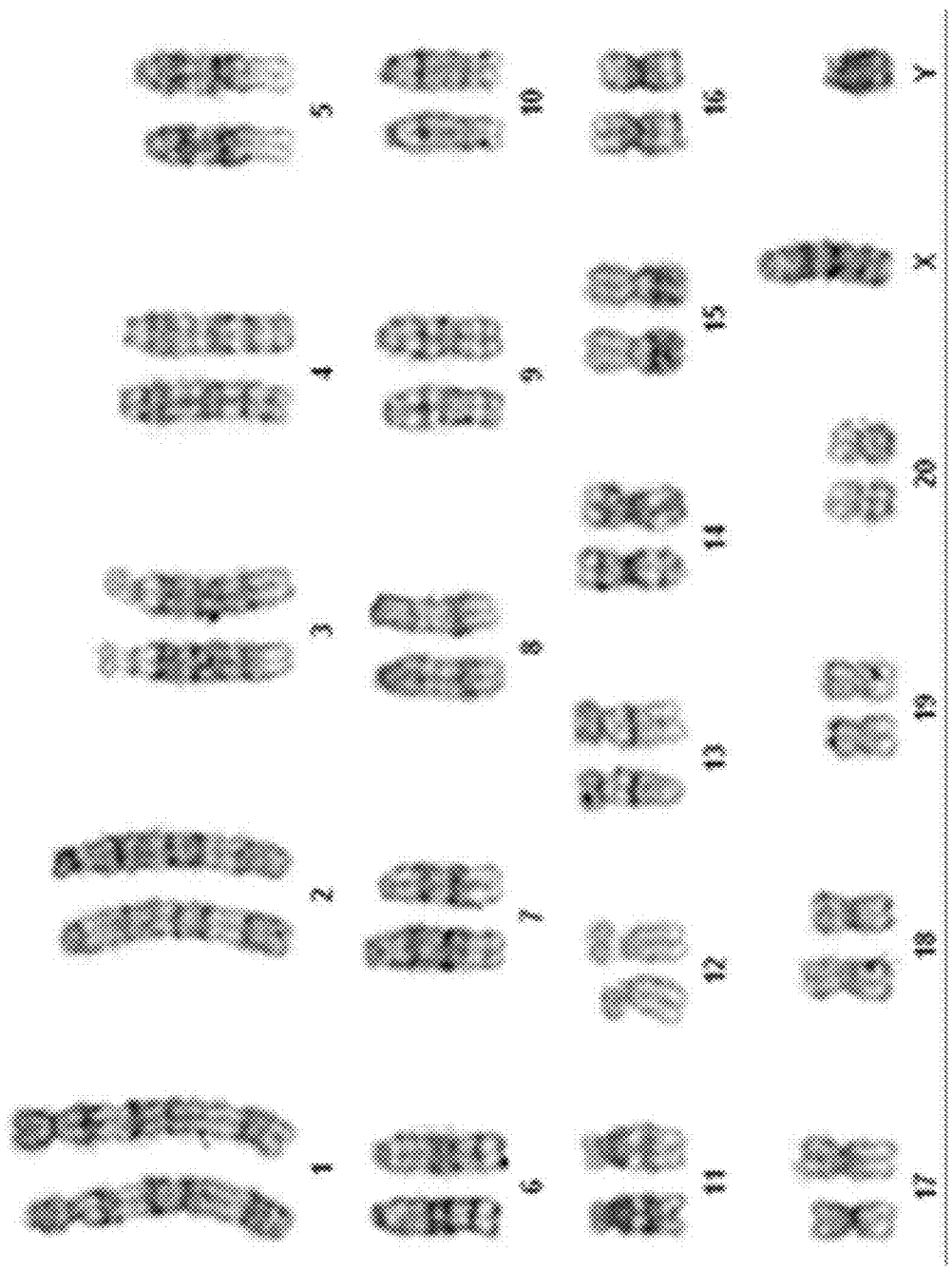

Cell Results: 42, XY

Cell Results: 42, XY

Cell Results: 42, XX

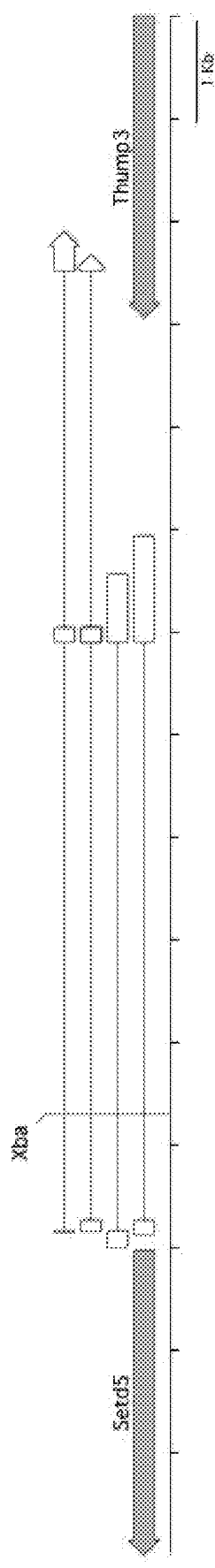
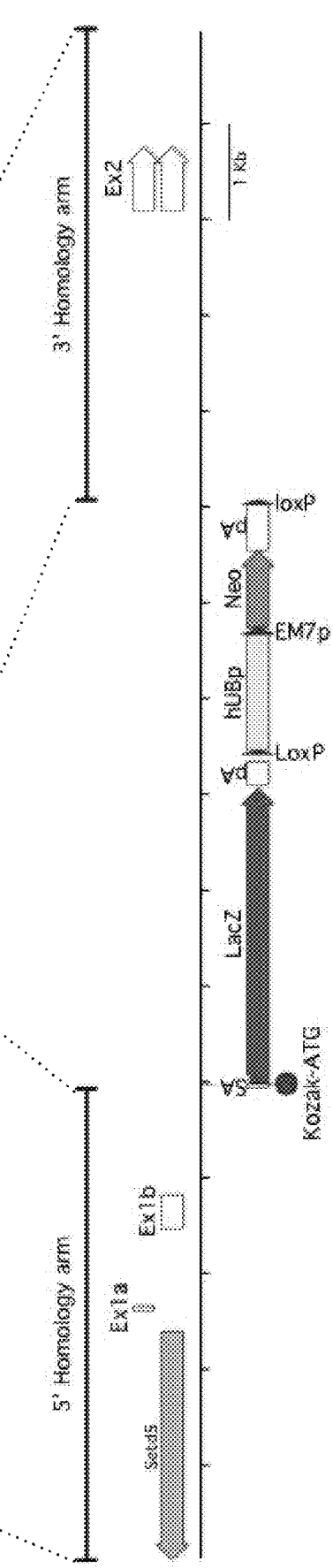
FIG. 12A
FIG. 12B
FIG. 12C

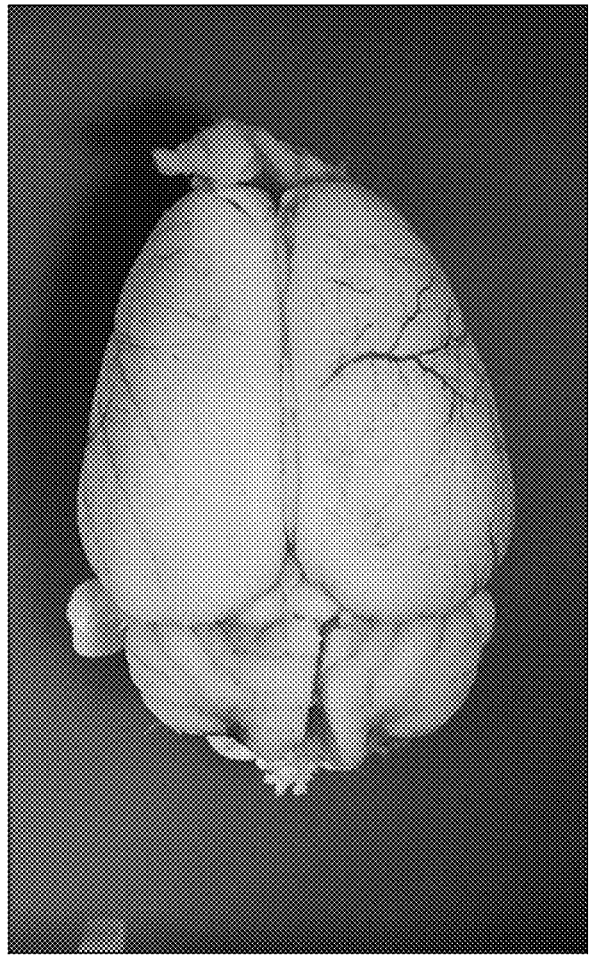
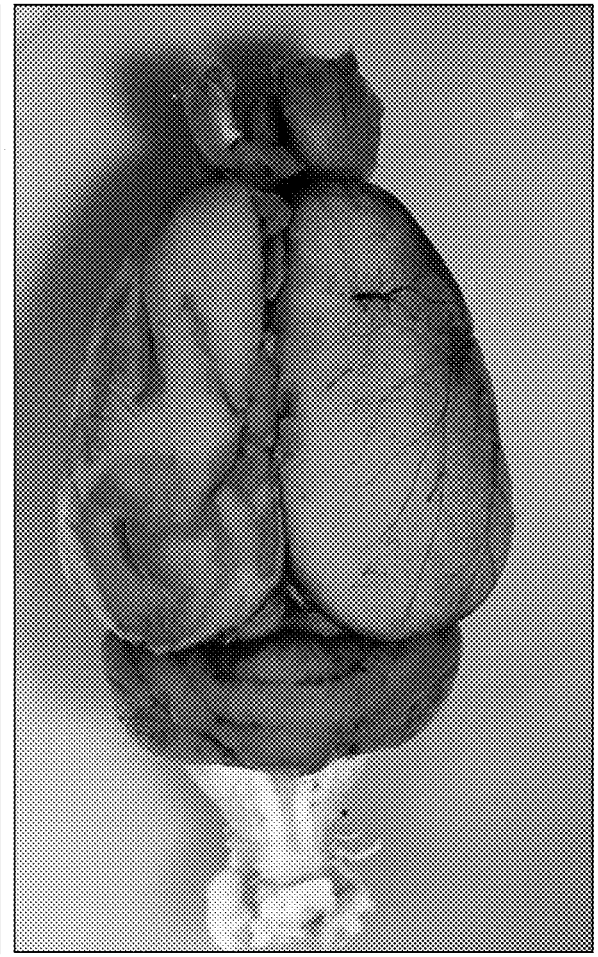
FIG. 13A
FIG. 13B

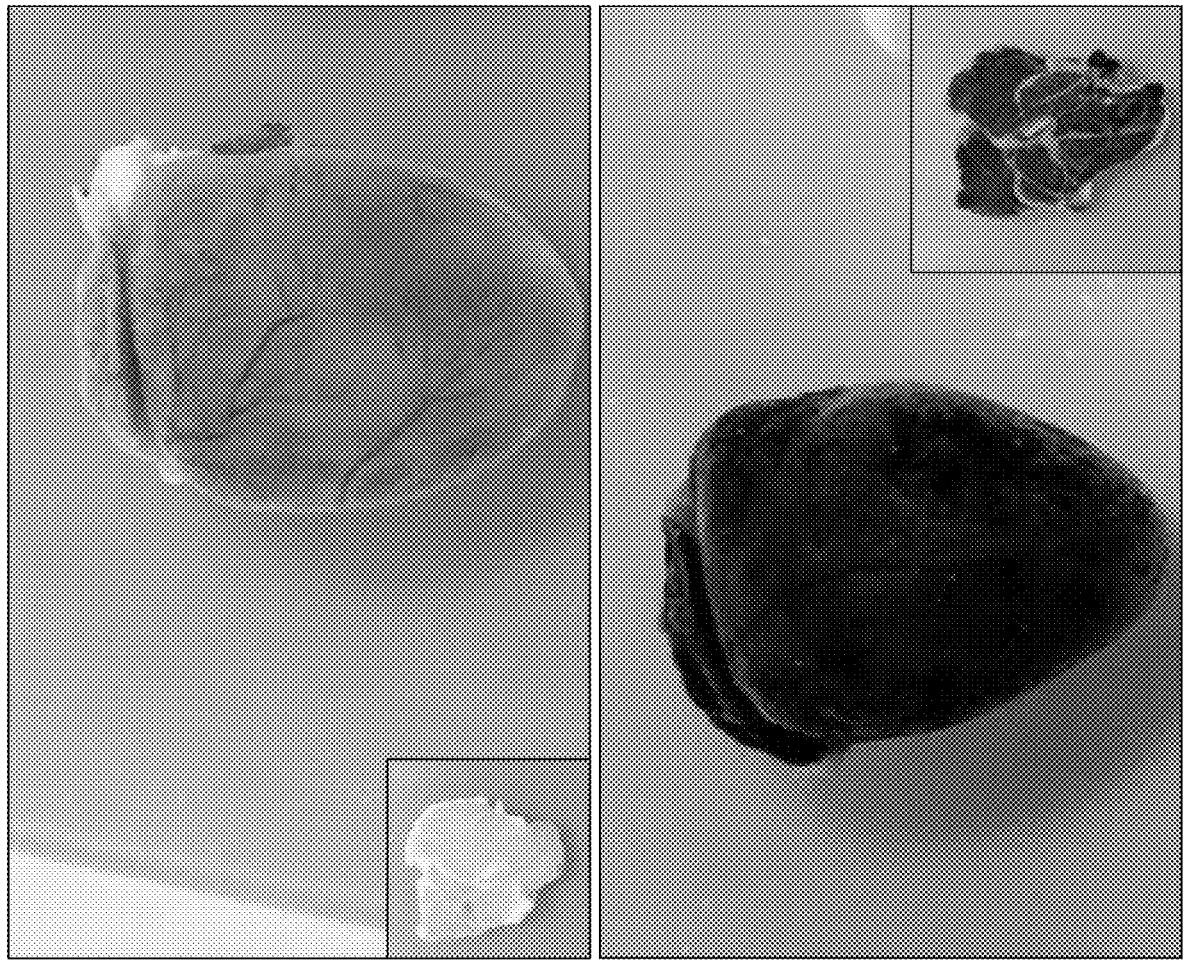

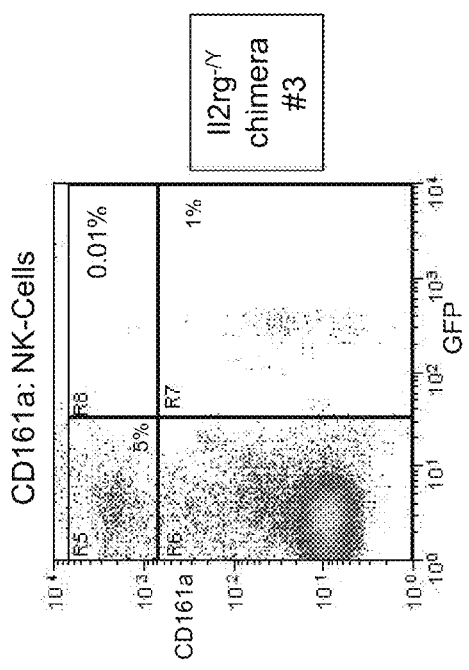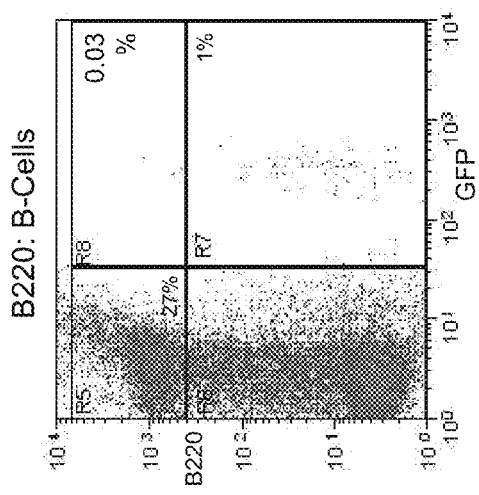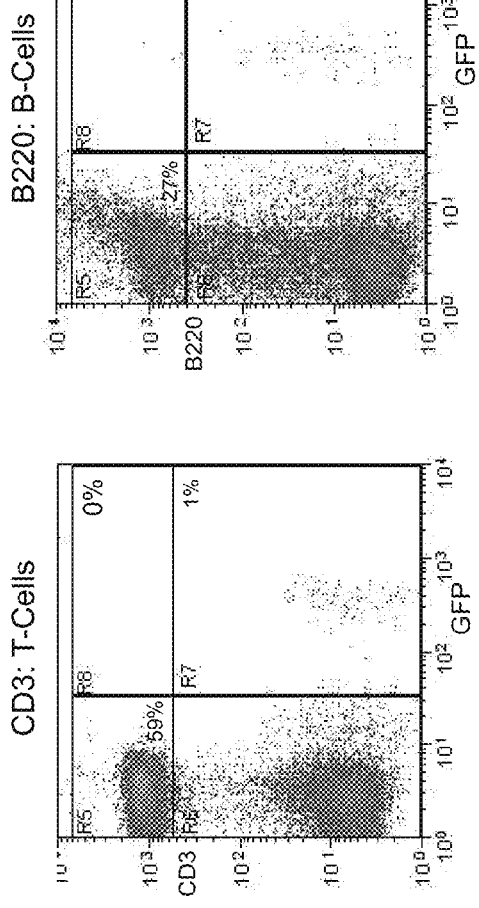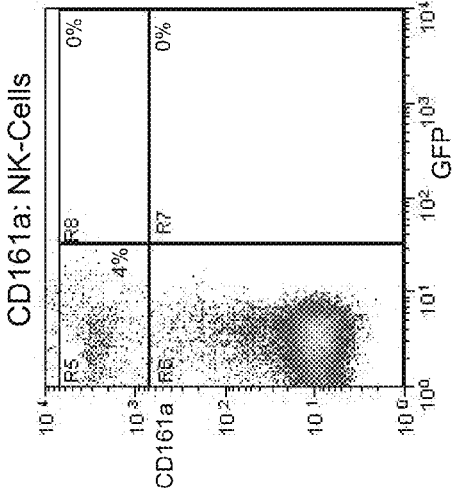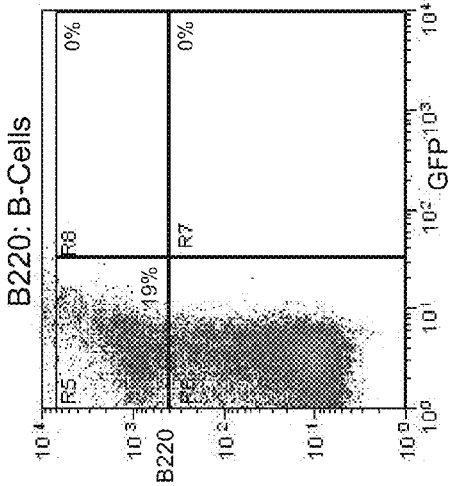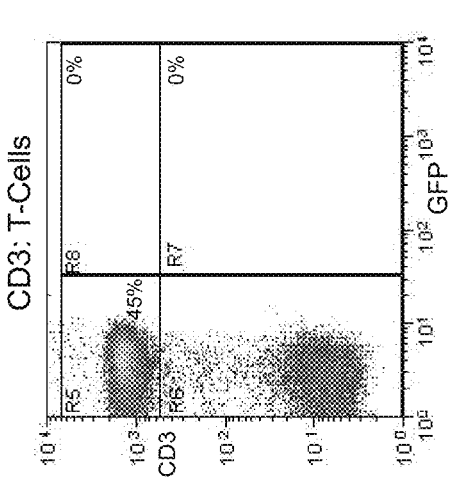
FIG. 29A  FIG. 29B  FIG. 29C
FIG. 29D  FIG. 29E  FIG. 29F Wild type ApoE+/-

Wild type

ApoE +/-

Wild type

ApoE+/−

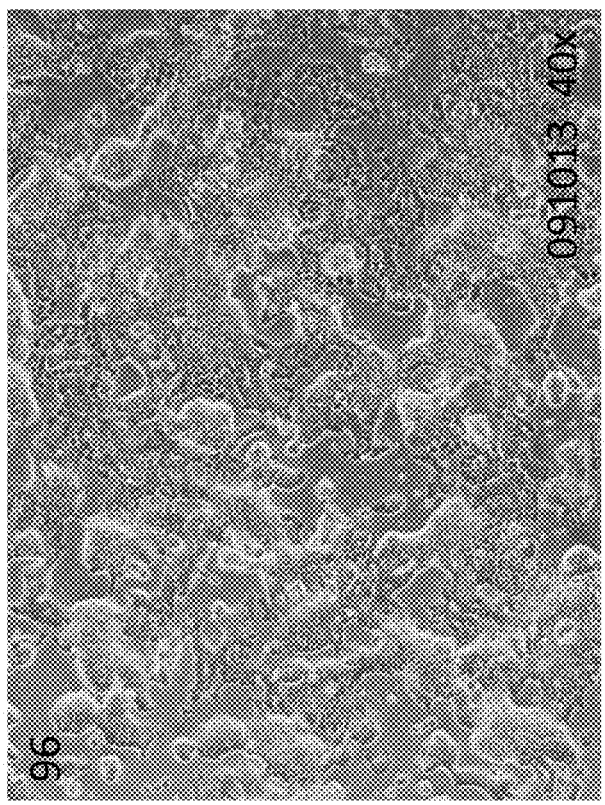
FIG. 52B
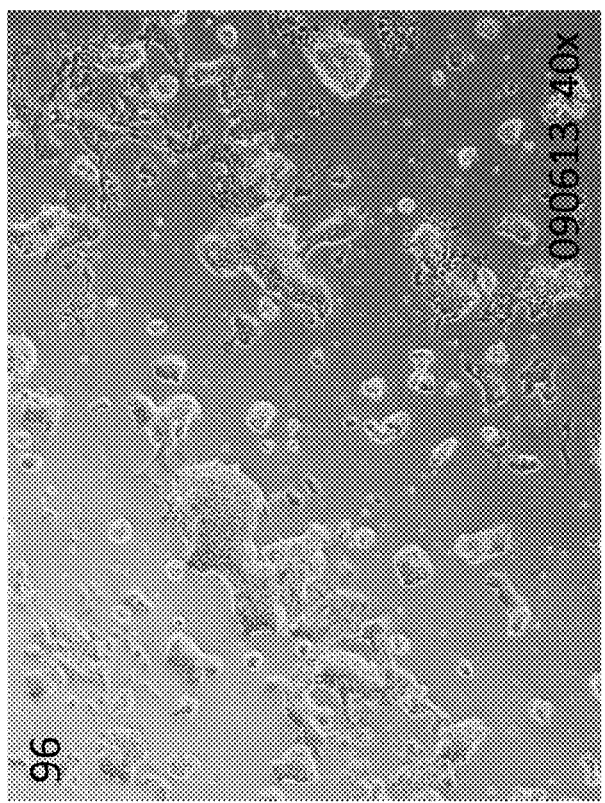
FIG. 52A

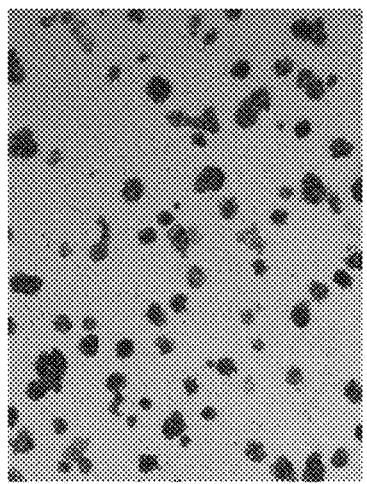
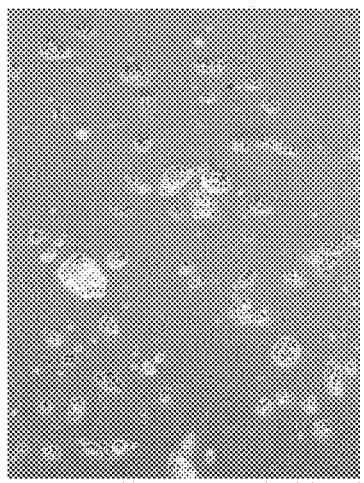
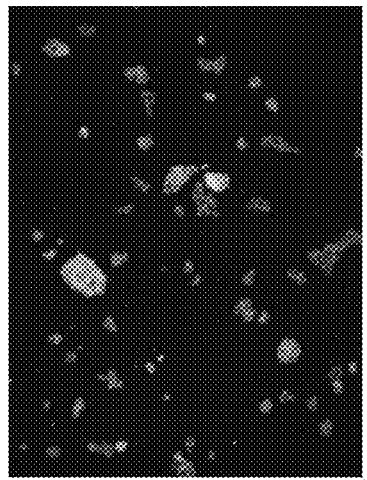
FIG. 54A
FIG. 54B
FIG. 54C

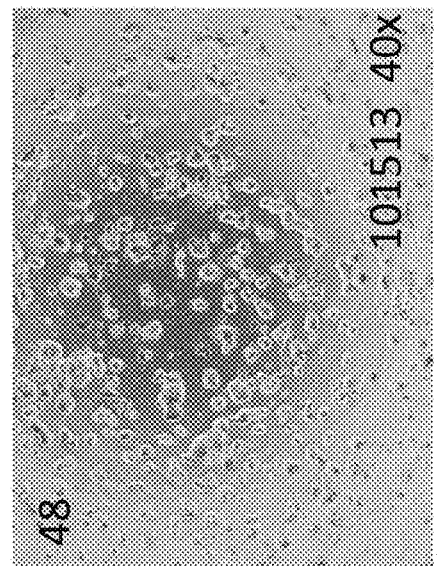
FIG. 55A
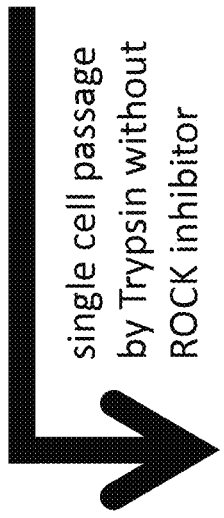
single cell passage by Trypsin without ROCK inhibitor
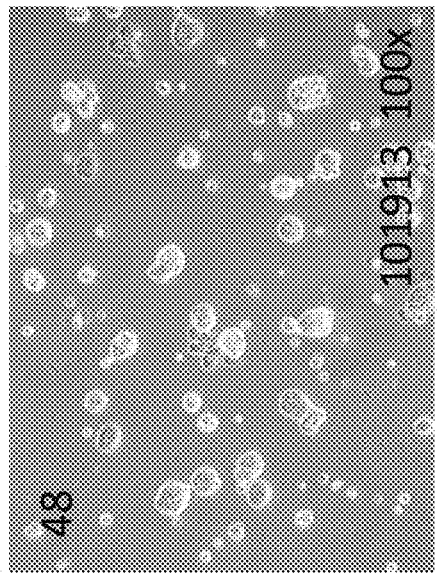
FIG. 55C
4 days after passage
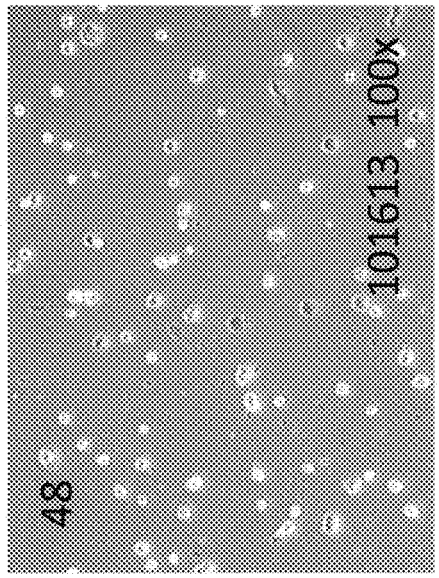
FIG. 55B
1 day after passage

METHODS AND COMPOSITIONS FOR THE TARGETED MODIFICATION OF A GENOME

CROSS REFERENCE TO RELATED APPLICATIONS

This application is a continuation of U.S. patent application Ser. No. 16/224,413, filed Dec. 18, 2018, which is a continuation of U.S. patent application Ser. No. 15/354,270, filed Nov. 17, 2016, which is a division of U.S. patent application Ser. No. 14/515,503, filed Oct. 15, 2014, which claims the benefit of U.S. Provisional Patent Application No. 61/914,768, filed Dec. 11, 2013, U.S. Provisional Patent Application No. 62/017,416, filed Jun. 26, 2014, U.S. Provisional Patent Application No. 62/029,261, filed Jul. 25, 2014, U.S. Provisional Patent Application No. 62/052,906, filed Sep. 19, 2014, U.S. Provisional Patent Application No. 62/059,527, filed Oct. 3, 2014, and U.S. Provisional Patent Application No. 62/064,384, filed Oct. 15, 2014, each of which is herein incorporated by reference in its entirety for all purposes.

REFERENCE TO A SEQUENCE LISTING SUBMITTED AS A TEXT FILE VIA EFS WEB

The official copy of the sequence listing is submitted electronically via EFS-Web as an ASCII formatted sequence listing with a file named 546745SEQLIST.TXT, created on Jun. 2, 2020, and having a size of 27.7 kilobytes, and is filed concurrently with the specification. The sequence listing contained in this ASCII formatted document is part of the specification and is herein incorporated by reference in its entirety.

BACKGROUND OF THE INVENTION

While rats have been regarded as an important animal model system that can recapitulate the pathology of various human diseases, including, but not limited to, cardiovascular (e.g., hypertension), metabolic (e.g., obesity, diabetes), neurological (e.g., pain pathologies), and a variety of cancers, the use of rats in modeling human diseases has been limited as compared to mice, due in part to unavailability of germline-transmittable pluripotent rat cells, which can sustain their pluripotency following a series of genetic modifications in vitro, e.g., one or more serial electroporations, and due in part to lack of efficient targeting technologies that allow introduction or deletion of large genomic DNA sequences, or replacement of large endogenous genomic DNA sequences with exogenous nucleic acid sequences in pluripotent rat cells.

There is a need in the art for compositions and methods that allow precise targeted changes in the genome of an organism, which can open or expand current areas of target discovery and validate therapeutic agents more quickly and easily.

SUMMARY

Methods are provided for modifying a genomic locus of interest in a eukaryotic cell via targeted genetic modification. Such a method comprises (a) introducing into the eukaryotic cell: (i) a large targeting vector (LTVEC) comprising a first nucleic acid flanked with a 5' homology arm and a 3' homology arm, wherein the LTVEC is at least 10 kb; (ii) a first expression construct comprising a first promoter operably linked to a second nucleic acid encoding a Cas protein, (iii) a second expression construct comprising a second promoter operably linked to a third nucleic acid encoding a guide RNA (gRNA) comprising a nucleotide sequence that hybridizes to a target sequence and a trans-activating CRISPR RNA (tracrRNA), wherein the first and the second promoters are active in the eukaryotic cell; and (b) identifying a modified eukaryotic cell comprising a targeted genetic modification at the genomic locus of interest.

In one embodiment, the targeted genetic modification is a biallelic genetic modification.

In one embodiment, the LTVEC is at least 15 kb, at least 20 kb, at least 30 kb, at least 40 kb, at least 50 kb, at least 60 kb, at least 70 kb, at least 80 kb, or at least 90 kb. In another embodiment, the LTVEC is at least 100 kb, at least 150 kb, or at least 200 kb.

In one embodiment, the eukaryotic cell is a mammalian cell. In one embodiment, the mammalian cell is a fibroblast.

In one embodiment, the eukaryotic cell is a pluripotent cell. In one embodiment, the pluripotent cell is a human pluripotent cell. In one embodiment the human pluripotent cell is a human embryonic stem (ES) cell or a human adult stem cell. In another embodiment, the human pluripotent cell is a developmentally restricted human progenitor cell. In another embodiment, the human pluripotent cell is a human induced pluripotent stem (iPS) cell.

In one embodiment, the Cas protein is Cas9.

In one embodiment, the target sequence is flanked by a Protospacer Adjacent Motif (PAM) sequence. In one embodiment, the target sequence is immediately flanked on the 3' end by a Protospacer Adjacent Motif (PAM) sequence.

In some embodiments, the sum total of the 5' and the 3' homology arms is from about 10 kb to about 150 kb. In some embodiments, the sum total of the 5' and the 3' homology arms of the LTVEC is from about 10 kb to about 20 kb, from about 20 kb to about 40 kb, from about 40 kb to about 60 kb, from about 60 kb to about 80 kb, from about 80 kb to about 100 kb, from about 100 kb to about 120 kb, or from about 120 kb to 150 kb.

The methods further provide that the targeted genetic modification comprises: (a) a replacement of an endogenous nucleic acid sequence with a homologous or an orthologous nucleic acid sequence; (b) a deletion of an endogenous nucleic acid sequence; (c) a deletion of an endogenous nucleic acid sequence, wherein the deletion ranges from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb; (d) insertion of an exogenous nucleic acid sequence; (e) insertion of an exogenous nucleic acid sequence ranging from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb; (f) insertion of an exogenous nucleic acid sequence comprising a homologous or an orthologous nucleic acid sequence; (g) insertion of a chimeric nucleic acid sequence comprising a human and a non-human nucleic acid sequence; (h) insertion of a conditional allele flanked with site-specific recombinase target sequences; (i) insertion of a selectable marker or a reporter gene operably linked to a third promoter active in the pluripotent cell; or (j) a combination thereof.

In one embodiment, the genomic locus of interest comprises (i) a 5' target sequence that is homologous to the 5' homology arm; and (ii) a 3' target sequence that is homologous to the 3' homology arm.

In some embodiments, the 5' target sequence and the 3' target sequence is separated by at least 5 kb but less than 3 Mb. In some embodiments, the 5' target sequence and the 3' target sequence is separated by at least 5 kb but less than 10 kb, at least 10 kb but less than 20 kb, at least 20 kb but less than 40 kb, at least 40 kb but less than 60 kb, at least 60 kb but less than 80 kb, at least about 80 kb but less than 100 kb, at least 100 kb but less than 150 kb, or at least 150 kb but less than 200 kb, at least about 200 kb but less than about 300 kb, at least about 300 kb but less than about 400 kb, at least about 400 kb but less than about 500 kb, at least about 500 kb but less than about 1 Mb, at least about 1 Mb but less than about 1.5 Mb, at least about 1.5 Mb but less than about 2 Mb, at least about 2 Mb but less than about 2.5 Mb, or at least about 2.5 Mb but less than about 3 Mb.

In one embodiment, the genomic locus of interest comprises the Interleukin-2 receptor gamma locus, the ApoE locus, the Rag1 locus, the Rag2 locus, or both of the Rag1 and the Rag2 loci.

In one embodiment, the first and the second expression constructs are on a single nucleic acid molecule.

Further provided is a method for modifying a genome, comprising exposing the genome to a Cas protein and a CRISPR RNA in the presence of a large targeting vector (LTVEC) comprising a nucleic acid sequence of at least 10 kb, wherein following exposure to the Cas protein, the CRISPR RNA, and the LTVEC, the genome is modified to contain at least 10 kb nucleic acid sequence.

In some such methods, the LTVEC comprises a nucleic acid sequence of at least 20 kb, at least 30 kb, at least 40 kb, at least 50 kb, at least 60 kb, at least 70 kb, at least 80 kb, or at least 90 kb. In some such methods, the LTVEC comprises a nucleic acid sequence of at least 100 kb, at least 150 kb, or at least 200 kb.

Further provided is a method for modifying a genome, comprising contacting the genome with a Cas protein, a CRISPR RNA that hybridizes to a target sequence, and a tracrRNA in the presence of a large targeting vector (LTVEC), wherein the LTVEC is at least 10 kb and comprises a first nucleic acid flanked with a 5' homology arm and a 3' homology arm, wherein following contacting with the Cas protein, CRISPR RNA, and tracrRNA in the presence of the LTVEC, the genome is modified at a genomic locus of interest to contain the first nucleic acid. The target sequence can be at or near the genomic locus of interest.

In some such methods, the genome is in a eukaryotic cell, and the Cas protein, the CRISPR RNA, the tracrRNA, and the LTVEC are introduced into the eukaryotic cell. Some such methods further comprise identifying a modified eukaryotic cell comprising a targeted genetic modification at the genomic locus of interest.

In some such methods, the CRISPR RNA and the tracrRNA are introduced together in the form of a single guide RNA (gRNA). In other methods, the CRISPR RNA and the tracrRNA are introduced separately.

In some such methods (a) the Cas protein is introduced into the eukaryotic cell in the form of a protein, a messenger RNA (mRNA) encoding the Cas protein, or a DNA encoding the Cas protein; (b) the CRISPR RNA is introduced into the eukaryotic cell in the form of an RNA or a DNA encoding the CRISPR RNA; and (c) the tracrRNA is introduced into the eukaryotic cell in the form of an RNA or a DNA encoding the tracrRNA.

In some methods (a) the DNA encoding the Cas protein is in the form of a first expression construct comprising a first promoter operably linked to a second nucleic acid encoding the Cas protein; (b) the DNA encoding the CRISPR RNA is in the form of a second expression construct comprising a second promoter operably linked to a third nucleic acid encoding the CRISPR RNA; and (c) the DNA encoding the tracrRNA is in the form of a third expression construct comprising a third promoter operably linked to a fourth nucleic acid encoding the tracrRNA, wherein the first, second, and third promoters are active in the eukaryotic cell. Optionally, the first, second, and/or third expression constructs are on a single nucleic acid molecule.

In some methods (a) the DNA encoding the Cas protein is in the form of a first expression construct comprising a first promoter operably linked to a second nucleic acid encoding the Cas protein; and (b) the DNA encoding the CRISPR RNA and the DNA encoding the tracrRNA are in the form of a second expression construct comprising a second promoter operably linked to a third nucleic acid encoding a gRNA comprising the CRISPR RNA and the tracrRNA; wherein the first and second promoters are active in the eukaryotic cell. Optionally, the first and the second expression constructs are on a single nucleic acid molecule.

In some methods, the Cas protein, the CRISPR RNA, and the tracrRNA are introduced into the eukaryotic cell as a protein-RNA complex.

In some methods, the targeted genetic modification comprises simultaneous deletion of an endogenous nucleic acid sequence at the genomic locus of interest and insertion of the first nucleic acid at the genomic locus of interest. In some methods, the deleted endogenous nucleic acid sequence is about 30 kb to about 110 kb, and the inserted first nucleic acid is about 40 kb to about 140 kb. In some methods, the deleted endogenous nucleic acid sequence is about 38 kb to about 110 kb, and the inserted first nucleic acid is about 43 kb to about 134 kb.

In some methods, the targeted genetic modification is a biallelic genetic modification. Optionally, the biallelic genetic modification comprises deletion of an endogenous nucleic acid sequence and insertion of the first nucleic acid at the genomic locus of interest in two homologous chromosomes.

In some methods, the modified eukaryotic cell is compound heterozygous at the genomic locus of interest. In some methods, the modified eukaryotic cell is hemizygous at the genomic locus of interest. Optionally, the targeted genetic modification at the genomic locus of interest in one chromosome comprises deletion of an endogenous nucleic acid sequence and insertion of the first nucleic acid. Optionally, the targeted genetic modification comprises: (1) deletion of an endogenous nucleic acid sequence at the genomic locus of interest in two homologous chromosomes; and (2) insertion of the first nucleic acid into the genomic locus of interest in a first chromosome and disruption of the genomic locus of interest in a second chromosome. The first chromosome can be one of the two homologous chromosomes, and the second chromosome can be the other homologous chromosome.

In some methods, the LTVEC is at least 15 kb, at least 20 kb, at least 30 kb, at least 40 kb, at least 50 kb, at least 60 kb, at least 70 kb, at least 80 kb, or at least 90 kb. Optionally, the LTVEC is at least 100 kb, at least 150 kb, or at least 200 kb.

In some methods, the first nucleic acid is at least 20 kb, at least 30 kb, at least 40 kb, at least 50 kb, at least 60 kb, at least 70 kb, at least 80 kb, at least 90 kb, at least 100 kb, at least 150 kb, at least 200 kb, at least 250 kb, or at least 300 kb. In some methods, the first nucleic acid is about 40 kb to about 140 kb. In some methods, the first nucleic acid is about 43 kb to about 134 kb.

In some methods, the eukaryotic cell is a mammalian cell, a fibroblast, a pluripotent cell, a non-human pluripotent cell, a rodent pluripotent cell, a mouse or rat embryonic stem (ES) cell, a human pluripotent cell, a human embryonic stem (ES) cell, a human adult stem cell, a developmentally restricted human progenitor cell, or a human induced pluripotent stem (iPS) cell.

In some methods, the Cas protein is Cas9. In some methods, the target sequence is immediately flanked by a Protospacer Adjacent Motif (PAM) sequence.

In some methods, the sum total of the 5' and the 3' homology arms of the LTVEC is from about 10 kb to about 150 kb. Optionally, the sum total of the 5' and the 3' homology arms of the LTVEC is from about 10 kb to about 20 kb, from about 20 kb to about 40 kb, from about 40 kb to about 60 kb, from about 60 kb to about 80 kb, from about 80 kb to about 100 kb, from about 100 kb to about 120 kb, or from about 120 kb to 150 kb.

In some methods, the targeted genetic modification comprises: (a) a replacement of an endogenous nucleic acid sequence with a homologous or an orthologous nucleic acid sequence; (b) a deletion of an endogenous nucleic acid sequence; (c) a deletion of an endogenous nucleic acid sequence, wherein the deletion ranges from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb; (d) insertion of an exogenous nucleic acid sequence; (e) insertion of an exogenous nucleic acid sequence ranging from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb; (f) insertion of an exogenous nucleic acid sequence comprising a homologous or an orthologous nucleic acid sequence; (g) insertion of a chimeric nucleic acid sequence comprising a human and a non-human nucleic acid sequence; (h) insertion of a conditional allele flanked with site-specific recombinase target sequences; (i) insertion of a selectable marker or a reporter gene operably linked to a third promoter active in the pluripotent cell; or (j) a combination thereof.

In some methods, the genomic locus of interest comprises (i) a 5' target sequence that is homologous to the 5' homology arm; and (ii) a 3' target sequence that is homologous to the 3' homology arm. Optionally, the 5' target sequence and the 3' target sequence are separated by at least 5 kb but less than 3 Mb. Optionally, the 5' target sequence and the 3' target sequence are separated by at least 5 kb but less than 10 kb, at least 10 kb but less than 20 kb, at least 20 kb but less than 40 kb, at least 40 kb but less than 60 kb, at least 60 kb but less than 80 kb, at least about 80 kb but less than 100 kb, at least 100 kb but less than 150 kb, or at least 150 kb but less than 200 kb, at least about 200 kb but less than about 300 kb, at least about 300 kb but less than about 400 kb, at least about 400 kb but less than about 500 kb, at least about 500 kb but less than about 1 Mb, at least about 1 Mb but less than about 1.5 Mb, at least about 1.5 Mb but less than about 2 Mb, at least about 2 Mb but less than about 2.5 Mb, or at least about 2.5 Mb but less than about 3 Mb. Optionally, the 5' target sequence and the 3' target sequence are separated by at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, or at least 200 kb. In some methods, the 5' and 3' target sequences are separated by about 30 kb to about 110 kb. In some methods, the 5' and 3' target sequences are separated by about 38 kb to about 110 kb.

In some methods, the genomic locus of interest comprises the Interleukin-2 receptor gamma locus, the ApoE locus, the Rag1 locus, the Rag2 locus, or both of the Rag1 and the Rag2 loci. In other methods, the genomic locus of interest comprises the Adamts5 locus, the Trpa1 locus, the Folh1 locus, or the Erbb4 locus. In yet other methods, the genomic locus of interest comprises the Lrp5 locus. In yet other methods, the genomic locus of interest comprises the C5 (Hc) locus, the Ror1 locus, or the Dpp4 locus.

Further provided is a method for producing an F0 generation non-human animal that comprises a targeted genetic modification at a genomic locus of interest, the method comprising: (a) contacting the genome in a non-human ES cell with a Cas protein, a CRISPR RNA, and a tracrRNA in the presence of a large targeting vector (LTVEC) to form a modified non-human ES cell, wherein the LTVEC is at least 10 kb and comprises a first nucleic acid flanked with a 5' homology arm and a 3' homology arm; (b) identifying the modified non-human ES cell comprising the targeted genetic modification at the genomic locus of interest; (c) introducing the modified non-human ES cell into a non-human host embryo; and (d) gestating the non-human host embryo in a surrogate mother, wherein the surrogate mother produces the F0 generation non-human animal comprising the targeted genetic modification at the genomic locus of interest.

In some such methods, the CRISPR RNA and the tracrRNA are introduced together in the form of a single guide RNA (gRNA). In other such methods, the CRISPR RNA and the tracrRNA are introduced separately.

In some such methods, (a) the Cas protein is introduced into the non-human ES cell in the form of a protein, a messenger RNA (mRNA) encoding the Cas protein, or a DNA encoding the Cas protein; (b) the CRISPR RNA is introduced into the non-human ES cell in the form of an RNA or a DNA encoding the CRISPR RNA; and (c) the tracrRNA is introduced into the non-human ES cell in the form of an RNA or a DNA encoding the tracrRNA.

In some such methods, (a) the DNA encoding the Cas protein is in the form of a first expression construct comprising a first promoter operably linked to a second nucleic acid encoding the Cas protein; (b) the DNA encoding the CRISPR RNA is in the form of a second expression construct comprising a second promoter operably linked to a third nucleic acid encoding the CRISPR RNA; and (c) the DNA encoding the tracrRNA is in the form of a third expression construct comprising a third promoter operably linked to a fourth nucleic acid encoding the tracrRNA, wherein the first, second, and third promoters are active in the non-human ES cell. Optionally, the first, second, and third expression constructs are on a single nucleic acid molecule.

In some such methods, (a) the DNA encoding the Cas protein is in the form of a first expression construct comprising a first promoter operably linked to a second nucleic acid encoding the Cas protein; and (b) the DNA encoding the CRISPR RNA and the DNA encoding the tracrRNA are in the form of a second expression construct comprising a second promoter operably linked to a third nucleic acid encoding a gRNA comprising the CRISPR RNA and the tracrRNA; wherein the first and second promoters are active in the non-human ES cell. Optionally, the first and the second expression constructs are on a single nucleic acid molecule.

In some such methods, the Cas protein, the CRISPR RNA, and the tracrRNA are introduced into the non-human ES cell as a protein-RNA complex.

In some such methods, the targeted genetic modification comprises simultaneous deletion of an endogenous nucleic acid sequence at the genomic locus of interest and insertion of the first nucleic acid at the genomic locus of interest.

In some such methods, the targeted genetic modification is a biallelic genetic modification. Optionally, the biallelic genetic modification comprises deletion of an endogenous nucleic acid sequence and insertion of the first nucleic acid at the genomic locus of interest in two homologous chromosomes.

In some such methods, the modified non-human ES cell is compound heterozygous at the genomic locus of interest. In some such methods, the modified non-human ES cell is hemizygous at the genomic locus of interest. Optionally, the targeted genetic modification at the genomic locus of interest in one chromosome comprises deletion of an endogenous nucleic acid sequence and insertion of the first nucleic acid. Optionally, the targeted genetic modification comprises: (1) deletion of an endogenous nucleic acid sequence at the genomic locus of interest in two homologous chromosomes; and (2) insertion of the first nucleic acid into the genomic locus of interest in a first chromosome and disruption of the genomic locus of interest in a second chromosome. The first chromosome can be one of the two homologous chromosomes, and the second chromosome can be the other homologous chromosome.

In some such methods, the Cas protein is Cas9.

Further provided are methods for modifying a genome at a genomic locus of interest in a eukaryotic cell, a mouse cell, or a human cell, comprising contacting the genome with a Cas protein, a CRISPR RNA that hybridizes to a target sequence at the genomic locus of interest, and a tracrRNA in the presence of a large targeting vector (LTVEC), wherein the LTVEC is at least 10 kb and comprises a first nucleic acid flanked with a 5' homology arm that is homologous to a 5' target sequence at the genomic locus of interest and a 3' homology arm that is homologous to a 3' target sequence at the genomic locus of interest, wherein the first nucleic acid is at least 30 kb and/or the 5' target sequence and the 3' target sequence are separated by at least 30 kb, wherein following contacting with the Cas protein, the CRISPR RNA, and the tracrRNA in the presence of the LTVEC, the genome is modified to comprise a targeted genetic modification comprising insertion of the first nucleic acid at the genomic locus of interest.

Any of the above methods can further comprise introducing the Cas protein, the CRISPR RNA, the tracrRNA, and the LTVEC into the eukaryotic cell, the mouse cell, or the human cell. Any of the above methods can further comprise identifying the modified eukaryotic cell, the modified mouse cell, or the modified human cell comprising the targeted genetic modification at the genomic locus of interest.

In some of the above methods, the CRISPR RNA and the tracrRNA are introduced together in the form of a single transcript. In some of the above methods, the CRISPR RNA and the tracrRNA are introduced separately.

In some of the above methods, (a) the Cas protein is introduced into the eukaryotic cell, the mouse cell, or the human cell in the form of a protein, a messenger RNA (mRNA) encoding the Cas protein, or a DNA encoding the Cas protein; (b) the CRISPR RNA is introduced into the eukaryotic cell, the mouse cell, or the human cell in the form of an RNA or a DNA encoding the CRISPR RNA; and (c) the tracrRNA is introduced into the eukaryotic cell, the mouse cell, or the human cell in the form of an RNA or a DNA encoding the tracrRNA. In some of the above methods, the Cas protein, the CRISPR RNA, and the tracrRNA are introduced into the eukaryotic cell, the mouse cell, or the human cell as a protein-RNA complex.

In some of the above methods, (a) the DNA encoding the Cas protein is in the form of a first expression construct comprising a first promoter operably linked to a second nucleic acid encoding the Cas protein; (b) the DNA encoding the CRISPR RNA is in the form of a second expression construct comprising a second promoter operably linked to a third nucleic acid encoding the CRISPR RNA; and (c) the DNA encoding the tracrRNA is in the form of a third expression construct comprising a third promoter operably linked to a fourth nucleic acid encoding the tracrRNA; wherein the first, second, and third promoters are active in the eukaryotic cell, the mouse cell, or the human cell. In some of the above methods, the first, second, and/or third expression constructs are on a single nucleic acid molecule.

In some of the above methods, (a) the DNA encoding the Cas protein is in the form of a first expression construct comprising a first promoter operably linked to a second nucleic acid encoding the Cas protein; and (b) the DNA encoding the CRISPR RNA and the DNA encoding the tracrRNA are in the form of a second expression construct comprising a second promoter operably linked to a third nucleic acid encoding a gRNA comprising the CRISPR RNA and the tracrRNA in a single transcript; wherein the first and second promoters are active in the eukaryotic cell, the mouse cell, or the human cell. In some of the above methods, the first and the second expression constructs are on a single nucleic acid molecule.

In some of the above methods, the LTVEC is at least 15 kb, at least 20 kb, at least 30 kb, at least 40 kb, at least 50 kb, at least 60 kb, at least 70 kb, at least 80 kb, or at least 90 kb. In some of the above methods, the LTVEC is at least 100 kb, at least 150 kb, or at least 200 kb.

In some of the above methods, the first nucleic acid is at least 20 kb, at least 30 kb, at least 40 kb, at least 50 kb, at least 60 kb, at least 70 kb, at least 80 kb, at least 90 kb, at least 100 kb, at least 150 kb, at least 200 kb, at least 250 kb, or at least 300 kb. In some of the above methods, the first nucleic acid is about 40 kb to about 140 kb.

In some of the above methods, the sum total of the 5' and the 3' homology arms of the LTVEC is from about 10 kb to about 150 kb. In some of the above methods, the sum total of the 5' and the 3' homology arms of the LTVEC is from about 10 kb to about 20 kb, from about 20 kb to about 40 kb, from about 40 kb to about 60 kb, from about 60 kb to about 80 kb, from about 80 kb to about 100 kb, from about 100 kb to about 120 kb, or from about 120 kb to 150 kb.

In some of the above methods, the 5' target sequence and the 3' target sequence are separated by at least 5 kb but less than 3 Mb. In some of the above methods, the 5' target sequence and the 3' target sequence are separated by at least 5 kb but less than 10 kb, at least 10 kb but less than 20 kb, at least 20 kb but less than 40 kb, at least 40 kb but less than 60 kb, at least 60 kb but less than 80 kb, at least about 80 kb but less than 100 kb, at least 100 kb but less than 150 kb, or at least 150 kb but less than 200 kb, at least about 200 kb but less than about 300 kb, at least about 300 kb but less than about 400 kb, at least about 400 kb but less than about 500 kb, at least about 500 kb but less than about 1 Mb, at least about 1 Mb but less than about 1.5 Mb, at least about 1.5 Mb but less than about 2 Mb, at least about 2 Mb but less than about 2.5 Mb, or at least about 2.5 Mb but less than about 3 Mb. In some of the above methods, the 5' target sequence and the 3' target sequence are separated by at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, or at least 200 kb. In some of the above methods, the 5' target sequence and the 3' target sequence are separated by from about 30 kb to about 110 kb.

In some of the above methods, the eukaryotic cell is not a rat cell. In some of the above methods, the eukaryotic cell is a pluripotent cell, a non-pluripotent cell, a mammalian cell, a human cell, a non-human mammalian cell, a rodent cell, a mouse cell, a hamster cell, a non-human pluripotent cell, a human pluripotent cell, a rodent pluripotent cell, or a fibroblast. In some of the above methods, the eukaryotic cell is a primary cell or an immortalized cell. In some of the above methods, the rodent pluripotent cell is a mouse or rat embryonic stem (ES) cell.

In some of the above methods, the mouse cell, or the human cell is a primary cell or an immortalized cell. In some of the above methods, the mouse cell, or the human cell is a pluripotent cell. In some of the above methods, the mouse pluripotent cell is a mouse embryonic stem (ES) cell. In some of the above methods, the human pluripotent cell is a human embryonic stem (ES) cell, a human adult stem cell, a developmentally restricted human progenitor cell, or a human induced pluripotent stem (iPS) cell. In some of the above methods, the human iPS cells is being maintained in a medium comprising a base medium and supplements, wherein the medium comprises: (a) a leukemia inhibitory factor (LIF) polypeptide; (b) a glycogen synthase kinase (GSK3) inhibitor; and (c) a MEK inhibitor; wherein the medium has an osmolality of about 175 mOsm/kg to about 280 mOsm/kg.

In some of the above methods, the Cas protein is Cas9. In some of the above methods, the target sequence is immediately flanked by a Protospacer Adjacent Motif (PAM) sequence.

In some of the above methods, the targeted genetic modification comprises simultaneous deletion of an endogenous nucleic acid sequence at the genomic locus of interest and insertion of the first nucleic acid at the genomic locus of interest in a single step. In some of the above methods, the deleted endogenous nucleic acid sequence is from about 30 kb to about 110 kb, and the inserted first nucleic acid is from about 40 kb to about 140 kb.

In some of the above methods, the targeted genetic modification is a biallelic genetic modification. In some of the above methods, the biallelic genetic modification comprises deletion of an endogenous nucleic acid sequence and insertion of the first nucleic acid at the genomic locus of interest in two homologous chromosomes. In some of the above methods, the modified eukaryotic cell, the modified mouse cell, or the modified human cell is compound heterozygous at the genomic locus of interest. In some of the above methods, the modified eukaryotic cell, the modified mouse cell, or the modified human cell is hemizygous at the genomic locus of interest. In some of the above methods, the targeted genetic modification at the genomic locus of interest in one chromosome comprises deletion of an endogenous nucleic acid sequence and insertion of the first nucleic acid. In some of the above methods, the targeted genetic modification comprises: (1) deletion of an endogenous nucleic acid sequence at the genomic locus of interest in first and second homologous chromosomes; and (2) insertion of the first nucleic acid into the genomic locus of interest in the first homologous chromosome and disruption of the genomic locus of interest in the second homologous chromosome.

In some of the above methods, the targeted genetic modification comprises: (a) a replacement of an endogenous nucleic acid sequence with a homologous or an orthologous nucleic acid sequence; (b) a deletion of an endogenous nucleic acid sequence; (c) a deletion of an endogenous nucleic acid sequence, wherein the deletion ranges from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb; (d) insertion of an exogenous nucleic acid sequence; (e) insertion of an exogenous nucleic acid sequence ranging from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb; (1) insertion of an exogenous nucleic acid sequence comprising a homologous or an orthologous nucleic acid sequence; (g) insertion of a chimeric nucleic acid sequence comprising a human and a non-human nucleic acid sequence; (h) insertion of a conditional allele flanked with site-specific recombinase target sequences; (i) insertion of a selectable marker or a reporter gene operably linked to a promoter active in the pluripotent cell; or (j) a combination thereof.

In some of the above methods, the genomic locus of interest comprises the Interleukin-2 receptor gamma locus, the ApoE locus, the Rag1 locus, the Rag2 locus, both of the Rag1 and the Rag2 loci, the Adamts5 locus, the Trpa1 locus, the Folh1 locus, the Erbb4 locus, the Lrp5 locus, the C5 (Hc) locus, the Ror1 locus, or the Dpp4 locus. In some of the above methods, the genomic locus of interest comprises extrachromosomal DNA.

Also provided are methods for producing an F0 generation non-human animal or mouse that comprises a targeted genetic modification at a genomic locus of interest, comprising: (a) modifying a non-human or mouse ES cell using any of the above methods; (b) identifying the modified non-human or mouse ES cell comprising the targeted genetic modification at the genomic locus of interest; (c) introducing the modified non-human or mouse ES cell into a non-human or mouse host embryo; and (d) gestating the non-human or mouse host embryo in a surrogate mother, wherein the surrogate mother produces the F0 generation non-human animal or mouse comprising the targeted genetic modification at the genomic locus of interest.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4 depicts the karyotype for line DA.2B, which is 42X,Y. Karyotyping was done because rat ESCs often become tetraploid; lines were thus pre-screened by counting metaphase chromosome spreads, and lines with mostly normal counts were then formally karyotyped.

FIG. 12A-C depict targeting of the rat Rosa26 locus, which lies between the Setd5 and Thumpd3 genes as in mouse, with the same spacing. FIG. 12A shows the structure of the mouse Rosa26 locus. Mouse Rosa26 transcripts consist of 2 or 3 exons.

FIG. 12B depicts the structure of the rat Rosa26 locus; the rat locus contains a second exon 1 (Ex1b) in addition to the homologous exon to mouse exon1 (Ex1a); no third exon has been identified in rat. FIG. 12C depicts a targeted rat Rosa26 allele; homology arms of 5 kb each were cloned by PCR using genomic DNA from DA rESC; the targeted allele contains a Splicing Acceptor (SA)-lacZ-hUB-neo cassette replacing a 117 bp deletion in the rat Rosa26 intron.

FIG. 21A provides a schematic for targeting the ApoE locus in rat ES cells using zinc-finger nucleases and a targeting vector comprising a reporter gene (LacZ) and a self-deleting cassette comprising a mouse Prm1 promoter operably linked to the Crei gene and a drug selection cassette comprising a human ubiquitin promoter operably linked to a neomycin resistance gene.

FIG. 29A-F show flow cytometry analysis of peripheral blood mononuclear cells (PBMCs) from an Il2rg−/y chimeric rat (FIG. 29A-C) and a WT DA rat (FIG. 29D-F). Flow cytometry analysis was for GFP expression and for T-cell marker CD3 (FIGS. 29A and 29D), B-cell marker B220 (FIGS. 29B and 29E), and NK cell marker CD161a (FIGS. 29C and 29F). Double-positive cells are shown in quadrant R8. FIG. 29A-F show that Il2rg−/y PBMCs do not express mature lymphocyte markers.

FIG. 43A-C show a brain from a wild type rat, and FIG. 43D-F show a brain from an ApoE+/− rat. FIGS. 43A and D show dorsal views, FIGS. 43B and E show ventral views, and FIGS. 43C and F show close-up views.

FIGS. 44A and B show a heart and blood vessels, respectively, from a wild type rat, and FIGS. 44C and D show a heart and blood vessels, respectively, from an ApoE+/− rat. Staining was present in the atria of the heart and in some vessels (e.g., vena cava).

FIGS. 45A and B show a liver from a wild type rat, and FIGS. 45C and D show a liver from an ApoE+/− rat. FIGS. 45B and D are close-ups of the livers.

grey boxes). Rag2 and Rag1 each comprise a single exon denoted by the unshaded arrows. The lower panel is the LTVEC. The 5' and 3' homology arms (48 kb and 15 kb, respectively) are denoted by the grey boxes. The LTVEC comprises a reporter gene (eGFP) and a puromycin resistance gene separated by an internal ribosome entry site (IRES) and operably linked to an actin promoter. The LTVEC further comprises a self-deleting cassette flanked by loxP sites (open arrows), which comprises a rat Prm1 promoter operably linked to the Crei gene and a drug selection cassette comprising a human ubiquitin promoter operably linked to a neomycin resistance gene.

Figure 51:
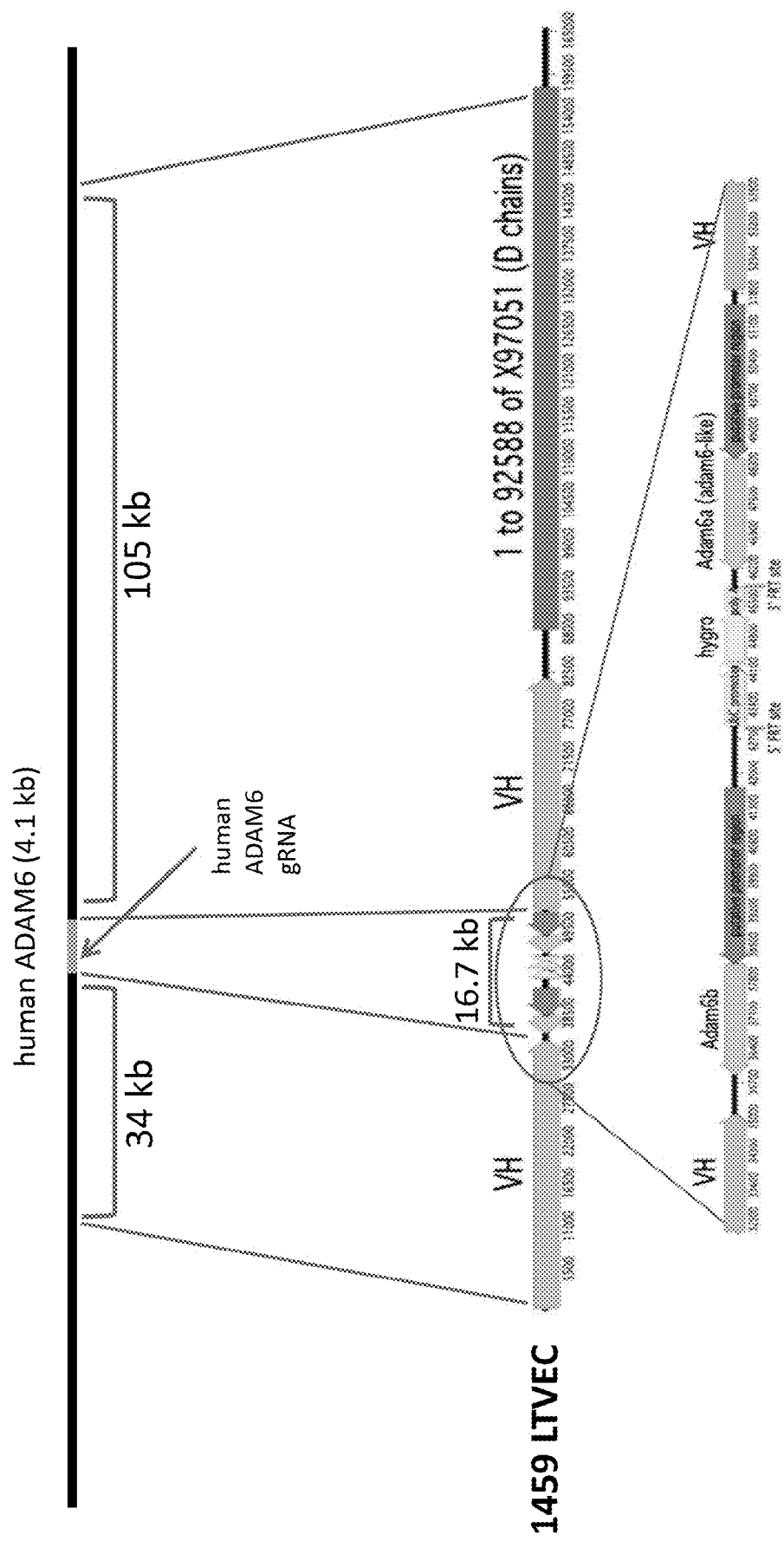

FIG. 51 depicts a schematic for replacement of a portion of the human ADAM6 locus with a nucleic acid comprising the mouse Adam6a and mouse Adam6b loci using an LTVEC and a guide RNA in human iPS cells. The target site for the guide RNA is indicated by the arrow.

FIG. 52A-B depict the morphology displayed by human iPS cells cultured for 8 days in 2i medium (FIG. 52A) and the morphology displayed by human iPS cells cultured for 12 days in 2i medium (FIG. 52B).

Figures 53A, 53B:
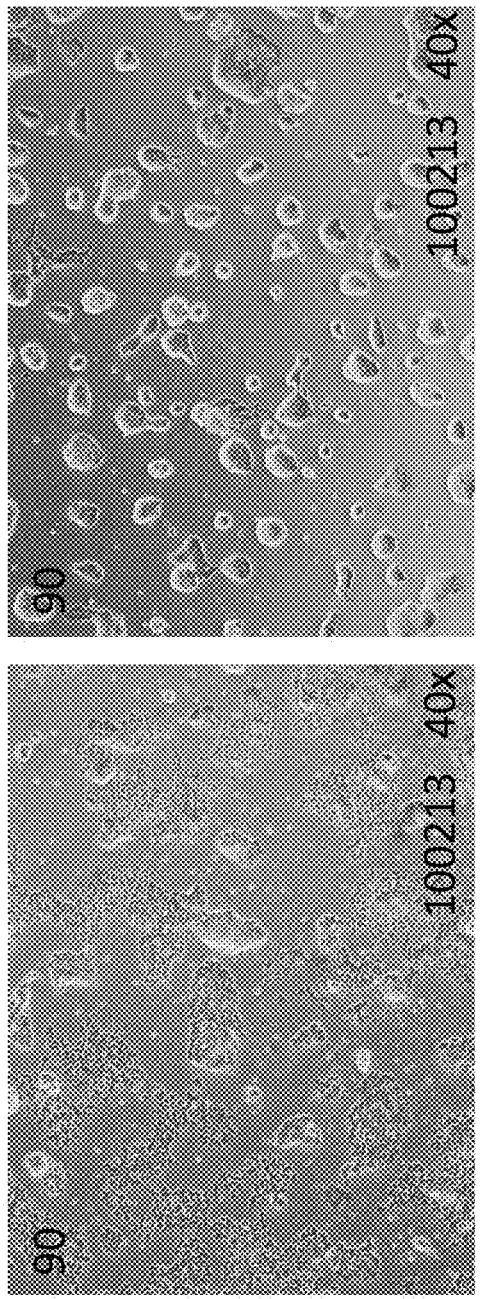
Figures 53C, 53D:
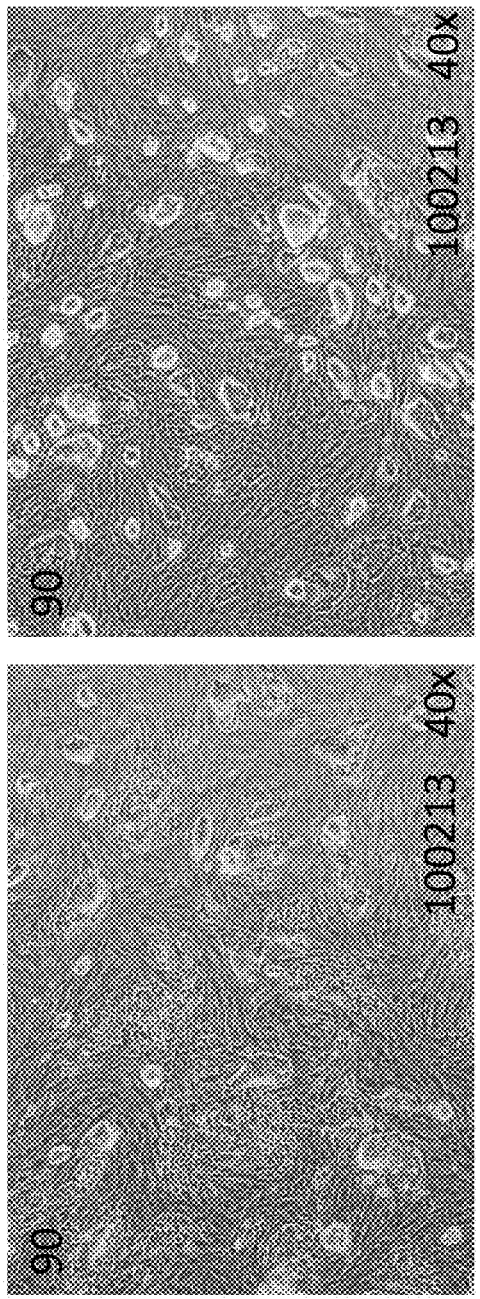

FIGS. 53A-53D depict the morphology of human iPS cells cultured in mTeSR™-hLIF medium or low osmolality VG2i medium for 6 days. FIGS. 53A and 53B depict the morphology of human iPS cells cultured in mTeSR™-hLIF medium (FIG. 53A) or VG2i medium (FIG. 53B) for 6 days. FIGS. 53C and 53D depict the morphology of human iPS cells cultured on newborn human foreskin fibroblast (NuFF) feeder cells in mTeSR™-hLIF medium (FIG. 53C) or VG2i medium (FIG. 53D) for 6 days.

FIG. 54A-C depict reprogrammed human iPS cells stained for pluripotency markers. FIG. 54A depicts reprogrammed human iPS cells cultured in VG2i medium that have been stained for alkaline phosphatase. FIGS. 54B and 54C depict reprogrammed human iPS cells cultured in VG2i medium that have been immunostained for the expression of NANOG.

FIGS. 55A-55C illustrate enzymatic dissociation and subculture of reprogrammed human iPS cells cultured in VG2i medium. FIG. 55A depicts reprogrammed human iPS cells cultured in VG2i medium prior to enzymatic dissociation with trypsin in the absence of a ROCK inhibitor. FIG. 55B depicts human iPS cells cultured in VG2i medium for 1 day after subculture. FIG. 55C depicts human iPS cells cultured in VG2i medium for 4 days after subculture.

DETAILED DESCRIPTION OF THE INVENTION

Compositions and methods are provided for modifying a rat, eukaryotic, non-rat eukaryotic, mammalian, non-human mammalian, human, rodent, non-rat rodent, mouse, or hamster genomic locus of interest via bacterial homologous recombination (BHR) in a prokaryotic cell. Compositions and methods are also provided for genetically modifying a genomic locus of interest, for example, rat, eukaryotic, non-rat eukaryotic, mammalian, non-human mammalian, human, rodent, non-rat rodent, or mouse genomic locus of interest using a large targeting vector (LTVEC) in combination with endonucleases. Compositions and methods are also provided for producing a genetically modified non-human animal, for example, a rat, mouse, rodent, or non-rat rodent, comprising one or more targeted genetic modifications. Also provided are isolated human and non-human totipotent or pluripotent stem cells, in particular rat embryonic stem cells, that are capable of sustaining pluripotency following one or more serial genetic modifications in vitro, and that are capable of transmitting the targeted genetic modifications to subsequent generations through germline.

Glossary

The term "embryonic stem cell" or "ES cell" as used herein includes an embryo-derived totipotent or pluripotent cell that is capable of contributing to any tissue of the developing embryo upon introduction into an embryo. The term "pluripotent cell" as used herein includes an undifferentiated cell that possesses the ability to develop into more than one differentiated cell types. The term "non-pluripotent cell" includes cells that are not pluripotent cells.

The term "homologous nucleic acid" as used herein includes a nucleic acid sequence that is either identical or substantially similar to a known reference sequence. In one embodiment, the term "homologous nucleic acid" is used to characterize a sequence having amino acid sequence that is at least 70%, at least 75%, at least 80%, at least 85%, at least 90%, at least 95%, at least 96%, at least 97%, at least 98%, at least 99%, or even 100% identical to a known reference sequence.

The term "orthologous nucleic acid" as used herein includes a nucleic acid sequence from one species that is functionally equivalent to a known reference sequence in another species.

The term "large targeting vector" or "LTVEC" as used herein includes large targeting vectors for eukaryotic cells that are derived from fragments of cloned genomic DNA larger than those typically used by other approaches intended to perform homologous gene targeting in eukaryotic cells. Examples of LTVEC, include, but are not limited to, bacterial homologous chromosome (BAC) and yeast artificial chromosome (YAC).

The term "modification of allele" (MOA) as used herein includes the modification of the exact DNA sequence of one allele of a gene(s) or chromosomal locus (loci) in a genome. Examples of "modification of allele (MOA)" as described herein includes, but is not limited to, deletions, substitutions, or insertions of as little as a single nucleotide or deletions of many kilobases spanning a gene(s) or chromosomal locus (loci) of interest, as well as any and all possible modifications between these two extremes.

The term "recombination site" as used herein includes a nucleotide sequence that is recognized by a site-specific recombinase and that can serve as a substrate for a recombination event.

"Serial" genetic modifications include two or more modifications conducted independently to a cell (e.g., a eukaryotic cell, a non-rat eukaryotic cell, a mammalian cell, a human cell, a non-human mammalian cell, a pluripotent cell, a non-pluripotent cell, a non-human pluripotent cell, a human pluripotent cell, a human ES cell, a human adult stem cell, a developmentally-restricted human progenitor cell, a human iPS cell, a human cell, a rodent cell, a non-rat rodent cell, a rat cell, a mouse cell, a hamster cell, a fibroblast, or a Chinese hamster ovary (CHO) cell). The first modification may be achieved by electroporation, or any other method known in the art. Then a second modification is made to the same cell genome employing a suitable second nucleic acid construct. The second modification may be achieved by a second electroporation, or any other method known in the art. In various embodiments, following the first and the second genetic modifications of the same cell, a third, a fourth, a fifth, a sixth, and so on, serial genetic modifications (one following another) may be achieved using, e.g., serial electroporation or any other suitable method (serially) known in the art.

The term "site-specific recombinase" as used herein includes a group of enzymes that can facilitate recombination between "recombination sites" where the two recombination sites are physically separated within a single nucleic acid molecule or on separate nucleic acid molecules. Examples of "site-specific recombinase" include, but are not limited to, Cre, Flp, and Dre recombinases.

The term "germline" in reference to a nucleic acid sequence includes a nucleic acid sequence that can be passed to progeny.

The phrase "heavy chain," or "immunoglobulin heavy chain" includes an immunoglobulin heavy chain sequence, including immunoglobulin heavy chain constant region sequence, from any organism. Heavy chain variable domains include three heavy chain CDRs and four FR regions, unless otherwise specified. Fragments of heavy chains include CDRs, CDRs and FRs, and combinations thereof. A typical heavy chain has, following the variable domain (from N-terminal to C-terminal), a $C_H1$ domain, a hinge, a $C_H2$ domain, and a $C_H3$ domain. A functional fragment of a heavy chain includes a fragment that is capable of specifically recognizing an epitope (e.g., recognizing the epitope with a $K_D$ in the micromolar, nanomolar, or picomolar range), that is capable of expressing and secreting from a cell, and that comprises at least one CDR. Heavy chain variable domains are encoded by variable region nucleotide sequence, which generally comprises $V_H$, $D_H$, and $J_H$ segments derived from a repertoire of $V_H$, $D_H$, and $J_H$ segments present in the germline. Sequences, locations and nomenclature for V, D, and J heavy chain segments for various organisms can be found in IMGT database, which is accessible via the internet on the world wide web (www) at the URL "imgt.org."

The phrase "light chain" includes an immunoglobulin light chain sequence from any organism, and unless otherwise specified includes human kappa (κ) and lambda (λ) light chains and a VpreB, as well as surrogate light chains. Light chain variable domains typically include three light chain CDRs and four framework (FR) regions, unless otherwise specified. Generally, a full-length light chain includes, from amino terminus to carboxyl terminus, a variable domain that includes FR1-CDR1-FR2-CDR2-FR3-CDR3-FR4, and a light chain constant region amino acid sequence. Light chain variable domains are encoded by the light chain variable region nucleotide sequence, which generally comprises light chain $V_L$ and light chain $J_L$ gene segments, derived from a repertoire of light chain V and J gene segments present in the germline. Sequences, locations and nomenclature for light chain V and J gene segments for various organisms can be found in IMGT database, which is accessible via the internet on the world wide web (www) at the URL "imgt.org." Light chains include those, e.g., that do not selectively bind either a first or a second epitope selectively bound by the epitope-binding protein in which they appear. Light chains also include those that bind and recognize, or assist the heavy chain with binding and recognizing, one or more epitopes selectively bound by the epitope-binding protein in which they appear.

The phrase "operably linked" comprises a relationship wherein the components operably linked function in their intended manner. In one instance, a nucleic acid sequence encoding a protein may be operably linked to regulatory sequences (e.g., promoter, enhancer, silencer sequence, etc.) so as to retain proper transcriptional regulation. In one instance, a nucleic acid sequence of an immunoglobulin variable region (or V(D)J segments) may be operably linked to a nucleic acid sequence of an immunoglobulin constant region so as to allow proper recombination between the sequences into an immunoglobulin heavy or light chain sequence.

1. Target Locus Comprising a Nucleic Acid

Various methods and compositions are provided, which allow for the integration of at least one insert nucleic acid at a target locus. As used herein, a "genomic locus of interest" comprises any segment or region of DNA within the genome that one desires to integrate an insert nucleic acid. The terms "genomic locus of interest" and "target genomic locus of interest" can be used interchangeable. The genomic locus of interest can be native to the cell, or alternatively can comprise a heterologous or exogenous segment of DNA that was integrated into the genome of the cell. Such heterologous or exogenous segments of DNA can include transgenes, expression cassettes, polynucleotide encoding selection makers, or heterologous or exogenous regions of genomic DNA. The term "locus" is a defined herein as a segment of DNA within the genomic DNA. Genetic modifications as described herein can include one or more deletions from a locus of interest, additions to a locus of interest, replacement of a locus of interest, and/or any combination thereof. The locus of interest can comprise coding regions or non-coding regulatory regions.

The genomic locus of interest can further comprise any component of a targeted integration system including, for example, a recognition site, a selection marker, a previously integrated insert nucleic acid, polynucleotides encoding nuclease agents, promoters, etc. Alternatively, the genomic locus of interest can be located within an extrachromosomal DNA within the cell, such as a yeast artificial chromosome (YAC), a bacterial artificial chromosome (BAC), a human artificial chromosome, or any other engineered genomic region contained in an appropriate host cell. In various embodiments, the targeted locus can comprise native, heterologous, or exogenous nucleic acid sequence from a prokaryote, a eukaryote, a non-rat eukaryote, yeast, bacteria, a non-human mammal, a non-human cell, a rodent, a non-rat rodent, a human, a rat, a mouse, a hamster, a rabbit, a pig, a bovine, a deer, a sheep, a goat, a chicken, a cat, a dog, a ferret, a primate (e.g., marmoset, rhesus monkey), domesticated mammal or an agricultural mammal or any other organism of interest or a combination thereof. In some embodiments, the genomic locus of interest comprises a nucleic acid sequence from a human, a mouse, or a combination thereof.

In specific embodiments, the target locus is from, for example, a eukaryotic cell, a non-rat eukaryotic cell, a mammalian cell, human cell, a non-human mammalian cell, a pluripotent cell, a non-pluripotent cell, a non-human pluripotent cell, a human pluripotent cell, a human ES cell, a human adult stem cell, a developmentally-restricted human progenitor cell, a human iPS cell, a human cell, a rodent cell, a non-rat rodent cell, a rat cell, a mouse cell, a hamster cell, a fibroblast, or a CHO cell.

In specific embodiments, the genomic locus of interest comprises a target locus of a "rat nucleic acid." Such a region comprises a nucleic acid from a rat that is integrated within the genome of a cell. Non-limiting examples of the target locus include a genomic locus that encodes a protein expressed in a B cell, a genomic locus that expresses a polypeptide in an immature B cell, a genomic locus that expresses a polypeptide in a mature B cell, an immunoglobulin (Ig) loci, or a T cell receptor loci, including, for example, a T cell receptor alpha locus. Additional examples of target genomic locus include an Fcer1a locus, a Tlr4 locus, a Prlr locus, a Notch4 locus, an Accn2 locus, an Adamts5 locus, a Trpa1 locus, Folh1 locus, an Lrp5 locus, an IL2 receptor locus, including, for example, an IL2 Receptor gamma (Il2rg) locus, an ApoE locus, a Rag1 locus, a Rag2 locus, a Rag1 Rag2 locus, and an Erbb4 locus. Any such target locus can be from a rat or can be from a eukaryotic cell, a non-rat eukaryotic cell, a mammalian cell, a human cell, or a non-human mammalian cell.

In one embodiment, the target locus encodes a mammalian immunoglobulin heavy chain variable region amino acid sequence. In one embodiment, the target locus encodes a rat immunoglobulin heavy chain variable region amino acid sequence. In one embodiment, the target locus comprises a genomic DNA sequence comprising an unrearranged rat, mouse, or human immunoglobulin heavy chain variable region nucleic acid sequence operably linked to an immunoglobulin heavy chain constant region nucleic acid sequence. In one embodiment, the immunoglobulin heavy chain constant region nucleic acid sequence is a rat, mouse, or human immunoglobulin heavy chain constant region nucleic acid sequence selected from a CH1, a hinge, a CH2, a CH3, and a combination thereof. In one embodiment, the heavy chain constant region nucleic acid sequence comprises a CH1-hinge-CH2-CH3. In one embodiment, the target locus comprises a rearranged rat, mouse, or human immunoglobulin heavy chain variable region nucleic acid sequence operably linked to an immunoglobulin heavy chain constant region nucleic acid sequence. In one embodiment, the immunoglobulin heavy chain constant region nucleic acid sequence is a rat, mouse, or human immunoglobulin heavy chain constant region nucleic acid sequence selected from a CH1, a hinge, a CH2, a CH3, and a combination thereof. In one embodiment, the heavy chain constant region nucleic acid sequence comprises a CH1-hinge-CH2-CH3.

In one embodiment, the target locus comprises a genomic DNA sequence that encodes a mammalian immunoglobulin light chain variable region amino acid sequence. In one embodiment, the genomic DNA sequence comprises an unrearranged mammalian λ and/or κ light chain variable region nucleic acid sequence.

In one embodiment, the genomic DNA sequence comprises a rearranged mammalian λ and/or κ light chain variable region nucleic acid sequence. In one embodiment, the unrearranged λ or κ light chain variable region nucleic acid sequence is operably linked to a mammalian immunoglobulin light chain constant region nucleic acid sequence selected from a λ light chain constant region nucleic acid sequence and a κ light chain constant region nucleic acid sequence. In one embodiment, the mammalian immunoglobulin light chain constant region nucleic acid sequence is a rat immunoglobulin light chain constant region nucleic acid sequence. In one embodiment, the mammalian immunoglobulin light chain constant region nucleic acid sequence is a mouse immunoglobulin light chain constant region nucleic acid sequence. In one embodiment, the mammalian immunoglobulin light chain constant region nucleic acid sequence is a human immunoglobulin light chain constant region nucleic acid sequence.

As used herein, an ApoE locus, an interleukin-2 receptor gamma (Il2rg) locus, a Rag2 locus, a Rag1 locus and/or a Rag2/Rag1 locus comprise the respective regions of the genome (i.e., a mammalian genome, a human genome or a non-human mammalian genome) in which each of these genes or gene combinations are located. Modifying any one of the ApoE locus, interleukin-2 receptor gamma (Il2rg) locus, Rag2 locus, Rag1 locus and/or Rag2/Rag1 locus (i.e., a mammalian, a human, or a non-human mammalian ApoE locus, the interleukin-2 receptor gamma locus, the Rag2 locus, the Rag1 locus and/or the combined Rag2/Rag1 locus) can comprise any desired alteration to the given locus. Non-limiting examples of modification to the given locus (i.e., a mammalian, a human, or a non-human mammalian locus) are discussed in further detail herein.

For example, in specific embodiments, one or more of the ApoE locus, interleukin-2 receptor gamma (Il2rg) locus, Rag2 locus, Rag1 locus and/or Rag2/Rag1 locus (i.e., a mammalian, a human, or a non-human mammalian ApoE locus, a mammalian, a human, or a non-human mammalian interleukin-2 receptor gamma locus, a mammalian, a human, or a non-human mammalian Rag2 locus, and/or the Rag2/Rag1 locus) is modified such that the activity and/or level of the encoded ApoE protein or the interleukin-2 receptor gamma protein or the Rag1 protein or the Rag2 protein or a combination of the Rag1 and Rag2 proteins are decreased. In other embodiments, the activity of the ApoE protein, the interleukin-2 receptor gamma protein, the Rag1 protein, or the Rag2 protein, or a combination of the Rag1 and Rag2 proteins is absent.

By "decreased" is intended any decrease in the level or activity of the gene/protein encoded at the locus of interest. For example, a decrease in activity can comprise either (1) a statistically significant decrease in the overall level or activity of a given protein (i.e., ApoE, interleukin-2 receptor gamma, Rag2, Rag2 or a combination of Rag1 and Rag2) including, for example, a decreased level or activity of 0.5%, 1%, 5%, 10%, 20%, 30%, 40%, 50%, 60%, 70%, 80%, 90%, 100%, 120% or greater when compared to an appropriate control. Methods to assay for a decrease in the concentration and/or the activity of anyone of ApoE, interleukin-2 receptor gamma, Rag1 and Rag2 are known in the art.

In other embodiments, one or more of the a mammalian, a human, or a non-human mammalian ApoE locus, the a mammalian, a human, or a non-human mammalian interleukin-2 receptor gamma locus, a mammalian, a human, or a non-human mammalian Rag2 locus, a mammalian, a human, or a non-human mammalian Rag1 locus and/or a mammalian, a human, or a non-human mammalian Rag2/Rag1 locus comprise a modification such that the activity and/or level of the encoded ApoE polypeptide, the interleukin-2 receptor gamma polypeptide, the Rag2 polypeptide, the Rag1 polypeptide, or both the Rag1 and Rag2 polypeptide is increased. By "increased" is intended any increase in the level or activity of the gene/polypeptide encoded at the locus of interest. For example, an increase in activity can comprise either (1) a statistically significant increase in the overall level or activity of a given protein (i.e., ApoE, interleukin-2 receptor gamma, Rag1, Rag2 or Rag1 and Rag2) including, for example, an increased level or activity of 0.5%, 1%, 5%, 10%, 20%, 30%, 40%, 50%, 60%, 70%, 80%, 90%, 100%, 120% or greater when compared to an appropriate control. Methods to assay for an increase in the concentration and/or the activity of anyone of the ApoE, Rag1, Rag2 and interleukin-2 receptor gamma proteins are known in the art.

The genetic modification to the a mammalian, a human, or a non-human mammalian ApoE locus, a mammalian, a human, or a non-human mammalian interleukin-2 receptor gamma locus, a mammalian, a human, or a non-human mammalian Rag2 locus, a mammalian, a human, or a non-human mammalian Rag1 locus and/or a mammalian, a human, or a non-human mammalian Rag2/Rag1 locus can comprise a deletion of an endogenous nucleic acid sequence at the genomic locus, an insertion of an exogenous nucleic acid at the genomic locus, or a combination thereof. The deletion and/or insertion can occur anywhere within the given locus as discussed elsewhere herein.

Further embodiments provided herein comprise the modification of one or more of the mammalian, human, or non-human mammalian ApoE locus, interleukin-2 receptor gamma locus, Rag2 locus, Rag1 locus and/or Rag2/Rag1 locus through the replacement of a portion of the ApoE locus, interleukin-2 receptor gamma (Il2rg) locus, Rag2 locus, Rag1 locus and/or Rag2/Rag1 locus with the corresponding homologous or orthologous portion of an ApoE locus, an interleukin-2 receptor gamma locus, a Rag2 locus, a Rag1 locus and/or a Rag2/Rag1 locus from another organism.

In still other embodiments, the modification of one or more of the mammalian, human, or non-human mammalian ApoE locus, the interleukin-2 receptor gamma locus, Rag2 locus, Rag1 locus, and/or Rag2/Rag1 locus is carried out through the replacement of a portion of the ApoE locus, interleukin-2 receptor gamma (Il2rg) locus, Rag2 locus, Rag1 locus and/or Rag2/Rag1 locus with an insert polynucleotide sharing across its full length least 80%, 85%, 90%, 91%, 92%, 93%, 94%, 95%, 96%, 97%, 98%, 99% to a portion of an ApoE locus, an interleukin-2 receptor gamma locus, a Rag2 locus, a Rag1 locus and/or a Rag2/Rag1 locus it is replacing.

The given insert polynucleotide and/or the corresponding region of the locus being deleted can be a coding region, an intron, an exon, an untranslated region, a regulatory region, a promoter, or an enhancer or any combination thereof or any portion thereof. Moreover, the given insert polynucleotide and/or the region of the locus, for example, being deleted can be of any desired length, including for example, between 10-100 nucleotides in length, 100-500 nucleotides in length, 500-1 kb nucleotide in length, 1 Kb to 1.5 kb nucleotide in length, 1.5 kb to 2 kb nucleotides in length, 2 kb to 2.5 kb nucleotides in length, 2.5 kb to 3 kb nucleotides in length, 3 kb to 5 kb nucleotides in length, 5 kb to 8 kb nucleotides in length, 8 kb to 10 kb nucleotides in length or more. In other instances, the size of the insertion or replacement is from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, from about 350 kb to about 400 kb, from about 400 kb to about 800 kb, from about 800 kb to 1 Mb, from about 300 kb to about 400 kb, from about 400 kb to about 500 kb, from 500 kb to 1 Mb, from about 1 Mb to about 1.5 Mb, from about 1.5 Mb to about 2 Mb, from about 2 Mb to about 2.5 Mb, from about 2.5 Mb to about 2.8 Mb, from about 2.8 Mb to about 3 Mb. In other embodiments, the given insert polynucleotide and/or the region of the locus being deleted is at least 100, 200, 300, 400, 500, 600, 700, 800, or 900 nucleotides or at least 1 kb, 2 kb, 3 kb, 4 kb, 5 kb, 6 kb, 7 kb, 8 kb, 9 kb, 10 kb, 11 kb, 12 kb, 13 kb, 14 kb, 15 kb, 16 kb or greater. In other embodiments, the given insert polynucleotide and/or the region of the locus being deleted is at least 10 kb, at least 20 kb, at least 30 kb, at least 40 kb, at least 50 kb, at least 60 kb, at least 70 kb, at least 80 kb, at least 90 kb, at least 100 kb, at least 150 kb, at least 200 kb, at least 250 kb, or at least 300 kb or greater.

The given insert polynucleotide can be from any organism, including, for example, a rodent, a non-rat rodent, a rat, a mouse, a hamster, a mammal, a non-human mammal, a eukaryote, a non-rat eukaryote, a human, an agricultural animal or a domestic animal.

As discussed in further detail herein, various methods are provided to generate targeted modifications of any locus of interest, including for example, targeted modifications in the ApoE locus, interleukin-2 receptor gamma (Il2rg) locus, Rag2 locus, Rag1 locus and/or Rag2/Rag1 locus. Further provided are genetically modified non-human animals, genetically modified non-human mammals, genetically modified non-rat eukaryotes, genetically modified non-pluripotent cells, or genetically modified pluripotent cells (e.g., a pluripotent cell, a non-human pluripotent cell, a human pluripotent cell, a human ES cell, a human adult stem cell, a developmentally-restricted human progenitor cell, or a human iPS cell), which comprise a deletion, an insertion, a replacement and/or any combination thereof at the interleukin-2 receptor gamma locus, at the ApoE locus, at the Rag2 locus, at the Rag1 locus, and/or at the Rag2/Rag1 locus. Such genetic modifications (including those that result in an absence, a decrease, an increase or a modulation in activity of the target locus) and are also capable of being transmitted through the germline. In specific embodiments, the genetic modifications result in a knockout of the desired target locus. Such non-human animals, for example, find use in in a variety of experimental systems as discussed elsewhere herein.

For example, ApoE (Apolipoprotein E) knockouts offer an animal model to study endothelial function, including, but not limited to, plaque formation, transcriptional changes (Whole Transcriptome Shotgun Sequencing (RNA-Seq), and ex vivo function. ApoE is an important transport molecule and can transport lipids, such as cholesterol, through the bloodstream. ApoE can also function in the nervous system, for example, to clear β-amyloid from the brain. Modifications in ApoE have been implicated in various conditions, including, for example, atherosclerosis, hyperlipidemia, and Alzheimer's disease. ApoE knockout animals display impaired clearing of lipoproteins from the blood and develop atherosclerosis. Thus, ApoE knockout animals provide a model to study conditions and/or processes such as, for example, endothelia function, plaque formation, transcriptional changes (RNA-Seq), hyperlipidemia, atherosclerosis and Alzheimer's disease. Assays to measure ApoE activity are known in the art. For example, a decrease in ApoE activity can be measured by assaying for a decrease in the ApoE levels in a blood sample obtained from a subject by immunoassays, such as by ELISA or by Immunoblotting techniques. Moreover, the large size of rats facilitates all these assays and improves the quality of the data.

RAG1 (Recombination-Activating Gene 1) and RAG2 (Recombination-Activating Gene 2) are enzymes that are part of a multi-subunit complex having VDJ recombination activity and play an important role in the rearrangement and recombination of immunoglobulin and T-cell receptor genes in lymphocytes. RAG1 and RAG2 induce a double stranded DNA cleavage to facilitate recombination and join of segments of the T cell receptor and B cell receptor (i.e., immunoglobulin) genes. Knockout of RAG1 and/or RAG2 causes a loss of B cells and T cells in the animal resulting in severe immunodeficiency. RAG1 and/or RAG2 knockout animals find use, for example, in studies of xenografts (i.e., human cell xenografts in rats), cancer, vaccine development, autoimmune disease, infectious disease and graft versus host disease (GVHD). Various assays to measure RAG1 and/or RAG2 activity are known in the art and include, for example, measuring recombination efficiency or assaying for the presence or absence of B cells and/or T cells in a subject.

The IL-2 receptor (IL-2R) is expressed on the surface of certain immune cells and binds to the cytokine interleukin-2 (IL-2). The IL-2R is an integral membrane protein comprising at least three separate subunit chains, including, an alpha chain (IL-2Ra, CD25), a beta chain (IL-2Rb, CD122) and a gamma chain (IL2-Rg, CD132). The IL-2 receptor gamma (also referred to as IL2r-γ or IL2Rg) chain is a common gamma chain that is shared by various cytokine receptors, including, for example, the receptors for IL-2, IL-4, IL-7, IL-9, IL-15 and IL-21. IL-2Rg comprises an ectodomain on the extracellular surface of the cell, which contributes to the binding of the ligand, a transmembrane domain, and an intracellular domain, which can interact with various molecules to induce intracellular signal transduction pathways. The Il2rg gene is found on the X-chromosome in mammals and certain mutations in the gamma chain gene in humans can cause human X-linked severe combined immunodeficiency (XSCID) characterized by a profound T-cell defect. In addition, the gamma chain ecto-domain can be shed off of the transmembrane receptor and released as a soluble gamma chain receptor. The soluble gamma chain receptor can be detected in the blood of a subject and can function to regulate cytokine signaling.

In some embodiments, the non-human IL-2Rg chain is replaced with the human IL2-Rg chain such that the genetically modified animal expresses a fully human IL-2Rg chain. In other instances, it may be useful to replace only the ectodomain of a non-human IL-2Rg chain with the ectodomain of the human IL-2Rg chain. In such cases, the resulting humanized IL-2Rg chain expressed in a non-human comprises a human ectodomain, with the remainder of the molecule being from the native organism.

The full-length humanization of IL-2Rg is useful because non-human mammals having this modified locus will produce human IL-2Rg. This will allow for the detection of human IL-2Rg in non-human mammals with antibodies specific to human IL-2Rg. The ecto-humanization (i.e., replacing the ecto-domain of IL-2Rg a non-human mammal with the human ecto-domain of IL-2Rg) will result in an IL-2Rg polypeptide that will bind the human ligands for IL2-Rg, but because the cytoplasmic domain is still from the non-human mammal, the ecto-humanized form of IL-2Rg will also interact with the non-human mammal signaling machinery.

2. Modifying a Target Locus

A. Targeting Vectors and Insert Nucleic Acids i. Insert Nucleic Acid

As used herein, the "insert nucleic acid" comprises a segment of DNA that one desires to integrate at the target locus. In one embodiment, the insert nucleic acid comprises one or more polynucleotides of interest. In other embodiments, the insert nucleic acid can comprise one or more expression cassettes. A given expression cassette can comprise a polynucleotide of interest, a polynucleotide encoding a selection marker and/or a reporter gene along with the various regulatory components that influence expression. Non-limiting examples of polynucleotides of interest, selection markers, and reporter genes that can be included within the insert nucleic acid are discussed in detail elsewhere herein.

In specific embodiments, the insert nucleic acid can comprise a nucleic acid from rat, which can include a segment of genomic DNA, a cDNA, a regulatory region, or any portion or combination thereof. In other embodiments, the insert nucleic acid can comprise a nucleic acid from a eukaryote, a non-rat eukaryote, a mammal, a human, a non-human mammal, a rodent, a non-rat rodent, a human, a rat, a mouse, a hamster, a rabbit, a pig, a bovine, a deer, a sheep, a goat, a chicken, a cat, a dog, a ferret, a primate (e.g., marmoset, rhesus monkey), a domesticated mammal, or an agricultural mammal or any other organism of interest. As outlined in further detail herein, the insert nucleic acid employed in the various methods and compositions can result in the "humanization" of the a target locus of interest.

In one embodiment, the insert nucleic acid comprises a knock-in allele of at least one exon of an endogenous gene. In one embodiment, the insert nucleic acid comprises a knock-in allele of the entire endogenous gene (i.e., "gene-swap knock-in").

In one embodiment, the insert nucleic acid comprises a regulatory element, including for example, a promoter, an enhancer, or a transcriptional repressor-binding element.

In further embodiments, the insert nucleic acid comprises a conditional allele. In one embodiment, the conditional allele is a multifunctional allele, as described in US 2011/0104799, which is incorporated by reference in its entirety. In specific embodiments, the conditional allele comprises: (a) an actuating sequence in sense orientation with respect to transcription of a target gene, and a drug selection cassette in sense or antisense orientation; (b) in antisense orientation a nucleotide sequence of interest (NSI) and a conditional by inversion module (COIN, which utilizes an exon-splitting intron and an invertible genetrap-like module; see, for example, US 2011/0104799, which is incorporated by reference in its entirety); and (c) recombinable units that recombine upon exposure to a first recombinase to form a conditional allele that (i) lacks the actuating sequence and the DSC, and (ii) contains the NSI in sense orientation and the COIN in antisense orientation.

The insert nucleic acid ranges from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb.

In one embodiment, the insert nucleic acid comprises a deletion of, for example, a eukaryotic cell, a non-rat eukaryotic cell, a mammalian cell, a human cell or a non-human mammalian cell genomic DNA sequence ranging from about 1 kb to about 200 kb, from about 2 kb to about 20 kb, or from about 0.5 kb to about 3 Mb. In one embodiment, the extent of the deletion of the genomic DNA sequence is greater than a total length of the 5' homology arm and the 3' homology arm. In one embodiment, the extent of the deletion of the genomic DNA sequence ranges from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 20 kb to about 30 kb, from about 30 kb to about 40 kb, from about 40 kb to about 50 kb, from about 50 kb to about 60 kb, from about 60 kb to about 70 kb, from about 70 kb to about 80 kb, from about 80 kb to about 90 kb, from about 90 kb to about 100 kb, from about 100 kb to about 110 kb, from about 110 kb to about 120 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, from about 190 kb to about 200 kb, from about 200 kb to about 250 kb, from about 250 kb to about 300 kb, from about 300 kb to about 350 kb, from about 350 kb to about 400 kb, from about 400 kb to about 800 kb, from about 800 kb to 1 Mb, from about 1 Mb to about 1.5 Mb, from about 1.5 Mb to about 2 Mb, from about 2 Mb, to about 2.5 Mb, from about 2.5 Mb to about 2.8 Mb, from about 2.8 Mb to about 3 Mb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb.

In one embodiment, the insert nucleic acid comprises an insertion or a replacement of a eukaryotic, a non-rat eukaryotic, a mammalian, a human or a non-human mammalian nucleic acid sequence with a homologous or orthologous human nucleic acid sequence. In one embodiment, the insert nucleic acid comprises an insertion or replacement of a DNA sequence with a homologous or orthologous human nucleic acid sequence at an endogenous locus that comprises the corresponding DNA sequence.

In one embodiment, the genetic modification is an addition of a nucleic acid sequence. In one embodiment, the added nucleotide sequence ranges from 5 kb to 200 kb.

In one embodiment, the insert nucleic acid comprises a genetic modification in a coding sequence. In one embodiment, the genetic modification comprises a deletion mutation of a coding sequence. In one embodiment, the genetic modification comprises a fusion of two endogenous coding sequences.

In one embodiment, the insert nucleic acid comprises an insertion or a replacement of a eukaryotic, a non-rat eukaryotic, a mammalian, a human, or a non-human mammalian, nucleic acid sequence with a homologous or orthologous human nucleic acid sequence. In one embodiment, the insert nucleic acid comprises an insertion or replacement of a rat DNA sequence with a homologous or orthologous human nucleic acid sequence at an endogenous rat locus that comprises the corresponding rat DNA sequence.

In one embodiment, the genetic modification comprises a deletion of a non-protein-coding sequence, but does not comprise a deletion of a protein-coding sequence. In one embodiment, the deletion of the non-protein-coding sequence comprises a deletion of a regulatory element. In one embodiment, the genetic modification comprises a deletion of a promoter. In one embodiment, the genetic modification comprises an addition of a promoter or a regulatory element. In one embodiment, the genetic modification comprises a replacement of a promoter or a regulatory element.

In one embodiment, the nucleic acid sequence of the targeting vector can comprise a polynucleotide that when integrated into the genome will produce a genetic modification of a region of the mammalian, human, or a non-human mammalian ApoE locus, wherein the genetic modification at the ApoE locus results in a decrease in ApoE activity, increase in ApoE activity, or a modulation of ApoE activity. In one embodiment, an ApoE knockout ("null allele) is generated.

In one embodiment, the nucleic acid sequence of the targeting vector can comprise a polynucleotide that when integrated into the genome will produce a genetic modification of a region of the mammalian, human cell, or non-human mammalian interleukin-2 receptor locus, wherein the genetic modification at the interleukin-2 receptor locus results in a decrease in interleukin-2 receptor activity. In one embodiment, an interleukin-2 receptor knockout ("null allele") is generated.

In further embodiments, the insert nucleic acid results in the replacement of a portion of the mammalian, human cell, or non-human mammalian ApoE locus, the interleukin-2 receptor gamma locus and/or Rag2 locus, and/or Rag1 locus and/or Rag2/Rag1 locus with the corresponding homologous or orthologous portion of an ApoE locus, an interleukin-2 receptor gamma locus, a Rag2 locus, a Rag1 locus and/or a Rag2/Rag1 locus from another organism.

Still other embodiments, the insert nucleic acid comprises a polynucleotide sharing across its full length least 80%, 85%, 90%, 91%, 92%, 93%, 94%, 95%, 96%, 97%, 98%, 99% to a portion of an ApoE locus, an interleukin-2 receptor gamma locus, a Rag2 locus, a Rag1 locus and/or a Rag2/Rag1 locus it is replacing.

The given insert polynucleotide and the corresponding region of the mammalian, human cell, or non-human mammalian locus being replaced can be a coding region, an intron, an exon, an untranslated region, a regulatory region, a promoter, or an enhancer or any combination thereof. Moreover, the given insert polynucleotide and/or the region of the mammalian, human cell, or non-human mammalian locus being deleted can be of any desired length, including for example, between 10-100 nucleotides in length, 100-500 nucleotides in length, 500-1 kb nucleotide in length, 1 Kb to 1.5 kb nucleotide in length, 1.5 kb to 2 kb nucleotides in length, 2 kb to 2.5 kb nucleotides in length, 2.5 kb to 3 kb nucleotides in length, 3 kb to 5 kb nucleotides in length, 5 kb to 8 kb nucleotides in length, 8 kb to 10 kb nucleotides in length or more. In other instances, the size of the insertion or replacement is from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, from about 350 kb to about 400 kb, from about 400 kb to about 800 kb, from about 800 kb to 1 Mb, from about 1 Mb to about 1.5 Mb, from about 1.5 Mb to about 2 Mb, from about 2 Mb, to about 2.5 Mb, from about 2.5 Mb to about 2.8 Mb, from about 2.8 Mb to about 3 Mb. In other embodiments, the given insert polynucleotide and/or the region of the mammalian, human cell, or non-human mammalian locus being deleted is at least 100, 200, 300, 400, 500, 600, 700, 800, or 900 nucleotides or at least 1 kb, 2 kb, 3 kb, 4 kb, 5 kb, 6 kb, 7 kb, 8 kb, 9 kb, 10 kb, 11 kb, 12 kb, 13 kb, 14 kb, 15 kb, 16 kb or greater.

In one embodiment, the promoter is constitutively active promoter.

In one embodiment, the promoter is an inducible promoter. In one embodiment, the inducible promoter is a chemically-regulated promoter. In one embodiment, the chemically-regulated promoter is an alcohol-regulated promoter. In one embodiment, the alcohol-regulated promoter is an alcohol dehydrogenase (alcA) gene promoter. In one embodiment, the chemically-regulated promoter is a tetracycline-regulated promoter. In one embodiment, the tetracycline-regulated promoter is a tetracycline-responsive promoter. In one embodiment, the tetracycline-regulated promoter is a tetracycline operator sequence (tetO). In one embodiment, the tetracycline-regulated promoter is a tet-On promoter. In one embodiment, the tetracycline-regulated promoter a tet-Off promoter. In one embodiment, the chemically-regulated promoter is a steroid regulated promoter. In one embodiment, the steroid regulated promoter is a promoter of a rat glucocorticoid receptor. In one embodiment, the steroid regulated promoter is a promoter of an estrogen receptor. In one embodiment, the steroid-regulated promoter is a promoter of an ecdysone receptor. In one embodiment, the chemically-regulated promoter is a metal-regulated promoter. In one embodiment, the metal-regulated promoter is a metalloprotein promoter. In one embodiment, the inducible promoter is a physically-regulated promoter. In one embodiment, the physically-regulated promoter is a temperature-regulated promoter. In one embodiment, the temperature-regulated promoter is a heat shock promoter. In one embodiment, the physically-regulated promoter is a light-regulated promoter. In one embodiment, the light-regulated promoter is a light-inducible promoter. In one embodiment, the light-regulated promoter is a light-repressible promoter.

In one embodiment, the promoter is a tissue-specific promoter. In one embodiment, the promoter is a neuron-specific promoter. In one embodiment, the promoter is a glia-specific promoter. In one embodiment, the promoter is a muscle cell-specific promoter. In one embodiment, the promoter is a heart cell-specific promoter. In one embodiment, the promoter is a kidney cell-specific promoter. In one embodiment, the promoter is a bone cell-specific promoter. In one embodiment, the promoter is an endothelial cell-specific promoter. In one embodiment, the promoter is an immune cell-specific promoter. In one embodiment, the immune cell promoter is a B cell promoter. In one embodiment, the immune cell promoter is a T cell promoter.

In one embodiment, the promoter is a developmentally-regulated promoter. In one embodiment, the developmentally-regulated promoter is active only during an embryonic stage of development. In one embodiment, the developmentally-regulated promoter is active only in an adult cell.

In specific embodiments, the promoter may be selected based on the cell type. Thus the various promoters find use in a eukaryotic cell, a non-rat eukaryotic cell, a mammalian cell, a non-human mammalian cell, a pluripotent cell, a non-pluripotent cell, a non-human pluripotent cell, a human pluripotent cell, a human ES cell, a human adult stem cell, a developmentally-restricted human progenitor cell, a human iPS cell, a human cell, a rodent cell, a non-rat rodent cell, a rat cell, a mouse cell, a hamster cell, a fibroblast or a CHO cell.

In some embodiments, the insert nucleic acid comprises a nucleic acid flanked with site-specific recombination target sequences. It is recognized the while the entire insert nucleic acid can be flanked by such site-specific recombination target sequences, any region or individual polynucleotide of interest within the insert nucleic acid can also be flanked by such sites. The site-specific recombinase can be introduced into the cell by any means, including by introducing the recombinase polypeptide into the cell or by introducing a polynucleotide encoding the site-specific recombinase into the host cell. The polynucleotide encoding the site-specific recombinase can be located within the insert nucleic acid or within a separate polynucleotide. The site-specific recombinase can be operably linked to a promoter active in the cell including, for example, an inducible promoter, a promoter that is endogenous to the cell, a promoter that is heterologous to the cell, a cell-specific promoter, a tissue-specific promoter, or a developmental stage-specific promoter. Site-specific recombination target sequences, which can flank the insert nucleic acid or any polynucleotide of interest in the insert nucleic acid can include, but are not limited to, loxP, lox511, lox2272, lox66, lox71, loxM2, lox5171, FRT, FRT11, FRT71, attp, att, FRT, rox, and a combination thereof.

In some embodiments, the site-specific recombination sites flank a polynucleotide encoding a selection marker and/or a reporter gene contained within the insert nucleic acid. In such instances following integration of the insert nucleic acid at the targeted locus the sequences between the site-specific recombination sites can be removed.

In one embodiment, the insert nucleic acid comprises a polynucleotide encoding a selection marker. The selection marker can be contained in a selection cassette. Such selection markers include, but are not limited to, neomycin phosphotransferase (neo$^r$), hygromycin B phosphotransferase (hyg$^r$), puromycin-N-acetyltransferase (puro$^r$), blasticidin S deaminase (bsr$^r$), xanthine/guanine phosphoribosyl transferase (gpt), or herpes simplex virus thymidine kinase (HSV-k), or a combination thereof. In one embodiment, the polynucleotide encoding the selection marker is operably linked to a promoter active in the cell, rat cell, pluripotent rat cell, the ES rat cell, a eukaryotic cell, a non-rat eukaryotic cell, a pluripotent cell, a non-pluripotent cell, a non-human pluripotent cell, a human pluripotent cell, a human ES cell, a human adult stem cell, a developmentally-restricted human progenitor cell, a human iPS cell, a mammalian cell, a non-human mammalian cell, a human cell, a rodent cell, a non-rat rodent cell, a mouse cell, a hamster cell, a fibroblast, or a CHO cell. When serially tiling polynucleotides of interest into a targeted locus, the selection marker can comprise a recognition site for a nuclease agent, as outlined above. In one embodiment, the polynucleotide encoding the selection marker is flanked with a site-specific recombination target sequences.

The insert nucleic acid can further comprise a reporter gene operably linked to a promoter, wherein the reporter gene encodes a reporter protein selected from the group consisting of or comprising LacZ, mPlum, mCherry, tdTomato, mStrawberry, J-Red, DsRed, mOrange, mKO, mCitrine, Venus, YPet, enhanced yellow fluorescent protein (eYFP), Emerald, enhanced green fluorescent protein (EGFP), CyPet, cyan fluorescent protein (CFP), Cerulean, T-Sapphire, luciferase, alkaline phosphatase, and/or a combination thereof. Such reporter genes can be operably linked to a promoter active in the cell. Such promoters can be an inducible promoter, a promoter that is endogenous to the reporter gene or the cell, a promoter that is heterologous to the reporter gene or to the cell, a cell-specific promoter, a tissue-specific promoter, or a developmental stage-specific promoter.

In one embodiment, nucleic acid insert can comprise a mammalian nucleic acid comprises a genomic locus that encodes a protein expressed in the nervous system, the skeletal system, the digestive system, the circulatory system, the muscular system, the respiratory system, the cardiovascular system, the lymphatic system, the endocrine system, the urinary system, the reproductive system, or a combination thereof. In one embodiment, the mammalian nucleic acid comprises a genomic locus that encodes a protein expressed in a bone marrow or a bone marrow-derived cell. In one embodiment, the nucleic acid comprises a genomic locus that encodes a protein expressed in a spleen cell.

In one embodiment, the mammalian nucleic acid comprises a genomic locus that encodes a protein expressed in the nervous system, the skeletal system, the digestive system, the circulatory system, the muscular system, the respiratory system, the cardiovascular system, the lymphatic system, the endocrine system, the urinary system, the reproductive system, or a combination thereof. In one embodiment, the mammalian nucleic acid comprises a genomic locus that encodes a protein expressed in a bone marrow or a bone marrow-derived cell. In one embodiment, the nucleic acid comprises a genomic locus that encodes a protein expressed in a spleen cell. In one embodiment, the genomic locus comprises a mouse genomic DNA sequence, a rat genomic DNA sequence, eukaryotic genomic DNA sequence, a non-rat eukaryotic genomic DNA sequence, a mammalian genomic DNA sequence, a human genomic DNA sequence, or non-human DNA sequence mammalian, or a combination thereof. In one embodiment, the genomic locus comprises, in any order, rat and human genomic DNA sequences. In one embodiment, the genomic locus comprises, in any order, mouse and human genomic DNA sequences. In one embodiment, the genomic locus comprises, in any order, mouse and rat genomic DNA sequences. In one embodiment, the genomic locus comprises, in any order, rat, mouse, and human genomic DNA sequences.

In one embodiment, the genomic locus comprises a mouse genomic DNA sequence, a rat genomic DNA sequence, a hamster genomic DNA sequence, a human genomic DNA sequence, eukaryotic genomic DNA sequence, a non-rat eukaryotic genomic DNA sequence, a mammalian genomic DNA sequence, or non-human DNA sequence mammalian, or a combination thereof. In one embodiment, the genomic locus comprises, in any order, rat and human genomic DNA sequences. In one embodiment, the genomic locus comprises, in any order, mouse and human genomic DNA sequences. In one embodiment, the genomic locus comprises, in any order, mouse and rat genomic DNA sequences. In one embodiment, the genomic locus comprises, in any order, rat, mouse, and human genomic DNA sequences.

In one embodiment, the genetic modification comprises at least one human disease allele of a human gene. In one embodiment, the human disease is a neurological disease. In one embodiment, the human disease is a cardiovascular disease. In one embodiment, the human disease is a kidney disease. In one embodiment, the human disease is a muscle disease. In one embodiment, the human disease is a blood disease. In one embodiment, the human disease is a cancer. In one embodiment, the human disease is an immune system disease.

In one embodiment, the human disease allele is a dominant allele. In one embodiment, the human disease allele is a recessive allele. In one embodiment, the human disease allele comprises a single nucleotide polymorphism (SNP) allele.

In one embodiment, the genetic modification produces a mutant form of a protein with an altered binding characteristic, altered localization, altered expression, and/or altered expression pattern.

In one embodiment, the insert nucleic acid comprises a selection cassette. In one embodiment, the selection cassette comprises a nucleic acid sequence encoding a selective marker, wherein the nucleic acid sequence is operably linked to a promoter active in rat ES cells. In one embodiment, the selective marker is selected from or comprises a hygromycin resistance gene or a neomycin resistance gene.

In one embodiment, the nucleic acid comprises a genomic locus that encodes a protein expressed in a B cell. In one embodiment, the nucleic acid comprises a genomic locus that encodes a protein expressed in an immature B cell. In one embodiment, the nucleic acid comprises a genomic locus that encodes a protein expressed in a mature B cell.

In one embodiment, the insert nucleic acid comprises a regulatory element. In one embodiment, the regulatory element is a promoter. In one embodiment, the regulatory element is an enhancer. In one embodiment, the regulatory element is a transcriptional repressor-binding element.

In one embodiment, the genetic modification comprises a deletion of a non-protein-coding sequence, but does not comprise a deletion of a protein-coding sequence. In one embodiment, the deletion of the non-protein-coding sequence comprises a deletion of a regulatory element. In one embodiment, the genetic modification comprises a deletion of a regulatory element. In one embodiment, the genetic modification comprises an addition of a promoter or a regulatory element. In one embodiment, the genetic modification comprises a replacement of a promoter or a regulatory element.

ii. Expression Cassettes

Provided herein are polynucleotides or nucleic acid molecules comprising the various components employed in a targeted genomic integration system provided herein (i.e., any one of or any combination of nuclease agents, recognition sites, insert nucleic acids, polynucleotides of interest, targeting vectors, selection markers, and other components).

The terms "polynucleotide," "polynucleotide sequence," "nucleic acid sequence," and "nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Polynucleotides can comprise deoxyribonucleotides and ribonucleotides include both naturally occurring molecules and synthetic analogues, and any combination these. The polynucleotides provided herein also encompass all forms of sequences including, but not limited to, single-stranded forms, double-stranded forms, hairpins, stem-and-loop structures, and the like.

Further provided are recombinant polynucleotides comprising the various components of the targeted genomic integration system. The terms "recombinant polynucleotide" and "recombinant DNA construct" are used interchangeably herein. A recombinant construct comprises an artificial or heterologous combination of nucleic acid sequences, e.g., regulatory and coding sequences that are not found together in nature. In other embodiments, a recombinant construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that is used to transform the host cells as is well known to those skilled in the art. For example, a plasmid vector can be used. Genetic elements required to successfully transform, select, and propagate host cells comprising any of the isolated nucleic acid fragments provided herein are also provided. Screening may be accomplished by Southern analysis of DNA, Northern analysis of mRNA expression, immunoblotting analysis of protein expression, or phenotypic analysis, among others.

In specific embodiments, one or more of the components of the targeted genomic integration system described herein can be provided in an expression cassette for expression in a prokaryotic cell, a eukaryotic cell, a non-rat eukaryotic cell, a bacterial, a yeast cell, or a mammalian cell or other organism or cell type of interest. The cassette can include 5' and 3' regulatory sequences operably linked to a polynucleotide provided herein. "Operably linked" comprises a relationship wherein the components operably linked function in their intended manner. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, operably linked means that the coding regions are in the same reading frame. In another instance, a nucleic acid sequence encoding a protein may be operably linked to regulatory sequences (e.g., promoter, enhancer, silencer sequence, etc.) so as to retain proper transcriptional regulation. In one instance, a nucleic acid sequence of an immunoglobulin variable region (or V(D)J segments) may be operably linked to a nucleic acid sequence of an immunoglobulin constant region so as to allow proper recombination between the sequences into an immunoglobulin heavy or light chain sequence.

The cassette may additionally contain at least one additional polynucleotide of interest to be co-introduced into the organism. Alternatively, the additional polynucleotide of interest can be provided on multiple expression cassettes. Such an expression cassette is provided with a plurality of restriction sites and/or recombination sites for insertion of a recombinant polynucleotide to be under the transcriptional regulation of the regulatory regions. The expression cassette may additionally contain selection marker genes.

The expression cassette can include in the 5'-3' direction of transcription, a transcriptional and translational initiation region (i.e., a promoter), a recombinant polynucleotide provided herein, and a transcriptional and translational termination region (i.e., termination region) functional in mammalian cell or a host cell of interest. The regulatory regions (i.e., promoters, transcriptional regulatory regions, and translational termination regions) and/or a polynucleotide provided herein may be native/analogous to the host cell or to each other. Alternatively, the regulatory regions and/or a polynucleotide provided herein may be heterologous to the host cell or to each other. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. Alternatively, the regulatory regions and/or a recombinant polynucleotide provided herein may be entirely synthetic.

The termination region may be native with the transcriptional initiation region, may be native with the operably linked recombinant polynucleotide, may be native with the host cell, or may be derived from another source (i.e., foreign or heterologous) to the promoter, the recombinant polynucleotide, the host cell, or any combination thereof.

In preparing the expression cassette, the various DNA fragments may be manipulated, so as to provide for the DNA sequences in the proper orientation. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the expression cassettes provided herein. The promoters can be selected based on the desired outcome. It is recognized that different applications can be enhanced by the use of different promoters in the expression cassettes to modulate the timing, location and/or level of expression of the polynucleotide of interest. Such expression constructs may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

The expression cassette containing the polynucleotides provided herein can also comprise a selection marker gene for the selection of transformed cells. Selectable marker genes are utilized for the selection of transformed cells or tissues.

Where appropriate, the sequences employed in the methods and compositions (i.e., the polynucleotide of interest, the nuclease agent, etc.) may be optimized for increased expression in the cell. That is, the genes can be synthesized using codons preferred in a given cell of interest including, for example, mammalian-preferred codons, human-preferred codons, rodent-preferred codons, non-rat-rodent-preferred codons, mouse-preferred codons, rat-preferred codons, hamster-preferred codons, etc. for improved expression.

The various methods and compositions provided herein can employ selection markers. Various selection markers can be used in the methods and compositions disclosed herein. Such selection markers can, for example, impart resistance to an antibiotic such as G418, hygromycin, blasticidin, neomycin, or puromycin. Such selection markers include neomycin phosphotransferase (neo$^r$), hygromycin B phosphotransferase (hyg$^r$), puromycin-N-acetyltransferase (puro$^r$), and blasticidin S deaminase (bsr$^r$). In still other embodiments, the selection marker is operably linked to an inducible promoter and the expression of the selection marker is toxic to the cell. Non-limiting examples of such selection markers include xanthine/guanine phosphoribosyl transferase (gpt), hypoxanthine-guanine phosphoribosyltransferase (HGPRT) or herpes simplex virus thymidine kinase (HSV-TK). The polynucleotide encoding the selection markers are operably linked to a promoter active in the cell.

iii. Targeting Vectors

Targeting vectors are employed to introduce the insert nucleic acid into the target locus of the rat, eukaryotic, non-rat eukaryotic, mammalian, non-human mammalian, human, rodent, non-rat rodent, mouse or hamster nucleic acid. The targeting vector comprises the insert nucleic acid and further comprises a 5' and a 3' homology arm, which flank the insert nucleic acid. The homology arms, which flank the insert nucleic acid, correspond to regions within the target locus of the rat, eukaryotic, non-rat eukaryotic, mammalian, non-human mammalian, human, rodent, non-rat rodent, mouse or hamster nucleic acid. For ease of reference, the corresponding cognate genomic regions within the targeted genomic locus are referred to herein as "target sites". For example, a targeting vector can comprise a first insert nucleic acid flanked by a first and a second homology arm complementary to a first and a second target site. As such, the targeting vector thereby aids in the integration of the insert nucleic acid into the target locus of the rat, eukaryotic, non-rat eukaryotic, mammalian, non-human mammalian, human, rodent, non-rat rodent, mouse or hamster nucleic acid through a homologous recombination event that occurs between the homology arms and the complementary target sites within the genome of the cell.

In one embodiment, the target locus of the rat, eukaryotic, non-rat eukaryotic, mammalian, non-human mammalian, human, rodent, non-rat rodent, mouse or hamster nucleic acid comprises a first nucleic acid sequence that is complementary to the 5' homology arm and a second nucleic acid sequence that is complementary to the 3' homology arm. In one embodiment, the first and the second nucleic acid sequences are separated by at least 5 kb. In another embodiment, the first and the second nucleic acid sequences are separated by at least 5 kb but less than 200 kb. In one embodiment, the first and the second nucleic acid sequences are separated by at least 10 kb. In one embodiment, the first and the second nucleic acid sequences are separated by at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, or at least 200 kb. In still further embodiments, the first and the second nucleic acid sequence is separated by at least 5 kb but less than 10 kb, at least 5 kb but less than 3 Mb, at least 10 kb but less than 20 kb, at least 20 kb but less than 40 kb, at least 40 kb but less than 60 kb, at least 60 kb but less than 80 kb, at least about 80 kb but less than 100 kb, at least 100 kb but less than 150 kb, or at least 150 kb but less than 200 kb, at least about 200 kb but less than about 300 kb, at least about 300 kb but less than about 400 kb, at least about 400 kb but less than about 500 kb, at least about 500 kb but less than about 1 Mb, at least about 1.5 Mb but less than about 2 Mb, at least about 1 Mb but less than about 1.5 Mb, at least about 2 Mb but less than 2.5 Mb, at least about 2.5 Mb but less than about 3 Mb, or at least about 2 Mb but less than about 3 Mb.

A homology arm of the targeting vector can be of any length that is sufficient to promote a homologous recombination event with a corresponding target site, including for example, at least 5-10 kb, 5-15 kb, 10-20 kb, 20-30 kb, 30-40 kb, 40-50 kb, 50-60 kb, 60-70 kb, 70-80 kb, 80-90 kb, 90-100 kb, 100-110 kb, 110-120 kb, 120-130 kb, 130-140 kb, 140-150 kb, 150-160 kb, 160-170 kb, 170-180 kb, 180-190 kb, 190-200 kb in length or greater. As outlined in further detail below, large targeting vectors can employ targeting arms of greater length. In a specific embodiment, the sum total of the 5' homology arm and the 3' homology arm is at least 10 kb or the sum total of the 5' homology arm and the 3' homology arm is at least about 16 kb to about 100 kb or about 30 kb to about 100 kb. In other embodiments, the size of the sum total of the total of the 5' and 3' homology arms of the LTVEC is about 10 kb to about 150 kb, about 10 kb to about 100 kb, about 10 kb to about 75 kb, about 20 kb to about 150 kb, about 20 kb to about 100 kb, about 20 kb to about 75 kb, about 30 kb to about 150 kb, about 30 kb to about 100 kb, about 30 kb to about 75 kb, about 40 kb to about 150 kb, about 40 kb to about 100 kb, about 40 kb to about 75 kb, about 50 kb to about 150 kb, about 50 kb to about 100 kb, or about 50 kb to about 75 kb, about 10 kb to about 30 kb, about 20 kb to about 40 kb, about 40 kb to about 60 kb, about 60 kb to about 80 kb, about 80 kb to about 100 kb, about 100 kb to about 120 kb, or from about 120 kb to about 150 kb. In one embodiment, the size of the deletion is the same or similar to the size of the sum total of the 5' and 3' homology arms of the LTVEC.

In one embodiment, the genomic locus of interest comprises (i) a 5' target sequence that is homologous to the 5' homology arm; and (ii) a 3' target sequence that is homologous to the 3' homology arm. In one embodiment, the 5' target sequence and the 3' target sequence are separated by at least 5 kb but less than 3 Mb. In still further embodiments, the 5' target sequence and the 3' target sequence are separated by at least 5 kb but less than 10 kb, at least 5 kb but less than 3 Mb, at least 10 kb but less than 20 kb, at least 20 kb but less than 40 kb, at least 40 kb but less than 60 kb, at least 60 kb but less than 80 kb, at least about 80 kb but less than 100 kb, at least 100 kb but less than 150 kb, or at least 150 kb but less than 200 kb, at least about 200 kb but less than about 300 kb, at least about 300 kb but less than about 400 kb, at least about 400 kb but less than about 500 kb, at least about 500 kb but less than about 1 Mb, at least about 1.5 Mb but less than about 2 Mb, at least about 1 Mb but less than about 1.5 Mb, at least about 2 Mb but less than 2.5 Mb, at least about 2.5 Mb but less than about 3 Mb, or at least about 2 Mb but less than about 3 Mb.

When nuclease agents are employed, the cognate genomic regions corresponding to the 5' and 3' homology arms of a targeting vector are "located in sufficient proximity" to nuclease target sites so as to promote the occurrence of a homologous recombination event between the cognate genomic regions and the homology arms upon a nick or double-strand break at the recognition site. For example, the nuclease target sites can be located anywhere between the cognate genomic regions corresponding to the 5' and 3' homology arms. In specific embodiments, the recognition site is immediately adjacent to at least one or both of the cognate genomic regions.

As used herein, a homology arm and a target site (i.e., cognate genomic region) "complement" or are "complementary" to one another when the two regions share a sufficient level of sequence identity to one another to act as substrates for a homologous recombination reaction. By "homology" is meant DNA sequences that are either identical or share sequence identity to a corresponding or "complementary" sequence. The sequence identity between a given target site and the corresponding homology arm found on the targeting vector can be any degree of sequence identity that allows for homologous recombination to occur. For example, the amount of sequence identity shared by the homology arm of the targeting vector (or a fragment thereof) and the target site (or a fragment thereof) can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination. Moreover, a complementary region of homology between the homology arm and the complementary target site can be of any length that is sufficient to promote homologous recombination at the cleaved recognition site. For example, a given homology arm and/or complementary target site can comprise complementary regions of homology that are at least 5-10 kb, 5-15 kb, 10-20 kb, 20-30 kb, 30-40 kb, 40-50 kb, 50-60 kb, 60-70 kb, 70-80 kb, 80-90 kb, 90-100 kb, 100-110 kb, 110-120 kb, 120-130 kb, 130-140 kb, 140-150 kb, 150-160 kb, 160-170 kb, 170-180 kb, 180-190 kb, 190-200 kb, 200 kb to 300 kb in length or greater (such as described in the LTVEC vectors described elsewhere herein) such that the homology arm has sufficient homology to undergo homologous recombination with the corresponding target sites within the genome of the cell. For ease of reference the homology arms are referred to herein as a 5' and a 3' homology arm. This terminology relates to the relative position of the homology arms to the insert nucleic acid within the targeting vector.

The homology arms of the targeting vector are therefore designed to be complementary to a target site with the targeted locus. Thus, the homology arms can be complementary to a locus that is native to the cell, or alternatively they can be complementary to a region of a heterologous or exogenous segment of DNA that was integrated into the genome of the cell, including, but not limited to, transgenes, expression cassettes, or heterologous or exogenous regions of genomic DNA. Alternatively, the homology arms of the targeting vector can be complementary to a region of a human artificial chromosome or any other engineered genomic region contained in an appropriate host cell. Still further, the homology arms of the targeting vector can be complementary to or be derived from a region of a BAC library, a cosmid library, or a P1 phage library. Thus, in specific embodiments, the homology arms of the targeting vector are complementary to a rat, eukaryotic, non-rat eukaryotic, mammalian, non-human mammalian, human, rodent, non-rat rodent, mouse or hamster genomic locus that is native, heterologous or exogenous to a given cell. In further embodiments, the homology arms are complementary to a rat, eukaryotic, non-rat eukaryotic, mammalian, non-human mammalian, human, rodent, non-rat rodent, mouse or hamster genomic locus that is not targetable using a conventional method or can be targeted only incorrectly or only with significantly low efficiency, in the absence of a nick or double-strand break induced by a nuclease agent. In one embodiment, the homology arms are derived from a synthetic DNA.

In still other embodiments, the 5' and 3' homology arms are complementary to the same genome as the targeted genome. In one embodiment, the homology arms are from a related genome, e.g., the targeted genome is a rat genome of a first strain, and the targeting arms are from a rat genome of a second strain, wherein the first strain and the second strain are different. In other embodiments, the homology arms are from the genome of the same animal or are from the genome of the same strain, e.g., the targeted genome is a rat genome of a first strain, and the targeting arms are from a rat genome from the same rat or from the same strain.

The targeting vector (such as a large targeting vector) can also comprise a selection cassette or a reporter gene as discussed elsewhere herein. The selection cassette can comprise a nucleic acid sequence encoding a selection marker, wherein the nucleic acid sequence is operably linked to a promoter. The promoter can be active in a prokaryotic cell of interest and/or active in a eukaryotic cell of interest. Such promoters can be an inducible promoter, a promoter that is endogenous to the reporter gene or the cell, a promoter that is heterologous to the reporter gene or to the cell, a cell-specific promoter, a tissue-specific promoter or a developmental stage-specific promoter. In one embodiment, the selection marker is selected from or comprises neomycin phosphotransferase (neo$^r$), hygromycin B phosphotransferase (hyg$^r$), puromycin-N-acetyltransferase (puro$^r$), blasticidin S deaminase (bsr$^r$), xanthine/guanine phosphoribosyl transferase (gpt), and herpes simplex virus thymidine kinase (HSV-k), and/or a combination thereof. The selection marker of the targeting vector can be flanked by the 5' and 3' homology arms or found either 5' or 3' to the homology arms.

In one embodiment, the targeting vector (such as a large targeting vector) comprises a reporter gene operably linked to a promoter, wherein the reporter gene encodes a reporter protein selected from the group consisting of or comprises LacZ, mPlum, mCherry, tdTomato, mStrawberry, J-Red, DsRed, mOrange, mKO, mCitrine, Venus, YPet, enhanced yellow fluorescent protein (EYFP), Emerald, enhanced green fluorescent protein (EGFP), CyPet, cyan fluorescent protein (CFP), Cerulean, T-Sapphire, luciferase, alkaline phosphatase, and/or a combination thereof. Such reporter genes can be operably linked to a promoter active in the cell. Such promoters can be an inducible promoter, a promoter that is endogenous to the report gene or the cell, a promoter that is heterologous to the reporter gene or to the cell, a cell-specific promoter, a tissue-specific promoter or a developmental stage-specific promoter.

In one embodiment, combined use of the targeting vector (including, for example, a large targeting vector) with the nuclease agent results in an increased targeting efficiency compared to use of the targeting vector alone. In one embodiment, when the targeting vector is used in conjunction with the nuclease agent, targeting efficiency of the targeting vector is increased at least by two-fold, at least three-fold, or at least 4-fold when compared to when the targeting vector is used alone.

When employing a targeting vector, the vector design can be such as to allow for the insertion of a given sequence that is from about 5 kb to about 200 kb as described herein. In one embodiment, the insertion is from about 5 kb to about 10 kb, from about 10 kb to about 20 kb, from about 20 kb to about 30 kb, from about 30 kb to about 40 kb, from about 40 kb to about 50 kb, from about 50 kb to about 60 kb, from about 60 kb to about 70 kb, from about 80 kb to about 90 kb, from about 90 kb to about 100 kb, from about 100 kb to about 110 kb, from about 110 kb to about 120 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb, from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb.

When employing a targeting vector, the vector design can be such as to allow for the replacement of a given sequence that is from about 5 kb to about 200 kb or from about 5 kb to about 3.0 Mb as described herein. In one embodiment, the replacement is from about 5 kb to about 10 kb, from about 10 kb to about 20 kb, from about 20 kb to about 30 kb, from about 30 kb to about 40 kb, from about 40 kb to about 50 kb, from about 50 kb to about 60 kb, from about 60 kb to about 70 kb, from about 80 kb to about 90 kb, from about 90 kb to about 100 kb, from about 100 kb to about 110 kb, from about 110 kb to about 120 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, from about 190 kb to about 200 kb, from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb.

In one embodiment, the targeting vector comprises a site-specific recombinase gene. In one embodiment, the site-specific recombinase gene encodes a Cre recombinase. In one embodiment, the Cre recombinase gene is Crei, wherein two exons encoding the Cre recombinase are separated by an intron to prevent its expression in a prokaryotic cell.

In one embodiment, the Cre recombinase gene further comprises a nuclear localization signal to facilitate localization of Cre (or any recombinase or nuclease agent) to the nucleus (e.g., the gene is an NL-Cre gene). In a specific embodiment, the Cre recombinase gene further comprises a nuclear localization signal and an intron (e.g., NL-Crei).

In various embodiments, a suitable promoter for expression of the nuclease agent (including the Cre or Crei recombinase discussed above) is selected from or comprises a Prm1, Blimp1, Gata6, Gata4, Igf2, Lhx2, Lhx5, and/or Pax3. In a specific embodiment, the promoter is the Gata6 or Gata4 promoter. The various promoters can be from any organism, including for example, a rodent such as a mouse or a rat, a non-rat rodent, a eukaryote, a non-rat eukaryote, a non-human mammal, a mammal, a human or a hamster. In another specific embodiment, the promoter is a Prm1 promoter. In another specific embodiment, the promoter is a rat Prm1 promoter. In another specific embodiment, the promoter is a mouse Prm1 promoter. In another specific embodiment, the promoter is a Blimp1 promoter or a fragment thereof, e.g., a 1 kb or 2 kb fragment of a Blimp1 promoter. See, for example, U.S. Pat. No. 8,697,851 and U.S. Application Publication 2013-0312129, both of which are herein incorporated by reference in their entirety.

iv. Large Targeting Vectors

The term "large targeting vector" or "LTVEC" as used herein comprises large targeting vectors that comprise homology arms that correspond to and are derived from nucleic acid sequences larger than those typically used by other approaches intended to perform homologous targeting in cells and/or comprising insert nucleic acids comprising nucleic acid sequences larger than those typically used by other approaches intended to perform homologous recombination targeting in cells. For example, the LTVEC make possible the modification of large loci that cannot be accommodated by traditional plasmid-based targeting vectors because of their size limitations. In specific embodiments, the homology arms and/or the insert nucleic acid of the LTVEC comprises genomic sequence of a eukaryotic cell or a non-rat eukaryotic cell. The size of the LTVEC is too large to enable screening of targeting events by conventional assays, e.g., southern blotting and long-range (e.g., 1 kb-5 kb) PCR. Examples of the LTVEC, include, but are not limited to, vectors derived from a bacterial artificial chromosome (BAC), a human artificial chromosome or a yeast artificial chromosome (YAC). Non-limiting examples of LTVECs and methods for making them are described, e.g., in U.S. Pat. Nos. 6,586,251, 6,596,541, 7,105,348, and WO 2002/036789 (PCT/US01/45375), and US 2013/0137101, each of which is herein incorporated by reference.

The LTVEC can be of any length, including, but not limited to, from about 20 kb to about 400 kb, from about 20 kb to about 30 kb, from about 30 kb to about 40 kb, from about 40 kb to about 50 kb, from about 50 kb to about 75 kb, from about 75 kb to about 100 kb, from about 100 kb to 125 kb, from about 125 kb to about 150 kb, from about 150 kb to about 175 kb, about 175 kb to about 200 kb, from about 200 kb to about 225 kb, from about 225 kb to about 250 kb, from about 250 kb to about 275 kb or from about 275 kb to about 300 kb, from about 200 kb to about 300 kb, from about 300 kb to about 350 kb, from about 350 kb to about 400 kb, from about 350 kb to about 550 kb. In one embodiment, the LTVEC is about 100 kb.

In some embodiments, the LTVEC is at least 10 kb, at least 15 kb, at least 20 kb, at least 30 kb, at least 40 kb, at least 50 kb, at least 60 kb, at least 70 kb, at least 80 kb, at least 90 kb, at least 100 kb, at least 150 kb or at least 200 kb.

In some embodiments, the LTVEC comprises a nucleic acid sequence of at least 20 kb, at least 30 kb, at least 40 kb, at least 50 kb, at least 60 kb, at least 70 kb, at least 80 kb, at least 90 kb, at least 100 kb, at least 150 kb or at least 200 kb.

In one embodiment, the LTVEC comprises an insert nucleic acid ranging from about 5 kb to about 200 kb, from about 5 kb to about 10 kb, from about 10 kb to about 20 kb, from about 20 kb to about 30 kb, from about 0.5 kb to about 30 kb, from about 0.5 kb to about 40 kb, from about 30 kb to about 150 kb, from about 0.5 kb to about 150 kb, from about 30 kb to about 40 kb, from about 40 kb to about 50 kb, from about 60 kb to about 70 kb, from about 80 kb to about 90 kb, from about 90 kb to about 100 kb, from about 100 kb to about 110 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb, from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb.

In one embodiment, the LTVEC comprises a nucleic acid sequence of at least 100 kb, at least 150 kb, or at least 200 kb.

When employing a LTVEC, the vector design can be such as to allow for the replacement of a given sequence that is from about 5 kb to about 200 kb or from about 5 kb to about 3 Mb as described herein. In one embodiment, the replacement is from about 5 kb to about 10 kb, from about 10 kb to about 20 kb, from about 20 kb to about 30 kb, from about 30 kb to about 40 kb, from about 40 kb to about 50 kb, from about 50 kb to about 60 kb, from about 60 kb to about 70 kb, from about 80 kb to about 90 kb, from about 90 kb to about 100 kb, from about 100 kb to about 110 kb, from about 110 kb to about 120 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, from about 190 kb to about 200 kb, from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb.

In one embodiment, the homology arms of the LTVEC are derived from a BAC library, a cosmid library, or a P1 phage library. In other embodiments, the homology arms are derived from the targeted genomic locus of the cell and in some instances the target genomic locus, which the LTVEC is designed to target is not targetable using a conventional method. In still other embodiments, the homology arms are derived from a synthetic DNA.

In one embodiment, a sum total of the 5' homology arm and the 3' homology arm in the LTVEC is at least 10 kb. In other embodiments, the sum total of the 5' and the 3' homology arms of the LTVEC is from about 10 kb to about 30 kb, from about 20 kb to about 40 kb, from about 40 kb to about 60 kb, from about 60 kb to about 80 kb, from about 80 kb to about 100 kb, from 100 kb to about 120 kb, from about 120 kb to about 140 kb, from about 140 kb to about 160 kb, from about 160 kb to about 180 kb, from about 180 kb to about 200 kb. In one embodiment the sum total of the 5' and the 3' homology arms of the LTVEC is from about 30 kb to about 100 kb. In other embodiments, the size of the sum total of the total of the 5' and 3' homology arms of the LTVEC is about 10 kb to about 150 kb, about 10 kb to about 100 kb, about 10 kb to about 75 kb, about 20 kb to about 150 kb, about 20 kb to about 100 kb, about 20 kb to about 75 kb, about 30 kb to about 150 kb, about 30 kb to about 100 kb, about 30 kb to about 75 kb, about 40 kb to about 150 kb, about 40 kb to about 100 kb, about 40 kb to about 75 kb, about 50 kb to about 150 kb, about 50 kb to about 100 kb, or about 50 kb to about 75 kb, about 10 kb to about 30 kb, about 20 kb to about 40 kb, about 40 kb to about 60 kb, about 60 kb to about 80 kb, about 80 kb to about 100 kb, about 100 kb to about 120 kb, or from about 120 kb to about 150 kb. In one embodiment, the size of the deletion is the same or similar to the size of the sum total of the 5' and 3' homology arms of the LTVEC.

In other embodiments, the 5' homology arm ranges from about 5 kb to about 100 kb. In one embodiment, the 3' homology arm ranges from about 5 kb to about 100 kb. In other embodiments, the sum total of the 5' and 3' homology arms are from about 5 kb to about 10 kb, from about 10 kb to about 20 kb, from about 20 kb to about 30 kb, from about 30 kb to about 40 kb, from about 40 kb to about 50 kb, from about 50 kb to about 60 kb, from about 60 kb to about 70 kb, from about 70 kb to about 80 kb, from about 80 kb to about 90 kb, from about 90 kb to about 100 kb, from about 100 kb to about 110 kb, from about 110 kb to about 120 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, from about 190 kb to about 200 kb, or from about 30 kb to about 100 kb, about 10 kb to about 30 kb, about 20 kb to about 40 kb, about 40 kb to about 60 kb, about 60 kb to about 80 kb, about 80 kb to about 100 kb, about 100 kb to about 120 kb, or from about 120 kb to about 150 kb.

In one embodiment, the LTVEC comprises an insert nucleic acid that is homologous or orthologous to a rat nucleic acid sequence flanked by the LTVEC homology arms. In one embodiment, the insert nucleic acid sequence is from a species other than a rat. In one embodiment, the insert nucleic acid sequence is from a eukaryote. In one embodiment, the insert nucleic acid that is homologous or orthologous to the rat nucleic acid sequence is a mammalian nucleic acid. In one embodiment, the insert nucleic acid that is homologous or orthologous to the rat nucleic acid sequence is a non-human mammalian nucleic acid. In one embodiment, the mammalian nucleic acid is a mouse nucleic acid. In one embodiment, the mammalian nucleic acid is a human nucleic acid. In one embodiment, the mammalian nucleic acid is a hamster nucleic acid. In one embodiment, the insert nucleic acid is a genomic DNA. In one embodiment, the insert is from 5 kb to 200 kb as described above.

In one embodiment, the LTVEC comprises a selection cassette or a reporter gene. Various forms of the selection cassette and reporter gene that can be employed are discussed elsewhere herein.

As described elsewhere herein, the LTVEC can also be used in the methods provided herein in combination with a nuclease agent that promotes a homologous recombination between the targeting vector and the target locus of a rat, eukaryotic, non-rat eukaryotic, mammalian, non-human mammalian, human, rodent, non-rat rodent, mouse or hamster nucleic acid in a pluripotent or non-pluripotent rat, eukaryotic, non-rat eukaryotic, mammalian, non-human mammalian, human, rodent, non-rat rodent, mouse or hamster cell.

In one embodiment, the large targeting vector (LTVEC) comprises a site-specific recombinase gene. In one embodiment, the site-specific recombinase gene encodes a Cre recombinase. In one embodiment, the Cre recombinase gene is Crei, wherein two exons encoding the Cre recombinase are separated by an intron to prevent its expression in a prokaryotic cell. In one embodiment, the Cre recombinase gene further comprises a nuclear localization signal to facilitate localization of Cre (or any recombinase or nuclease agent) to the nucleus (e.g., the gene is an NL-Cre gene). In a specific embodiment, the Cre recombinase gene further comprises a nuclear localization signal and an intron (e.g., NL-Crei)

In various embodiments, a suitable promoter for expression of the nuclease agent (including the Cre or Crei recombinase discussed above) is selected from or comprises a Prm1, Blimp1, Gata6, Gata4, Igf2, Lhx2, Lhx5, and/or Pax3. In a specific embodiment, the promoter is the Gata6 or Gata4 promoter. The various promoters can be from any organism, including for example, a rodent such as a mouse or a rat, a non-rat rodent, a eukaryote, a non-rat eukaryote, a non-human mammal, a mammal, a human or a hamster. In another specific embodiment, the promoter is a Prm1 promoter. In another specific embodiment, the promoter is a rat Prm1 promoter. In another specific embodiment, the promoter is a mouse Prm1 promoter. In another specific embodiment, the promoter is a Blimp1 promoter or a fragment thereof, e.g., a 1 kb or 2 kb fragment of a Blimp1 promoter. See, for example, U.S. Pat. No. 8,697,851 and U.S. Application Publication 2013-0312129, both of which are herein incorporated by reference in their entirety.

In one embodiment, the LTVEC comprises an insert nucleic acid that can produce a deletion, addition, replacement or a combination thereof of a region of the rat, a eukaryotic, a non-rat eukaryotic, a mammalian, non-human mammalian, a human, a rodent, a non-rat rodent, a mouse or a hamster ApoE locus, the Il2rg locus, the Rag2 locus, the Rag1 locus and/or the Rag2/Rag1 locus as discussed in detail elsewhere herein. In specific embodiments, the genetic modification at the ApoE locus results in a decrease, an increase or a modulation in ApoE activity, IL-2Rg activity, Rag2 activity, Rag1 activity and/or Rag2 and Rag1 activity. In one embodiment, an ApoE knockout, and Il2rg knockout, a Rag2 knockout, a Rag1 knockout, a Rag2/Rag1 knockout is generated. As discussed below, nuclease agents can be employed with any of the LTVEC targeting systems to target any genomic locus of interest.

In another embodiment, the genome is exposed to a Cas protein and a CRISPR RNA in the presence of a large targeting vector (LTVEC) comprising a nucleic acid sequence of at least 10 kb. In such cases, following exposure to the Cas protein, the CRISPR RNA, and the LTVEC, the genome is modified to contain at least 10 kb of nucleic acid sequence. In specific embodiments, the LTVEC comprises a nucleic acid sequence of at least 20 kb, at least 30 kb, at least 40 kb, at least 50 kb, at least 60 kb, at least 70 kb, at least 80 kb, at least 90 kb, at least 100 kb, at least 150 kb or at least 200 kb.

v. Nuclease Agents and Recognition Sites for Nuclease Agents

As outlined in detail above, nuclease agents may be utilized in the methods and compositions disclosed herein to aid in the modification of the target locus both in a prokaryotic cell or within a pluripotent or non-pluripotent rat, eukaryotic, non-rat eukaryotic, mammalian, non-human mammalian, human, rodent, non-rat rodent, mouse or hamster cell. Such a nuclease agent may promote homologous recombination between the targeting vector and the target locus. In one embodiment, the nuclease agent comprises an endonuclease agent.

As used herein, the term "recognition site for a nuclease agent" comprises a DNA sequence at which a nick or double-strand break is induced by a nuclease agent. The recognition site for a nuclease agent can be endogenous (or native) to the cell or the recognition site can be exogenous to the cell. In specific embodiments, the recognition site is exogenous to the cell and thereby is not naturally occurring in the genome of the cell. In still further embodiments, the recognition site is exogenous to the cell and to the polynucleotides of interest that one desired to be positioned at the target genomic locus. In further embodiments, the exogenous or endogenous recognition site is present only once in the genome of the host cell. In specific embodiments, an endogenous or native site that occurs only once within the genome is identified. Such a site can then be used to design nuclease agents that will produce a nick or double-strand break at the endogenous recognition site.

The length of the recognition site can vary, and includes, for example, recognition sites that are at least 4, 6, 8, 10, 12, 14, 16, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or more nucleotides in length. In one embodiment, each monomer of the nuclease agent recognizes a recognition site of at least 9 nucleotides. In other embodiments, the recognition site is from about 9 to about 12 nucleotides in length, from about 12 to about 15 nucleotides in length, from about 15 to about 18 nucleotides in length, or from about 18 to about 21 nucleotides in length, and any combination of such subranges (e.g., 9-18 nucleotides). The recognition site could be palindromic, that is, the sequence on one strand reads the same in the opposite direction on the complementary strand. It is recognized that a given nuclease agent can bind the recognition site and cleave that binding site or alternatively, the nuclease agent can bind to a sequence that is the different from the recognition site. Moreover, the term recognition site comprises both the nuclease agent binding site and the nick/cleavage site irrespective whether the nick/cleavage site is within or outside the nuclease agent binding site. In another variation, the cleavage by the nuclease agent can occur at nucleotide positions immediately opposite each other to produce a blunt end cut or, in other cases, the incisions can be staggered to produce single-stranded overhangs, also called "sticky ends", which can be either 5' overhangs, or 3' overhangs.

Any nuclease agent that induces a nick or double-strand break into a desired recognition site can be used in the methods and compositions disclosed herein. A naturally-occurring or native nuclease agent can be employed so long as the nuclease agent induces a nick or double-strand break in a desired recognition site. Alternatively, a modified or engineered nuclease agent can be employed. An "engineered nuclease agent" comprises a nuclease that is engineered (modified or derived) from its native form to specifically recognize and induce a nick or double-strand break in the desired recognition site. Thus, an engineered nuclease agent can be derived from a native, naturally-occurring nuclease agent or it can be artificially created or synthesized. The modification of the nuclease agent can be as little as one amino acid in a protein cleavage agent or one nucleotide in a nucleic acid cleavage agent. In some embodiments, the engineered nuclease induces a nick or double-strand break in a recognition site, wherein the recognition site was not a sequence that would have been recognized by a native (non-engineered or non-modified) nuclease agent. Producing a nick or double-strand break in a recognition site or other DNA can be referred to herein as "cutting" or "cleaving" the recognition site or other DNA.

Active variants and fragments of the exemplified recognition sites are also provided. Such active variants can comprise at least 65%, 70%, 75%, 80%, 85%, 90%, 91%, 92%, 93%, 94%, 95%, 96%, 97%, 98%, 99% or more sequence identity to the given recognition site, wherein the active variants retain biological activity and hence are capable of being recognized and cleaved by a nuclease agent in a sequence-specific manner. Assays to measure the double-strand break of a recognition site by a nuclease agent are known in the art and generally measure the ability of a nuclease to cut the recognition site.

The recognition site of the nuclease agent can be positioned anywhere in or near the target locus. The recognition site can be located within a coding region of a gene, or within regulatory regions, which influence expression of the gene. Thus, a recognition site of the nuclease agent can be located in an intron, an exon, a promoter, an enhancer, a regulatory region, or any non-protein coding region.

In one embodiment, the nuclease agent is a Transcription Activator-Like Effector Nuclease (TALEN). TAL effector nucleases are a class of sequence-specific nucleases that can be used to make double-strand breaks at specific target sequences in the genome of a prokaryotic or eukaryotic organism. TAL effector nucleases are created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See, WO 2010/079430; Morbitzer et al. (2010) *PNAS* 10.1073/pnas.1013133107; Scholze & Boch (2010) *Virulence* 1:428-432; Christian et al. *Genetics* (2010) 186:757-761; Li et al. (2010) *Nuc. Acids Res*. (2010) doi:10.1093/nar/gkq704; and Miller et al. (2011) *Nature Biotechnology* 29:143-148; all of which are herein incorporated by reference.

Examples of suitable TAL nucleases, and methods for preparing suitable TAL nucleases, are disclosed, e.g., in US Patent Application No. 2011/0239315 A1, 2011/0269234 A1, 2011/0145940 A1, 2003/0232410 A1, 2005/0208489 A1, 2005/0026157 A1, 2005/0064474 A1, 2006/0188987 A1, and 2006/0063231 A1 (each hereby incorporated by reference). In various embodiments, TAL effector nucleases are engineered that cut in or near a target nucleic acid sequence in, e.g., a genomic locus of interest, wherein the target nucleic acid sequence is at or near a sequence to be modified by a targeting vector. The TAL nucleases suitable for use with the various methods and compositions provided herein include those that are specifically designed to bind at or near target nucleic acid sequences to be modified by targeting vectors as described herein.

In one embodiment, each monomer of the TALEN comprises 12-25 TAL repeats, wherein each TAL repeat binds a 1 bp subsite. In one embodiment, the nuclease agent is a chimeric protein comprising a TAL repeat-based DNA binding domain operably linked to an independent nuclease. In one embodiment, the independent nuclease is a FokI endonuclease. In one embodiment, the nuclease agent comprises a first TAL-repeat-based DNA binding domain and a second TAL-repeat-based DNA binding domain, wherein each of the first and the second TAL-repeat-based DNA binding domain is operably linked to a FokI nuclease, wherein the first and the second TAL-repeat-based DNA binding domain recognize two contiguous target DNA sequences in each strand of the target DNA sequence separated by about 6 bp to about 40 bp cleavage site, and wherein the FokI nucleases dimerize and make a double strand break at a target sequence.

In one embodiment, the nuclease agent comprises a first TAL-repeat-based DNA binding domain and a second TAL-repeat-based DNA binding domain, wherein each of the first and the second TAL-repeat-based DNA binding domain is operably linked to a FokI nuclease, wherein the first and the second TAL-repeat-based DNA binding domain recognize two contiguous target DNA sequences in each strand of the target DNA sequence separated by a 5 bp or 6 bp cleavage site, and wherein the FokI nucleases dimerize and make a double strand break.

The nuclease agent employed in the various methods and compositions disclosed herein can further comprise a zinc-finger nuclease (ZFN). In one embodiment, each monomer of the ZFN comprises 3 or more zinc finger-based DNA binding domains, wherein each zinc finger-based DNA binding domain binds to a 3 bp subsite. In other embodiments, the ZFN is a chimeric protein comprising a zinc finger-based DNA binding domain operably linked to an independent nuclease. In one embodiment, the independent endonuclease is a FokI endonuclease. In one embodiment, the nuclease agent comprises a first ZFN and a second ZFN, wherein each of the first ZFN and the second ZFN is operably linked to a FokI nuclease, wherein the first and the second ZFN recognize two contiguous target DNA sequences in each strand of the target DNA sequence separated by about 6 bp to about 40 bp cleavage site or about a 5 bp to about 6 bp cleavage site, and wherein the FokI nucleases dimerize and make a double strand break. See, for example, US20060246567; US20080182332; US20020081614; US20030021776; WO/2002/057308A2; US20130123484; US20100291048; and, WO/2011/017293A2, each of which is herein incorporated by reference.

In one embodiment of the methods provided herein, the nuclease agent comprises (a) a chimeric protein comprising a zinc finger-based DNA binding domain fused to a FokI endonuclease; or (b) a chimeric protein comprising a Transcription Activator-Like Effector Nuclease (TALEN) fused to a FokI endonuclease.

In still another embodiment, the nuclease agent is a meganuclease. Meganucleases have been classified into four families based on conserved sequence motifs, the families are the LAGLIDADG (SEQ ID NO: 16), GIY-YIG, H-N-H, and His-Cys box families. These motifs participate in the coordination of metal ions and hydrolysis of phosphodiester bonds. HEases are notable for their long recognition sites, and for tolerating some sequence polymorphisms in their DNA substrates. Meganuclease domains, structure and function are known, see for example, Guhan and Muniyappa (2003) Crit Rev Biochem Mol Biol 38:199-248; Lucas et al., (2001) Nucleic Acids Res 29:960-9; Jurica and Stoddard, (1999) Cell Mol Life Sci 55:1304-26; Stoddard, (2006) Q Rev Biophys 38:49-95; and Moure et al., (2002) Nat Struct Biol 9:764. In some examples a naturally occurring variant, and/or engineered derivative meganuclease is used. Methods for modifying the kinetics, cofactor interactions, expression, optimal conditions, and/or recognition site specificity, and screening for activity are known, see for example, Epinat et al., (2003) Nucleic Acids Res 31:2952-62; Chevalier et al., (2002) Mol Cell 10:895-905; Gimble et al., (2003) Mol Biol 334:993-1008; Seligman et al., (2002) Nucleic Acids Res 30:3870-9; Sussman et al., (2004) J Mol Biol 342:31-41; Rosen et al., (2006) Nucleic Acids Res 34:4791-800; Chames et al., (2005) Nucleic Acids Res 33:e178; Smith et al., (2006) Nucleic Acids Res 34:e149; Gruen et al., (2002) Nucleic Acids Res 30:e29; Chen and Zhao, (2005) Nucleic Acids Res 33:e154; WO2005105989; WO2003078619; WO2006097854; WO2006097853; WO2006097784; and WO2004031346.

Any meganuclease can be used herein, including, but not limited to, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, PI-PspI, F-SceI, F-SceII, F-SuvI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NcIIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp6803I, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, I-ZbiIP, PI-Mtul, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, PI-TliII, or any active variants or fragments thereof.

In one embodiment, the meganuclease recognizes double-stranded DNA sequences of 12 to 40 base pairs. In one embodiment, the meganuclease recognizes one perfectly matched target sequence in the genome. In one embodiment, the meganuclease is a homing nuclease. In one embodiment, the homing nuclease is a LAGLIDADG (SEQ ID NO: 16) family of homing nuclease. In one embodiment, the LAGLIDADG (SEQ ID NO: 16) family of homing nuclease is selected from I-SceI, I-CreI, and I-Dmol.

Nuclease agents can further comprise restriction endonucleases, which include Type I, Type II, Type III, and Type IV endonucleases. Type I and Type III restriction endonucleases recognize specific recognition sites, but typically cleave at a variable position from the nuclease binding site, which can be hundreds of base pairs away from the cleavage site (recognition site). In Type II systems the restriction activity is independent of any methylase activity, and cleavage typically occurs at specific sites within or near to the binding site. Most Type II enzymes cut palindromic sequences, however Type IIa enzymes recognize non-palindromic recognition sites and cleave outside of the recognition site, Type IIb enzymes cut sequences twice with both sites outside of the recognition site, and Type IIs enzymes recognize an asymmetric recognition site and cleave on one side and at a defined distance of about 1-20 nucleotides from the recognition site. Type IV restriction enzymes target methylated DNA. Restriction enzymes are further described and classified, for example in the REBASE database (webpage at rebase.neb.com; Roberts et al., (2003) Nucleic Acids Res 31:418-20), Roberts et al., (2003) Nucleic Acids Res 31:1805-12, and Belfort et al., (2002) in Mobile DNA II, pp. 761-783, Eds. Craigie et al., (ASM Press, Washington, DC).

The nuclease agent employed in the various methods and compositions can also comprise a CRISPR/Cas system. Such systems can employ, for example, a Cas9 nuclease, which in some instances, is codon-optimized for the desired cell type in which it is to be expressed. Such systems can also employ a guide RNA (gRNA) that comprises two separate molecules. An exemplary two-molecule gRNA comprises a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA" or "scaffold") molecule. A crRNA comprises both the DNA-targeting segment (single stranded) of the gRNA and a stretch of nucleotides that forms one half of a double stranded RNA (dsRNA) duplex of the protein-binding segment of the gRNA. A corresponding tracrRNA (activator-RNA) comprises a stretch of nucleotides that forms the other half of the dsRNA duplex of the protein-binding segment of the gRNA. Thus, a stretch of nucleotides of a crRNA are complementary to and hybridize with a stretch of nucleotides of a tracrRNA to form the dsRNA duplex of the protein-binding domain of the gRNA. As such, each crRNA can be said to have a corresponding tracrRNA. The crRNA additionally provides the single stranded DNA-targeting segment. Accordingly, a gRNA comprises a sequence that hybridizes to a target sequence, and a tracrRNA. Thus, a crRNA and a tracrRNA (as a corresponding pair) hybridize to form a gRNA. If used for modification within a cell, the exact sequence and/or length of a given crRNA or tracrRNA molecule can be designed to be specific to the species in which the RNA molecules will be used.

Naturally occurring genes encoding the three elements (Cas9, tracrRNA and crRNA) are typically organized in operon(s). Naturally occurring CRISPR RNAs differ depending on the Cas9 system and organism but often contain a targeting segment of between 21 to 72 nucleotides length, flanked by two direct repeats (DR) of a length of between 21 to 46 nucleotides (see, e.g., WO2014/131833). In the case of *S. pyogenes*, the DRs are 36 nucleotides long and the targeting segment is 30 nucleotides long. The 3' located DR is complementary to and hybridizes with the corresponding tracrRNA, which in turn binds to the Cas9 protein.

Alternatively, the system further employs a fused crRNA-tracrRNA construct (i.e., a single transcript) that functions with the codon-optimized Cas9. This single RNA is often referred to as a guide RNA or gRNA. Within a gRNA, the crRNA portion is identified as the 'target sequence' for the given recognition site and the tracrRNA is often referred to as the 'scaffold.' Briefly, a short DNA fragment containing the target sequence is inserted into a guide RNA expression plasmid. The gRNA expression plasmid comprises the target sequence (in some embodiments around 20 nucleotides), a form of the tracrRNA sequence (the scaffold) as well as a suitable promoter that is active in the cell and necessary elements for proper processing in eukaryotic cells. Many of the systems rely on custom, complementary oligos that are annealed to form a double stranded DNA and then cloned into the gRNA expression plasmid. The gRNA expression cassette and the Cas9 expression cassette are then introduced into the cell. See, for example, Mali P et al. (2013) *Science* 2013 Feb. 15; 339(6121):823-6; Jinek M et al. *Science* 2012 Aug. 17; 337(6096):816-21; Hwang W Y et al. *Nat Biotechnol* 2013 March; 31(3):227-9; Jiang W et al. *Nat Biotechnol* 2013 March; 31(3):233-9; and Cong L et al. *Science* 2013 Feb. 15; 339(6121):819-23, each of which is herein incorporated by reference. See also, for example, WO/2013/176772A1, WO/2014/065596A1, WO/2014/089290A1, WO/2014/093622A2, WO/2014/099750A2, and WO/2013142578A1, each of which is herein incorporated by reference.

In some embodiments, the Cas9 nuclease can be provided in the form of a protein. In some embodiments, the Cas9 protein can be provided in the form of a complex with the gRNA. In other embodiments, the Cas9 nuclease can be provided in the form of a nucleic acid encoding the protein. The nucleic acid encoding the Cas9 nuclease can be RNA (e.g., messenger RNA (mRNA)) or DNA.

In some embodiments, the gRNA can be provided in the form of RNA. In other embodiments, the gRNA can be provided in the form of DNA encoding the RNA. In some embodiments, the gRNA can be provided in the form of separate crRNA and tracrRNA molecules, or separate DNA molecules encoding the crRNA and tracrRNA, respectively.

In one embodiment, the method for modifying a genomic locus of interest in a cell further comprises introducing into the cell: (a) a first expression construct comprising a first promoter operably linked to a first nucleic acid sequence encoding a Clustered Regularly Interspaced Short Palindromic Repeats (CRISPR)-associated (Cas) protein; (b) a second expression construct comprising a second promoter operably linked to a genomic target sequence linked to a guide RNA (gRNA), wherein the genomic target sequence is flanked by a Protospacer Adjacent Motif Optionally, the genomic target sequence is flanked on the 3'end by a Protospacer Adjacent Motif (PAM) sequence. In one embodiment, the cell comprises a eukaryotic cell, a non-rat eukaryotic cell, a mammalian cell, a human cell, a non-human mammalian cell, a pluripotent cell, a non-pluripotent cell, a non-human pluripotent cell, a human pluripotent cell, a human ES cell, a human adult stem cell, a developmentally-restricted human progenitor cell, a human iPS cell, a human cell, a rodent cell, a non-rat rodent cell, a rat cell, a mouse cell, a hamster cell, a fibroblast, or a CHO cell.

In one embodiment, the genomic target sequence comprises the nucleotide sequence of GNNNNNNNNNNNNNNNNNNNNGG ($GN_{1-20}GG$; SEQ ID NO: 1). In one embodiment, the genomic target sequence comprises SEQ ID NO: 23, wherein N is between 1 and 20 nucleotides in length. In another embodiment, the genomic target sequence comprises between 14 and 20 nucleotides in length of SEQ ID NO: 1.

In one embodiment, the gRNA comprises a third nucleic acid sequence encoding a Clustered Regularly Interspaced Short Palindromic Repeats (CRISPR) RNA (crRNA) and a trans-activating CRISPR RNA (tracrRNA). In specific embodiments, the Cas protein is Cas9.

In some embodiments, the gRNA comprises (a) the chimeric RNA of the nucleic acid sequence 5'-GUUUUA-GAGCUAGAAAUAGCAAGUUAAAAU AAGGCUA-GUCCGUUAUCAACUUGAAAAAGUGGCACCGAGU-CGGUGCUUUU-3' (SEQ ID NO: 2); or (b) the chimeric RNA of the nucleic acid sequence 5'-GUUUUAGAGCUA-GAAAUAGCAAGUUAAAAUAAGGCUAGUCCG-3' (SEQ ID NO: 3).

In another embodiment, the crRNA comprises 5'-GUUUUAGAGCUAGAAAUAGCAAGUUAAAAU-3' (SEQ ID NO: 4); 5'-GUUUUAGAGCUA-GAAAUAGCAAGUUAAAAUAAG (SEQ ID NO: 5); or 5'-GAGUCCGAGCAGAAGAAGAAGUUUA-3' (SEQ ID NO: 6).

In yet other embodiments, the tracrRNA comprises, 5'-AAGGCUAGUCCG-3' (SEQ ID NO: 7) or 5'-AAGGC-

UAGUCCGU UAUCAACUUGAAAAAGUGGCACCGA-GUCGGUGCUUUU-3' (SEQ ID NO: 8).

In one embodiment, the Cas protein is a type I Cas protein. In one embodiment, the Cas protein is a type II Cas protein. In one embodiment, the type II Cas protein is Cas9. In one embodiment, the first nucleic acid sequence encodes a human codon-optimized Cas protein.

In certain embodiments, the Cas protein is a "nickase" that can create single strand breaks (i.e., "nicks") at the target site without cutting both strands of double stranded DNA (dsDNA). Cas9, for example, comprises two nuclease domains—a RuvC-like nuclease domain and an HNH-like nuclease domain—which are responsible for cleavage of opposite DNA strands. Mutation in either of these domains can create a nickase. Examples of mutations creating nickases can be found, for example, WO/2013/176772A1 and WO/2013/142578A1, each of which is herein incorporated by reference.

In certain embodiments, two separate Cas proteins (e.g., nickases) specific for a target site on each strand of dsDNA can create overhanging sequences complementary to overhanging sequences on another nucleic acid, or a separate region on the same nucleic acid. The overhanging ends created by contacting a nucleic acid with two nickases specific for target sites on both strands of dsDNA can be either 5' or 3' overhanging ends. For example, a first nickase can create a single strand break on the first strand of dsDNA, while a second nickase can create a single strand break on the second strand of dsDNA such that overhanging sequences are created. The target sites of each nickase creating the single strand break can be selected such that the overhanging end sequences created are complementary to overhanging end sequences on a different nucleic acid molecule. The complementary overhanging ends of the two different nucleic acid molecules can be annealed by the methods disclosed herein. In some embodiments, the target site of the nickase on the first strand is different from the target site of the nickase on the second strand.

In one embodiment, the first nucleic acid comprises a mutation that disrupts at least one amino acid residue of nuclease active sites in the Cas protein, wherein the mutant Cas protein generates a break in only one strand of the target DNA region, and wherein the mutation diminishes nonhomologous recombination in the target DNA region.

In one embodiment, the first nucleic acid that encodes the Cas protein further comprises a nuclear localization signal (NLS). In one embodiment, the nuclear localization signal is a SV40 nuclear localization signal.

In one embodiment, the second promoter that drives the expression of the genomic target sequence and the guide RNA (gRNA) is an RNA polymerase III promoter. In one embodiment, the RNA polymerase III promoter is a human U6 promoter. In one embodiment, the RNA polymerase III promoter is a rat U6 polymerase III promoter. In one embodiment, the RNA polymerase III promoter is a mouse U6 polymerase III promoter.

In one embodiment, the nucleic acid sequences encoding crRNA and the tracrRNA are linked via a synthetic loop, wherein, upon expression, the crRNA and the tracrRNA forms a crRNA:tracrRNA duplex.

The CRISPR/Cas system as described above can be used in combination with large targeting vectors with any of the following cell types: a eukaryotic cell, a non-rat eukaryotic cell, a mammalian cell, a non-human mammalian cell, a pluripotent cell, a non-pluripotent cell, a non-human pluripotent cell, a human pluripotent cell, a human ES cell, a human adult stem cell, a developmentally-restricted human progenitor cell, a human iPS cell, a human cell, a rodent cell, a non-rat rodent cell, a rat cell, a mouse cell, a hamster cell, a fibroblast or a CHO cell.

In one embodiment, the first expression construct and the second expression construct are expressed from a same plasmid.

In one embodiment, the first and the second expression constructs are introduced together with the LTVEC. In one embodiment, the first and the second expression constructs are introduced separately from the LTVEC over a period of time.

In one embodiment, the method comprises introducing a plurality of the second construct and a plurality of the LTVEC for multiplex editing of distinct target loci as described herein.

Active variants and fragments of nuclease agents (i.e., an engineered nuclease agent) are also provided. Such active variants can comprise at least 65%, 70%, 75%, 80%, 85%, 90%, 91%, 92%, 93%, 94%, 95%, 96%, 97%, 98%, 99% or more sequence identity to the native nuclease agent, wherein the active variants retain the ability to cut at a desired recognition site and hence retain nick or double-strand-break-inducing activity. For example, any of the nuclease agents described herein can be modified from a native endonuclease sequence and designed to recognize and induce a nick or double-strand break at a recognition site that was not recognized by the native nuclease agent. Thus in some embodiments, the engineered nuclease has a specificity to induce a nick or double-strand break at a recognition site that is different from the corresponding native nuclease agent recognition site. Assays for nick or double-strand-break-inducing activity are known and generally measure the overall activity and specificity of the endonuclease on DNA substrates containing the recognition site.

The nuclease agent may be introduced into the cell by any means known in the art. The polypeptide encoding the nuclease agent may be directly introduced into the cell. Alternatively, a polynucleotide encoding the nuclease agent can be introduced into the cell. When a polynucleotide encoding the nuclease agent is introduced into the cell, the nuclease agent can be transiently, conditionally or constitutively expressed within the cell. Thus, the polynucleotide encoding the nuclease agent can be contained in an expression cassette and be operably linked to a conditional promoter, an inducible promoter, a constitutive promoter, or a tissue-specific promoter. Such promoters of interest are discussed in further detail elsewhere herein. Alternatively, the nuclease agent is introduced into the cell as an mRNA encoding or comprising a nuclease agent.

In one embodiment, the crRNA and the tracrRNA are expressed as separate RNA transcripts.

In specific embodiments, the polynucleotide encoding the nuclease agent is stably integrated in the genome of the cell and operably linked to a promoter active in the cell. In other embodiments, the polynucleotide encoding the nuclease agent is in the same targeting vector comprising the insert nucleic acid, while in other instances the polynucleotide encoding the nuclease agent is in a vector or a plasmid that is separate from the targeting vector comprising the insert nucleic acid.

When the nuclease agent is provided to the cell through the introduction of a polynucleotide encoding the nuclease agent, such a polynucleotide encoding a nuclease agent can be modified to substitute codons having a higher frequency of usage in the cell of interest, as compared to the naturally occurring polynucleotide sequence encoding the nuclease agent. For example the polynucleotide encoding the nuclease agent can be modified to substitute codons having a higher frequency of usage in a given prokaryotic or eukaryotic cell of interest, including a bacterial cell, a yeast cell, a human cell, a non-human cell, a non-rat eukaryotic cell, a mammalian cell, a rodent cell, a non-rat rodent cell, a mouse cell, a rat cell, a hamster cell or any other host cell of interest, as compared to the naturally occurring polynucleotide sequence.

In one embodiment, the endonuclease agent is introduced together with the LTVEC. In one embodiment, the endonuclease agent is introduced separately from the LTVEC over a period of time. In one embodiment, the endonuclease agent is introduced prior to the introduction of the LTVEC. In one embodiment, the endonuclease agent is introduced into the rat, eukaryotic, non-rat eukaryotic, mammalian, non-human mammalian, human, rodent, non-rat rodent, mouse or hamster ES cell following introduction of the LTVEC.

In one embodiment, the endonuclease agent is an expression construct comprising a nucleic acid sequence encoding an endonuclease, wherein the nucleic acid sequence is operably linked to a promoter. In one embodiment, the promoter is a constitutively active promoter. In one embodiment, the promoter is an inducible promoter. In one embodiment, the promoter is active in the pluripotent or non-pluripotent rat, eukaryotic, non-rat eukaryotic, mammalian, non-human mammalian, human, rodent, non-rat rodent, mouse or hamster cell. In one embodiment, the endonuclease agent is an mRNA encoding an endonuclease.

B. Methods for Integrating a Polynucleotide of Interest into a Target Locus

Methods for modifying a target locus of interest are provided. In one embodiment, a target locus in a pluripotent or non-pluripotent rat, eukaryotic, non-rat eukaryotic, mammalian, non-human mammalian, human, rodent, non-rat rodent, mouse or hamster cell is targeted for genetic modification. Such a method comprises: (a) introducing into the pluripotent or non-pluripotent rat, eukaryotic, non-rat eukaryotic, mammalian, non-human mammalian, human, rodent, non-rat rodent, mouse or hamster cell a targeting vector comprising an insert nucleic acid flanked with a 5' rat, eukaryotic, non-rat eukaryotic, mammalian, non-human mammalian, human, rodent, non-rat rodent, mouse or hamster homology arm and a 3' rat, eukaryotic, non-rat eukaryotic, mammalian, non-human mammalian, human, rodent, non-rat rodent, mouse or hamster homology arm; and (b) identifying a genetically modified pluripotent or non-pluripotent rat, eukaryotic, non-rat eukaryotic, mammalian, non-human mammalian, human, rodent, non-rat rodent, mouse or hamster cell comprising the targeted genetic modification at the target locus, wherein the targeted genetic modification is capable of being transmitted through the germline. In specific embodiments, the sum total of the 5' homology arm and the 3' homology arm is at least 10 kb and/or a large targeting vector is employed.

In other embodiments, the size of the sum total of the total of the 5' and 3' homology arms of the LTVEC is about 10 kb to about 150 kb, about 10 kb to about 100 kb, about 10 kb to about 75 kb, about 20 kb to about 150 kb, about 20 kb to about 100 kb, about 20 kb to about 75 kb, about 30 kb to about 150 kb, about 30 kb to about 100 kb, about 30 kb to about 75 kb, about 40 kb to about 150 kb, about 40 kb to about 100 kb, about 40 kb to about 75 kb, about 50 kb to about 150 kb, about 50 kb to about 100 kb, or about 50 kb to about 75 kb, about 10 kb to about 30 kb, about 20 kb to about 40 kb, about 40 kb to about 60 kb, about 60 kb to about 80 kb, about 80 kb to about 100 kb, about 100 kb to about 120 kb, or from about 120 kb to about 150 kb. In one embodiment, the size of the deletion is the same or similar to the size of the sum total of the 5' and 3' homology arms of the LTVEC.

The pluripotent cell, for example, a rat cell, can be an embryonic stem cell, for example, a rat embryonic stem cell. In a specific embodiment, (a) the rat ES cell is derived from a DA strain or an ACI strain; or (b) the rat ES cell is characterized by expression of a pluripotency marker comprising Oct-4, Sox-2, alkaline phosphatase, or a combination thereof. In other instances, the rat embryonic stem cell employed comprises a rat ES cell as described in U.S. patent application Ser. No. 14/185,103, filed on Feb. 20, 2014, herein incorporated by reference in its entirety.

Any pluripotent or non-pluripotent cell can be used in the methods provided herein. For example, the pluripotent or non-pluripotent cell can be from a eukaryote, a non-rat eukaryote, a non-human mammal, a mammal, a rodent, a non-rat rodent, a rat, a mouse, a human or a hamster.

As described elsewhere herein, the insert nucleic acid can be any nucleic acid sequence. In non-limiting embodiments, (a) the insert nucleic acid comprises a replacement of an endogenous rat, eukaryotic, non-rat eukaryotic, mammalian, human, rodent, non-rat rodent, mouse or hamster nucleic acid sequence with a homologous or a orthologous mammalian nucleic acid sequence; (b) the insert nucleic acid comprises a deletion of an endogenous rat, eukaryotic, non-rat eukaryotic, mammalian, human, rodent, non-rat rodent, mouse or hamster nucleic acid sequence; (c) the insert nucleic acid comprises a deletion of an endogenous rat, eukaryotic, non-rat eukaryotic, mammalian, non-human mammalian, human, rodent, non-rat rodent, mouse or hamster nucleic acid sequence, wherein the deletion ranges from 5 kb to 200 kb or from 5 kb to 3 Mb (as discussed in detail elsewhere herein); (d) the insert nucleic acid comprises an addition of an exogenous nucleic acid sequence (including for example an exogenous nucleic acid sequence ranging from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb); (e) the insert nucleic acid comprises an exogenous nucleic acid sequence comprising a homologous or an orthologous nucleic acid sequence; (f) the homologous or the orthologous nucleic acid sequence of (a) wherein the nucleic acid sequence is a human nucleic acid sequence; (g) the insert nucleic acid comprises the homologous or the orthologous nucleic acid sequence of (a) wherein the nucleic acid sequence is a chimeric nucleic acid sequence comprising a human and a rat nucleic acid sequence; (h) the insert nucleic acid comprises the exogenous nucleic acid sequence of (e), wherein the insert nucleic acid ranges from about 5 kb to about 200 kb; (i) the insert nucleic acid comprises a conditional allele flanked with site-specific recombinase target sequences; (j) the insert nucleic acid comprises a reporter gene operably linked to a promoter; (k) the insert nucleic acid comprises one or more unrearranged human immunoglobulin heavy chain $V_H$ gene segments, one or more unrearranged human immunoglobulin heavy chain D gene segments, and one or more unrearranged human immunoglobulin heavy chain $J_H$ gene segments, which are operably linked to a rodent heavy chain constant region nucleic acid sequence; (l) the insert nucleic acid comprises a rearranged human immunoglobulin heavy chain variable region nucleic acid sequence operably linked to a rodent heavy chain constant region nucleic acid sequence; (m) the insert nucleic acid comprises one or more unrearranged human immunoglobulin $V_\kappa$ or $V_\lambda$ gene segments and one or more unrearranged human immunoglobulin $J_\kappa$ or $J_\lambda$ gene segments, which are operably linked to a mammalian immunoglobulin λ or κ light chain light chain constant region nucleic acid sequence; (n) the insert nucleic acid comprises a rearranged human immunoglobulin λ or κ light chain variable region nucleic acid sequence operably linked to a mammalian immunoglobulin λ or κ light chain light chain constant region nucleic acid sequence; (o) the mammalian heavy chain constant region nucleic acid sequence of (k) and/or (l) comprises a rat constant region nucleic acid sequence, a human constant region nucleic acid sequence, or a combination thereof; or (p) the mammalian immunoglobulin λ or κ light chain constant region nucleic acid of (m) and/or (n) comprises a rat constant region nucleic acid sequence, a human constant region nucleic acid sequence, or a combination thereof.

In one embodiment, the insert nucleic acid comprises one or more functional human $V_H$ gene segments comprising $V_H1$-2, $V_H1$-3, $V_H1$-8, $V_H1$-18, $V_H1$-24, $V_H1$-45, $V_H1$-46, $V_H1$-58, $V_H1$-69, $V_H2$-5, $V_H2$-26, $V_H2$-70, $V_H3$-7, $V_H3$-9, $V_H3$-11, $V_H3$-13, $V_H3$-15, $V_H3$-16, $V_H3$-20, $V_H3$-21, $V_H3$-23, $V_H3$-30, $V_H3$-30-3, $V_H3$-30-5, $V_H3$-33, $V_H3$-35, $V_H3$-38, $V_H3$-43, $V_H3$-48, $V_H3$-49, $V_H3$-53, $V_H3$-64, $V_H3$-66, $V_H3$-72, $V_H3$-73, $V_H3$-74, $V_H4$-4, $V_H4$-28, $V_H4$-30-1, $V_H4$-30-2, $V_H4$-30-4, $V_H4$-31, $V_H4$-34, $V_H4$-39, $V_H4$-59, $V_H4$-61, $V_H5$-51, $V_H6$-1, $V_H7$-4-1, $V_H7$-81, or a combination thereof.

In one embodiment, the insert nucleic acid comprises one or more functional human D gene segments comprising D1-1, D1-7, D1-14, D1-20, D1-26, D2-2, D2-8, D2-15, D2-21, D3-3, D3-9, D3-10, D3-16, D3-22, D4-4, D4-11, D4-17, D4-23, D5-12, D5-5, D5-18, D5-24, D6-6, D6-13, D6-19, D6-25, D7-27, or a combination thereof.

In one embodiment, the insert nucleic acid comprises one or more functional $J_H$ gene segments comprising $J_H1$, $J_H2$, $J_H3$, $J_H4$, $J_H5$, $J_H6$, or a combination thereof. In one embodiment, the insert nucleic acid comprises one or more human Vκ gene segments comprising Vκ4-1, Vκ5-2, Vκ7-3, Vκ2-4, Vκ1-5, Vκ1-9, Vκ2-10, Vκ3-11, Vκ1-12, Vκ1-13, Vκ2-14, Vκ3-15, Vκ1-16, Vκ1-17, Vκ2-18, Vκ2-19, Vκ3-20, Vκ6-21, Vκ1-22, Vκ1-23, Vκ2-24, Vκ3-25, Vκ2-26, Vκ1-27, Vκ2-28, Vκ2-29, Vκ2-30, Vκ3-31, Vκ1-32, Vκ1-33, Vκ3-34, Vκ1-35, Vκ2-36, Vκ1-37, Vκ2-38, Vκ1-39, Vκ2-40, or a combination thereof.

In one embodiment, the insert nucleic acid comprises one or more human Vλ gene segments comprising Vλ3-1, Vλ4-3, Vλ2-8, Vλ3-9, Vλ3-10, Vλ2-11, Vλ3-12, Vλ2-14, Vλ3-16, Vλ2-18, Vλ3-19, Vλ3-21, Vλ3-22, Vλ2-23, Vλ3-25, Vλ3-27, or a combination thereof.

In one embodiment, the insert nucleic acid comprises one or more human Jκ gene segments comprising Jκ1, Jκ2, Jκ3, Jκ4, Jκ5, or a combination thereof.

In specific embodiments, upon modification of the target locus in a pluripotent or non-pluripotent rat, eukaryotic, non-rat eukaryotic, mammalian, non-human mammal, human, rodent, non-rat rodent, mouse or hamster cell, the genetic modification is transmitted through the germline.

In one embodiment, the insert nucleic acid sequence comprises a polynucleotide that when integrated into the genome will produce a genetic modification of a region of the rat, eukaryotic, non-rat eukaryotic, mammalian, non-human mammal, human, rodent, non-rat rodent, mouse or hamster ApoE locus, wherein the genetic modification at the ApoE locus results in a decrease in ApoE activity, an increase in ApoE activity or a modulation of ApoE activity. In one embodiment, an ApoE knockout is generated.

In one embodiment, the insert nucleic acid sequence comprises a polynucleotide that when integrated into the genome will produce a genetic modification of a region of the rat, eukaryotic, non-rat eukaryotic, mammal, human, non-human mammal, rodent, non-rat rodent, mouse or hamster interleukin-2 receptor gamma locus, wherein the genetic modification at the interleukin-2 receptor gamma locus results in a decrease in interleukin-2 receptor activity, an increase in interleukin-2 receptor gamma activity, or a modulation of interleukin-2 receptor activity. In one embodiment, an interleukin-2 receptor knockout is generated.

In still another embodiment, the insert nucleic acid sequence comprises a polynucleotide that when integrated into the genome will produce a genetic modification of a region of the rat, eukaryotic, non-rat eukaryotic, mammal, non-human mammal, human, rodent, non-rat rodent, mouse or hamster Rag1 locus, the rat, eukaryotic, non-rat eukaryotic, non-human mammal, mammalian, human, rodent, non-rat rodent, mouse or hamster Rag2 locus and/or the rat, eukaryotic, non-rat eukaryotic, mammalian, non-human mammal, human, rodent, non-rat rodent, mouse or hamster Rag2/Rag1 locus, wherein the genetic modification at the rat, eukaryotic, non-rat eukaryotic, mammalian, non-human mammal, human, rodent, non-rat rodent, mouse or hamster Rag1, Rag2 and/or Rag2/Rag1 locus results in a decrease in Rag1, Rag2 or Rag1 and Rag2 protein activity, an increase in Rag1, Rag2 or Rag1 and Rag2 protein activity, or a modulation in Rag1, Rag2 or Rag1 and Rag2 protein activity. In one embodiment, a Rag1, Rag2 or Rag2/Rag1 knockout is generated.

In further embodiments, the insert nucleic acid results in the replacement of a portion of the rat, eukaryotic, non-rat eukaryotic, mammalian, non-human mammal, human, rodent, non-rat rodent, mouse or hamster ApoE locus, the interleukin-2 receptor gamma locus and/or Rag2 locus, and/or Rag1 locus and/or Rag2/Rag1 locus with the corresponding orthologous portion of an ApoE locus, an interleukin-2 receptor gamma locus, a Rag2 locus, a Rag1 locus and/or a Rag2/Rag1 locus from another organism.

In still other embodiments, the insert nucleic acid comprises a polynucleotide sharing across its full length least 80%, 85%, 90%, 91%, 92%, 93%, 94%, 95%, 96%, 97%, 98%, 99% to a portion of an ApoE locus, an interleukin-2 receptor gamma locus, a Rag2 locus, a Rag1 locus and/or a Rag2/Rag1 locus it is replacing.

The given insert polynucleotide and the corresponding region of the rat, eukaryotic, non-rat eukaryotic, mammal, non-human mammal, human, rodent, non-rat rodent, mouse or hamster locus being replaced can be a coding region, an intron, an exon, an untranslated region, a regulatory region, a promoter, or an enhancer or any combination thereof. Moreover, the given insert polynucleotide and/or the region of the rat, eukaryotic, non-rat eukaryotic, mammalian, human, non-human mammal, rodent, non-rat rodent, mouse or hamster locus being replaced can be of any desired length, including for example, between 10-100 nucleotides in length, 100-500 nucleotides in length, 500-1 kb nucleotide in length, 1 kb to 1.5 kb nucleotide in length, 1.5 kb to 2 kb nucleotides in length, 2 kb to 2.5 kb nucleotides in length, 2.5 kb to 3 kb nucleotides in length, 3 kb to 5 kb nucleotides in length, 5 kb to 8 kb nucleotides in length, 8 kb to 10 kb nucleotides in length or more. In other instances, the size of the insertion or replacement is from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, from about 350 kb to about 400 kb, from about 400 kb to about 800 kb, from about 800 kb to 1 Mb, from about 1 Mb to about 1.5 Mb, from about 1.5 Mb to about 2 Mb, from about 2 Mb, to about 2.5 Mb, from about 2.5 Mb to about 2.8 Mb, from about 2.8 Mb to about 3 Mb. In other embodiments, the given insert polynucleotide and/or the region of the rat, eukaryotic, non-rat eukaryotic, non-human mammal, mammal, human, rodent, non-rat rodent, mouse or hamster locus being replaced is at least 100, 200, 300, 400, 500, 600, 700, 800, or 900 nucleotides or at least 1 kb, 2 kb, 3 kb, 4 kb, 5 kb, 6 kb, 7 kb, 8 kb, 9 kb, 10 kb, 11 kb, 12 kb, 13 kb, 14 kb, 15 kb, 16 kb or greater.

i. Methods for Modifying a Target Locus of a Nucleic Acid Via Bacterial Homologous Recombination (BHR)

Methods and compositions are provided for modifying a target locus of a eukaryotic, non-rat eukaryotic, a mammalian, a human or a non-human mammalian nucleic acid, via bacterial homologous recombination (BHR) in a prokaryotic cell. Such methods find use in utilizing bacterial homologous recombination in a prokaryotic cell to genetically modify a target locus of a eukaryotic, non-rat eukaryotic, a mammalian, a human or a non-human mammalian nucleic acid in order to create a targeting vector. Such a targeting vector comprising the genetically modified target locus can be introduced into a eukaryotic cell, for example, a eukaryotic cell, non-rat eukaryotic cell, a mammalian cell, a human cell, a non-human mammalian cell, a pluripotent cell, a non-pluripotent cell, a non-human pluripotent cell, a human pluripotent cell, a human ES cell, a human adult stem cell, a developmentally-restricted human progenitor cell, a human iPS cell, a human cell, a rodent cell, a non-rat rodent cell, a rat cell, a mouse cell, a hamster cell, a fibroblast, or a CHO cell. "Homologous recombination" includes the exchange of DNA fragments between two DNA molecules at cross-over sites within regions of homology. Thus, "bacterial homologous recombination" or "BHR" includes homologous recombination that occurs in bacteria.

Methods for modifying a target locus of a nucleic acid from a eukaryotic cell, non-rat eukaryotic cell, a mammalian cell, a human cell, a non-human mammalian cell, a pluripotent cell, a non-pluripotent cell, a non-human pluripotent cell, a human pluripotent cell, a human ES cell, a human adult stem cell, a developmentally-restricted human progenitor cell, a human iPS cell, a human cell, a rodent cell, a non-rat rodent cell, a rat cell, a mouse cell, a hamster cell, a fibroblast, or a CHO cell via bacterial homologous recombination (BHR) are provided. The methods comprise introducing into a prokaryotic cell a targeting vector comprising an insert nucleic acid flanked with a 5' homology arm and a 3' homology arm, wherein the prokaryotic cell comprises a target locus of a nucleic acid and is capable of expressing a recombinase that mediates the BHR at the target locus. Such targeting vectors can include any of the large targeting vectors described herein.

In one embodiment, the method comprises introducing into a prokaryotic cell: (i) a first construct comprising a nucleic acid having a DNA sequence of interest; (ii) a second targeting construct comprising an insert nucleic acid flanked with a 5' homology arm and a 3' homology arm, and (iii) a third construct encoding a recombinase that mediates bacterial homologous recombination. In one embodiment, the first, the second, and the third construct are introduced into the prokaryotic cell separately over a period of time. In one embodiment, the prokaryotic cell comprises a nucleic acid that encodes the recombinase, and the method does not require introduction of the third construct. In one embodiment, the recombinase is expressed under the control of an inducible promoter.

In one embodiment the first construct comprising the nucleic acid, is derived from a bacterial artificial chromosome (BAC) or yeast artificial chromosome (YAC). A prokaryotic cell comprising the insert nucleic acid at the target genomic locus can be selected. This method can be serially repeated as disclosed herein to allow the introduction of multiple insert nucleic acids at the targeted locus in the prokaryotic cell. Once the target nucleic acid locus is "built" within the prokaryotic cell, a targeting vector comprising the modified target locus can be isolated from the prokaryotic cell and introduced into a target genomic locus within a eukaryotic cell, non-rat eukaryotic cell, a mammalian cell, a human cell, a non-human mammalian cell, a pluripotent cell, a non-pluripotent cell, a non-human pluripotent cell, a human pluripotent cell, a human ES cell, a human adult stem cell, a developmentally-restricted human progenitor cell, a human iPS cell, a human cell, a rodent cell, a non-rat rodent cell, a rat cell, a mouse cell, a hamster cell, a fibroblast, or a CHO cell.

Preferred rat cells for receiving targeting vectors are described in U.S. application Ser. No. 14/185,703, filed Feb. 20, 2014, the contents of which are summarized herein. These rat cells are pluripotent rat cells capable of sustaining their pluripotency following one or more targeted genetic modifications in vitro, and are capable of transmitting the targeted genetic modifications through the germline.

Electroporated pluripotent cells, for example, are plated at a high density for the selection of drug-resistant cells comprising the targeting vector. The drug selection process removes the majority of the plated cells (~99%), leaving behind individual colonies, each of which is a clone derived from a single cell. Of the remaining cells, most cells (~80-100%) contain the targeting vector (comprising a drug selection cassette) integrated at a random location in the genome. Therefore, the colonies are picked individually and genotyped to identify ES cells harboring the targeting vector at the correct genomic location (e.g., using the modification of allele assay described below).

A high-throughput quantitative assay, namely, modification of allele (MOA) assay, can be used for genotyping. Such an assay allows a large-scale screening of a modified allele(s) in a parental chromosome following a genetic modification. The MOA assay can be carried out via various analytical techniques, including, but not limited to, a quantitative PCR, e.g., a real-time PCR (qPCR). For example, the real-time PCR comprises a first primer set that recognizes the target locus and a second primer set that recognizes a non-targeted reference locus. In addition, the primer set comprises a fluorescent probe that recognizes the amplified sequence. In one embodiment, the quantitative assay is carried out via Invader Probes®. In one embodiment, the quantitative assay is carried out via MMP Assays®. In one embodiment, the quantitative assay is carried out via TaqMan® Molecular Beacon. In one embodiment, the quantitative assay is carried out via Eclipse™ probe technology. (See, for example, US2005/0144655, which is incorporated by reference herein in its entirety).

The selected pluripotent cell (i.e., a non-human pluripotent cell, a non-human ES cell) comprising the targeted genetic modification can then be introduced into a host embryo, for example, a pre-morula stage or blastocyst stage embryo and implanted in the uterus of a surrogate mother to generate a founder non-human animal (F0 animal). Subsequently, the founder animal, for example, can be bred to a wild-type animal to create F1 progeny heterozygous for the genetic modification. Mating of the heterozygous F1 animal can produce progeny homozygous for the genetic modification. Mating of the heterozygous F1 animal can produce progeny homozygous for the genetic modification. In some embodiments, various genetic modifications of the target loci described herein can be carried out using a large targeting vector (LTVEC) as described in detail elsewhere herein. For example, an LTVEC can be derived from Bacterial Artificial Chromosome (BAC) DNA using VELOCIGENE® genetic engineering technology (see, e.g., U.S. Pat. No. 6,586,251 and Valenzuela, D. M. et al. (2003), High-throughput engineering of the mouse genome coupled with high-resolution expression analysis, Nature Biotechnology 21(6): 652-659, which is incorporated herein by reference in their entireties).

Use of bacterial homologous recombination (BHR) to generate a large targeting vector (LTVEC) circumvents the limitations of plasmids in accommodating a large genomic DNA fragment and consequent low efficiency of introducing a targeted modification into an endogenous locus in pluripotent or non-pluripotent cells. One or more targeted genetic modifications can be performed in generating a LTVEC. An exemplary LTVEC produced in the prokaryotic cell can comprises an insert nucleic acid that carries a genomic sequence with one or more genetic modifications or an exogenous nucleic acid (e.g., a homolog or ortholog of a rat nucleic acid), which is flanked by homologous arms, complementary to specific genomic regions.

Host prokaryotic cells comprising the various targeting vectors described herein are also provided. Such prokaryotic cells include, but are not limited to, bacteria such as *E. coli*. In one embodiment, a host prokaryotic cell comprises a targeting vector comprising an insert nucleic acid flanked with a 5' homology arm and a 3' homology arm, wherein the insert nucleic acid ranges from about 5 kb to about 200 kb.

The host prokaryotic cell can further comprise a nucleic acid that encodes a recombinase polypeptide or the nucleic acid that encodes the recombinase polypeptide is operably linked to an inducible promoter.

Further provided are various methods and compositions, which employ the LTVEC as described herein in combination with a prokaryotic cell in order to produce targeted genetic modifications. Such compositions and methods are discussed elsewhere herein.

Methods for modifying a target locus of a nucleic acid via bacterial homologous recombination (BHR) are provided that comprise introducing into a prokaryotic cell a targeting vector comprising an insert nucleic acid flanked with a 5' homology arm and a 3' homology arm, wherein the prokaryotic cell comprises nucleic acids corresponding to the 5' and 3' homology arms and the prokaryotic cell is capable of expressing a recombinase that mediates the BHR at the target locus. Such targeting vectors can include any of the large targeting vectors described herein. Such methods can employ a LTVEC as discussed in detail herein and further employ the CRISPR/Cas system as discussed elsewhere herein.

In one embodiment, the CRISPR/Cas system can be controlled by a promoter active in a prokaryotic cell, such as, for example, *E. coli*.

ii. Methods for Modifying a Target Locus of Interest in a Pluripotent Cell or Non-Pluripotent Cell.

Further provided is a method for modifying a target locus of interest in a pluripotent cell or non-pluripotent cell via targeted genetic modification, comprising (a) introducing into the pluripotent cell or non-pluripotent cell a targeting vector comprising an insert nucleic acid flanked with a 5' homology arm and a 3' homology arm, wherein the sum total of the 5' homology arm and the 3' homology arm is at least 10 kb; and (b) identifying a genetically modified pluripotent or non-pluripotent cell comprising the targeted genetic modification at the target locus of interest. In one embodiment, the sum total of the 5' homology arm and the 3' homology arm is at least about 16 kb to about 30 kb. In specific embodiments, the targeted genetic modification is capable of being transmitted through the germline. Such targeting vectors can include any of the large targeting vectors described herein.

Various cells can also be used in the methods for modifying a target locus of interest provided herein. In specific embodiments, the cell is a eukaryotic cell, non-rat eukaryotic cell, a pluripotent cell, a non-pluripotent cell, a non-human pluripotent cell, a human pluripotent cell, a human ES cell, a human adult stem cell, a developmentally restricted human progenitor cell, a human induced pluripotent cell (iPS) cell, a mammalian cell, a human cell, a fibroblast, a rodent cell, a non-rat rodent cell, a mouse cell, a hamster cell or a CHO cell.

In one aspect, a method for modifying a genomic locus of interest in a pluripotent cell via targeted genetic modification is provided, comprising: (a) providing a pluripotent cell that is able to sustain its pluripotency following at least one targeted genetic modification of its genome and is able to transmit the targeted modification to a germline of an F1 generation; (b) introducing a large targeting vector (LTVEC) into the pluripotent cell, wherein the LTVEC comprises an insert nucleic acid flanked with a 5' homology arm and a 3' homology arm, wherein the 5' homology arm and the 3' homology arm comprise a genomic DNA fragment; and (c) identifying a genetically modified pluripotent cell comprising the targeted genetic modification.

Various methods can be used to identify cells having the insert nucleic acid integrated at the target locus of interest. Insertion of the insert nucleic acid at the target locus of interest results in a "modification of allele". The term "modification of allele" and methods for the detection of the modified allele are discussed in further detail elsewhere herein.

In one aspect, a method for modifying a genomic locus of interest in a non-pluripotent cell or a pluripotent cell via endonuclease-mediated gene targeting is provided, the method comprising: (a) providing an isolated non-pluripotent cell or an isolated pluripotent cell that is able to transmit the genetically modified genome to a germline of an F1 generation; (b) introducing into the non-pluripotent cell or the pluripotent cell an endonuclease agent; wherein the endonuclease agent makes a nick or a double strand break at a target DNA sequence located in the genomic locus of interest, and wherein the nick or the double strand break at the target DNA sequence in the non-pluripotent cell or the pluripotent cell induces: (i) non-homologous end joining (NHEJ)-mediated DNA repair of the nick or the double strand break, wherein the NHEJ-mediated DNA repair generates a mutant allele comprising an insertion or a deletion of a nucleic acid sequence at the target DNA sequence; or (ii) homologous recombination-mediated DNA repair that results in restoration of a wild-type nucleic acid sequence; and (c) identifying the modified genomic locus of interest.

In one aspect, a method for modifying a genomic locus of interest in an isolated embryonic stem cell (ES) via a nuclease agent is provided, comprising: (a) providing an isolated ES cell that is able to transmit the targeted genetic modification to a germline of an F1 generation; (b) introducing into the ES cell: (i) a large targeting vector (LTVEC) comprising an insert nucleic acid flanked with a 5' homology arm and a 3' homology arm, wherein the insert is a nucleic acid sequence that is at least 5 kb; and (ii) an endonuclease agent, wherein the endonuclease agent makes a nick or a double strand break at a target DNA sequence located in the genomic locus of interest, and wherein the target sequence is not present in the insert nucleic acid; and (c) identifying the targeted genetic modification in the embryonic stem (ES) cell.

In one aspect, a method for modifying a genomic locus of interest in a non-pluripotent cell or a pluripotent cell via RNA-guided genome engineering is provided, the method comprising: (a) providing a non-pluripotent cell or a pluripotent cell that is able to transmit the genetically modified genome to a germline of an F1 generation; (b) introducing into the non-pluripotent cell or the pluripotent cell: (i) a first expression construct comprising a first promoter operably linked to a first nucleic acid sequence encoding a Clustered Regularly Interspaced Short Palindromic Repeats (CRISPR)-associated (Cas) protein, (ii) a second expression construct comprising a second promoter operably linked to a genomic target sequence linked to a guide RNA (gRNA), wherein the genomic target sequence is flanked by a Protospacer Adjacent Motif (PAM) sequence. Optionally the genomic target sequence is flanked on the 3'end by a Protospacer Adjacent Motif (PAM) sequence. In one embodiment, the Cas protein and the CRISPR RNA and/or tracrRNA do not naturally occur together (e.g., the Cas protein and CRISPR RNA do not naturally occur together). In one embodiment, the genomic target sequence comprises the nucleotide sequence of GNNNNNNNNNNNNNNNNNNNGG (GN$_{1-20}$ GG; SEQ ID NO: 1). In one embodiment, the genomic target sequence comprises SEQ ID NO: 1, wherein N is between 14 and 20 nucleotides in length. In one embodiment, the gRNA comprises a third nucleic acid sequence encoding a Clustered Regularly Interspaced Short Palindromic Repeats (CRISPR) RNA (crRNA) and a fourth nucleic acid sequence encoding a trans-activating CRISPR RNA (tracrRNA). In one embodiment, upon expression, the Cas protein forms a CRISPR-Cas complex comprising the crRNA and the tracrRNA, and the CRISPR-Cas complex makes a nick or a double strand break at a target DNA sequence located in the genomic locus of interest, and wherein the nick or the double strand break at the target DNA sequence in the non-pluripotent cell or the pluripotent cell induces: (i) non-homologous end joining (NHEJ)-mediated DNA repair of the nick or the double strand break created by the CRISPR-Cas complex, wherein the NHEJ generates a mutant allele comprising an insertion or a deletion of a nucleic acid sequence at the target DNA sequence; or (ii) homologous recombination-mediated DNA repair that results in restoration of a wild-type nucleic acid sequence; and (c) identifying the modified the genomic locus of interest.

In one aspect, a method for modifying a genomic locus of interest in a non-pluripotent cell or a pluripotent cell via RNA-guided genome engineering is provided, the method comprising introducing into the non-pluripotent cell or the pluripotent cell that is able to transmit the modified genome through the germline: (i) a Clustered Regularly Interspaced Short Palindromic Repeats (CRISPR)-associated (Cas) protein or a nucleic acid encoding the Cas protein; and (ii) a gRNA or a DNA encoding the gRNA, wherein the gRNA comprises a nucleotide sequence that hybridizes to a genomic target sequence and a trans-activating CRISPR RNA (tracrRNA); wherein the genomic target sequence is flanked by a Protospacer Adjacent Motif (PAM) sequence.

In some embodiments, the Cas protein can be introduced into the non-pluripotent cell or the pluripotent cell as an isolated protein. In some embodiments, the Cas protein can further comprise a cell-penetrating domain that facilitates cellular uptake of the protein. In other embodiments, the Cas protein can be introduced into the cell as a messenger RNA (mRNA) molecule encoding the Cas protein. In other embodiments, the Cas protein can be introduced into the cell as a DNA molecule encoding the Cas protein. For example, the DNA molecule encoding the Cas protein can be provided in a construct and be operably linked to a promoter capable of expressing in the non-pluripotent cell or the pluripotent cell. In certain embodiments, the nucleic acid encoding the Cas protein is codon-optimized for expression in the non-pluripotent cell or the pluripotent cell.

In some embodiments, the gRNA can be introduced into the non-pluripotent cell or the pluripotent cell as a RNA molecule. For example, the gRNA molecule can be transcribed in vitro. In other embodiments, the gRNA can be introduced into the non-pluripotent cell or the pluripotent cell as a DNA molecule encoding the gRNA. For example, the DNA molecule encoding the gRNA can be in a construct and be operably linked to a promoter capable of expressing the gRNA in the non-pluripotent cell or the pluripotent cell. In other embodiments, the gRNA can be chemically synthesized.

In some embodiments, the gRNA can be introduced into the non-pluripotent cell or the pluripotent cell as a fused crRNA-tracrRNA molecule (i.e., a single transcript). In other embodiments, the gRNA can be introduced into the non-pluripotent cell or the pluripotent cell as separate crRNA and tracrRNA molecules (i.e., separate transcripts). In other embodiments, the gRNA can be introduced into the non-pluripotent cell or the pluripotent cell as separate DNA molecules encoding the crRNA and tracrRNA, respectively. For example, the separate DNA molecules encoding the crRNA and tracrRNA can be in separate constructs and be operably linked to promoters capable of expressing in the non-pluripotent cell or the pluripotent cell. In any of the above embodiments, any combination of the constructs can be in separate nucleic acid molecules or together in a single nucleic acid molecule In some embodiments, the Cas protein and the gRNA can be introduced into the non-pluripotent cell or the pluripotent cell simultaneously or sequentially. Likewise, the crRNA and the tracrRNA of the gRNA can be introduced into the non-pluripotent cell or the pluripotent cell simultaneously or sequentially. The ratio of the Cas protein (or encoding nucleic acid) to the gRNA (or encoding DNA) and/or the ratio of the crRNA to the tracrRNA can be about stoichiometric such that they can form an RNA-protein complex.

In certain embodiments, the Cas protein can be introduced into the non-pluripotent cell or the pluripotent cell in the form of a complex with the gRNA.

In one embodiment, the pluripotent cell is an induced pluripotent stem cell (iPS). In one embodiment, the pluripotent cell is a developmentally restricted progenitor cell.

The presence of a nick or a double-strand break in the recognition site within the selection marker, in various embodiments, increases the efficiency and/or frequency of recombination between a targeting vector (such as a LTVEC) and the targeted locus of interest. In one embodiment, the recombination is homologous recombination. In another embodiment, the recombination is an insertion by non-homologous end joining. In various embodiments, in the presence of the nick or double strand break, targeting efficiency of a targeting vector (such as a LTVEC) at the target genomic locus is at least about 2-fold higher, at least about 3-fold higher, at least about 4-fold higher than in the absence of the nick or double-strand break (using, e.g., the same targeting vector and the same homology arms and corresponding target sites at the genomic locus of interest but in the absence of an added nuclease agent that makes the nick or double strand break).

In one embodiment, the targeted genetic modification at the target locus is biallelic. By "biallelic" is meant that both alleles of a gene comprise the targeted genetic modification. The targeted genetic modification can be the same or different in each allele. For example, a biallelic modification can result from the same modification being made to corresponding alleles on corresponding homologous chromosomes, or from different modifications being made to corresponding alleles on corresponding homologous chromosomes. Thus, a biallelic modification can result, for example, in homozygosity for a specific modification at a genomic locus of interest (i.e., the specific modification in both alleles), compound heterozygosity at a genomic locus of interest (e.g., the specific modification in one allele and inactivation or disruption of the other allele), or hemizygosity at a genomic locus of interest (e.g., the specific modification in one allele and loss of the other allele). In certain embodiments, the combined use of a targeting vector (including, for example, an LTVEC) with a nuclease agent results in biallelic targeted genetic modification of the genomic locus of interest in a cell as compared to use of the targeting vector alone. When the targeting vector is used in conjunction with a nuclease agent, biallelic targeting efficiency is increased at least by two-fold, at least three-fold, at least 4-fold or more as compared to when the targeting vector is used alone. In further embodiments, the biallelic targeting efficiency is at least 0.2%, 0.3%, 0.4%, 0.5%, 0.6%, 0.7%, 0.8%, 0.9%, 1%, 2%, 3%, 4% or 5% or higher.

The biallelic targeted genetic modification at the target locus can result in a homozygous genetically modified cell. By "homozygous" is meant that both alleles of the target locus (i.e., the alleles on both homologous chromosomes) have been modified in the same way. In certain embodiments, the combined use of a targeting vector (including, for example, an LTVEC) with a nuclease agent results in biallelic homozygous targeted genetic modification of the genomic locus of interest in a cell. In one embodiment, the biallelic genetic modification comprises deletion of an endogenous nucleic acid sequence at the genomic locus of interest in two homologous chromosomes (i.e., a pair of first and second chromosomes) and insertion of the insert nucleic acid at the genomic locus of interest in two homologous chromosomes (i.e., the pair of first and second homologous chromosomes). In some embodiments, the insert nucleic acid replaces the endogenous nucleic acid sequence at the genomic locus of interest in both homologous chromosomes. In one embodiment, the insert nucleic acid is homologous or orthologous to the deleted endogenous nucleic acid sequence.

In one embodiment, the targeted genetic modification at the target locus results in a hemizygous genetically modified cell. By "hemizygous" is meant that only one allele (i.e., the allele on one of two homologous chromosomes) of the target locus is present or only one allele is capable of being expressed and functional. In other embodiments, the targeted genetic modification results more generally in compound heterozygosity. Compound heterozygosity includes situations in which both alleles of the target locus (i.e., the alleles on both homologous chromosomes) have been modified, but they have been modified in different ways (e.g., an insertion in one allele and inactivation or disruption of the other allele). In certain embodiments, the combined use of a targeting vector (including, for example, an LTVEC) with a nuclease agent results in hemizygous targeted genetic modification of the genomic locus of interest in a cell. In certain embodiments, the combined use of a targeting vector (including, for example, an LTVEC) with a nuclease agent results in targeted genetic modifications that create compound heterozygosity at a genomic locus of interest in a cell. In one embodiment, the targeted genetic modification at the genomic locus of interest in one chromosome comprises deletion of an endogenous nucleic acid sequence and insertion of the insert nucleic acid. In other embodiments, the targeted genetic modification comprises: (1) deletion of an endogenous nucleic acid sequence at the genomic locus of interest in two homologous chromosomes; and (2) insertion of the insert nucleic acid into the genomic locus of interest in a first chromosome and disruption of the genomic locus of interest in a second chromosome. The first chromosome can be the first of the two homologous chromosomes, and the second chromosome can be the second of the two homologous chromosomes. In other embodiments, the targeted modification comprises: (1) deletion of an endogenous nucleic acid sequence at the genomic locus of interest and insertion of the insert nucleic acid into the genomic locus of interest in the first homologous chromosome; and (2) disruption of the genomic locus of interest in the second homologous chromosome. Disruption of the endogenous nucleic acid sequence can result, for example, when a double-strand break at the genomic locus of interest created by the nuclease agent is repaired by non-homologous end joining (NHEJ)-mediated DNA repair, which generates a mutant allele comprising an insertion or a deletion of a nucleic acid sequence at the genomic locus of interest and thereby causes disruption of the genomic locus of interest. Examples of disruption include alteration of a regulatory element (e.g., promoter or enhancer) at the genomic locus of interest, a missense mutation, a truncation mutation, a null mutation, or an insertion or deletion of small number of nucleotides (e.g., causing a frameshift mutation). Another example of disruption is a nonsense mutation. Disruption can result in inactivation (i.e., loss of function) or loss of the allele.

Homozygous and hemizygous targeted genetic modifications are advantageous because when genetically modified cells containing these mutations are used to generate genetically modified animals as discussed below, the process for generating genetically modified animals that are non-heterozygous (i.e., homozygous or hemizygous) for the intended targeted genetic modification is more efficient and less-time consuming because fewer breeding steps are required. Targeted genetic modifications resulting in compound heterozygosity or hemizygosity (e.g., an insertion in one allele and inactivation, disruption, or loss of the other allele) can be advantageous for the same reason.

Various cell types can also be used in any of the various methods described herein above for modifying a genomic locus via a nuclease agent. In specific embodiments, the cell is a eukaryotic cell, non-rat eukaryotic cell, a pluripotent cell, a non-pluripotent cell, a non-human pluripotent cell, a human pluripotent cell, a human ES cell, a human adult stem cell, a developmentally restricted human progenitor cell, a human induced pluripotent cell (iPS) cell, a mammalian cell, a human cell, a fibroblast, a rodent cell, non-rat rodent cell, a mouse cell, a hamster cell or a CHO cell.

Compositions are provided which comprise a genetically modified non-human animal, having a targeted genetic modification in the interleukin-2 receptor gamma locus or in the ApoE locus. The various methods and compositions provided herein allows for these modified loci to be transmitted through the germline.

In specific embodiments, a genetically modified non-human animal, or a genetically modified pluripotent or non-pluripotent cell comprises a genomic locus having a targeted genetic modification in the interleukin-2 gamma receptor locus or having a targeted genetic modification in the ApoE locus, wherein the interleukin-2 gamma receptor genomic locus or the ApoE locus comprise: (i) a deletion of at least a portion of the interleukin-2 gamma receptor locus or at least a portion of the ApoE locus; (ii) an insertion of a heterologous nucleic acid sequence into the ApoE locus or into the interleukin-2 gamma receptor locus; or (iii) a combination thereof, wherein the genetically modified genomic locus is capable of being transmitted through the germline.

Methods are further provided that allow for such genetically modified non-human animals, and for such genetically modified pluripotent cells to be made. Such methods include a method for modifying an ApoE genomic locus or an interleukin-2 gamma receptor locus in a pluripotent cell via targeted genetic modification. The method comprises (a) introducing into the pluripotent cell a targeting vector comprising an insert nucleic acid flanked with a 5' homology arm, to the ApoE locus and a 3' homology arm, to the ApoE locus, (b) identifying a genetically modified pluripotent cell comprising the targeted genetic modification at the ApoE genomic locus of interest, wherein the targeted genetic modification is capable of being transmitted through germline.

Additional methods include (a) introducing into the pluripotent cell a targeting vector comprising an insert nucleic acid flanked with a 5' homology arm to the interleukin-2 receptor gamma locus and a 3' homology arm to the interleukin-2 receptor gamma locus, (b) identifying a genetically modified pluripotent cell comprising the targeted genetic modification at the interleukin-2 receptor gamma locus, wherein the targeted genetic modification is capable of being transmitted through germline.

iii. Methods of Integrating Multiple Polynucleotides of Interest at the Targeted Locus The various methods and compositions provided herein allow for the targeted integration of multiple polynucleotides of interest with a given target locus. The various methods set forth above can be sequentially repeated to allow for the targeted integration of any number of insert nucleic acids into a given targeted locus. Thus, the various methods provide for the insertion of at least 1, 2, 3, 4, 5, 6, 7, 8, 9, 10, 11, 12, 13, 14, 15, 16, 17, 18, 19, 20 or more insert nucleic acids into the target locus. In particular embodiments, such sequential tiling methods allow for the reconstruction of large genomic regions from a eukaryotic cell, for example, non-rat eukaryotic cell, a mammalian cell (i.e., a human, a non-human, a rodent, a non-rat rodent, a mouse, a monkey, a rat, a hamster, a domesticated mammal or an agricultural animal) into a targeted locus. In such instances, the transfer and reconstruction of genomic regions that include both coding and non-coding regions allow for the complexity of a given region to be preserved by retaining, at least in part, the coding regions, the non-coding regions and the copy number variations found within the native genomic region. Thus, the various methods provide, for example, methods to generate "heterologous" or "exogenous" genomic regions within any eukaryotic cell, any non-rat eukaryotic cell, any mammalian cell or animal of interest, particularly within a prokaryotic host cell or within a non-pluripotent cell, a pluripotent cell or an ES cell. In one non-limiting example, a "humanized" genomic region within a non-human animal (i.e., within a rat) is generated. Methods to generate genomic regions within any cell are provided herein. In specific embodiments, the cell is a eukaryotic cell, a non-rat eukaryotic cell, a pluripotent cell, a non-pluripotent cell, a non-human pluripotent cell, a human pluripotent cell, a human ES cell, a human adult stem cell, a developmentally restricted human progenitor cell, a human induced pluripotent cell (iPS) cell, a mammalian cell, a human cell, a fibroblast, a rodent cell, a non-rat rodent cell, a mouse cell, a hamster cell or a CHO cell.

3. A Humanized Genomic Locus

Provided herein are various methods and compositions comprising a humanized genomic locus. As used herein, by "humanized" genomic locus is meant a region of a non-human genome comprising at least one human nucleic acid sequence. The humanized genomic locus can comprise a region of DNA from any organism that has a human DNA sequence inserted therein. In specific embodiments, the organism is a eukaryote, a non-rat eukaryote, a non-human mammal, a mammal, a human, a rodent, a non-rat rodent, a rat, a mouse or a hamster. For example, a "humanized rat locus" comprises a region of rat DNA that has a human DNA sequence inserted therein.

The human DNA sequence can be a naturally occurring human DNA sequence or it can be modified from its native form. In specific embodiments, the human DNA shares at least 85%, 90%, 91%, 92%, 93%, 94%, 95%, 96%, 97%, 98%, or 99% sequence identity to a native human sequence. If a human sequence is not a native human sequence it at least has greater sequence identity to a native human sequence than it does to an orthologous non-human sequence. Moreover, the human DNA sequence can comprise a cDNA, a region of human genomic DNA, a non-coding regulatory region, or any portion of a coding, genomic, or regulatory region of the human DNA. The human DNA sequence inserted into the non-human locus can comprise any of the insert polynucleotides as described elsewhere herein. In specific embodiments, the human DNA sequence is orthologous to the non-human target locus, while in other instances, the human DNA sequence is homologous to the non-human target locus.

In one embodiment, the targeted genetic modification is an insertion or a replacement of an endogenous nucleic acid sequence, with a homologous or orthologous human nucleic acid sequence. In one embodiment, the targeted genetic modification comprises an insertion or replacement of an endogenous nucleic acid sequence with a homologous or orthologous human nucleic acid sequence at an endogenous locus that comprises the corresponding non-human nucleic acid sequence.

Methods for making a humanized locus comprise introducing into the target locus comprising a nucleic acid a human nucleic acid sequence. In one embodiment, a method of making a humanized non-human animal provided. Such a method comprises (a) modifying a genome of a non-human pluripotent cell or non-pluripotent cell with a targeting vector comprising an insert nucleic acid that comprises a human nucleic acid sequence to form a donor cell; (b) introducing the donor cell into a host embryo; and (c) gestating the host embryo in a surrogate mother; wherein the surrogate mother produces a progeny that comprises the human nucleic acid sequence. In specific embodiments, the humanized locus is capable of being transmitted through the germline. In a further embodiment, the targeting vector comprises a large targeting vector (LTVEC) and the insert nucleic acid that comprises a human nucleic acid sequence is at least 5 kb.

In other methods, the humanized genomic locus is made by modifying a target locus of a nucleic acid via bacterial homologous recombination (BHR). The method comprises introducing into a prokaryotic cell a targeting vector comprising an insert nucleic acid flanked with a 5' homology arm and a 3' homology arm, wherein the insert nucleic acid comprises a human nucleic acid sequence, and wherein the prokaryotic cell comprises a nucleic acid and is capable of expressing a recombinase that mediates the BHR at the target locus.

The humanized genomic locus can comprise (a) an insertion of a homologous or orthologous human nucleic acid sequence; (b) a replacement of an endogenous nucleic acid sequence with a homologous or orthologous human nucleic acid sequence; or (c) a combination thereof. In specific embodiments, the humanized genomic locus is capable of being transmitted through the germline. In still other embodiments, the human orthologous sequence replaces the corresponding sequence found in the non-human locus.

Any human nucleic acid sequence can be used in the methods and compositions provided herein. Non-limiting examples of human nucleic acid sequences that can be used in the methods and compositions are discussed in detail elsewhere herein.

The human nucleic acid sequence for insertion into a locus of interest can be any size. In one embodiment, the human nucleic acid sequence can be from about 500 nucleotides to about 200 kb, from about 500 nucleotides to about 5 kb, from about 5 kb to about 200 kb, from about 5 kb to about 10 kb, from about 10 kb to about 20 kb, from about 20 kb to about 30 kb, from about 30 kb to about 40 kb, from about 40 kb to about 50 kb, from about 60 kb to about 70 kb, from about 80 kb to about 90 kb, from about 90 kb to about 100 kb, from about 100 kb to about 110 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb. In a specific embodiment, the human nucleic acid sequence is at least 5 kb.

In one embodiment, a genomic locus is provided wherein the homologous or orthologous human nucleic acid sequence comprises (a) one or more unrearranged human immunoglobulin heavy chain $V_H$ gene segments, one or more unrearranged human immunoglobulin heavy chain D gene segments, and one or more unrearranged human immunoglobulin heavy chain $J_H$ gene segments, which are operably linked to a mammalian heavy chain constant region nucleic acid sequence; (b) a rearranged human immunoglobulin heavy chain variable region nucleic acid sequence operably linked to a mammalian immunoglobulin heavy chain constant region nucleic acid sequence; (c) one or more unrearranged human immunoglobulin $V_\kappa$ or $V_\lambda$ gene segments and one or more unrearranged human immunoglobulin $J_\kappa$ or $J_\lambda$ gene segments, which are operably linked to a mammalian, immunoglobulin λ or κ light chain light chain constant region nucleic acid sequence; or (d) a rearranged human immunoglobulin λ or κ light chain variable region nucleic acid sequence operably linked to a mammalian immunoglobulin λ or κ light chain light chain constant region nucleic acid sequence.

In another embodiment, a genomic locus is provided wherein (a) the mammalian immunoglobulin heavy chain constant region nucleic acid sequence is a constant region nucleic acid sequence, a human constant region nucleic acid sequence, or a combination thereof; or (b) the mammalian immunoglobulin λ or κ light chain light chain constant region nucleic acid sequence is a rat constant region nucleic acid sequence, a human constant region nucleic acid sequence, or a combination thereof.

In a specific embodiment, a genomic locus is provided wherein the immunoglobulin heavy chain constant region nucleic acid sequence is selected from or comprises a $C_H1$, a hinge, a $C_H2$, a $C_H3$, and/or a combination thereof.

In one embodiment, the genomic locus comprises one or more functional human $V_H$ gene segments comprising $V_H1$-2, $V_H1$-3, $V_H1$-8, $V_H1$-18, $V_H1$-24, $V_H1$-45, $V_H1$-46, $V_H1$-58, $V_H1$-69, $V_H2$-5, $V_H2$-26, $V_H2$-70, $V_H3$-7, $V_H3$-9, $V_H3$-11, $V_H3$-13, $V_H3$-15, $V_H3$-16, $V_H3$-20, $V_H3$-21, $V_H3$-23, $V_H3$-30, $V_H3$-30-3, $V_H3$-30-5, $V_H3$-33, $V_H3$-35, $V_H3$-38, $V_H3$-43, $V_H3$-48, $V_H3$-49, $V_H3$-53, $V_H3$-64, $V_H3$-66, $V_H3$-72, $V_H3$-73, $V_H3$-74, $V_H4$-4, $V_H4$-28, $V_H4$-30-1, $V_H4$-30-2, $V_H4$-30-4, $V_H4$-31, $V_H4$-34, $V_H4$-39, $V_H4$-59, $V_H4$-61, $V_H5$-51, $V_H6$-1, $V_H7$-4-1, $V_H7$-81, or a combination thereof.

In one embodiment, the genomic locus comprises one or more functional human D gene segments comprising D1-1, D1-7, D1-14, D1-20, D1-26, D2-2, D2-8, D2-15, D2-21, D3-3, D3-9, D3-10, D3-16, D3-22, D4-4, D4-11, D4-17, D4-23, D5-12, D5-5, D5-18, D5-24, D6-6, D6-13, D6-19, D6-25, D7-27, or a combination thereof.

In one embodiment, the genomic locus comprises one or more functional $J_H$ gene segments comprising $J_H1$, $J_H2$, $J_H3$, $J_H4$, $J_H5$, $J_H6$, and/or a combination thereof. In one embodiment, the insert nucleic acid comprises one or more human Vκ gene segments comprises Vκ4-1, Vκ5-2, Vκ7-3, Vκ2-4, Vκ1-5, Vκ3-7, Vκ2-10, Vκ3-11, Vκ1-12, Vκ1-13, Vκ2-14, Vκ3-15, Vκ1-16, Vκ1-17, Vκ2-18, Vκ2-19, Vκ3-20, Vκ6-21, Vκ1-22, Vκ1-23, Vκ2-24, Vκ3-25, Vκ2-26, Vκ1-27, Vκ2-28, Vκ2-29, Vκ2-30, Vκ3-31, Vκ1-32, Vκ1-33, Vκ3-34, Vκ1-35, Vκ2-36, Vκ1-37, Vκ2-38, Vκ1-39, Vκ2-40, or a combination thereof.

In one embodiment, the genomic locus comprises one or more human Vλ gene segments comprising Vλ3-1, Vλ4-3, Vλ2-8, Vλ3-9, Vλ3-10, Vλ2-11, Vλ3-12, Vλ2- 14, Vλ3-16, Vλ2-18, Vλ3-19, Vλ3-21, Vλ3-22, Vλ2-23, Vλ3-25, Vλ3-27, or a combination thereof.

In one embodiment, the genomic locus comprises one or more human Jκ gene segments comprising Jκ1, Jκ2, Jκ3, Jκ4, Jκ5, or a combination thereof.

In yet another embodiment, the genomic locus, comprises a humanized genomic locus comprising a human interleukin-2 receptor (IL2R) nucleic acid sequence or a variant or a fragment thereof is provided. In specific embodiments, the IL2R nucleic acid sequence comprises an interleukin-2 receptor alpha, an interleukin-2 receptor beta, or an interleukin-2 receptor gamma nucleic acid sequence or variants or fragments thereof.

In further embodiments, a genomic locus, comprises a humanized genomic locus comprising of a portion of the human ApoE locus, the human interleukin-2 receptor gamma locus, the human Rag2 locus, the human Rag1 locus and/or the human Rag2/Rag1 locus replacing the corresponding homologous or orthologous portion of the non-human ApoE locus, interleukin-2 receptor gamma locus, Rag2 locus, Rag1 locus and/or Rag2/Rag1 locus. In one embodiment, the non-human ecto-domain of IL-2Rg is replaced with the ecto-domain of human IL-2Rg, with the remainder of the molecule being from the non-human.

In another embodiment, a genetically modified non-human animal, comprising a humanized genomic locus is provided. Such genetically modified non-human animals comprise (a) an insertion of a homologous or orthologous human nucleic acid sequence; (b) a replacement of nucleic acid sequence with a homologous or orthologous human nucleic acid sequence at an endogenous genomic locus; or (c) a combination thereof, wherein the humanized genomic locus is capable of being transmitted through the germline.

Genetically modified animals, including non-human animals) comprising any of the various humanized genomic loci provided herein and described above are also provided.

4. Polynucleotides of Interest

Any polynucleotide of interest may be contained in the various insert nucleic acids and thereby integrated at the target locus. The methods disclosed herein, provide for at least 1, 2, 3, 4, 5, 6 or more polynucleotides of interest to be integrated into the targeted genomic locus.

The polynucleotide of interest within the insert nucleic acid when integrated at the target genomic locus can introduce one or more genetic modifications into the cell. The genetic modification can comprise a deletion of an endogenous nucleic acid sequence and/or the addition of an exogenous or heterologous or orthologous polynucleotide into the target genomic locus. In one embodiment, the genetic modification comprises a replacement of an endogenous nucleic acid sequence with an exogenous polynucleotide of interest at the target genomic locus. Thus, methods provided herein allow for the generation of a genetic modification comprising a knockout, a deletion, an insertion, a replacement ("knock-in"), a point mutation, a domain swap, an exon swap, an intron swap, a regulatory sequence swap, a gene swap, or a combination thereof. Such modifications may occur upon integration of the first, second, third, fourth, fifth, six, seventh, or any subsequent insert nucleic acids into the target genomic locus.

The polynucleotide of interest within the insert nucleic acid and/or integrated at the target locus can comprise a sequence that is native to the cell it is introduced into; the polynucleotide of interest can be heterologous to the cell it is introduced to; the polynucleotide of interest can be exogenous to the cell it is introduced into; the polynucleotide of interest can be orthologous to the cell it is introduced into; or the polynucleotide of interest can be from a different species than the cell it is introduced into. As used herein "native" in reference to a sequence inserted at the target locus is a sequence that is native to the cell having the target locus or native to the cell from which the target locus was derived (i.e., from a rat). As used herein, "heterologous" in reference to a sequence includes a sequence that originates from a foreign species, or, if from the same species, is substantially different or modified from its native form in composition and/or genomic locus by deliberate human intervention. As used herein, "exogenous" in reference to a sequence is a sequence that originates from a foreign species. The polynucleotide of interest can be from any organism of interest including, but not limited to, non-human, a rodent, a non-rat rodent, a hamster, a mouse, a rat, a human, a monkey, an agricultural mammal or a non-agricultural mammal. The polynucleotide of interest can further comprise a coding region, a non-coding region, a regulatory region, or a genomic DNA. Thus, the 1st, 2nd, 3rd, 4th, 5th, 6th, 7th, and/or any of the subsequent insert nucleic acids can comprise such sequences.

In one embodiment, the polynucleotide of interest within the insert nucleic acid and/or integrated at the target locus is native to a mouse nucleic acid sequence, a human nucleic acid, a non-human nucleic acid, a eukaryotic nucleic acid, a non-rat eukaryotic nucleic acid, a non-human mammalian nucleic acid, a mammalian nucleic acid, a rodent nucleic acid, a non-rat rodent nucleic acid, a rat nucleic acid, a hamster nucleic acid, a monkey nucleic acid, an agricultural mammal nucleic acid, or a non-agricultural mammal nucleic acid. In still further embodiments, the polynucleotide of interest integrated at the target locus is a fragment of a genomic nucleic acid. In one embodiment, the genomic nucleic acid is a mouse genomic nucleic acid, a human genomic nucleic acid, a non-human nucleic acid, a eukaryotic nucleic acid, a non-rat eukaryotic nucleic acid, a non-human mammalian nucleic acid, a mammalian nucleic acid, a rodent nucleic acid, a non-rat rodent nucleic acid, a rat nucleic acid, a hamster nucleic acid, a monkey nucleic acid, an agricultural mammal nucleic acid or a non-agricultural mammal nucleic acid or a combination thereof.

In one embodiment, the polynucleotide of interest can range from about 500 nucleotides to about 200 kb as described above. The polynucleotide of interest can be from about 500 nucleotides to about 5 kb, from about 5 kb to about 200 kb, from about 5 kb to about 10 kb, from about 10 kb to about 20 kb, from about 20 kb to about 30 kb, from about 30 kb to about 40 kb, from about 40 kb to about 50 kb, from about 60 kb to about 70 kb, from about 80 kb to about 90 kb, from about 90 kb to about 100 kb, from about 100 kb to about 110 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb, from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb.

The polynucleotide of interest within the insert nucleic acid and/or inserted at the target genomic locus can encode a polypeptide, can encode an miRNA, or it can comprise any regulatory regions or non-coding regions of interest including, for example, a regulatory sequence, a promoter sequence, an enhancer sequence, a transcriptional repressor-binding sequence, or a deletion of a non-protein-coding sequence, but does not comprise a deletion of a protein-coding sequence. In addition, the polynucleotide of interest within the insert nucleic acid and/or inserted at the target genomic locus can encode a protein expressed in the nervous system, the skeletal system, the digestive system, the circulatory system, the muscular system, the respiratory system, the cardiovascular system, the lymphatic system, the endocrine system, the urinary system, the reproductive system, or a combination thereof. In one embodiment, the polynucleotide of interest within the insert nucleic acid and/or inserted at the target genomic locus encodes a protein expressed in a bone marrow or a bone marrow-derived cell. In one embodiment, the polynucleotide of interest within the insert nucleic acid and/or integrated at the target locus encodes a protein expressed in a spleen cell. In still further embodiments, the polynucleotide of interest within the insert nucleic acid and/or inserted at the target locus encodes a protein expressed in a B cell, encodes a protein expressed in an immature B cell or encodes a protein expressed in a mature B cell.

The polynucleotide of interest within the insert polynucleotide can comprise a portion of an ApoE locus, an Il2rg locus, a Rag1 locus, a Rag2 locus and/or a Rag2/Rag1 locus. Such portions of these given loci are discussed elsewhere herein, as are the various homologous and orthologous regions from any organism of interest that can be employed.

In one embodiment, polynucleotide of interest within the insert nucleic acid and/or inserted at the target locus comprises a genomic nucleic acid sequence that encodes an immunoglobulin heavy chain variable region amino acid sequence. The phrase "heavy chain," or "immunoglobulin heavy chain" are described elsewhere herein.

In one embodiment, the polynucleotide of interest within the insert nucleic acid and/or integrated at the target locus comprises a genomic nucleic acid sequence that encodes a human immunoglobulin heavy chain variable region amino acid sequence.

In one embodiment, the genomic nucleic acid sequence comprises one or more unrearranged human immunoglobulin heavy chain $V_H$ gene segments, one or more unrearranged human immunoglobulin heavy chain D gene segments, and one or more unrearranged human immunoglobulin heavy chain $J_H$ gene segments, which are operably linked to a mammalian heavy chain constant region nucleic acid sequence. In one embodiment, the genomic nucleic acid sequence comprises a rearranged human immunoglobulin heavy chain variable region nucleic acid sequence operably linked to a mammalian heavy chain constant region nucleic acid sequence. In one embodiment, the genomic nucleic acid sequence comprises one or more unrearranged human immunoglobulin $V_\kappa$ or $V_\lambda$ gene segments and one or more unrearranged human immunoglobulin $J_\kappa$ or $J_\lambda$ gene segments, which are operably linked to a mammalian immunoglobulin λ or κ light chain light chain constant region nucleic acid sequence. In one embodiment, the genomic nucleic acid sequence comprises a rearranged human immunoglobulin λ or κ light chain variable region nucleic acid sequence operably linked to a mammalian immunoglobulin λ or κ light chain light chain constant region nucleic acid sequence. In one embodiment, the heavy chain constant region nucleic acid sequence comprises a rat constant region nucleic acid sequence, a human constant region nucleic acid sequence, or a combination thereof. In one embodiment, the immunoglobulin λ or κ light chain constant region nucleic acid comprises a rat constant region nucleic acid sequence, a human constant region nucleic acid sequence, or a combination thereof.

In one embodiment, the immunoglobulin heavy chain constant region nucleic acid sequence is selected from or comprises a $C_H1$, a hinge, a $C_H2$, a $C_H3$, and/or a combination thereof. In one embodiment, the heavy chain constant region nucleic acid sequence comprises a $C_H1$-hinge-$C_H2$-$C_H3$.

In one embodiment, the polynucleotide of interest within the insert nucleic acid and/or integrated at the target locus comprises a genomic nucleic acid sequence that encodes an immunoglobulin light chain variable region amino acid sequence. The phrase "light chain" includes an immunoglobulin light chain sequence from any organism, and is described elsewhere herein.

In one embodiment, the polynucleotide of interest within the insert nucleic acid and/or integrated at the target genomic locus comprises a genomic nucleic acid sequence that encodes a human immunoglobulin light chain variable region amino acid sequence.

In one embodiment, the genomic nucleic acid sequence comprises one or more unrearranged human immunoglobulin $V_\kappa$ or $V_\lambda$ gene segments and one or more unrearranged human immunoglobulin $J_\kappa$ or $J_\lambda$ gene segments, which are operably linked to a rodent immunoglobulin λ or κ light chain light chain constant region nucleic acid sequence. In one embodiment, the genomic nucleic acid sequence comprises a rearranged human immunoglobulin λ or κ light chain variable region nucleic acid sequence operably linked to a rodent immunoglobulin λ or κ light chain light chain constant region nucleic acid sequence. In one embodiment, the light chain constant region nucleic acid sequence comprises a rat constant region nucleic acid sequence, a human constant region nucleic acid sequence, or a combination thereof. In one embodiment, the immunoglobulin λ or κ light chain constant region nucleic acid comprises a rat constant region nucleic acid sequence, a human constant region nucleic acid sequence, or a combination thereof.

The polynucleotide of interest within the insert nucleic acid and/or integrated at the target locus can encode an extracellular protein or a ligand for a receptor. In specific embodiments, the encoded ligand is a cytokine. Cytokines of interest includes a chemokine selected from or comprising CCL, CXCL, CX3CL, and/or XCL. The cytokine can also comprise a tumor necrosis factor (TNF). In still other embodiments, the cytokine is an interleukin (IL). In one embodiment, the interleukin is selected from or comprises IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, and/or IL-36. In one embodiment, the interleukin is IL-2. In specific embodiments, such polynucleotides of interest within the insert nucleic acid and/or integrated at the target genomic locus are from a human and, in more specific embodiments, can comprise human genomic sequence.

The polynucleotide of interest within the insert nucleic acid and/or integrated at the target genomic locus can encode Apolipoprotein E (ApoE).

The polynucleotide of interest within the insert nucleic acid and/or integrated at the target locus can encode a cytoplasmic protein or a membrane protein. In one embodiment, the membrane protein is a receptor, such as, a cytokine receptor, an interleukin receptor, an interleukin 2 receptor-alpha, an interleukin-2 receptor beta, an interleukin-2 receptor gamma or receptor tyrosine kinase. In other instances, the polynucleotide of interest within the insert nucleic acid and/or integrated at the target locus can comprise an orthologous or homologous region of the target locus.

The polynucleotide of interest within the insert nucleic acid and/or integrated at the target locus can comprise a polynucleotide encoding at least a region of a T cell receptor, including the T cell receptor alpha. In specific methods each of the insert nucleic acids comprise a genomic region of the T cell receptor locus (i.e., the T cell receptor alpha locus) such that upon completion of the serial integration, a portion or the entirety of the genomic T cell receptor locus has been integrated at the target locus. Such insert nucleic acids can comprise at least one or more of a variable segment or a joining segment of a T cell receptor locus (i.e., of the T cell receptor alpha locus). In still further embodiments, the polynucleotide of interest encoding the region of the T cell receptor can be from, for example, a eukaryote, a non-rat eukaryote, a mammal, a non-human mammal, rodent, non-rat rodent, mouse, rat, a human, a monkey, a hamster, an agricultural mammal or a domestic mammal polynucleotide encoding a mutant protein.

In other embodiments, the polynucleotide of interest integrated at the target locus encodes a nuclear protein. In one embodiment, the nuclear protein is a nuclear receptor. In specific embodiments, such polynucleotides of interest within the insert nucleic acid and/or integrated at the target locus are from a human and, in more specific embodiments, can comprise human genomic sequence.

The polynucleotide of interest within the insert nucleic acid and/or integrated at the target genomic locus can comprise a genetic modification in a coding sequence. Such genetic modifications include, but are not limited to, a deletion mutation of a coding sequence or the fusion of two coding sequences.

The polynucleotide of interest within the insert nucleic acid and/or integrated at the target locus can comprise a polynucleotide encoding a mutant protein, including, for example, a human mutant protein. In one embodiment, the mutant protein is characterized by an altered binding characteristic, altered localization, altered expression, and/or altered expression pattern. In one embodiment, the polynucleotide of interest within the insert nucleic acid and/or integrated at the target locus comprises at least one disease allele, including for example, an allele of a neurological disease, an allele of a cardiovascular disease, an allele of a kidney disease, an allele of a muscle disease, an allele of a blood disease, an allele of a cancer-causing gene, or an allele of an immune system disease. In such instances, the disease allele can be a dominant allele or the disease allele is a recessive allele. Moreover, the disease allele can comprises a single nucleotide polymorphism (SNP) allele. The polynucleotide of interest encoding the mutant protein can be from any organism, including, but not limited to, a eukaryote, a non-rat eukaryote, a mammal, a non-human mammal, rodent, non-rat rodent, mouse, rat, a human, a hamster, a monkey, an agricultural mammal or a domestic mammal polynucleotide encoding a mutant protein.

In one embodiment, the genetic modification produces a mutant form of a protein with an altered binding characteristic, altered localization, altered expression, and/or altered expression pattern.

In one embodiment, the genetic modification produces a deletion, addition, replacement or a combination thereof of a region of the ApoE locus, for example, the rat ApoE locus, wherein the genetic modification at the ApoE locus results in a decrease in ApoE activity. In one embodiment, an ApoE knockout is generated.

In one embodiment, the genetic modification produces a deletion, addition, replacement or a combination thereof of a region of the Rag1 locus, for example, the rat Rag1 locus, wherein the genetic modification at the Rag1 locus results in a decrease in Rag1 activity. In one embodiment, a Rag1 knockout is generated. In one embodiment, the genetic modification produces a deletion, addition, replacement or a combination thereof of a region of the Rag2 locus, for example, the rat Rag2 locus, wherein the genetic modification at the Rag2 locus results in a decrease in Rag2 activity. In one embodiment, a Rag2 knockout is generated. In one embodiment, the genetic modification produces a deletion, addition, replacement or a combination thereof of a region of the Rag1/Rag2 locus, for example, the rat Rag1/Rag2 locus, wherein the genetic modification at the Rag1/Rag2 locus results in a decrease in Rag1 activity and a decrease in Rag2 activity. In one embodiment, a Rag11Rag2 knockout is generated.

In one embodiment, the genetic modification produces a deletion, addition, replacement or a combination thereof of a region of the interleukin-2 receptor gamma locus, for example, the rat interleukin-2 receptor gamma locus, wherein the genetic modification at the interleukin-2 receptor gamma locus results in a decrease in interleukin-2 receptor gamma. In one embodiment, an interleukin-2 receptor gamma knockout is generated.

As discussed elsewhere herein, further embodiments provided herein comprises one or more of the ApoE locus, the interleukin-2 receptor gamma locus, the Rag2 locus, the Rag1 locus and/or the Rag2/Rag1 locus, for example, the rat ApoE locus, the rat interleukin-2 receptor gamma locus, the Rag2 locus, the Rag1 locus and/or the Rag2/Rag1 locus, is modified through the replacement of a portion of the rat ApoE locus, the interleukin-2 receptor gamma locus, the Rag2 locus, the Rag1 locus and/or Rag2/Rag1 locus with the corresponding orthologous portion of an ApoE locus, an interleukin-2 receptor gamma locus, a Rag2 locus, a Rag1 locus and/or a Rag2/Rag1 locus from another organism.

In one embodiment, multiple genetic modifications are generated. In one embodiment, a genetic modification produces a deletion, addition, replacement or a combination thereof of a region of interleukin-2 receptor gamma locus, for example, the rat interleukin-2 receptor gamma locus, wherein the genetic modification at the interleukin-2 receptor gamma locus results in a decrease in interleukin-2 receptor gamma and a second genetic modification produces a deletion, addition, replacement or a combination thereof of a region of the rat Rag2 locus, wherein the genetic modification at the Rag2 locus results in a decrease in Rag2 activity. In one embodiment, an interleukin-2 receptor gamma/Rag2 knockout is generated. Such a rat has a SCID phenotype.

In one embodiment, the mammalian nucleic acid comprises a genomic locus that encodes a protein expressed in the nervous system, the skeletal system, the digestive system, the circulatory system, the muscular system, the respiratory system, the cardiovascular system, the lymphatic system, the endocrine system, the urinary system, the reproductive system, or a combination thereof. In one embodiment, the mammalian nucleic acid comprises a genomic locus that encodes a protein expressed in a bone marrow or a bone marrow-derived cell. In one embodiment, the nucleic acid comprises a genomic locus that encodes a protein expressed in a spleen cell. In one embodiment, the genomic locus comprises a mouse genomic DNA sequence, a rat genomic DNA sequence, a human genomic DNA sequence, or a combination thereof. In one embodiment, the genomic locus comprises, in any order, rat and human genomic DNA sequences. In one embodiment, the genomic locus comprises, in any order, mouse and human genomic DNA sequences. In one embodiment, the genomic locus comprises, in any order, mouse and rat genomic DNA sequences. In one embodiment, the genomic locus comprises, in any order, rat, mouse, and human genomic DNA sequences.

In one embodiment, the insert nucleic acid comprises a genetic modification in a coding sequence of a gene. In one embodiment, the genetic modification comprises a deletion mutation in the coding sequence. In one embodiment, the genetic modification comprises a fusion of two endogenous coding sequences.

In one embodiment, the genetic modification comprises a deletion of a non-protein-coding sequence, but does not comprise a deletion of a protein-coding sequence. In one embodiment, the deletion of the non-protein-coding sequence comprises a deletion of a regulatory element. In one embodiment, the genetic modification comprises an addition of a promoter. In one embodiment, the genetic modification comprises a replacement of a promoter or regulatory element. In one embodiment, the regulatory element is an enhancer. In one embodiment, the regulatory element is a transcriptional repressor-binding element.

In one embodiment, the genetic modification comprises placement of a human nucleic acid sequence encoding a mutant human protein. In one embodiment, the genetic modification comprises at least one human disease allele of a human gene. In one embodiment, the human disease is a neurological disease. In one embodiment, the human disease is a cardiovascular disease. In one embodiment, the human disease is a kidney disease. In one embodiment, the human disease is a muscle disease. In one embodiment, the human disease is a blood disease. In one embodiment, the human disease is a cancer. In one embodiment, the human disease is an immune system disease. In one embodiment, the human disease allele is a dominant allele. In one embodiment, the human disease allele is a recessive allele. In one embodiment, the human disease allele comprises a single nucleotide polymorphism (SNP) allele.

The polynucleotide of interest within the insert nucleic acid and/or integrated at the target locus can also comprise a regulatory sequence, including for example, a promoter sequence, an enhancer sequence, or a transcriptional repressor-binding sequence. In specific embodiments, the polynucleotide of interest within the insert nucleic acid and/or integrated at the target genomic locus comprises a polynucleotide having a deletion of a non-protein-coding sequence, but does not comprise a deletion of a protein-coding sequence. In one embodiment, the deletion of the non-protein-coding sequence comprises a deletion of a regulatory sequence. In another embodiment, the deletion of the regulatory element comprises a deletion of a promoter sequence. In one embodiment, the deletion of the regulatory element comprises a deletion of an enhancer sequence. Such a polynucleotide of interest can be from any organism, including, but not limited to, a eukaryote, a non-rat eukaryote, a mammal, a non-human mammal, rodent, non-rat rodent, mouse, rat, a human, a monkey, an agricultural mammal or a domestic mammal polynucleotide encoding a mutant protein.

5. Methods of Introducing Sequences and Generation of Transgenic Animals

As outlined above, methods and compositions are provided herein to allow for the targeted integration of one or more polynucleotides of interest into a target locus. Such systems employ a variety of components and for ease of reference, herein the term "targeted integration system" generically comprises all the components required for an integration event (i.e., in non-limiting examples, the various nuclease agents, recognition sites, insert DNA polynucleotides, targeting vectors, target genomic locus, and/or polynucleotides of interest).

The methods provided herein comprise introducing into a cell one or more polynucleotides or polypeptide constructs comprising the various components of the targeted genomic integration system. "Introducing" means presenting to the cell the sequence (polypeptide or polynucleotide) in such a manner that the sequence gains access to the interior of the cell. The methods provided herein do not depend on a particular method for introducing any component of the targeted genomic integration system into the cell, only that the polynucleotide gains access to the interior of a least one cell. Methods for introducing polynucleotides into various cell types are known in the art and include, but are not limited to, stable transfection methods, transient transfection methods, and virus-mediated methods.

Any cells from any organism can be used in the methods provided herein. In specific embodiments the cells are from a eukaryote, a non-rat eukaryote, a mammal, a non-human mammal, a human, a rodent, a non-rat rodent, a rat, a mouse or a hamster. In specific embodiments, the cells are a eukaryotic cell, a non-rat eukaryotic cell, a pluripotent cell, a non-pluripotent cell, a non-human pluripotent cell, a non-human mammalian cell, a human pluripotent cell, a human ES cell, a human adult stem cell, a developmentally restricted human progenitor cell, a human induced pluripotent cell (iPS) cell, a mammalian cell, a human cell, a fibroblast, a rodent cell, a non-rat rodent cell, a rat cell, a mouse cell, a hamster cell or a CHO cell.

In some embodiments, the cells employed in the methods and compositions have a DNA construct stably incorporated into their genome. "Stably incorporated" or "stably introduced" means the introduction of a polynucleotide into the cell such that the nucleotide sequence integrates into the genome of the cell and is capable of being inherited by progeny thereof. Any protocol may be used for the stable incorporation of the DNA constructs or the various components of the targeted genomic integration system.

Transfection protocols as well as protocols for introducing polypeptides or polynucleotide sequences into cells may vary. Non-limiting transfection methods include chemical-based transfection methods include the use of liposomes; nanoparticles; calcium phosphate (Graham et al. (1973). Virology 52 (2): 456-67, Bacchetti et al. (1977) Proc Natl Acad Sci USA 74 (4): 1590-4 and, Kriegler, M (1991). Transfer and Expression: A Laboratory Manual. New York: W. H. Freeman and Company. pp. 96-97); dendrimers; or cationic polymers such as DEAE-dextran or polyethylenimine. Non chemical methods include electroporation; Sono-poration; and optical transfection. Particle-based transfection include the use of a gene gun, magnet assisted transfection (Bertram, J. (2006) Current Pharmaceutical Biotechnology 7, 277-28). Viral methods can also be used for transfection.

In one embodiment, the introducing one or more of the polynucleotides into a cell is mediated by electroporation, by intracytoplasmic injection, by a viral infection, by an adenovirus, by lentivirus, by retrovirus, by transfection, by lipid-mediated transfection or is mediated via Nucleofection™.

In one embodiment, introduction one or more of the polynucleotides into a cell further comprises: introducing an expression construct comprising a nucleic acid sequence of interest operably linked to a promoter. In one embodiment, the promoter is a constitutively-active promoter. In one embodiment, the promoter is an inducible promoter. In one embodiment, the promoter is active in a stem cell, for example, an embryonic stem cell.

In one embodiment, the expression construct is introduced together with the LTVEC. In one embodiment, the expression construct is introduced separately from the LTVEC over a period of time.

In one embodiment, the introduction of the one or more polynucleotides into the cell can be performed multiple times over a period of time. In one embodiment, the introduction of the one or more polynucleotides into the cell are performed at least two times over a period of time, at least three times over a period of time, at least four times over a period of time, at least five times over a period of time, at least six times over a period of time, at least seven times over a period of time, at least eight times over a period of time, at least nine times over a period of times, at least ten times over a period of time, at least eleven times, at least twelve times over a period of time, at least thirteen times over a period of time, at least fourteen times over a period of time, at least fifteen times over a period of time, at least sixteen times over a period of time, at least seventeen times over a period of time, at least eighteen times over a period of time, at least nineteen times over a period of time, or at least twenty times over a period of time.

In one embodiment, the nuclease agent is introduced into the cell simultaneously with the targeting vector or the large targeting vector (LTVEC). Alternatively, the nuclease agent is introduced separately from the targeting vector or the LTVEC over a period of time. In one embodiment, the nuclease agent is introduced prior to the introduction of the targeting vector or the LTVEC, while in other embodiments, the nuclease agent is introduced following introduction of the targeting vector or the LTVEC.

In one embodiment, screening step comprises a quantitative assay for assessing modification of allele (MOA) of a parental chromosome. In one embodiment, the quantitative assay is carried out via a quantitative PCR. In one embodiment, the quantitative PCR is a real-time PCR (qPCR). In one embodiment, the real-time PCR comprises a first primer set that recognizes the target locus and a second primer set that recognizes a non-targeted reference locus. In one embodiment, the primer set comprises a fluorescent probe that recognizes the amplified sequence. In one embodiment, the quantitative assay is carried out via fluorescence-mediated in situ hybridization (FISH). In one embodiment, the quantitative assay is carried out via comparative genomic hybridization. In one embodiment, the quantitative assay is carried out via isothermic DNA amplification. In one embodiment, the quantitative assay is carried out via isothermic DNA amplification. In one embodiment, the quantitative assay is carried out via quantitative hybridization to an immobilized probe(s). In one embodiment, the quantitative assay is carried out via Invader Probes®. In one embodiment, the quantitative assay is carried out via MMP Assays®. In one embodiment, the quantitative assay is carried out via TaqMan® Molecular Beacon. In one embodiment, the quantitative assay is carried out via Eclipse™ probe technology. (See, for example, US2005/0144655, which is incorporated by reference herein in its entirety).

Further provided is a method for making a humanized non-human animal, comprising: (a) modifying a genome of a pluripotent cell with a targeting vector comprising an insert nucleic acid that comprises a human nucleic acid sequence to form a donor cell; (b) introducing the donor cell into a host embryo; and (c) gestating the host embryo in a surrogate mother; wherein the surrogate mother produces a progeny that comprises the human nucleic acid sequence. In one embodiment, the donor cell is introduced into a host embryo that is at the blastocyst stage or at a pre-morula stage (i.e., a 4 cell stage or an 8 cell stage). Moreover, step (a) can also be performed with a large targeting vector (LTVEC) and/or a human nucleic acid sequence at least 5 kb in length. In still further embodiments, the genetic modification is capable of being transmitted through the germline.

Genetically modified non-human animals can be generated employing the various methods disclosed herein. Such methods comprise (1) integrating one or more polynucleotide of interest at the target locus of a pluripotent cell to generate a genetically modified pluripotent cell comprising the insert nucleic acid in the targeted genomic locus employing the methods disclosed herein; (2) selecting the genetically modified pluripotent cell having the one or more polynucleotides of interest at the target genomic locus; (3) introducing the genetically modified pluripotent cell into a host embryo; and (4) implanting the host embryo comprising the genetically modified pluripotent cell into a surrogate mother. A progeny from the genetically modified pluripotent cell is generated. In one embodiment, the donor cell is introduced into a host embryo at the blastocyst stage or at the pre-morula stage (i.e., the 4 cell stage or the 8 cell stage). Progeny that are capable of transmitting the genetic modification though the germline are generated. The pluripotent cell can be an ES cell as discussed elsewhere herein.

Nuclear transfer techniques can also be used to generate the genetically modified non-human animals. Briefly, methods for nuclear transfer include the steps of: (1) enucleating an oocyte; (2) isolating a donor cell or nucleus to be combined with the enucleated oocyte; (3) inserting the cell or nucleus into the enucleated oocyte to form a reconstituted cell; (4) implanting the reconstituted cell into the womb of an animal to form an embryo; and (5) allowing the embryo to develop. In such methods oocytes are generally retrieved from deceased animals, although they may be isolated also from either oviducts and/or ovaries of live animals. Oocytes can be matured in a variety of medium known to those of ordinary skill in the art prior to enucleation. Enucleation of the oocyte can be performed in a number of manners well known to those of ordinary skill in the art. Insertion of the donor cell or nucleus into the enucleated oocyte to form a reconstituted cell is usually by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell is typically activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, are typically cultured in medium well known to those of ordinary skill in the art and then transferred to the womb of an animal. See, for example, US20080092249, WO/1999/005266A2, US20040177390, WO/2008/017234A1, and U.S. Pat. No. 7,612,250, each of which is herein incorporated by reference.

In one aspect, a method for making a genetically modified non-human animal is provided, comprising modifying a genomic locus of interest in a pluripotent cell employing endonuclease-mediated gene targeting to introduce a modification at a genomic locus of interest to form a modified pluripotent cell, maintaining the modified pluripotent cell under conditions sufficient to maintain pluripotency, employing the modified pluripotent cell as a donor cell in a host embryo, and gestating the host embryo comprising the modified pluripotent cell in a surrogate mother, wherein the host embryo is gestated by the surrogate mother and a genetically modified progeny is born.

In one embodiment, the target sequence is located in an intron. In one embodiment, the target sequence is located in an exon. In one embodiment, the target sequence is located in a promoter. In one embodiment, the target sequence is located in a promoter regulatory region. In one embodiment, the target sequence is located in an enhancer region.

In one embodiment, introducing step is performed multiple times over a period of time using a plurality of endonucleases that recognize distinct target sequences. In one embodiment, step is performed at least two times over a period of time using a plurality of endonucleases that recognize distinct target sequences, at least three times over a period of time using a plurality of endonucleases that recognize distinct target sequences, at least four times over a period of time using a plurality of endonucleases that recognize distinct target sequences, at least five times over a period of time using a plurality of endonucleases that recognize distinct target sequences, at least six times over a period of time using a plurality of endonucleases that recognize distinct target sequences, at least seven times over a period of time using a plurality of endonucleases that recognize distinct target sequences, at least eight times over a period of time using a plurality of endonucleases that recognize distinct target sequences, at least nine times over a period of time using a plurality of endonucleases that recognize distinct target sequences, at least ten times over a period of time using a plurality of endonucleases that recognize distinct target sequences, at least eleven times over a period of time using a plurality of endonucleases that recognize distinct target sequences, at least twelve times over a period of time using a plurality of endonucleases that recognize distinct target sequences, at least thirteen times over a period of time using a plurality of endonucleases that recognize distinct target sequences, at least fourteen times over a period of time using a plurality of endonucleases that recognize distinct target sequences, at least fifteen times over a period of time using a plurality of endonucleases that recognize distinct target sequences, at least sixteen times over a period of time using a plurality of endonucleases that recognize distinct target sequences, at least seventeen times over a period of time using a plurality of endonucleases that recognize distinct target sequences, at least eighteen times over a period of time using a plurality of endonucleases that recognize distinct target sequences, at least nineteen times over a period of time using a plurality of endonucleases that recognize distinct target sequences, or at least twenty times over a period of time using a plurality of endonucleases that recognize distinct target sequences.

In one embodiment, introducing step is mediated by electroporation, by intracytoplasmic injection, by an adenovirus, by lentivirus, by retrovirus, by transfection, by lipid-mediated transfection or is mediated via Nucleofection™.

In one embodiment, the method further comprises introducing an exogenous nucleic acid into the genetically modified pluripotent cell. In one embodiment, the exogenous nucleic acid is a transgene. In one embodiment, the exogenous nucleic acid is introduced into an endogenous locus. In one embodiment, the exogenous nucleic acid is introduced ectopically (e.g., at a locus different from its endogenous locus).

In one aspect, a method for making a genetically modified non-human animal is provided, comprising modifying a genomic locus of interest in a pluripotent cell employing RNA-guided genome engineering to introduce a modification at a genomic locus of interest to form a modified pluripotent cell, maintaining the modified pluripotent cell under conditions sufficient to maintain pluripotency, employing the modified pluripotent cell as a donor cell in a host embryo and gestating the host embryo comprising the modified pluripotent cell in a surrogate mother, wherein the host embryo is gestated by the surrogate mother and a genetically modified progeny is born.

In one embodiment, the method has a targeting rate ranging from about 2% to about 80%.

In one embodiment, the method comprises co-introducing a plurality of the second expression construct comprising distinct genomic target sequences for multiplex editing of distinct genomic loci. In one embodiment, the method comprises introducing a plurality of the second expression construct comprising distinct genomic target sequences for multiplex editing of distinct genomic loci over a period of time.

In one embodiment, introducing step is performed multiple times over a period of time. In one embodiment, introducing step (b) is performed at least two times over a period of time, at least three times over a period of time, at least four times over a period of time, at least five times over a period of time, at least six times over a period of time, at least seven times over a period of time, at least eight times over a period of time, at least nine times over a period of time, at least ten times over a period of time, at least eleven times over a period of time, at least twelve times over a period of time, at least thirteen times over a period of time, at least fourteen times over a period of time, at least fifteen times over a period of time, at least sixteen times over a period of time, at least seventeen times over a period of time, at least eighteen times over a period of time, at least nineteen times over a period of time, at least twenty times over a period of time.

In one embodiment, the first expression construct and the second expression construct are expressed from a same plasmid.

In one embodiment, introducing step is mediated by electroporation, by intracytoplasmic injection, by an adenovirus, by lentivirus, by retrovirus, by transfection, by lipid-mediated transfection or is mediated via Nucleofection™.

In one embodiment, the method further comprises introducing an exogenous nucleic acid into the pluripotent cell comprising the mutant allele.

In one embodiment, the exogenous nucleic acid is a transgene. In one embodiment, the exogenous nucleic acid is introduced into an endogenous locus. In one embodiment, the exogenous nucleic acid is placed ectopically (e.g., at a locus different from its endogenous locus).

In one embodiment, the method further comprises introducing an exogenous nucleic acid into the genetically modified pluripotent cell. In one embodiment, the exogenous nucleic acid is a transgene. In one embodiment, the exogenous nucleic acid is introduced into an endogenous locus. In one embodiment, the exogenous nucleic acid is introduced ectopically (e.g., at a locus different from its endogenous locus).

In one aspect, a method for making a humanized non-human animal is provided, comprising modifying a genome of a pluripotent cell with an LTVEC comprising an insert that comprises a human sequence of at least 5 kb, and employing the pluripotent cell as a donor cell, introducing the donor cell into a host embryo, and gestating the host embryo in a surrogate mother, wherein the surrogate mother births a progeny that comprises the humanization.

Other methods for making a genetically modified non-human animal comprising in its germline one or more genetic modifications as described herein is provided, comprising: (a) modifying a targeted locus contained in a prokaryotic cell employing the various methods described herein; (b) selecting a modified prokaryotic cell comprising the genetic modification at the targeted locus; (c) isolating the genetically modified targeting vector from the genome of the modified prokaryotic cell; (d) introducing the genetically modified targeting vector into a pluripotent cell to generate a genetically modified pluripotent cell comprising the insert nucleic acid at the targeted genomic locus; (e) selecting the genetically modified pluripotent cell; (f) introducing the genetically modified pluripotent cell into a host embryo at a pre-morula stage; and (g) implanting the host embryo comprising the genetically modified pluripotent cell into a surrogate mother to generate an F0 generation derived from the genetically modified pluripotent cell. In such methods the targeting vector can comprise a large targeting vector. The pluripotent cell can be an ES cell. In further methods, the isolating step (c) further comprises (c1) linearizing the genetically modified targeting vector (i.e., the genetically modified LTVEC). In still further embodiments, the introducing step (d) further comprises (d1) introducing a nuclease agent as described herein into the pluripotent cell. In one embodiment, selecting steps (b) and/or (e) are carried out by applying a selectable agent as described herein to the prokaryotic cell or the pluripotent cell. In one embodiment, selecting steps (b) and/or (e) are carried out via a modification of allele (MOA) assay as described herein.

Further methods for modifying a target genomic locus of a mammalian cell via bacterial homologous recombination (BHR) in a prokaryotic cell are provided and comprise: (a) providing a prokaryotic cell comprising a target locus comprising a nucleic acid, (b) introducing into the prokaryotic cell a targeting vector comprising an insert nucleic acid flanked with a 5' homology arm and a 3' homology arm, wherein the insert nucleic acid comprises a mammalian region (including, for example, a DNA insert from a human), and (c) selecting a targeted prokaryotic cell comprising the insert nucleic acid at the target locus, wherein the prokaryotic cell is capable of expressing a recombinase that mediates the BHR. Step (a1) can comprise providing a prokaryotic cell comprising a target locus comprising a nucleic acid comprising a first polynucleotide comprising a first recognition site for a first nuclease agent, and step (b1) can further comprise expressing in the prokaryotic cell a nuclease agent that makes a nick or double-strand break at or near the first recognition site. Steps (a)-(c) can be serially repeated as disclosed herein to allow the introduction of multiple insert nucleic acids at the targeted locus in the prokaryotic cell. Once the targeted genomic locus is "built" with the prokaryotic cell, a targeting vector comprising the modified target locus can be isolated from the prokaryotic cell and introduced into a target genomic locus within a pluripotent cell. Pluripotent cells (i.e., ES cells) comprising the modified genomic locus can then be made into genetically modified non-human animals.

In some embodiments, various genetic modifications of the target genomic loci described herein can be carried out by a series of homologous recombination reactions (BHR) in bacterial cells using an LTVEC derived from Bacterial Artificial Chromosome (BAC) DNA using VELOCIGENE® genetic engineering technology (see, e.g., U.S. Pat. No. 6,586,251 and Valenzuela, D. M. et al. (2003), High-throughput engineering of the mouse genome coupled with high-resolution expression analysis, *Nature Biotechnology* 21(6): 652-659, which is incorporated herein by reference in their entireties).

In some embodiments, targeted ES cells comprising various genetic modifications as described herein are used as insert ES cells and introduced into a pre-morula stage embryo from a corresponding organism, e.g., an 8-cell stage mouse embryo, via the VELOCIMOUSE® method (see, e.g., U.S. Pat. Nos. 7,576,259, 7,659,442, 7,294,754, and US 2008-0078000 A1, all of which are incorporated by reference herein in their entireties). The embryo comprising the genetically modified ES cells is incubated until the blastocyst stage and then implanted into a surrogate mother to produce an F0. Animals bearing the genetically modified genomic locus can be identified via modification of allele (MOA) assay as described herein. The resulting F0 generation non-human animal derived from the genetically modified ES cells is crossed to a wild-type non-human animal to obtain F1 generation offspring. Following genotyping with specific primers and/or probes, F1 non-human animals that are heterozygous for the genetically modified genomic locus are crossed to each other to produce animals that are homozygous for the genetically modified genomic locus. Alternatively, an F0 female non-human animal and an F0 male non-human animal each having the genetic modification can be crossed to obtain an F1 non-human animal homozygous for the genetic modification.

In one aspect, a genetically modified rat genome, for example, is provided, comprising a targeted modification of an endogenous nucleic acid sequence with a homologous or orthologous nucleic acid sequence from another organism.

In one embodiment, the homologous or orthologous nucleic acid sequence is of a length from about 5 kb to about 200 kb. In one embodiment, the homologous or orthologous non-rat nucleic acid sequence ranges from about 5 kb to about 10 kb. In one embodiment, the homologous or orthologous non-rat nucleic acid sequence ranges from about 10 kb to about 20 kb. In one embodiment, the homologous or orthologous non-rat nucleic acid sequence ranges from about 20 kb to about 30 kb. In one embodiment, the homologous or orthologous non-rat nucleic acid sequence ranges from about 30 kb to about 40 kb. In one embodiment, the homologous or orthologous non-rat nucleic acid sequence ranges from about 40 kb to about 50 kb. In one embodiment, the homologous or orthologous non-rat nucleic acid sequence ranges from about 50 kb to about 60 kb. In one embodiment, the homologous or orthologous non-rat nucleic acid sequence ranges from about 60 kb to about 70 kb. In one embodiment, the homologous or orthologous non-rat nucleic acid sequence ranges from about 70 kb to about 80 kb. In one embodiment, the homologous or orthologous non-rat nucleic acid sequence ranges from about 80 kb to about 90 kb. In one embodiment, the homologous or orthologous non-rat nucleic acid sequence ranges from about 90 kb to about 100 kb. In one embodiment, the homologous or orthologous non-rat nucleic acid sequence ranges from about 100 kb to about 110 kb. In one embodiment, the homologous or orthologous non-rat nucleic acid sequence ranges from about 110 kb to about 120 kb. In one embodiment, the homologous or orthologous non-rat nucleic acid sequence ranges from about 120 kb to about 130 kb. In one embodiment, the homologous or orthologous non-rat nucleic acid sequence ranges from about 140 kb to about 150 kb. In one embodiment, the homologous or orthologous non-rat nucleic acid sequence ranges from about 150 kb to about 160 kb. In one embodiment, the homologous or orthologous non-rat nucleic acid sequence ranges from about 160 kb to about 170 kb. In one embodiment, the homologous or orthologous non-rat nucleic acid sequence ranges from about 170 kb to about 180 kb. In one embodiment, the homologous or orthologous non-rat nucleic acid sequence ranges from about 180 kb to about 190 kb. In one embodiment, the homologous or orthologous non-rat nucleic acid sequence ranges from about 190 kb to about 200 kb. Various polynucleotides of interest that can be employed in the insert nucleic acid are described elsewhere herein.

Further methods for targeted genome modification of a non-human animal are provided. Such methods can comprise (a) modifying a genomic locus of interest in a non-human pluripotent cell according to any of the various methods provided herein for modifying a genomic locus of interest, thereby producing a genetically modified non-human pluripotent cell comprising a targeted genome modification; (b) introducing the modified non-human pluripotent cell of step (a) into a non-human host embryo; and (c) gestating the non-human host embryo comprising the modified pluripotent cell in a surrogate mother, wherein the surrogate mother produces F0 progeny comprising the targeted genome modification, and wherein the targeted genome modification is capable of being transmitted through the germline.

In some embodiments, the targeted genome modification comprises simultaneous deletion of an endogenous nucleic acid sequence at the genomic locus of interest and insertion of an exogenous nucleic acid at the genomic locus of interest (i.e., deletion and insertion in a single step). In some embodiments, the targeted genome modification comprises a biallelic genetic modification. The biallelic genetic modification can comprise deletion of an endogenous nucleic acid sequence and insertion of an exogenous nucleic acid at the genomic locus of interest in two homologous chromosomes (i.e., a pair of first and second homologous chromosomes).

In other embodiments, the targeted genome modification creates a modified pluripotent cell that is compound heterozygous at the genomic locus of interest. In other embodiments, the targeted genome modification creates a modified pluripotent cell that is hemizygous at the genomic locus of interest. In some embodiments, the targeted genetic modification at the genomic locus of interest in one chromosome comprises deletion of an endogenous nucleic acid sequence and insertion of an exogenous nucleic acid. For example, the targeted genetic modification can comprise: (1) deletion of an endogenous nucleic acid sequence at the genomic locus of interest in two homologous chromosomes; and (2) insertion of an exogenous nucleic acid into the genomic locus of interest in a first chromosome and disruption of the genomic locus of interest in a second chromosome. The first chromosome can be the first of the two homologous chromosomes, and the second chromosome can be the second of the two homologous chromosomes.

6. Cells

The various methods and compositions described herein employ a genomic locus targeting system in a cell. In one embodiment, the cell is a pluripotent cell. In one embodiment, the cell is a non-pluripotent cell. In one embodiment, the pluripotent cell is a non-human pluripotent cell. In one embodiment, the non-human pluripotent cell is a mammalian pluripotent cell. In one embodiment, the pluripotent cell is a human induced pluripotent stem (iPS) cell.

In other embodiments, the cell is a eukaryotic cell, a non-rat eukaryotic cell, a human pluripotent cell, a human ES cell, a human adult stem cell, a developmentally restricted human progenitor cell, a non-human mammalian cell, a mammalian cell, a human cell, a fibroblast, a rodent cell, a non-rat rodent cell, a rat cell, a mouse cell, a hamster cell or a CHO cell.

In one embodiment, a eukaryotic cell is a primary cell. Primary cells include cells or cultures of cells that have been isolated directly from an organism, organ, or tissue. Primary cells include cells that are neither transformed nor immortal. They include any cell obtained from an organism, organ, or tissue which was not previously passed in tissue culture or has been previously passed in tissue culture but is incapable of being indefinitely passed in tissue culture. Such cells can be isolated by conventional techniques and include, for example, hematopoietic cells, endothelial cells, epithelial cells, fibroblasts, mesenchymal cells, keratinocytes, melanocytes, monocytes, mononuclear cells, adipocytes, preadipocytes, neurons, glial cells, hepatocytes, skeletal myoblasts, and smooth muscle cells. In some embodiments, primary cells are derived from connective tissues, muscle tissues, nervous system tissues, or epithelial tissues.

In another embodiment, a eukaryotic cell is an immortalized cell. Immortalized cells include cells from a multicellular organism that would normally not proliferate indefinitely but, due to mutation or alteration, have evaded normal cellular senescence and instead can keep undergoing division. Such mutations or alterations can occur naturally or be intentionally induced. Examples of immortalized cells include Chinese hamster ovary (CHO) cells, human embryonic kidney cells (e.g., HEK 293 cells), and mouse embryonic fibroblast cells (e.g., 3T3 cells). Numerous types of immortalized cells are well known in the art.

In some embodiments, immortalized cells are derived from cancer cells. In another embodiment, a primary or immortalized cell is one that is typically used for culturing or for expressing recombinant genes or proteins.

In other embodiments, the pluripotent cell is able to sustain its pluripotency following at least one targeted genetic modification of its genome and is able to transmit the targeted modification to a germline of an F1 generation.

In one embodiment, the pluripotent cell is a non-human fertilized egg at the single cell stage. In one embodiment, the non-human fertilized egg is a mammalian fertilized egg. In one embodiment, the mammalian fertilized egg is a rodent fertilized egg at the single cell stage. In one embodiment, the mammalian fertilized egg is a rat or mouse fertilized egg at the single cell stage.

The various cells employed in the method and compositions disclosed herein can also comprise prokaryotic cells, such as a bacterial cell, including *E. coli*. In specific embodiments, the prokaryotic cell is a recombination-competent strain of *E. coli*. In one embodiment, the prokaryotic cell comprises a nucleic acid that encodes the recombinase, while in other instances, the prokaryotic cell does not comprise the nucleic acid that encodes the recombinase, and the nucleic acid encoding the recombinase is introduced into the prokaryotic cell. In one embodiment, the nucleic acid encoding the recombinase comprises a DNA or an mRNA. In some embodiments, the nucleic acid encoding the recombinase is pABG. In one embodiment, the recombinase is expressed under the control of an inducible promoter. In one embodiment, expression of the recombinase is controlled by arabinose.

A. Low Osmolality Medium for Making and Maintaining Human Induced Pluripotent Stem Cells A cell culture medium is provided for use in the methods and compositions of the invention. In one embodiment, the medium is suitable for making a population of human iPS cells. In another embodiment, the medium is suitable for maintaining human iPS cells in culture. In some embodiments, the human iPS cells are naïve or naïve-looking.

The medium provided herein comprises at least a base medium, supplements, a leukemia inhibitory factor (LIF) polypeptide, a glycogen synthase kinase 3 (GSK3) inhibitor, and a MEK inhibitor.

The present medium is a low osmolality medium. In one example, the osmolality is between about 175-280 mOsm/kg. In further examples, the osmolality of the medium is about 180-270 mOsm/kg, about 200-250 mOsm/kg, about 220-240 mOsm/kg, or about 225-235 mOsm. In a particular embodiment, the osmolality of the medium is about 233 mOsm/kg.

The base medium provided for the invention is a low osmolality base medium to which supplements are added. The present base medium differs from base media typically used to maintain human iPS cells in culture, which include Dulbecco's Modified Eagle's Medium (DMEM), in various forms (e.g., Invitrogen DMEM, Cat. No. 1 1971-025), and a low salt DMEM available commercially as KO-DMEM™ (Invitrogen Cat. No. 10829-018).

The base medium provided herein is a low osmolality medium but exhibits characteristics that are not limited to low osmolality. For example, the DMEM formulation shown in Table A can be made suitable for the purposes of the invention by altering the sodium chloride and/or sodium bicarbonate concentrations as provided herein, which will result in a different osmolality as compared with the standard DMEM base medium or low-salt DMEM base medium (KO-DMEM) shown in Table A.

TABLE A

DMEM base medium formulation.

| Component | Mg/L | mM |
|---|---|---|
| Glycine | 30 | 0.4 |
| L-Arginine•HCl | 84 | 0.398 |
| L-Cystine•2HCl | 63 | 0.201 |
| L-Glutamine | 584 | 4 |
| L-Histidine•HCl•H2O | 42 | 0.2 |
| L-Isoleucine | 105 | 0.802 |
| L-Leucine | 105 | 0.802 |
| L-Lysine•HCl | 146 | 0.798 |
| L-Methionine | 30 | 0.201 |
| L-Phenylalanine | 66 | 0.4 |
| L-Serine | 42 | 0.4 |
| L-Threonine | 95 | 0.798 |
| L-Tryptophan | 16 | 0.0784 |
| L-Tyrosine disodium salt dihydrate | 104 | 0.398 |
| L-Valine | 94 | 0.803 |
| Choline chloride | 4 | 0.0286 |
| D-Calcium pantothenate | 4 | $8.39 \times 10^{-3}$ |
| Folic Acid | 4 | $9.07 \times 10^{-3}$ |
| Niacinamide | 4 | 0.0328 |
| Pyridoxine•HCl | 4 | 0.0196 |
| Riboflavin | 0.4 | $1.06 \times 10^{-3}$ |
| Thiamine•HCl | 4 | 0.0119 |
| i-Inositol | 7.2 | 0.04 |
| Calcium Chloride (CaCl$_2$) (anhydrous) | 200 | 1.8 |
| Ferric Nitrate (Fe(NO$_3$)$_3$•9H$_2$O) | 0.1 | $2.48 \times 10^{-4}$ |
| Magnesium Sulfate (MgSO$_4$) (anhyd.) | 97.67 | 0.814 |
| Potassium Chloride (KCl) | 400 | 5.33 |
| D-Glucose (Dextrose) | 4500 | 25 |
| Phenol Red | 15 | 0.0399 |
| NaCL/NaHCO$_3$ Content of DMEM | | |
| Sodium Bicarbonate (NaHCO$_3$) | 3700 | 44.05 |
| Sodium Chloride (NaCl) | 6400 | 110.34 |
| NaCl/NaHCO$_3$ Content of Low salt DMEM (KO-DMEM) | | |
| Sodium Bicarbonate (NaHCO$_3$) | 2200 | 26 |
| Sodium Chloride (NaCl) | 5100 | 87.7 |
| NaCl/NaHCO$_3$ Content of Low osmolality DMEM | | |
| Sodium Bicarbonate (NaHCO$_3$) | 2200 | 26 |
| Sodium Chloride (NaCl) | 3000 | 50 |

The present base medium can include a salt of an alkaline metal and a halide, such as sodium chloride (NaCl). Exemplary concentrations of NaCl in the base medium include 50±5 mM or about 3 mg/mL.

In another embodiment, the base medium exhibits a concentration of a salt of carbonic acid. The salt of carbonic acid can be a sodium salt. In such an example, the sodium salt can be sodium bicarbonate. In a particular embodiment, sodium bicarbonate is present in the base medium at a concentration of about 26±5 mM or about 2.2 mg/mL.

In yet another embodiment, the base medium is a low osmolality base medium. The osmolality of the base medium can be within a range of about 175-280 mOsm/kg, about 180-250 mOsm/kg, about 190-225 mOsm/kg, or about 195-205 mOsm/kg. An exemplary osmolality of the base medium can be 200, 214, 216, or 218 mOsm/kg. In a particular example, the osmolality of the base medium is 200 mOsm/kg. The osmolality can be determined when cells are cultured in different concentrations of $CO_2$. In some examples, cells are cultured at 3% $CO_2$ or 5% $CO_2$.

In a preferred embodiment, the base medium comprises NaCl at a concentration of 3.0 mg/mL, sodium bicarbonate at a concentration of about 2.2 mg/mL, and has an osmolality of 200 mOsm/kg.

Supplements formulated with the base medium of the invention are suitable for making, maintaining, or enriching populations of human iPS cells disclosed herein. Such supplements are indicated as "supplements" or "+ supplements" in this disclosure. The term "supplements" or the phrase "+ supplements," includes one or more additional elements added to the components of the base medium described in Table A. For example, supplements can include, without limitation, F-12® medium (Gibco), N2® supplement (Gibco; 100× solution), NEUROBASAL® medium (Gibco), B-27® supplement (Gibco; 50× solution), L-glutamine, glucose, 2-mercaptoethanol, a Leukemia Inhibitory Factor (LIF) polypeptide, a glycogen synthase kinase 3 inhibitor, a MEK inhibitor, or any combination thereof.

In a particular embodiment, the LIF polypeptide is a human LIF (hLIF) polypeptide. In some examples, a hLIF polypeptide is used at a concentration of about 1-1000 units/mL, about 20-800 units/mL, about 50-500 units/mL, about 75-250 units/mL, or about 100 units/mL.

In another particular embodiment, the GSK3 inhibitor comprises CHIR99021. In some examples, CHIR99021 is used at a concentration of about 0.1 to 10 µM, about 1-5 µM, about 2-4 µM, or about 3 µM.

In another particular embodiment, the MEK inhibitor comprises PD0325901. In some examples, PD0325901 is used at a concentration of about 0.1-5 µM, about 0.2-1 µM, about 0.3-0.7 µM, or about 0.5 µM.

An exemplary medium comprises a low osmolality base medium described herein at about 24.75% (v/v), F-12 medium at about 24.75% (v/v), N2 supplement at about 0.5% (v/v), NEUROBASAL medium at about 49% (v/v), B-27 supplement at about 1% (v/v), L-glutamine at about 2 mM, 2-mercaptoethanol at about 0.1 mM, hLIF at about 100 units/mL, CHIR99021 at about 3 µM, and PD0325901 at about 0.5 µM.

In another particular embodiment, the medium may or may not comprise basic fibroblast growth factor (bFGF, also known as FGF2 or FGF-β). Preferably the present medium does not comprise bFGF.

B. Human Induced Pluripotent Stem Cells

Methods and compositions are provided herein for making a population of human iPS cells. Methods and compositions are further provided for maintaining human iPS cells in culture. Human iPS cells that are produced or maintained in culture are also provided.

The term "pluripotent cell" or "pluripotent stem cell" includes an undifferentiated cell that possesses the ability to develop into more than one differentiated cell type. Such pluripotent cells can be, for example, a mammalian embryonic stem (ES cell) cell or a mammalian induced pluripotent stem cell (iPS cell). Examples of pluripotent cells include human iPS cells.

The term "embryonic stem cell" or "ES cell" means an embryo-derived totipotent or pluripotent stem cell, derived from the inner cell mass of a blastocyst, that can be maintained in an in vitro culture under suitable conditions. ES cells are capable of differentiating into cells of any of the three vertebrate germ layers, e.g., the endoderm, the ectoderm, or the mesoderm. ES cells are also characterized by their ability propagate indefinitely under suitable in vitro culture conditions. See, for example, Thomson et al. (Science (1998) Vol. 282(5391), pp. 1145-1147).

The term "induced pluripotent stem cell" or "iPS cell" includes a pluripotent stem cell that can be derived directly from a differentiated adult cell. Human iPS cells can be generated by introducing specific sets of reprogramming factors into a non-pluripotent cell which can include, for example, Oct3/4, Sox family transcription factors (e.g., Sox1, Sox2, Sox3, Sox15), Myc family transcription factors (e.g., c-Myc, 1-Myc, n-Myc), Krüppel-like family (KLF) transcription factors (e.g., KLF1, KLF2, KLF4, KLF5), and/or related transcription factors, such as NANOG, LIN28, and/or Glis1. Human iPS cells can also be generated, for example, by the use of miRNAs, small molecules that mimic the actions of transcription factors, or lineage specifiers. Human iPS cells are characterized by their ability to differentiate into any cell of the three vertebrate germ layers, e.g., the endoderm, the ectoderm, or the mesoderm. Human iPS cells are also characterized by their ability propagate indefinitely under suitable in vitro culture conditions. See, for example, Takahashi and Yamanaka (Cell (2006) Vol. 126(4), pp. 663-676).

The terms "naïve" and "primed" identify different pluripotency states of human iPS cells. The term "naïve-looking" identifies a cell expressing a pluripotent state that exhibits one or more characteristics of a naïve pluripotent cell. Naïve-looking human iPS cells can also be referred to as "naïve-like" human iPS cells. In some embodiments, naïve-looking human iPS cells exhibit one or more morphological characteristics of naïve human iPS cells, such as a morphology characterized by compact dome-shaped colonies. In some embodiments, naïve-looking human iPS cells express one or more of the pluripotency markers described herein. In some embodiments, naïve or naïve-looking human iPS cells are naïve human iPS cells. In other embodiments, naïve or naïve-looking human iPS cells are naïve-looking iPS cells.

Characteristics of naïve and primed iPS cells are described in the art. See, for example, Nichols and Smith (Cell Stem Cell (2009) Vol. 4(6), pp. 487-492). Naïve human iPS cells exhibit a pluripotency state similar to that of ES cells of the inner cell mass of a pre-implantation embryo. Such naïve cells are not primed for lineage specification and commitment. Female naïve iPS cells are characterized by two active X chromosomes. In culture, self-renewal of naïve human iPS cells is dependent on leukemia inhibitory factor (LIF) and other inhibitors. Cultured naïve human iPS cells display a clonal morphology characterized by rounded dome-shaped colonies and a lack of apico-basal polarity. Cultured naïve cells can further display one or more pluripotency makers as described elsewhere herein. Under appropriate conditions, the doubling time of naïve human iPS cells in culture can be between 16 and 24 hours.

Primed human iPS cells express a pluripotency state similar to that of post-implantation epiblast cells. Such cells are primed for lineage specification and commitment. Female primed iPS cells are characterized by one active X chromosome and one inactive X chromosome. In culture, self-renewal of primed human iPS cells is dependent on fibroblast growth factor (FGF) and activin. Cultured primed human iPS cells display a clonal morphology characterized by an epithelial monolayer and display apico-basal polarity. Under appropriate conditions, the doubling time of primed human iPS cells in culture can be 24 hours or more.

In one embodiment, human iPS cells can be derived from non-pluripotent cells transformed to express a pluripotent state. Such transformed cells include, for example, cells that have been transformed to express reprogramming genes that induce pluripotency. A pluripotent state can include, for example, expression of one or more of the pluripotency markers described herein. Such cells (such as human foreskin fibroblasts) can be transformed to express reprogramming genes, or any additional genes of interest, by any means known in the art. See, for example, Takahashi and Yamanaka (Cell (2006) Vol. 126(4), pp. 663-676). For example, they can be introduced into the cells using one or more plasmids, lentviral vectors, or retroviral vectors. In some cases, the vectors integrate into the genome and can be removed after reprogramming is complete. In particular embodiments, the non-pluripotent cells are transformed with reprogramming genes comprising Oct4, Sox2, Klf4, Myc, or any combination thereof. In some examples, the transformed cells comprise primed human iPS cells.

In some embodiments, the human iPS cells cultured in the low osmolality medium described herein express one or more phenotypes, gene expression profiles, or markers characteristic of a naïve state. In one example, the human iPS cells express one or more pluripotency markers whose expression is indicative of a naïve state. Such pluripotency markers can include alkaline phosphatase, NANOG, 5T4, ABCG2, Activin RIB/ALK-4, Activin RIIB, E-Cadherin, Cbx2, CD9, CD30/TNFRSF8, CD117/c-kit, CDX2, CHD1, Cripto, DNMT3B, DPPA2, DPPA4, DPPA5/ESG1, EpCAM/TROP1, ERR beta/NR3B2, ESGP, F-box protein 15/FBXO15, FGF-4, FGF-5, FoxD3, GBX2, GCNF/NR6A1, GDF-3, Gi24/VISTA/B7-H5, integrin alpha 6/CD49f, integrin alpha 6 beta 1, integrin alpha 6 beta 4, integrin beta 1/CD29, KLF4, KLF5, L1TD1, Lefty, Lefty-1, Lefty-A, LIN-28A, LIN-28B, LIN-41, cMaf, cMyc, Oct-3/4, Oct-4A, Podocalyxin, Rex-1/ZFP42, Smad2, Smad2/3, SOX2, SSEA-1, SSEA-3, SSEA-4, STAT3, Stella/Dppa3, SUZ12, TBX2, TBX3, TBX5, TERT, TEX19, TEX19.1, THAP11, TRA-1-60(R), TROP-2, UTF1, and/or ZIC3. In a specific example, the expressed pluripotency marker is alkaline phosphatase, NANOG, or both.

In another embodiment, human iPS cells cultured in the low osmolality medium described herein display morphological characteristics indicative of a naïve state. An exemplary morphology is characterized by cells having compact dome-shaped colonies in culture.

In another embodiment, human iPS cells cultured in the low osmolality medium described herein can be mechanically or enzymatically dissociated into a single-cell suspension, passaged, and/or subcultured. In one example, enzymatic dissociation can be performed using trypsin. When cultured in the present low osmolality medium, human iPS cells can provide greater transformation efficiency due to enhanced dissociation into a single-cell suspension. With other types of medium (e.g., mTeSR™ medium or 2i medium) typically used to maintain human iPS cells in culture, dissociation of human iPS cells must be performed mechanically or with enzymes such as collagenase that are less harsh than trypsin. Consequently, the cells are not dissociated as effectively or as completely. In contrast, with the present low osmolality medium, trypsin can be used to dissociate the cells, and the enhanced dissociation results in increased transformation efficiency. Furthermore, unlike with other types of medium typically used to maintain human iPS cells in culture (e.g., mTeSR™ medium or 2i medium), enzymatic dissociation of human iPS cells cultured with the present low osmolality medium (preferably a low osmolality medium not comprising bFGF) can be performed in the absence of one or more inhibitors that are generally necessary for the passage of such cells. An exemplary inhibitor that can be omitted is a Rho-associated protein kinase (ROCK) inhibitor. A ROCK inhibitor is generally necessary when passaging human iPS cells to inhibit the activation of pro-apoptotic pathways.

In a further embodiment, subcultured human iPS cells cultured in the low osmolality medium described herein can maintain a naïve or naïve-looking state following enzymatic dissociation and subculture. In some examples, subcultured human iPS cells can continue to display a morphology characterized by compact dome-shaped colonies. Subcultured human iPS cells can also continue to express one or pluripotency markers as described herein.

C. Methods for Making and Maintaining a Population of Human Induced Pluripotent Stem Cells Methods and compositions are provided for making human iPS cells in an in vitro culture. Methods and compositions are further provided for maintaining human iPS cells in an in vitro culture.

The term "making" includes culturing non-pluripotent cells transformed to express one or more reprogramming factors as described herein, under suitable conditions to induce a change in cell phenotype, gene expression, or both, such that the cells display a naïve or naïve-looking state, i.e., express one or more characteristics of naïve human iPS cells. A naïve or naïve-looking state can be expressed in response to particular culture conditions, e.g., culture in a low osmolality medium as described herein. In some examples, the proportion of cells expressing a naïve or naïve-looking state is at least about 30%, 40%, 50%, 60%, 70%, 80%, 90%, 95%, and up to 100% of the cells in culture.

In one embodiment, the method enriches an in vitro culture for a population of naïve or naïve-looking human iPS cells. In such an embodiment, naïve or naïve-looking human iPS cells can be propagated in culture preferentially over cells that do not express a naïve or naïve-looking state. In another embodiment, naïve or naïve-looking human iPS cells can be selected from a culture, be enzymatically dissociated, and subcultured to produce an enriched population of naïve or naïve-looking human iPS cells.

In one embodiment, non-pluripotent cells transformed to express a pluripotent state, are cultured in vitro in a medium provided herein that is suitable for inducing expression of a naïve or naïve-looking state for a period of at least 1, 2, 5, 7, 10, 14, 21, or 28 days, or any period of time sufficient to induce expression of a naïve or naïve-looking state in culture. Transformed cells can be cultured in the present medium for at least 1, 2, 3, or 4 weeks. Sometimes transformed cells are cultured for 1-4 weeks. Expression of a naïve or naïve-looking state can be determined by observing morphological characteristics or the expression of pluripotency markers, characteristic of a naïve or naïve-looking state, that are described elsewhere herein.

In one embodiment, non-pluripotent cells transformed to express a pluripotent state, are cultured in the present low osmolality medium until they express characteristics of a naïve or naïve-looking state. Cells can then be cultured in the present medium to maintain a naïve or naïve-looking state. In another embodiment, non-pluripotent cells transformed to express a pluripotent state, are first cultured in a high osmolality medium prior to culturing in the present low osmolality medium. Such high osmolality medium exhibits an osmolality higher than the present low osmolality medium and can comprise bFGF. Some high osmolality medium comprises one or more of bovine serum albumin, bFGF, transforming growth factor β (TGFβ), lithium chloride, pipecolic acid, and gamma-aminobutyric acid (GABA). Examples of a high osmolality medium include mTeSR™ medium (Stemcell Technologies).

In some embodiments, non-pluripotent cells transformed to express a pluripotent state, can first be cultured in high osmolality medium comprising bFGF until they begin to express characteristics of a naïve or naïve-looking state, at which time the cells are cultured in the present low osmolality medium. In one example, cells can be cultured in high osmolality medium comprising bFGF for a period of at least 1, 2, 5, 10, 30, 60, or 90 days, a period of 1, 2, 4, 8, or 12 weeks, or a period between 1 day to 3 months. An exemplary time period for culture in a high osmolality medium comprising bFGF is 2 months.

In other embodiments, non-pluripotent cells transformed to express a pluripotent state, can first be cultured in high osmolality medium comprising bFGF until they begin to display a morphology characterized by three-dimensional cell clumps, at which time cells are cultured in the present low osmolality medium. In such embodiments, cells displaying three-dimensional clumps can be selected, dissociated (e.g., with trypsin), and transferred to a new culture in the low osmolality medium described herein.

The terms "maintain," "maintaining," and "maintenance" include the preservation of at least one or more of the characteristics or phenotypes of the human iPS cells described herein. Such characteristics can include maintaining pluripotency, cell morphology, gene expression profiles, and/or other functional characteristics of naïve cells. The terms "maintain," "maintaining," and "maintenance" can also encompass the propagation of cells and/or an increase in the number of naïve cells being cultured. The terms include culture conditions that prevent cells from converting to a primed or non-pluripotent state. The terms further include culture conditions that permit the cells to remain pluripotent and/or naïve, while the cells may or may not continue to divide and increase in number.

In one embodiment, human iPS cells are cultured in vitro in a medium provided herein that is suitable for maintaining such cells in a naïve or naïve-looking state. In a particular example, human iPS cells can be cultured in a suitable medium for a period of 1, 2, 5, 7, 10, 14, 21, or 28 days, or for a period of about 2 weeks, about 3 weeks, about 4 weeks, or more, so long as the cultured cells are maintained in a naïve or naïve-looking state. Cells can be cultured for at least 1, 2, 3 or 4 weeks. Sometimes cells are cultured for 1-4 weeks. Human iPS cells can be maintained, for example, for any period of time sufficient for propagation of the cells in culture, genetic modification of the cells, and/or subculture of the cells.

In another embodiment, human iPS cells or non-pluripotent cells transformed to express a pluripotent state, can be cultured on a substrate or feeder cell layer suitable for in vitro culture. In a particular example, cells are cultured on MATRIGEL™ (BD Biosciences). In another example, cells are cultured on newborn human foreskin fibroblast (NuFF) feeder cells. In another example, cells are cultured on GELTREX™ (Life Technologies).

In a further embodiment, the doubling time of human iPS cells cultured in the present low osmolality medium is reduced as compared to primed human iPS cells or non-pluripotent cells transformed to express a pluripotent state. In a particular example, the doubling time of the present human iPS cells is between about 16-24 hours.

7. Sequence Identity

The methods and compositions provided herein employ a variety of different components of the targeted genomic integration system (i.e., nuclease agents, recognition sites, insert nucleic acids, polynucleotides of interest, targeting vectors, selection markers and other components). It is recognized throughout the description that some components of the targeted genomic integration system can have active variants and fragments. Such components include, for example, nuclease agents (i.e., engineered nuclease agents), nuclease agent recognition sites, polynucleotides of interest, target sites and corresponding homology arms of the targeting vector. Biological activity for each of these components is described elsewhere herein.

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. "Equivalent program" means any sequence comparison program that, for any two sequences in question, generates an alignment having identical nucleotide or amino acid residue matches and an identical percent sequence identity when compared to the corresponding alignment generated by GAP Version 10.

Unless defined otherwise, all technical and scientific terms used herein have the same meaning as commonly understood by one of ordinary skill in the art to which this invention belongs. Although any methods and materials similar or equivalent to those described herein also can be used in the practice or testing of the described invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural references unless the context clearly dictates otherwise. All technical and scientific terms used herein have the same meaning.

The publications discussed herein are provided solely for their disclosure prior to the filing date of the present application. Nothing herein is to be construed as an admission that the described invention is not entitled to antedate such publication by virtue of prior invention. Further, the dates of publication provided may be different from the actual publication dates, which may need to be independently confirmed.

The described invention may be embodied in other specific forms without departing from the spirit or essential attributes thereof and, accordingly, reference should be made to the appended claims, rather than to the foregoing specification, as indicating the scope of the invention.

Non-limiting embodiments include:

1. A method for targeted modification of a genomic locus of interest in a pluripotent rat cell, comprising (a) introducing into the pluripotent rat cell a large targeting vector (LTVEC) comprising an insert nucleic acid flanked with a 5' rat homology arm and a 3' rat homology arm, wherein the sum total of the 5' and the 3' homology arms is at least 10 kb but less than 150 kb; and (b) identifying a genetically modified pluripotent rat cell comprising the targeted genetic modification at the genomic locus of interest, wherein the targeted genetic modification is capable of being transmitted through the germline.
2. The method of embodiment 1, wherein the targeted genetic modification is biallelic.
3. The method of embodiment 1 or 2, wherein the pluripotent rat cell is a rat embryonic stem (ES) cell.
4. The method of embodiment 1, 2 or 3, wherein the pluripotent rat cell is derived from a DA strain or an ACI strain.
5. The method of any one of embodiments 1-4, wherein the pluripotent rat cell is characterized by expression of at least one pluripotency marker comprising Dnmt3L, Eras, Err-beta, Fbxo15, Fgf4, Gdf3, Klf4, Lef1, LIF receptor, Lin28, Nanog, Oct4, Sox15, Sox2, Utf1, or a combination thereof.
6. The method of any one of embodiments 1-4 wherein the pluripotent rat cell is characterized by one of more of the following characteristics:
   (a) lack of expression of one or more pluripotency markers comprising c-Myc, Ecat1, and/or Rexo1; (b) lack of expression of mesodermal markers comprising Brachyury and/or Bmpr2; (c) lack of expression of one or more endodermal markers comprising Gata6, Sox17 and/or Sox7; or (d) lack of expression of one or more neural markers comprising Nestin and/or Pax6.

7. The method of any one of embodiments 1-6, wherein the sum total of the 5' and the 3' homology arms of the LTVEC is from about 10 kb to about 30 kb, from about 20 kb to about 40 kb, from about 40 kb to about 60 kb, from about 60 kb to about 80 kb, from about 80 kb to about 100 kb, from about 100 kb to about 120 kb, or from about 120 kb to 150 kb.

8. The method of any one of embodiments 1-6, wherein the sum total of the 5' and the 3' homology arms of the LTVEC is from about 16 kb to about 150 kb.

9. The method of any one of embodiments 1-8, wherein the targeted genetic modification comprises: (a) a replacement of an endogenous rat nucleic acid sequence with a homologous or an orthologous nucleic acid sequence; (b) a deletion of an endogenous rat nucleic acid sequence; (c) a deletion of an endogenous rat nucleic acid sequence, wherein the deletion ranges from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb; (d) an exogenous nucleic acid sequence ranging from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb; (e) an exogenous nucleic acid sequence comprising a homologous or an orthologous nucleic acid sequence; (f) a chimeric nucleic acid sequence comprising a human and a rat nucleic acid sequence; (g) a conditional allele flanked with site-specific recombinase target sequences; or (h) a reporter gene operably linked to a promoter active in a rat cell.

10. The method of any one of embodiments 1-9, wherein the genomic locus of interest comprises (i) a first nucleic acid sequence that is complementary to the 5' rat homology arm; and (ii) a second nucleic acid sequence that is complementary to the 3' rat homology arm.

11. The method of embodiment 10, wherein the first and the second nucleic acid sequence is separated by at least 5 kb but less than 3 Mb.

12. The method of embodiment 10, wherein the first and the second nucleic acid sequence is separated by at least 5 kb but less than 10 kb, at least 10 kb but less than 20 kb, at least 20 kb but less than 40 kb, at least 40 kb but less than 60 kb, at least 60 kb but less than 80 kb, at least about 80 kb but less than 100 kb, at least 100 kb but less than 150 kb, or at least 150 kb but less than 200 kb, at least about 200 kb but less than about 300 kb, at least about 300 kb but less than about 400 kb, at least about 400 kb but less than about 500 kb, at least about 500 kb but less than about 1 Mb, at least about 1 Mb but less than about 1.5 Mb, at least about 1.5 Mb but less than about 2 Mb, at least about 2 Mb but less than about 2.5 Mb, or at least about 2.5 Mb but less than about 3 Mb.

13. The method of any one of embodiment 1-12, wherein introducing step (a) further comprises introducing a second nucleic acid encoding a nuclease agent that promotes a homologous recombination between the targeting construct and the genomic locus of interest in the pluripotent rat cell.

14. The method of embodiment 13, wherein the nuclease agent comprises (a) a chimeric protein comprising a zinc finger-based DNA binding domain fused to a FokI endonuclease; or (b) a chimeric protein comprising a Transcription Activator-Like Effector Nuclease (TALEN) fused to a FokI endonuclease.

15. The method of any one of embodiments 1-12, wherein introducing step (a) further comprises introducing into the pluripotent rat cell: (i) a first expression construct comprising a first promoter operably linked to a first nucleic acid sequence encoding a Clustered Regularly Interspaced Short Palindromic Repeats (CRISPR)-associated (Cas) protein, (ii) a second expression construct comprising a second promoter operably linked to a genomic target sequence linked to a guide RNA (gRNA), wherein the genomic target sequence is immediately flanked on the 3' end by a Protospacer Adjacent Motif (PAM) sequence.

16. The method of embodiment 15, wherein the genomic locus of interest comprises the nucleotide sequence of SEQ ID NO: 1.

17. The method of embodiment 15 or 16, wherein the gRNA comprises a third nucleic acid sequence encoding a Clustered Regularly Interspaced Short Palindromic Repeats (CRISPR) RNA (crRNA) and a trans-activating CRISPR RNA (tracrRNA).

18. The method of embodiment 15, 16 or 17, wherein the Cas protein is Cas9.

19. The method of embodiment 15, 16, 17, or 18, wherein the gRNA comprises: (a) the chimeric RNA of the nucleic acid sequence of SEQ ID NO: 2; or (b) the chimeric RNA of the nucleic acid sequence of SEQ ID NO: 3.

20. The method of embodiment 17, wherein the crRNA comprises SEQ ID NO: 4; SEQ ID NO: 5; or SEQ ID NO: 6.

21. The method of embodiment 17, wherein the tracrRNA comprises SEQ ID NO: 7 or SEQ ID NO: 8.

22. A modified rat genomic locus comprising: (i) an insertion of a homologous or orthologous human nucleic acid sequence; (ii) a replacement of an endogenous rat nucleic acid sequence with the homologous or orthologous human nucleic acid sequence; or (iii) a combination thereof, wherein the modified rat genomic locus is capable of being transmitted through the germline.

23. The modified rat genomic locus of embodiment 22, wherein the size of the insertion or replacement is from about 5 kb to about 400 kb.

24. The rat genomic locus of embodiment 22, wherein the size of the insertion or replacement is from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb.

25. A method for making a humanized rat, comprising: (a) targeting a genomic locus of interest in a pluripotent rat cell with a targeting construct comprising a human nucleic acid to form a genetically modified pluripotent rat cell; (b) introducing the genetically modified pluripotent rat cell into a host rat embryo; and (c) gestating the host rat embryo in a surrogate mother; wherein the surrogate mother produces rat progeny comprising a modified genomic locus that comprises: (i) an insertion of a human nucleic acid sequence; (ii) a replacement of the rat nucleic acid sequence at the genomic locus of interest with a homologous or orthologous human nucleic acid sequence; (iii) a chimeric nucleic acid sequence comprising a human and a rat nucleic acid sequence; or (iv) a combination thereof, wherein the modified genomic locus is capable of being transmitted through the germline.

26. The method of embodiment 25, wherein the targeting construct is a large targeting vector (LTVEC), and the sum total of the 5' and the 3' homology arms of the LTVEC is at least 10 kb but less than 150 kb.

27. The method of embodiment 26, wherein the sum total of the 5' and the 3' homology arms of the targeting construct is from about 10 kb to about 30 kb, from about 20 kb to 40 kb, from about 40 kb to about 60 kb, from about 60 kb to about 80 kb, or from about 80 kb to about 100 kb, from about 100 kb to about 120 kb, or from about 120 kb to 150 kb.

28. The method of embodiment 25, 26 or 27, wherein the human nucleic acid sequence is at least 5 kb but less than 400 kb.

29. The method of embodiment 25, 26, or 27, wherein the human nucleic acid sequence is at least 5 kb but less than 10 kb, at least 10 kb but less than 20 kb, at least 20 kb but less than 40 kb, at least 40 kb but less than 60 kb, at least 60 kb but less than 80 kb, at least about 80 kb but less than 100 kb, at least 100 kb but less than 150 kb, at least 150 kb but less than 200 kb, at least 200 kb but less than 250 kb, at least 250 kb but less than 300 kb, at least 300 kb but less than 350 kb, or at least 350 kb but less than 400 kb.

30. The method of any one of embodiments 25-29, wherein the pluripotent rat cell is a rat embryonic stem (ES) cell.

31. The method of any one of embodiments 25-30, wherein the pluripotent rat cell is derived from a DA strain or an ACI strain.

32. The method of any one of embodiments 25-31, wherein the pluripotent rat cell is characterized by expression of at least one pluripotency marker comprising Dnmt3L, Eras, Err-beta, Fbxo15, Fgf4, Gdf3, Klf4, Lef1, LIF receptor, Lin28, Nanog, Oct4, Sox15, Sox2, Utf1, or a combination thereof.

33. The method of any one of embodiment 25-31, wherein the pluripotent rat cell is characterized by one or more of the following features: (a) lack of expression of one or more pluripotency markers comprising c-Myc, Ecat1, and/or Rexo1; (b) lack of expression of one or more mesodermal markers comprising Brachyury and/or Bmpr2; (c) lack of expression of one or more endodermal markers comprising Gata6, Sox17, and/or Sox7; or (d) lack of expression of one or more neural markers comprising Nestin and/or Pax6.

34. A modified rat comprising a humanized genomic locus, wherein the humanized genomic locus comprises: (i) an insertion of a homologous or orthologous human nucleic acid sequence; (ii) a replacement of a rat nucleic acid sequence at an endogenous genomic locus with a homologous or orthologous human nucleic acid sequence; (iii) a chimeric nucleic acid sequence comprising a human and a rat nucleic acid sequence or (iv) a combination thereof, wherein the humanized genomic locus is capable of being transmitted through the germline.

35. A rat or rat cell comprising a targeted genetic modification in its genomic locus, wherein the genomic locus is an Interleukin-2 receptor gamma locus, an ApoE locus, a Rag1 locus, a Rag2 locus, or a Rag2/Rag1 locus, wherein the targeted genetic modification comprises: (a) a deletion of an endogenous rat nucleic acid sequence at the genomic locus; (b) an insertion of a homologous nucleic acid, an orthologous nucleic acid, or a chimeric nucleic acid comprising a human and a rat nucleic acid sequence, or (c) a combination thereof, wherein the targeted genetic modification is transmissible through the germline of the rat or a rat propagated from the rat cell.

36. The rat or rat cell of embodiment 35, wherein (a) the deletion of the endogenous rat nucleic acid at the genomic locus is at least about 10 kb; or (b) the deletion of the endogenous rat nucleic acid at the genomic locus is from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb; (c) the insertion of the exogenous nucleic acid sequence at the genomic locus is at least about 5 kb; or (d) the insertion of the exogenous nucleic acid sequence at the genomic locus is from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb.

37. The rat or rat cell of embodiment 35 or 36, wherein (a) the targeted genetic modification at the Interleukin-2 receptor gamma locus results in a decrease in or absence of Interleukin-2 receptor gamma protein activity; (b) the targeted genetic modification at the ApoE locus results in a decrease in or absence of ApoE protein activity; (c) the targeted genetic modification at the Rag1 locus results in a decrease in or absence of Rag1 protein activity; (d) the targeted genetic modification at the Rag2 locus results in a decrease in or absence of Rag2 protein activity; or (e) the targeted genetic modification at the Rag2/Rag1 locus results in a decrease in or absence of Rag2 protein activity and Rag1 activity.

38. The rat or rat cell of embodiment 35, 36, or 37, wherein the targeted genetic modification of the Interleukin-2 receptor gamma locus comprises: (a) a deletion of the entire rat Interleukin-2 receptor gamma coding region or a portion thereof; (b) a replacement of the entire rat Interleukin-2 receptor gamma coding region or a portion thereof with a human Interleukin-2 receptor gamma coding region or a portion thereof; (c) a replacement of an ecto-domain of the rat Interleukin-2 receptor gamma coding region with the ecto-domain of a human Interleukin-2 receptor gamma; or (d) at least a 3 kb deletion of the Interleukin-2 receptor gamma locus.

39. The rat or rat cell of any one of embodiments 35-37, wherein the targeted genetic modification of the ApoE locus comprises: (a) a deletion of the entire ApoE coding region or a portion thereof; or (b) at least a 1.8 kb deletion of the ApoE locus comprising the ApoE coding region.

40. The rat or rat cell of any one of embodiments 35-37, wherein the targeted genetic modification of the Rag2 locus comprises: (a) a deletion of the entire Rag2 coding region or a portion thereof; (b) at least a 5.7 kb deletion of the Rag2 locus comprising the Rag2 coding region.

41. The rat or rat cell of any one of embodiments 35-37, wherein the targeted genetic modification of the Rag2/Rag1 locus comprises: (a) a deletion of the entire Rag2 coding region or a portion thereof and a deletion of the entire Rag1 coding region or portion thereof; or (b) a deletion of at least 16 kb of the Rag2/Rag1 locus comprising the Rag2 coding region.

42. The rat or rat cell of any one of embodiment 35-41, wherein the targeted genetic modification comprises an insertion of an expression cassette comprising a selective marker at the Interleukin-2 receptor gamma locus, the ApoE locus, the Rag1 locus, the Rag2 locus, or the Rag2/Rag1 locus.

43. The rat or rat cell of any one of embodiments 42, wherein the expression cassette comprises a lacZ gene operably linked to the endogenous promoter at the genomic locus and a human ubiquitin promoter operably linked to a selective marker.

44. The rat or rat cell of any one of embodiments 35-43, wherein the targeted genetic modification in the Interleukin-2 receptor gamma locus, the ApoE locus, the Rag1 locus, the Rag2 locus or the Rag2/Rag1 locus comprises the insertion of a self-deleting selection cassette.

45. The rat or rat cell of embodiment 44, wherein the self-deleting selection cassette comprises a selective marker gene operably linked to a promoter active in the rat cell and a recombinase gene operably linked to a male germ cell-specific promoter, wherein the self-deleting cassette is flanked by recombination recognition sites recognized by the recombinase.

46. The rat or rat cell of embodiment 45, wherein (a) the male germ cell-specific promoter is a Protamine-1 promoter; or (b) the recombinase gene encodes Cre, and the recombination recognition sites are loxP sites.

47. The rat or rat cell of any one of embodiments 35-46, wherein the insertion of the exogenous nucleic acid sequence at the genomic locus comprises a reporter nucleic acid operably linked to an endogenous Interleukin-2 receptor gamma promoter, an endogenous ApoE promoter, an endogenous Rag1 promoter, or an endogenous Rag2 promoter.

48. The rat or rat cell of embodiment 47, wherein the reporter nucleic acid encodes a reporter comprising β-galactosidase, mPlum, mCherry, tdTomato, mStrawberry, J-Red, DsRed, mOrange, mKO, mCitrine, Venus, YPet, enhanced yellow fluorescent protein (EYFP), Emerald, enhanced green fluorescent protein (EGFP), CyPet, cyan fluorescent protein (CFP), Cerulean, T-Sapphire, luciferase, alkaline phosphatase, or a combination thereof.

49. The rat cell of any one of embodiments 35-48, wherein the rat cell is a pluripotent rat cell or a rat embryonic stem (ES) cell.

50. The rat cell of embodiment 49, wherein the pluripotent rat cell or the rat embryonic stem (ES) cell (a) is derived from a DA strain or an ACI strain; (b) is characterized by expression of at least one pluripotency marker comprising Dnmt3L, Eras, Err-beta, Fbxo15, Fgf4, Gdf3, Klf4, Lef1, LIF receptor, Lin28, Nanog, Oct4, Sox15, Sox2, Utf1, or a combination thereof; or (c) is characterized by one or more of the following characteristics: (i) lack of expression of one or more pluripotency markers comprising c-Myc, Ecat1, and/or Rexo1; (ii) lack of expression of mesodermal markers comprising Brachyury and/or Bmpr2; (iii) lack of expression of one or more endodermal markers comprising Gata6, Sox17 and/or Sox7; or (iv) lack of expression of one or more neural markers comprising Nestin and/or Pax6.

51. A method for modifying a target genomic locus in an Interleukin-2 receptor gamma locus, an ApoE locus, a Rag1 locus, a Rag2 locus or a Rag2/Rag1 locus in a pluripotent rat cell, the method comprising: (a) introducing into the pluripotent rat cell a targeting vector comprising an insert nucleic acid flanked with 5' and 3' rat homology arms homologous to the target genomic locus, (b) identifying a genetically modified pluripotent rat cell comprising a targeted genetic modification at the target genomic locus, wherein the targeted genetic modification is capable of being transmitted through the germline of a rat propagated from the pluripotent rat cell.

52. The method of embodiment 51, wherein the targeting vector is a large targeting vector (LTVEC) wherein the sum total of the 5' and the 3' rat homology arms is at least about 10 kb but less than about 150 kb.

53. The method of embodiment 51 or 52, wherein introducing the targeting vector into the pluripotent rat cell leads to: (i) a deletion of an endogenous rat nucleic acid sequence at the target genomic locus; (ii) an insertion of an exogenous nucleic acid sequence at the target genomic locus; or (iii) a combination thereof.

54. The method of embodiment 53, wherein (a) the deletion of the endogenous rat nucleic acid at the genomic locus is at least about 10 kb; or (b) the deletion of the endogenous rat nucleic acid at the genomic locus is from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb; (c) the insertion of the exogenous nucleic acid sequence at the genomic locus is at least about 5 kb; or. (d) the insertion of the exogenous nucleic acid sequence at the genomic locus is from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb.

55. The method of any one of embodiment 51-54, wherein (a) the targeted genetic modification at the Interleukin-2 receptor gamma locus results in a decrease in or absence of Interleukin-2 receptor gamma protein activity; (b) the targeted genetic modification at the ApoE locus results in a decrease in or absence of ApoE protein activity; (c) the targeted genetic modification at the Rag1 locus results in a decrease in or absence of Rag1 protein activity; (d) the targeted genetic modification at the Rag2 locus results in a decrease in or absence of Rag2 protein activity; or (e) the targeted genetic modification at the Rag2/Rag1 locus results in a decrease in or absence of Rag2 protein activity and i Rag1 protein activity.

56. The method of any one of embodiment 51-54, wherein the targeted genetic modification of the Interleukin-2 receptor gamma locus comprises (a) a deletion of the entire rat Interleukin-2 receptor gamma coding region or a portion thereof; (b) a replacement of the entire rat Interleukin-2 receptor gamma coding region or a portion thereof with a human Interleukin-2 receptor gamma coding region or a portion thereof; (c) a replacement of an ecto-domain of the rat Interleukin-2 receptor gamma coding region with the ecto-domain of a human Interleukin-2 receptor gamma; or (d) at least a 3 kb deletion of the Interleukin-2 receptor gamma locus comprising the Interleukin-2 receptor gamma coding region.

57. The method of any one of embodiment 51-55, wherein the targeted genetic modification of the ApoE locus comprises: (a) a deletion of the entire ApoE coding region or a portion thereof; or (b) at least a 1.8 kb deletion of the ApoE locus comprising the ApoE coding region.

58. The method of any one of embodiment 51-55, wherein the targeted genetic modification of the Rag2 locus comprises: (a) a deletion of the entire Rag2 coding region or a portion thereof; or (b) at least a 5.7 kb deletion of the Rag2 locus comprising the Rag2 coding region.

59. The method of any one of embodiment 51-55, wherein the targeted genetic modification of the Rag1/Rag2 locus comprises: (a) a deletion of the entire Rag2 coding region or a portion thereof and a deletion of the entire Rag1 coding region or portion thereof; or (b) a deletion of at least 16 kb of the Rag2/Rag1 locus comprising the Rag2 and Rag1 coding regions.

60. The method of any one of embodiment 51-59, wherein the insert nucleic acid comprises an expression cassette comprising a polynucleotide encoding a selective marker.

61. The method embodiment 60, wherein the expression cassette comprises a lacZ gene operably linked to an endogenous promoter at the genomic locus and a human ubiquitin promoter operably linked to a selective marker gene.

62. The method of any one of embodiments 51-60, wherein the insert nucleic acid comprises a self-deleting selection cassette.

63. The method of embodiment 62, wherein the self-deleting selection cassette comprises a selective marker operably linked to a promoter active in the rat pluripotent cell and a polynucleotide encoding a recombinase operably linked to a male germ cell-specific promoter, wherein the self-deleting cassette is flanked by recombination recognition sites recognized by the recombinase.

64. The method of embodiment 63, wherein (a) the male germ cell-specific promoter is a Protamine-1 promoter; or (b) the recombinase gene encodes Cre and the recombination recognition sites are loxP sites.

65. The method of embodiment 53, wherein the insertion of the exogenous nucleic acid sequence at the genomic locus comprises a reporter nucleic acid sequence operably linked to an endogenous Interleukin-2 receptor gamma promoter, an endogenous ApoE promoter, an endogenous Rag1 promoter, or an endogenous Rag2 promoter.

66. The method of embodiment 65, wherein the reporter nucleic acid sequence encodes a reporter comprising β-galactosidase, mPlum, mCherry, tdTomato, mStrawberry, J-Red, DsRed, mOrange, mKO, mCitrine, Venus, YPet, enhanced yellow fluorescent protein (EYFP), Emerald, enhanced green fluorescent protein (EGFP), CyPet, cyan fluorescent protein (CFP), Cerulean, T-Sapphire, luciferase, alkaline phosphatase, or a combination thereof.

67. The method of any one of embodiment 51-66, wherein the pluripotent rat cell is a rat embryonic stem (ES) cell.

68. The method of any one of embodiment 51-67, wherein the pluripotent rat cell (a) is derived from a DA strain or an ACI strain; or (b) is characterized by expression of a pluripotency marker comprising Oct-4, Sox-2, alkaline phosphatase, or a combination thereof; or (c) is characterized by one or more of the following characteristics: (i) lack of expression of one or more pluripotency markers comprising c-Myc, Ecat1, and/or Rexo1; (ii) lack of expression of mesodermal markers comprising Brachyury and/or Bmpr2; (iii) lack of expression of one or more endodermal markers comprising Gata6, Sox17 and/or Sox7; or (iv) lack of expression of one or more neural markers comprising Nestin and/or Pax6.

69. The method of any one of embodiment 51-68, further comprising identifying the targeted genetic modification at the target genomic locus, wherein the identification step employs a quantitative assay for assessing a modification of allele (MOA) at the target genomic locus.

70. The method of any one of embodiment 51-69, wherein introducing step (a) further comprises introducing a second nucleic acid encoding a nuclease agent that promotes a homologous recombination between the targeting vector and the target genomic locus in the pluripotent rat cell.

71. The method of embodiment 70, wherein the nuclease agent comprises a chimeric protein comprising a zinc finger-based DNA binding domain fused to a FokI endonuclease.

72. The method of embodiment 71, wherein the method results in bi-allelic modification of the target genomic locus.

73. The method of any one of embodiment 51-70, wherein introducing step (a) further comprises introducing into the pluripotent rat cell: (i) a first expression construct comprising a first promoter operably linked to a first nucleic acid sequence encoding a Clustered Regularly Interspaced Short Palindromic Repeats (CRISPR)-associated (Cas) protein, (ii) a second expression construct comprising a second promoter operably linked to a genomic target sequence linked to a guide RNA (gRNA), wherein the genomic target sequence is immediately flanked on the 3' end by a Protospacer Adjacent Motif (PAM) sequence.

74. The method of embodiment 73, wherein the genomic locus of interest comprises the nucleotide sequence of SEQ ID NO: 1.

75. The method of embodiment 73 or 74, wherein the gRNA comprises a third nucleic acid sequence encoding a Clustered Regularly Interspaced Short Palindromic Repeats (CRISPR) RNA (crRNA) and a trans-activating CRISPR RNA (tracrRNA).

76. The method of embodiment 73, wherein the Cas protein is Cas9.

77. The method of embodiment 73, 74, or 75, wherein the gRNA comprises: (a) the chimeric RNA of the nucleic acid sequence of SEQ ID NO: 2; or (b) the chimeric RNA of the nucleic acid sequence of SEQ ID NO: 3.

78. The method of embodiment 75, wherein the crRNA comprises SEQ ID NO: 4; SEQ ID NO: 5; or SEQ ID NO: 6.

79. The method of embodiment 75, wherein the tracrRNA comprises SEQ ID NO: 7 or SEQ ID NO: 8.

80. The rat or rat cell of any one of embodiments 35-50, wherein the rat or rat cell comprises targeted genetic modifications at the Interleukin-2 receptor gamma locus, the ApoE locus, the Rag1 locus, the Rag2 locus, and/or the Rag2/Rag1 locus.

81. The rat or rat cell of embodiment 80, wherein the rat or rat cell comprises targeted genetic modifications at the Interleukin-2 receptor gamma locus and the Rag2/Rag1 locus.

Additional non-limiting embodiments include:

1. A method for modifying a genomic locus of interest in a eukaryotic cell, comprising: (a) introducing into the eukaryotic cell: (i) a large targeting vector (LTVEC) comprising a first nucleic acid flanked with a 5' homology arm and a 3' homology arm, wherein the LTVEC is at least 10 kb; (ii) a first expression construct comprising a first promoter operably linked to a second nucleic acid encoding a Cas protein, (iii) a second expression construct comprising a second promoter operably linked to a third nucleic acid encoding a guide RNA (gRNA) comprising a nucleotide sequence that hybridizes to a target sequence and a trans-activating CRISPR RNA (tracrRNA), wherein the first and the second promoters are active in the eukaryotic cell; and (b) identifying a modified eukaryotic cell comprising a targeted genetic modification at the genomic locus of interest.

2. The method of embodiment 1, wherein the targeted genetic modification is a biallelic genetic modification.

3. The method of embodiment 1, wherein the LTVEC is at least 15 kb, at least 20 kb, at least 30 kb, at least 40 kb, at least 50 kb, at least 60 kb, at least 70 kb, at least 80 kb, or at least 90 kb.

4. The method of embodiment 1, wherein the LTVEC is at least 100 kb, at least 150 kb, or at least 200 kb.

5. The method of embodiment 1, wherein the eukaryotic cell is a mammalian cell.

6. The method of embodiment 5, wherein the mammalian cell is a fibroblast.

7. The method of embodiment 1, wherein the eukaryotic cell is a pluripotent cell.

8. The method of embodiment 7, wherein the pluripotent cell is a human pluripotent cell.

9. The method of embodiment 8, wherein the human pluripotent cell is a human embryonic stem (ES) cell or a human adult stem cell.

10. The method of embodiment 8, wherein the human pluripotent cell is a developmentally restricted human progenitor cell.

11. The method of embodiment 8, wherein the human pluripotent cell is a human induced pluripotent stem (iPS) cell.

12. The method of embodiment 1, wherein the Cas protein is Cas9.

13. The method of embodiment 1, wherein the target sequence is immediately flanked on the 3' end by a Protospacer Adjacent Motif (PAM) sequence.

14. The method of embodiment 1, wherein the sum total of the 5' and the 3' homology arms is from about 10 kb to about 150 kb.

15. The method of embodiment 1, wherein the sum total of the 5' and the 3' homology arms of the LTVEC is from about 10 kb to about 20 kb, from about 20 kb to about 40 kb, from about 40 kb to about 60 kb, from about 60 kb to about 80 kb, from about 80 kb to about 100 kb, from about 100 kb to about 120 kb, or from about 120 kb to 150 kb.

16. The method of embodiment 1, wherein the targeted genetic modification comprises: (a) a replacement of an endogenous nucleic acid sequence with a homologous or an orthologous nucleic acid sequence; (b) a deletion of an endogenous nucleic acid sequence; (c) a deletion of an endogenous nucleic acid sequence, wherein the deletion ranges from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb; (d) insertion of an exogenous nucleic acid sequence; (e) insertion of an exogenous nucleic acid sequence ranging from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb; (f) insertion of an exogenous nucleic acid sequence comprising a homologous or an orthologous nucleic acid sequence; (g) insertion of a chimeric nucleic acid sequence comprising a human and a non-human nucleic acid sequence; (h) insertion of a conditional allele flanked with site-specific recombinase target sequences; (i) insertion of a selectable marker or a reporter gene operably linked to a third promoter active in the pluripotent cell; or (j) a combination thereof.

17. The method of embodiment 1, wherein the genomic locus of interest comprises (i) a 5' target sequence that is homologous to the 5' homology arm; and (ii) a 3' target sequence that is homologous to the 3' homology arm.
18. The method of embodiment 17, wherein the 5' target sequence and the 3' target sequence is separated by at least 5 kb but less than 3 Mb.
19. The method of embodiment 17, wherein the 5' target sequence and the 3' target sequence is separated by at least 5 kb but less than 10 kb, at least 10 kb but less than 20 kb, at least 20 kb but less than 40 kb, at least 40 kb but less than 60 kb, at least 60 kb but less than 80 kb, at least about 80 kb but less than 100 kb, at least 100 kb but less than 150 kb, or at least 150 kb but less than 200 kb, at least about 200 kb but less than about 300 kb, at least about 300 kb but less than about 400 kb, at least about 400 kb but less than about 500 kb, at least about 500 kb but less than about 1 Mb, at least about 1 Mb but less than about 1.5 Mb, at least about 1.5 Mb but less than about 2 Mb, at least about 2 Mb but less than about 2.5 Mb, or at least about 2.5 Mb but less than about 3 Mb.
20. The method of embodiment 1, wherein the genomic locus of interest comprises the Interleukin-2 receptor gamma locus, the ApoE locus, the Rag1 locus, the Rag2 locus, or both of the Rag1 and the Rag2 loci.
21. The method of embodiment 1, wherein the first and the second expression constructs are on a single nucleic acid molecule.
22. A method for modifying a genome, comprising exposing the genome to a Cas protein and a CRISPR RNA in the presence of a large targeting vector (LTVEC) comprising a nucleic acid sequence of at least 10 kb, wherein following exposure to the Cas protein, the CRISPR RNA, and the LTVEC, the genome is modified to contain at least 10 kb nucleic acid sequence.
23. The method of embodiment 22, wherein the LTVEC comprises a nucleic acid sequence of at least 20 kb, at least 30 kb, at least 40 kb, at least 50 kb, at least 60 kb, at least 70 kb, at least 80 kb, or at least 90 kb.
24. The method of embodiment 22, wherein the LTVEC comprises a nucleic acid sequence of at least 100 kb, at least 150 kb, or at least 200 kb.
25. A method for modifying a genome, comprising contacting the genome with a Cas protein, a CRISPR RNA that hybridizes to a target sequence, and a tracrRNA in the presence of a large targeting vector (LTVEC), wherein the LTVEC is at least 10 kb and comprises a first nucleic acid flanked with a 5' homology arm and a 3' homology arm, wherein following contacting with the Cas protein, CRISPR RNA, and tracrRNA in the presence of the LTVEC, the genome is modified at a genomic locus of interest to contain the first nucleic acid.
26. The method of embodiment 25, wherein the genome is in a eukaryotic cell, and the Cas protein, the CRISPR RNA, the tracrRNA, and the LTVEC are introduced into the eukaryotic cell
27. The method of embodiment 26, further comprising identifying a modified eukaryotic cell comprising a targeted genetic modification at the genomic locus of interest.
28. The method of embodiment 26 or 27, wherein the CRISPR RNA and the tracrRNA are introduced together in the form of a single guide RNA (gRNA).
29. The method of embodiment 26 or 27, wherein the CRISPR RNA and the tracrRNA are introduced separately.
30. The method of any one of embodiments 26-29, wherein: (a) the Cas protein is introduced into the eukaryotic cell in the form of a protein, a messenger RNA (mRNA) encoding the Cas protein, or a DNA encoding the Cas protein; (b) the CRISPR RNA is introduced into the eukaryotic cell in the form of an RNA or a DNA encoding the CRISPR RNA; and (c) the tracrRNA is introduced into the eukaryotic cell in the form of an RNA or a DNA encoding the tracrRNA.
31. The method of embodiment 30, wherein the Cas protein, the CRISPR RNA, and the tracrRNA are introduced into the eukaryotic cell as a protein-RNA complex.
32. The method of embodiment 30, wherein: (a) the DNA encoding the Cas protein is in the form of a first expression construct comprising a first promoter operably linked to a second nucleic acid encoding the Cas protein; (b) the DNA encoding the CRISPR RNA is in the form of a second expression construct comprising a second promoter operably linked to a third nucleic acid encoding the CRISPR RNA; and (c) the DNA encoding the tracrRNA is in the form of a third expression construct comprising a third promoter operably linked to a fourth nucleic acid encoding the tracrRNA, wherein the first, second, and third promoters are active in the eukaryotic cell.
33. The method of embodiment 32, wherein the first, second, and/or third expression constructs are on a single nucleic acid molecule.
34. The method of embodiment 30, wherein: (a) the DNA encoding the Cas protein is in the form of a first expression construct comprising a first promoter operably linked to a second nucleic acid encoding the Cas protein; and (b) the DNA encoding the CRISPR RNA and the DNA encoding the tracrRNA are in the form of a second expression construct comprising a second promoter operably linked to a third nucleic acid encoding a gRNA comprising the CRISPR RNA and the tracrRNA; wherein the first and second promoters are active in the eukaryotic cell.
35. The method of embodiment 34, wherein the first and the second expression constructs are on a single nucleic acid molecule.
36. The method of any one of embodiments 27-35, wherein the targeted genetic modification comprises simultaneous deletion of an endogenous nucleic acid sequence at the genomic locus of interest and insertion of the first nucleic acid at the genomic locus of interest.
37. The method of any one of embodiments 27-36, wherein the targeted genetic modification is a biallelic genetic modification.
38. The method of embodiment 37, wherein the biallelic genetic modification comprises deletion of an endogenous nucleic acid sequence and insertion of the first nucleic acid at the genomic locus of interest in two homologous chromosomes.
39. The method of any one of embodiments 27-36, wherein the modified eukaryotic cell is hemizygous at the genomic locus of interest.
40. The method of embodiment 39, wherein the targeted genetic modification at the genomic locus of interest in one chromosome comprises deletion of an endogenous nucleic acid sequence and insertion of the first nucleic acid.
41. The method of embodiment 39, wherein the targeted genetic modification comprises: (1) deletion of an endogenous nucleic acid sequence at the genomic locus of interest in two homologous chromosomes; and (2) insertion of the first nucleic acid into the genomic locus of interest in a first chromosome and disruption of the genomic locus of interest in a second chromosome.

42. The method of any one of embodiments 25-41, wherein the LTVEC is at least 15 kb, at least 20 kb, at least 30 kb, at least 40 kb, at least 50 kb, at least 60 kb, at least 70 kb, at least 80 kb, or at least 90 kb.
43. The method of any one of embodiments 25-42, wherein the LTVEC is at least 100 kb, at least 150 kb, or at least 200 kb.
44. The method of any one of embodiments 25-43, wherein the first nucleic acid is at least 20 kb, at least 30 kb, at least 40 kb, at least 50 kb, at least 60 kb, at least 70 kb, at least 80 kb, at least 90 kb, at least 100 kb, at least 150 kb, at least 200 kb, at least 250 kb, or at least 300 kb.
45. The method of any one of embodiments 26-44, wherein the eukaryotic cell is a mammalian cell.
46. The method of embodiment 45, wherein the mammalian cell is a fibroblast.
47. The method of any one of embodiments 26-43, wherein the eukaryotic cell is a pluripotent cell.
48. The method of embodiment 47, wherein the pluripotent cell is a non-human pluripotent cell.
49. The method of embodiment 48, wherein the non-human pluripotent cell is a rodent pluripotent cell.
50. The method of embodiment 49, wherein the rodent pluripotent cell is a mouse or rat embryonic stem (ES) cell.
51. The method of embodiment 47, wherein the pluripotent cell is a human pluripotent cell.
52. The method of embodiment 51, wherein the human pluripotent cell is a human embryonic stem (ES) cell or a human adult stem cell.
53. The method of embodiment 51, wherein the human pluripotent cell is a developmentally restricted human progenitor cell.
54. The method of embodiment 51, wherein the human pluripotent cell is a human induced pluripotent stem (iPS) cell.
55. The method of any one of embodiments 25-54, wherein the Cas protein is Cas9.
56. The method of any one of embodiments 25-55, wherein the target sequence is immediately flanked by a Protospacer Adjacent Motif (PAM) sequence.
57. The method of any one of embodiments 25-56, wherein the sum total of the 5' and the 3' homology arms of the LTVEC is from about 10 kb to about 150 kb.
58. The method of any one of embodiments 25-57, wherein the sum total of the 5' and the 3' homology arms of the LTVEC is from about 10 kb to about 20 kb, from about 20 kb to about 40 kb, from about 40 kb to about 60 kb, from about 60 kb to about 80 kb, from about 80 kb to about 100 kb, from about 100 kb to about 120 kb, or from about 120 kb to 150 kb.
59. The method of any one of embodiments 27-58, wherein the targeted genetic modification comprises: (a) a replacement of an endogenous nucleic acid sequence with a homologous or an orthologous nucleic acid sequence; (b) a deletion of an endogenous nucleic acid sequence; (c) a deletion of an endogenous nucleic acid sequence, wherein the deletion ranges from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb; (d) insertion of an exogenous nucleic acid sequence; (e) insertion of an exogenous nucleic acid sequence ranging from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb; (f) insertion of an exogenous nucleic acid sequence comprising a homologous or an orthologous nucleic acid sequence; (g) insertion of a chimeric nucleic acid sequence comprising a human and a non-human nucleic acid sequence; (h) insertion of a conditional allele flanked with site-specific recombinase target sequences; (i) insertion of a selectable marker or a reporter gene operably linked to a third promoter active in the pluripotent cell; or (j) a combination thereof.
60. The method of any one of embodiments 25-59, wherein the genomic locus of interest comprises (i) a 5' target sequence that is homologous to the 5' homology arm; and (ii) a 3' target sequence that is homologous to the 3' homology arm.
61. The method of embodiment 60, wherein the 5' target sequence and the 3' target sequence are separated by at least 5 kb but less than 3 Mb.
62. The method of embodiment 60, wherein the 5' target sequence and the 3' target sequence are separated by at least 5 kb but less than 10 kb, at least 10 kb but less than 20 kb, at least 20 kb but less than 40 kb, at least 40 kb but less than 60 kb, at least 60 kb but less than 80 kb, at least about 80 kb but less than 100 kb, at least 100 kb but less than 150 kb, or at least 150 kb but less than 200 kb, at least about 200 kb but less than about 300 kb, at least about 300 kb but less than about 400 kb, at least about 400 kb but less than about 500 kb, at least about 500 kb but less than about 1 Mb, at least about 1 Mb but less than about 1.5 Mb, at least about 1.5 Mb but less than about 2 Mb, at least about 2 Mb but less than about 2.5 Mb, or at least about 2.5 Mb but less than about 3 Mb.
63. The method of embodiment 60, wherein the 5' target sequence and the 3' target sequence are separated by at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, or at least 200 kb.
64. The method of any one of embodiments 25-63, wherein the genomic locus of interest comprises the Interleukin-2 receptor gamma locus, the ApoE locus, the Rag1 locus, the Rag2 locus, or both of the Rag1 and the Rag2 loci.
65. The method of any one of embodiments 25-63, wherein the genomic locus of interest comprises the Adamts5 locus, the Trpa1 locus, the Folh1 locus, or the Erbb4 locus.

66. The method of any one of embodiments 25-63, wherein the genomic locus of interest comprises the Lrp5 locus.

67. A method for producing an F0 generation non-human animal that comprises a targeted genetic modification at a genomic locus of interest, the method comprising: (a) contacting the genome in a non-human ES cell with a Cas protein, a CRISPR RNA, and a tracrRNA in the presence of a large targeting vector (LTVEC) to form a modified non-human ES cell, wherein the LTVEC is at least 10 kb and comprises a first nucleic acid flanked with a 5' homology arm and a 3' homology arm; (b) identifying the modified non-human ES cell comprising the targeted genetic modification at the genomic locus of interest; (c) introducing the modified non-human ES cell into a non-human host embryo; and (d) gestating the non-human host embryo in a surrogate mother, wherein the surrogate mother produces the F0 generation non-human animal comprising the targeted genetic modification at the genomic locus of interest.

68. The method of embodiment 67, wherein the CRISPR RNA and the tracrRNA are introduced together in the form of a single guide RNA (gRNA).

69. The method of embodiment 67, wherein the CRISPR RNA and the tracrRNA are introduced separately.

70. The method of any one of embodiments 67-69, wherein: (a) the Cas protein is introduced into the non-human ES cell in the form of a protein, a messenger RNA (mRNA) encoding the Cas protein, or a DNA encoding the Cas protein; (b) the CRISPR RNA is introduced into the non-human ES cell in the form of an RNA or a DNA encoding the CRISPR RNA; and (c) the tracrRNA is introduced into the non-human ES cell in the form of an RNA or a DNA encoding the tracrRNA.

71. The method of embodiment 70, wherein the Cas protein, the CRISPR RNA, and the tracrRNA are introduced into the non-human ES cell as a protein-RNA complex.

72. The method of embodiment 70, wherein: (a) the DNA encoding the Cas protein is in the form of a first expression construct comprising a first promoter operably linked to a second nucleic acid encoding the Cas protein; (b) the DNA encoding the CRISPR RNA is in the form of a second expression construct comprising a second promoter operably linked to a third nucleic acid encoding the CRISPR RNA; and (c) the DNA encoding the tracrRNA is in the form of a third expression construct comprising a third promoter operably linked to a fourth nucleic acid encoding the tracrRNA, wherein the first, second, and third promoters are active in the non-human ES cell.

73. The method of embodiment 72, wherein the first, second, and third expression constructs are on a single nucleic acid molecule.

74. The method of embodiment 70, wherein: (a) the DNA encoding the Cas protein is in the form of a first expression construct comprising a first promoter operably linked to a second nucleic acid encoding the Cas protein; and (b) the DNA encoding the CRISPR RNA and the DNA encoding the tracrRNA are in the form of a second expression construct comprising a second promoter operably linked to a third nucleic acid encoding a gRNA comprising the CRISPR RNA and the tracrRNA; wherein the first and second promoters are active in the non-human ES cell.

75. The method of embodiment 74, wherein the first and the second expression constructs are on a single nucleic acid molecule.

76. The method of any one of embodiments 67-75, wherein the targeted genetic modification comprises simultaneous deletion of an endogenous nucleic acid sequence at the genomic locus of interest and insertion of the first nucleic acid at the genomic locus of interest.

77. The method of any one of embodiments 67-76, wherein the targeted genetic modification is a biallelic genetic modification.

78. The method of embodiment 77, wherein the biallelic genetic modification comprises deletion of an endogenous nucleic acid sequence and insertion of the first nucleic acid at the genomic locus of interest in two homologous chromosomes.

79. The method of any one of embodiments 67-76, wherein the modified non-human ES cell is hemizygous at the genomic locus of interest.

80. The method of embodiment 79, wherein the targeted genetic modification at the genomic locus of interest in one chromosome comprises deletion of an endogenous nucleic acid sequence and insertion of the first nucleic acid.

81. The method of embodiment 79, wherein the targeted genetic modification comprises: (1) deletion of an endogenous nucleic acid sequence at the genomic locus of interest in two homologous chromosomes; and (2) insertion of the first nucleic acid into the genomic locus of interest in a first chromosome and disruption of the genomic locus of interest in a second chromosome.

82. The method of any one of embodiments 67-81, wherein the Cas protein is Cas9.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Figure 1:
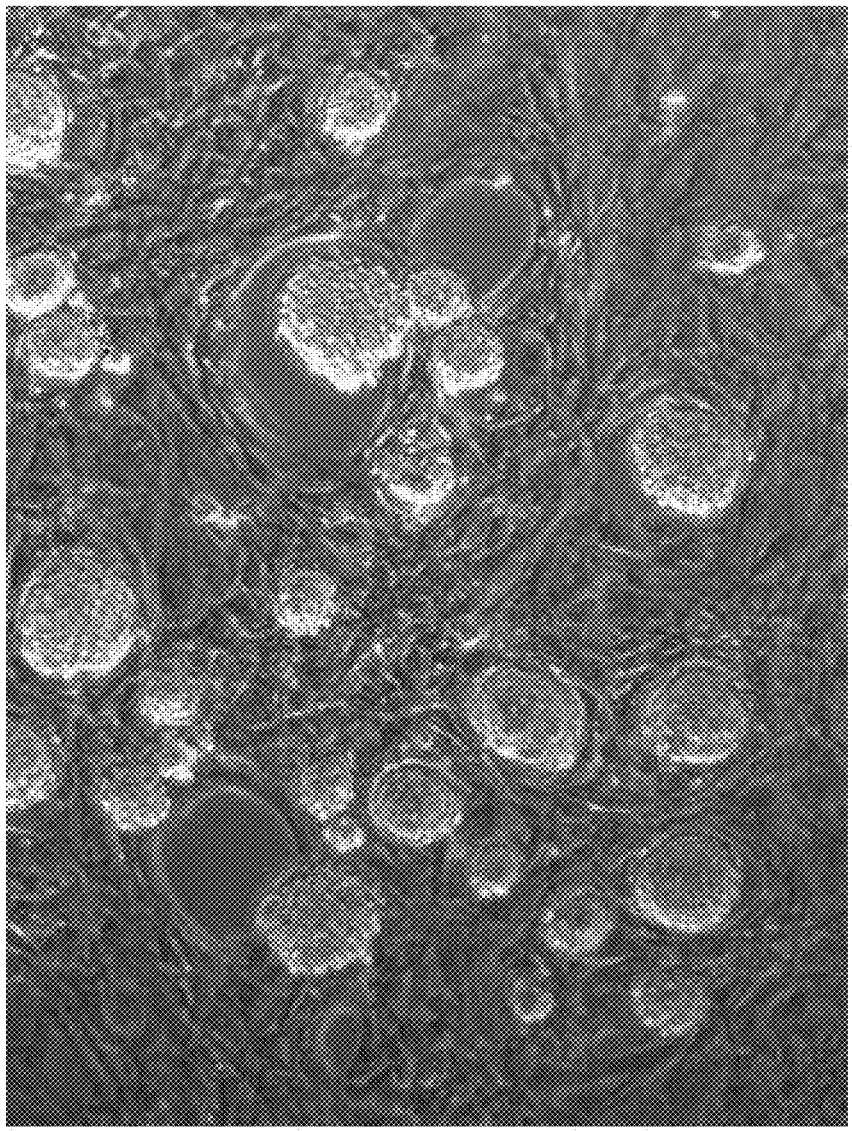
FIG. 1 depicts rat ESCs, which grow as compact spherical colonies that routinely detach and float in the dish.
Figure 2:
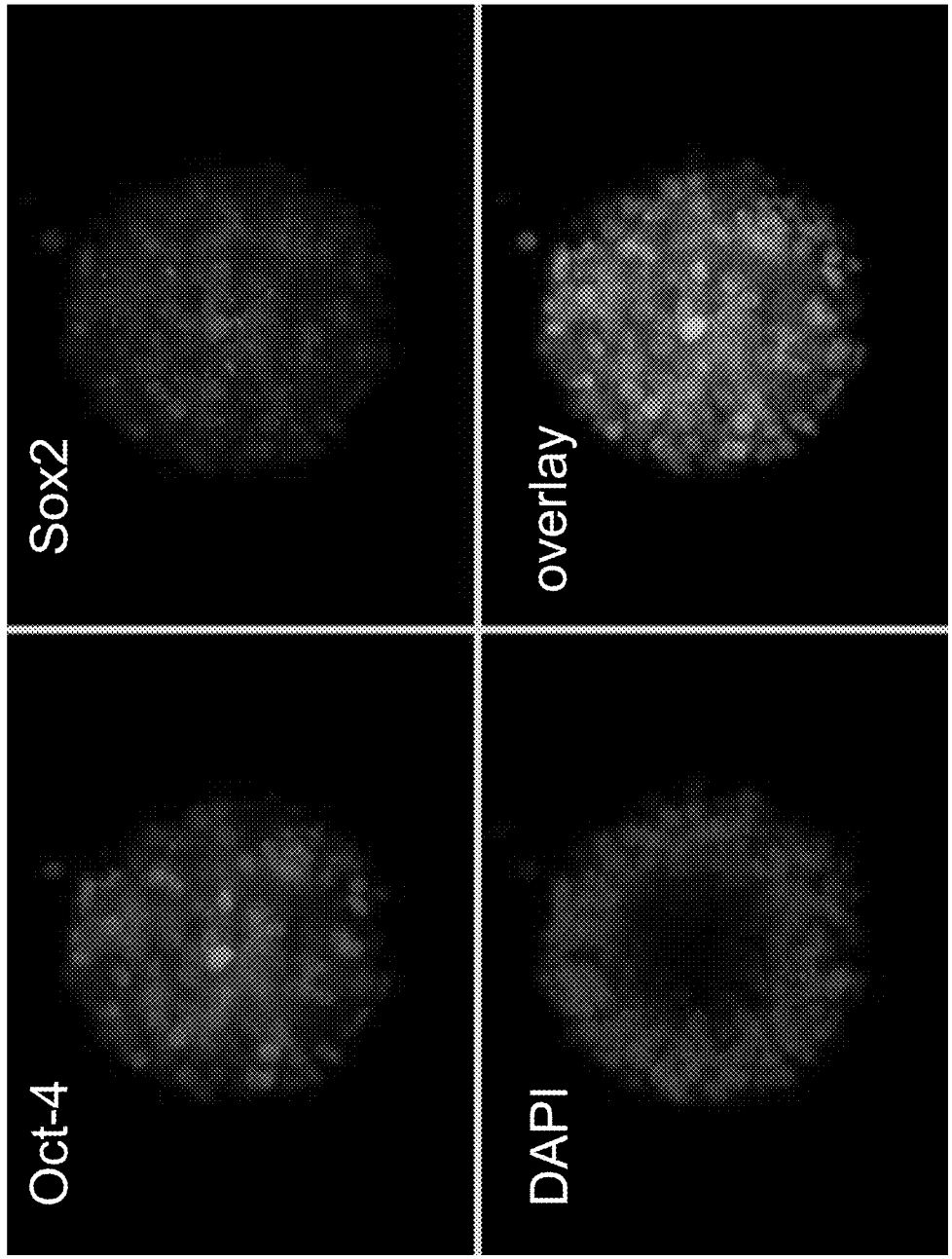
FIG. 2A through D depict various pluripotency markers expressed by rat ESCs: A depicts Oct-4 (green); B depicts Sox-2 (red); C depicts DAPI (blue); D depicts an overlay of pluripotency markers expressed by rESCs.
Figure 3:
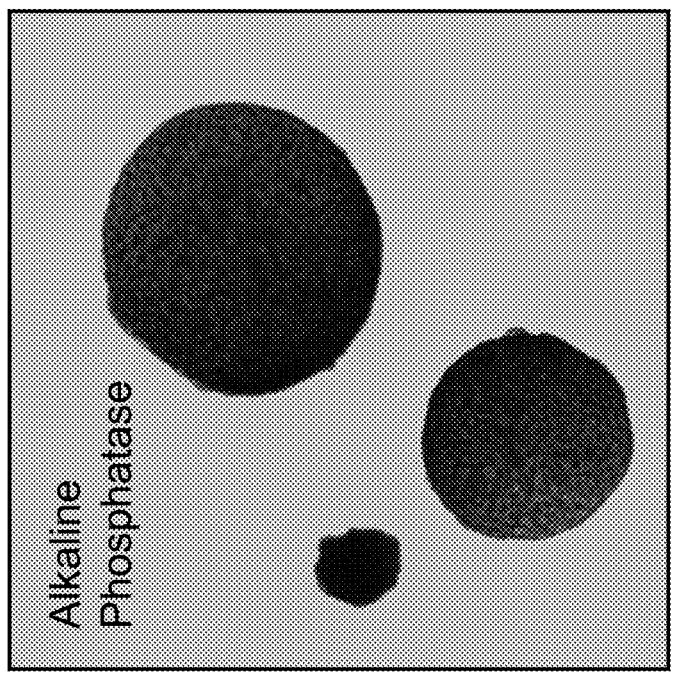
FIG. 3 depicts that the rat ESCs express light levels of alkaline phosphatase (a pluripotency marker).
Figure 8:
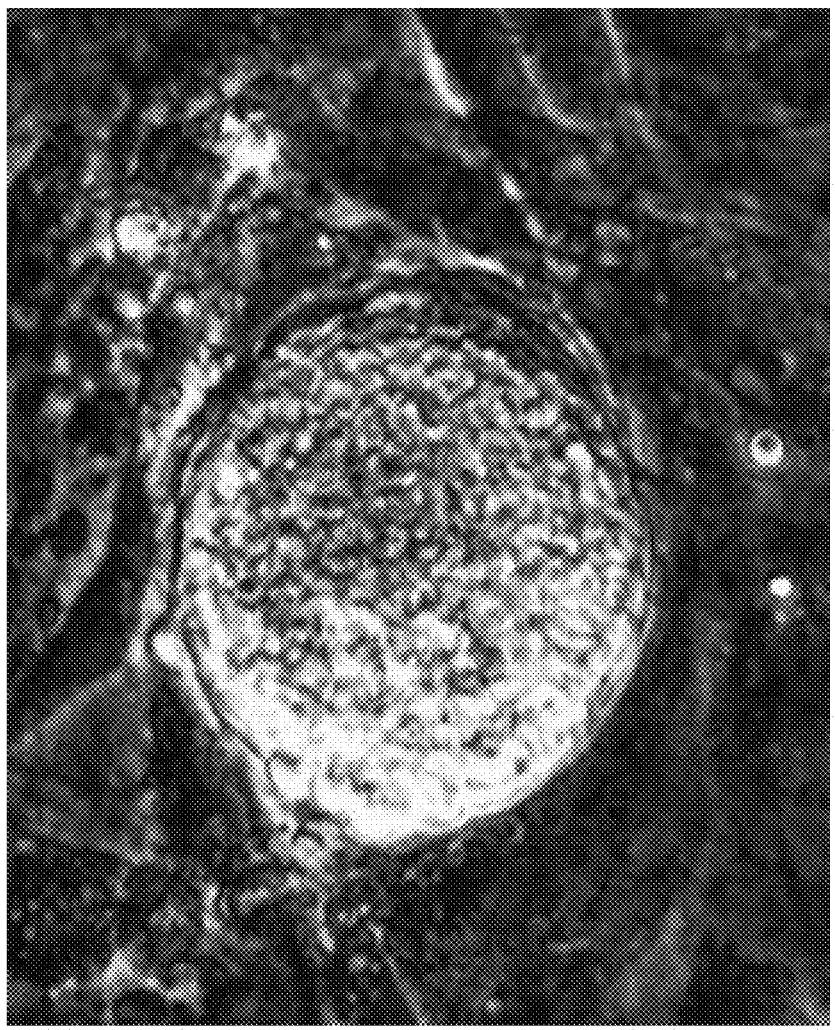
FIG. 8 depicts a closer view of a rat ESC of FIG. 1.

Example 1. Rat ES Cell Derivation and Characterization 1.1. Rat ES Cell Characterization As shown in FIG. 1, rat ESCs grow as compact spherical colonies, which routinely detach and float in the dish (close-up, FIG. 8). Rat ESCs express pluripotency markers including Oct-4 (FIG. 2A) and Sox2 (FIG. 2B), and express high levels of alkaline phosphatase (FIG. 3). Karyotype for line DA.2B is 42X,Y (FIG. 4). Rat ESCs often become tetraploid; thus, lines were pre-screened by counting metaphase chromosome spreads; lines with mostly normal counts were then formally karyotyped.

ACI blastocysts were collected from super-ovulated females obtained commercially. DA blastocysts were cultured from frozen 8-cell embryos obtained commercially. Zona pellucidae were removed with Acid Tyrodes; and blastocysts were plated onto mitotically inactivated MEFs. Outgrowths were picked and expanded using standard methods. All blastocysts were plated, cultured and expanded using 2i media (Li et al. (2008) Germline competent embryonic stem cells derived from rat blastocysts, Cell 135:1299-1310; incorporated herein by reference in its entirety).

TABLE 1

Rat ES Cell Derivation

|  | ACI | DA |
|---|---|---|
| Embryo source | Blastocysts (Superovulation) | Frozen 8-cell embryos cultured to blastocyst |
| Blastocysts plated: | 107 | 22 |
| Outgrowths: | 32 (30% of blasts) | 10 (45% of blasts) |
| Lines: | 16 (50% of outgrowths) | 9 (90% of outgrowths) |
| Karyotyped: | 3; all 42X, Y | 6: 3 42X, X<br>3 42X, Y |
| GLT validated: | 1 (ACI.G1) | 1 42X, X (DA.2C)<br>1 42X, Y (DA.2B) |

1.2. Rat Production

Figure 9:
FIG. 9 depicts production of chimeras by blastocyst injection and transmission of the rat ESC genome through the germline. Chimeras were produced by blastocyst injection using parental ACI.G1 rat ESCs. High percentage chimeras usually have albino snouts.
Figure 10:
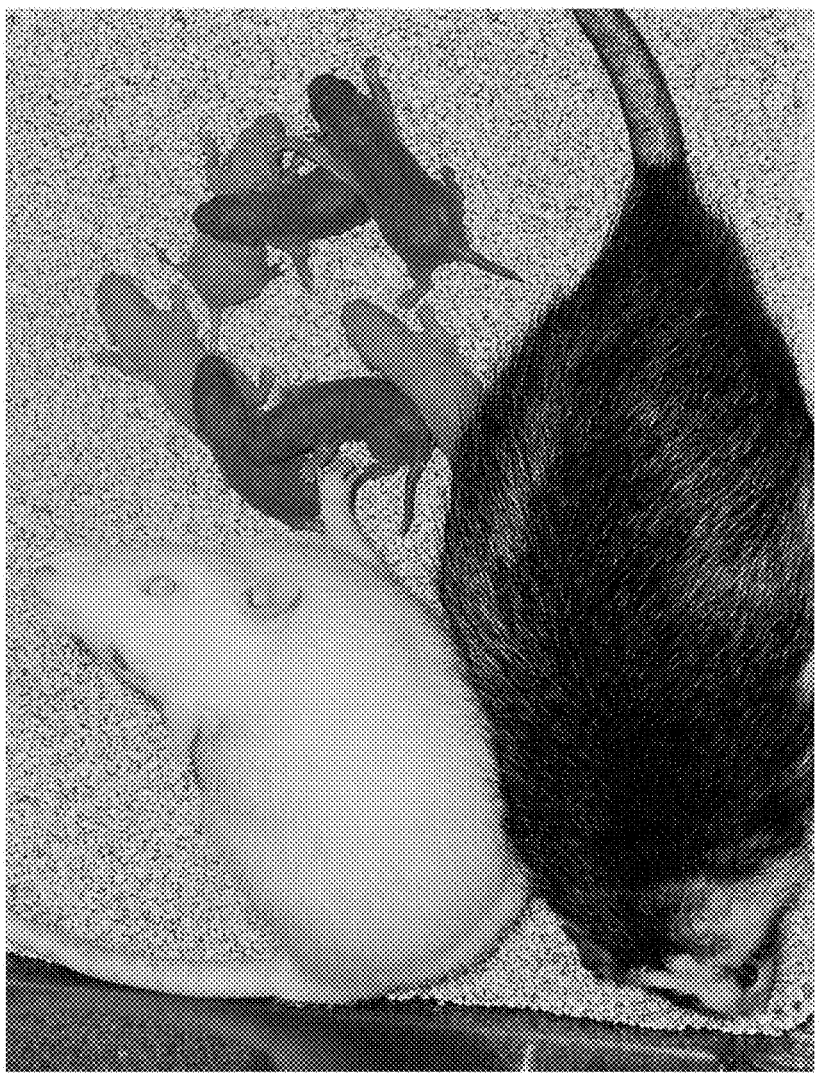
FIG. 10 depicts F1 agouti pups with albino littermates, sired by ACI/SD chimera labeled with an asterisk (*) in FIG. 9.

Chimeric rats were produced by blastocyst injection and transmission of the rat ESC genome. Chimeras produced by blastocyst microinjection using parental ACI.G1 rat ESCs are shown in FIG. 9. F1 agouti pups with albino littermates, sired by the ACI/SD chimera labeled with an asterisk (*) in FIG. 9 are shown in FIG. 10.

Germline Transmission of Parental Rat ESC.

Three euploid rat ESC lines were evaluated for pluripotency by microinjection into albino SD blastocysts. Chimeras were identified by agouti coat color, which indicates rat ESC contribution (see FIG. 10). For each line, a majority of chimeras transmitted the rESC genome to F1 offspring (Table 2).

TABLE 2

Germline Transmission of Parental rESC

| Line (Karyotype) | Chimeras bred | Germline transmitters | Total pups from GLT chimeras | rESC-derived pups | GLT efficiency (%) |
|---|---|---|---|---|---|
| ACI.G1 (XY) | 5 | 3 (60%) | 103 | 11 | 11 |
| DA.2B (XY) | 5 | 4 (80%) | 129 | 11 | 9 |
| DA.2C (XX) | 3 | 2 (66%) | 45 | 7 | 16 |

1.3. Derivation of Rat Embryonic Stem Cells.

Superovulation Protocol, Rats

Day 0: injected with pregnant mare serum: IP, 20 U (0.4 ml).

Day 1: no action

Day 2: (46 hr. later): injected with hCG, IP, 50 U (1 ml). set up single female matings.

Day 3: checked plugs. Females were plugged. This is day 0.5.

Day 6 (e3.5): Euthanized females and flushed embryos.

ES Cell Derivation Protocol (Superovulation)

Day 0:

1) Euthanized female rat with $CO_2$.
2) Swabbed ventral abdomen with 70% ethanol; using scissors, opened the ventral body wall to expose the viscera.
3) Dissected out the oviducts and uterine horns and placed them into a tissue culture dish containing warm N2B27 media. Washed out as much blood as possible and transferred to a new dish with N2B27.
4) Using a 1 ml syringe and a blunt 27 g needle, flushed media through the uterine horns and oviducts to eject blastocysts into the media.
5) Collected the blastocysts with a mouth pipet and transfer to embryo culture dish containing KSOM+2i (1 µMPD0325901, 3 µM CHIR99021). KSOM is a culture medium produced by Millipore. Catalog number is MR-106-D.
6) Cultured overnight at 37°; 7.5% $CO_2$.

ES Cell Derivation Protocol (Frozen Embryos)

Day 0:

1) Thawed frozen 8-cell embryos (commercially obtained) into M2 medium. Cultured 10 minutes at room temperature.
2) Transferred to KSOM+2i and culture overnight.

ES Cell Derivation Protocol (Same for Both)

Day 1:

1) Transferred cavitated embryos to 2i medium & culture overnight.
2) Continued culturing un-cavitated embryos in KSOM+2i Day 2:

1) Transferred all remaining embryos to 2i medium (whether or not they've cavitated).
2) Cultured overnight; continued culturing earlier embryos in 2i medium.

Day 3:

1) Transferred embryos for 30-60 seconds with Acid Tyrodes to remove the zona pellucida.
2) Washed embryos 3× in 2i medium to remove Acid Tyrodes.
3) Deposited each embryo into a separate well of a 96-well feeder plate (the well contains a monolayer of mitotically inactivated mouse embryonic fibroblasts (MEFs).
4) Cultured overnight in 2i medium.

Day 4-5:

1) Monitored plated embryos for the presence of an outgrowth (an amorphous undifferentiated mass of cells). Outgrowths are ready for transfer when they are approximately twice the size of the plated embryo.
2) Each day: remove spent media with a micropipet and replace with fresh 2i media.
3) Transferred outgrowths to new feeder wells:
   a. Removed spent media and gently wash well with PBS.
   b. Removed PBS and add 30 µl 0.05% trypsin; incubate for 10 minutes.
   c. Stopped trypsin reaction by adding 30 µl 2i+ 10% FBS.
   d. Gently dissociated the cells with a micropipettor and transferred entire contents of the well to a new well in a 24-well feeder plate. This was Passage 1 (P1).
   e. Cultured overnight in 2i medium.

Day 5-8: (timing depends on how fast each line expands)

1) Changed media each day (2i media) and monitored for the presence of colonies with an ESC morphology.
2) When colonies appear, continued culturing until colonies expand to ~50% confluency.
3) Trypsinized and passaged colonies as before; plated on feeders, 1 well per line, in a 6-well dish. This was Passage 2 (P2).

Ongoing:

1) Continued feeding and monitoring each line until approximately 50% confluent.

2) Trypsinized cells as usual.
3) stopped trypsin with 2i+ 10% FBS; pelleted the cells by centrifugation (5', 1200 rpm in Beckman-Coulter table-top centrifuge).
4) Aspirated the supernatant and gently resuspend the cells in 400 μl Freezing Medium (70% 2i, 20% FBS, 10% DMSO).
5) Distributed the cells into 2 vials and freeze at −80°. This was Passage 3 (P3).
6) For long-term storage, transferred the vials to liquid N2 storage.

The 2i media was prepared as follows in Table 3.

| Reagent | Vendor | Concentration |
| --- | --- | --- |
| DMEM/F12 basal media | Invitrogen/Life Technologies | 1x |
| Neurobasal media | Invitrogen/Life Technologies | 1x |
| Penicillin/streptomycin | Invitrogen/Life Technologies | 1% |
| L-Glutamine | Invitrogen/Life Technologies | 4 mM |
| 2-Mercaptoethanol | Invitrogen/Life Technologies | 0.1 mM |
| N2 supplement | Invitrogen/Life Technologies | 1x |
| B27 supplement | Invitrogen/Life Technologies | 1x |
| LIF | Millipore | 100 U/ml |
| PD0325901 (MEK inhibitor). | Stemgent | 1 uM |
| CHIR99021 (GSK inhibitor). | Stemgent | 3 uM |

Materials:
Pregnant Mare's Serum Gonadotropin (PMSG)
Human Pregnancy Urine Chorionic Gonadotropin (HCG)
Female Rats (5-12 weeks old)
Male rats (12 wks. to 8 mos. old), one per cage
Syringes/needles
Animal room with lights on 6:00-18:00
Procedure:
Day 1: 8:00-10:00 AM
Inject females with 20 IU PMSG (0.4 ml), IP
Discard unused PMSG.
Day 3: 8:00-10:00 AM (48 hours after PMSG injection)
Inject females with 50 IU HCG (1 ml), IP
Place one female per male in mating cage.
Discard unused HCG.
Day 4: 8:00-10:00 AM (24 hrs. after HCG injection)
Check females for plugs.
Hormone Suppliers
PMSG: Sigma # G-4877 (1000 IU). Resuspend in PBS to a final [ ] of 50 IU/ml. Store at −20° in 1 ml aliquots.
HCG: Sigma # CG-5 (5000 IU). Resuspend in PBS to a final [ ] of 50 IU/ml. Store at −20° in 1 ml aliquots.

1.4. Karyotyping of Rat Embryonic Stem Cell Lines

The rat ES cell lines generated herein were karyotyped, and the results are summarized in Tables 4-7.

TABLE 4

| ACI.G1 Karyotyping Results | Number of cells |
| --- | --- |
| Number of cells karyotyped | 7 |
| Number of cells analyzed | 20 |
| Number of 42, XY cells | 18 |
| Number of abnormal cells | 2 |
| 40, XY, −5, −9 | 1 |

TABLE 4-continued

Figure 5A:
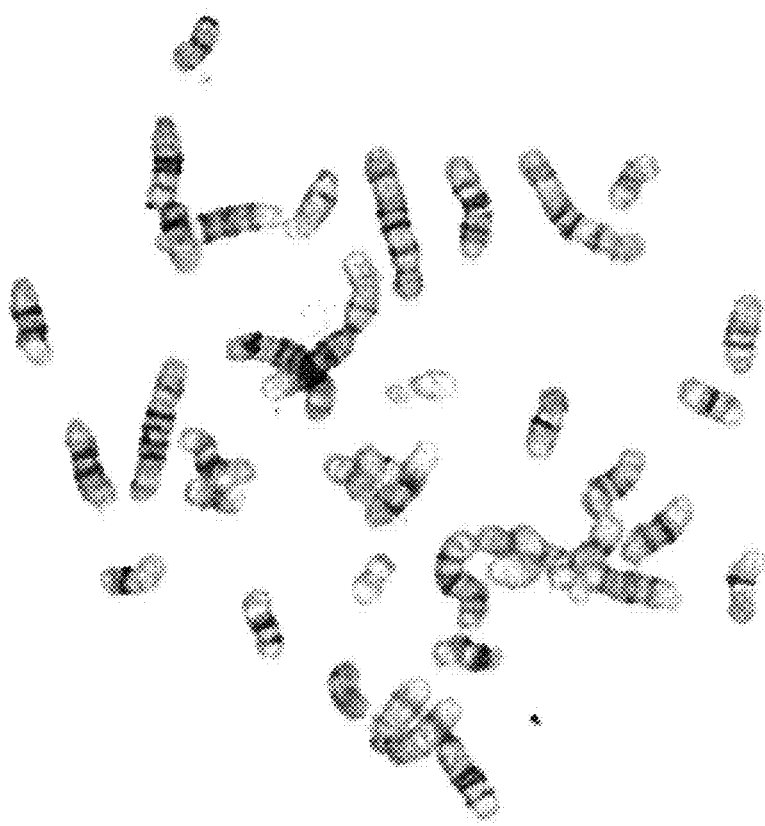
FIG. 5A-B provides photographs showing the analysis of the chromosome number of the ACI.G1 rat ES cell line.
Figure 5B:
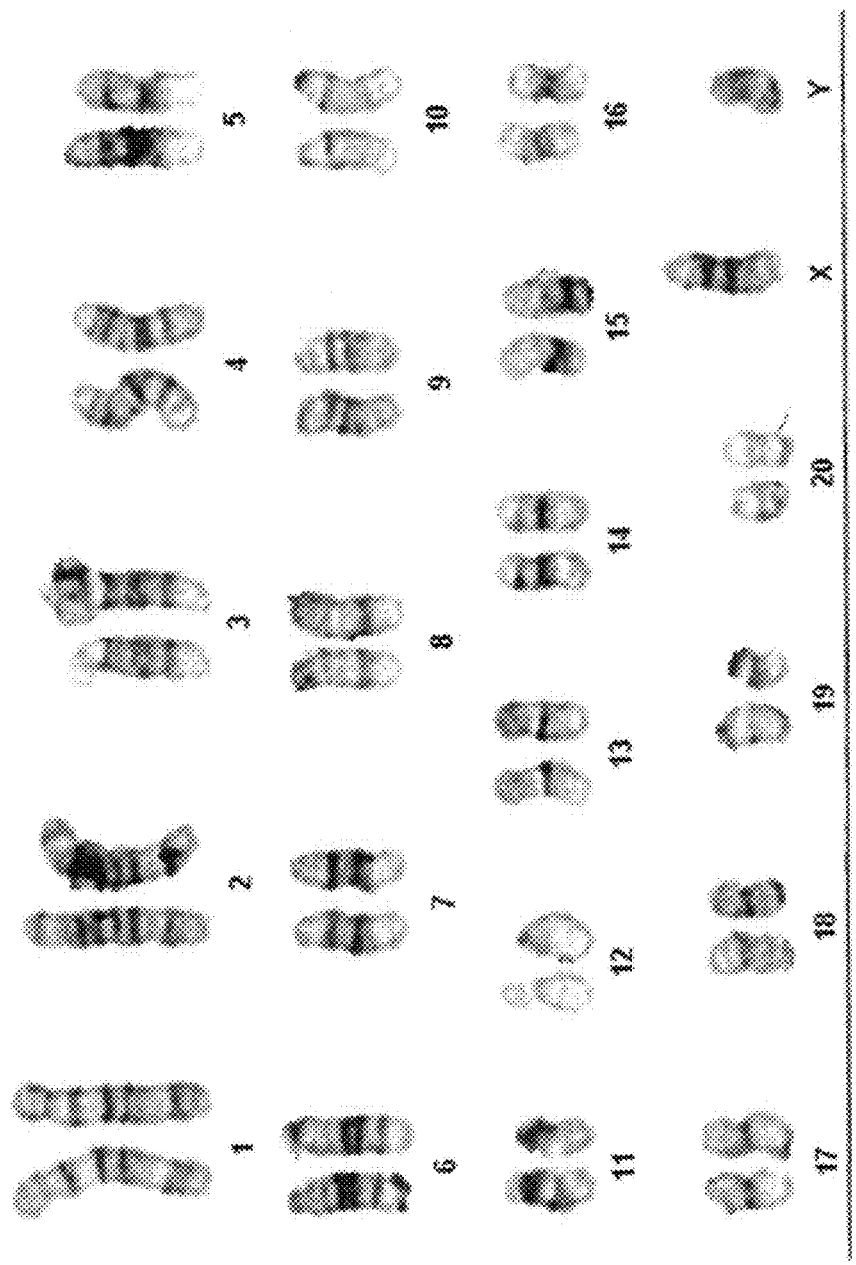

| ACI.G1 Karyotyping Results | Number of cells |
| --- | --- |
| 41, XY, −14 | 1 |
| 42, XY | 18 |
| Other notes: | |
| Two analyzed cells were missing different autosomes, which may be a sporadic occurrence due to technical artifact. 90% of analyzed cells had a normal male 42, XY karyotype. | |
| FIG. 5 provides a photograph showing the analysis of the chromosome number of the ACI.G1 rat ES cell line. | |

TABLE 5

Figure 6A:
FIG. 6A-B provides photographs showing the analysis of the chromosome number of the DA.2B rat ES cell line.
Figure 6B:
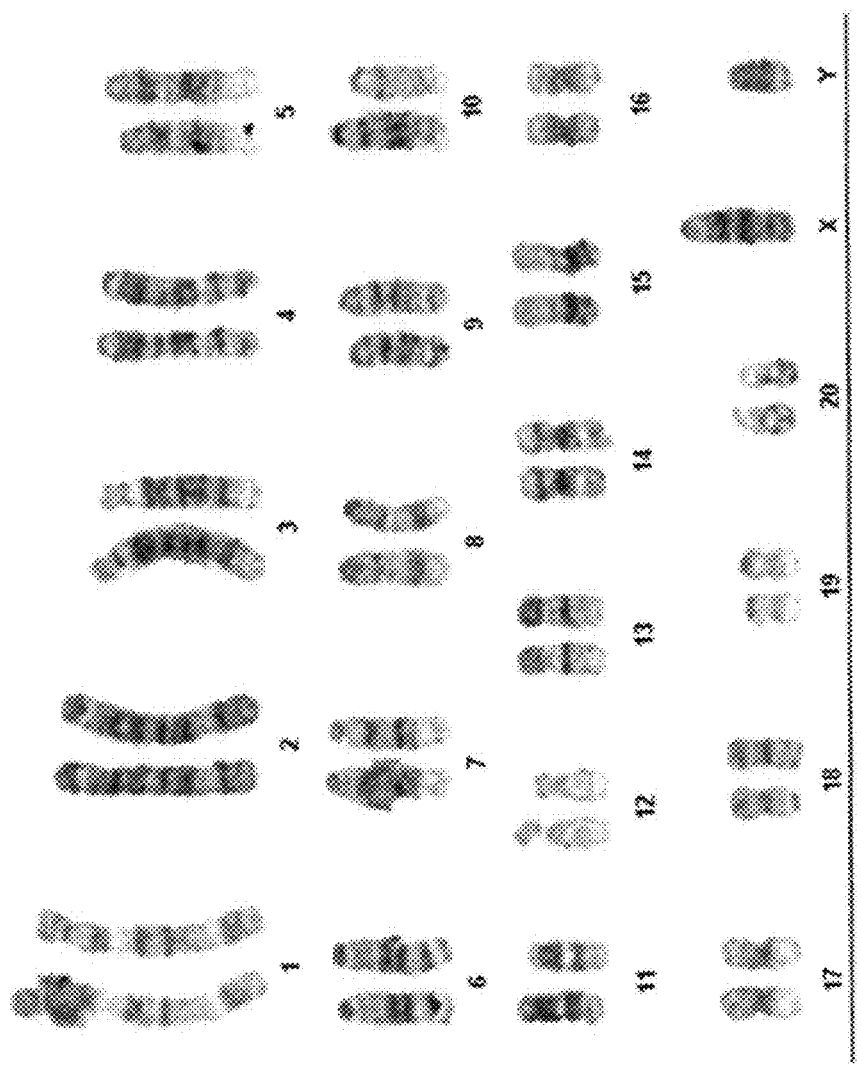

| DA.2B Karyotyping Results | Number of cells |
| --- | --- |
| Number of cells karyotyped | 6 |
| Number of cells analyzed | 20 |
| Number of 42, XY cells | 20 |
| Number of abnormal cells | 0 |
| 42, XY | 20 |
| Other notes: | |
| All analyzed cells had a normal diploid 42, XY karyotype. | |
| FIG. 6 provides a photograph showing the analysis of the chromosome number of the DA.2B rat ES cell line. | |

TABLE 6

Figure 7A:
FIG. 7A-B provides photographs showing the analysis of the chromosome number of the DA.2C rat ES cell line.
Figure 7B:
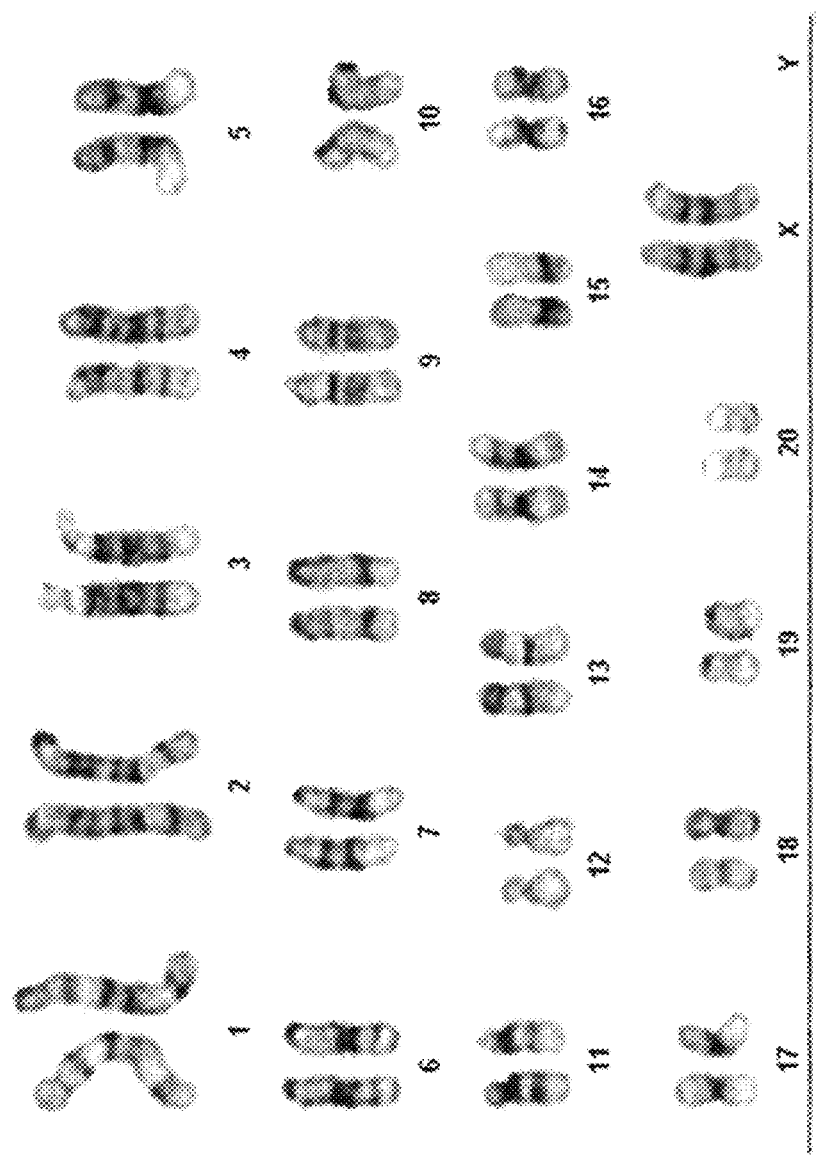

| DA.2C Karyotyping Results | Number of cells |
| --- | --- |
| Number of cells karyotyped | 5 |
| Number of cells analyzed | 20 |
| Number of 42, XX cells | 20 |
| Number of abnormal cells | 0 |
| 42, XX | |
| Other notes: | |
| 100% of analyzed cells had normal female XX rat karyotype. | |
| FIG. 7 provides a photograph showing the analysis of the chromosome number of the DA.2C rat ES cell line. | |

TABLE 7

| strain | Blastocysts plated | Lines established | Lines Karyotyped | Karyotypes |
| --- | --- | --- | --- | --- |
| BN × SDF1 | 41 | 8 (20%) | 5 | all lines were high % complex polyploid |
| ACI | 27 | 16 (60%) | 3 | G1: 90% 42 XY; others were 70-85% euploid |
| DA | 20 | 9 (45%) | 6 | 2B: 100% 42 XY; 2C: 100% 42 XX; others were 95-100% euploid |
| F344 | 4 | 1 (25%) | 0 | |
| Totals | 92 | 34 (37%) | | |

1.5. Electroporation of Vector into Rat Embryonic Stem Cell

1. Passaged rat ES cells 24-48 hrs prior to electroporation.
2. Changed media to RVG2i+ROCKi (10 μM Y-27632) 24 hr. prior to electroporation
3. Changed media 30' prior to trypsinization.
4. Aliquoted DNA to be electroporated.
5. Allowed DNA to warm at RT for >10 min.
6. Heated DNA for 5' @ 62° C. Place DNA on ice.

7. Trypsinized cells:
   a. Collected floating colonies. Washed plate to collect as many floaters as possible.
   b. Pelleted colonies: 3' @ 750 rpm.
   c. Washed pellet 1× with 5-10 ml PBS and re-spin/pellet
   d. Aspirated supernatant; add 500λ trypsin, 0.05%+1% chicken serum.
      i. Did not pool more than 110 cm plate of colonies per tube. If there are too many colonies packed into the bottom of the tube during trypsinization they will clump and most of the cells will be lost.
   e. 4' @ 37°. Pipetted colonies several times to minimize clumping.
   f. Repeated steps 1-2 X: 4' @ 37°.
   g. Stopped trypsin with 500λ RVG2i+ 10% FBS.
8. Pelleted cells: 5' @ 1200 rpm.
9. Resuspend cells in 10 ml PBS. Count two 20λ aliquots to determine total cell number.
10. Pelleted cells (5'/1200 rpm); calculate total cell number and total resuspension volume to achieve correct cell concentration (target #/75 μl EP buffer).
11. Resuspend in a minimal volume of EP buffer; measure total volume and adjust to target volume with EP buffer. Electroporation buffer is sold by Millipore. The catalog # is ES-003-D. See, Valenzuela et al. (2003) *Nature Biotechnology* 21:652-659, which is herein incorporated by reference.
12. Add 75λ cells to 50×DNA; transfer the 125λ cells/DNA solution to one well of a BTX 48-well cuvette.
    a. Filled the empty wells in the same column with 125λ EP buffer.
13. Pulsed the cuvette once in the BTX electroporator:
    a. Settings: 400V; Ω; 100 μF (settings may vary)
14. Placed cuvette on ice for 15' to recover.
15. Removed cells into 5 ml RVG2i+ 10 μM ROCKi.
16. Added to 15 cm plate with 20 ml RVG2i+ 10 μM ROCKi. Plate has 2×neoR MEFs (or other MEFs depending on project). The neoR selectable marker is the neomycin phosphotransferase (neo) gene of Beck et al. (1982) Gene, 19:327-36 or in U.S. Pat. No. 7,205,148 or 6,596,541, each of which are herein incorporated by reference.
17. Incubated @ 37°. Begin selection 48 hrs later.
ROCK inhibitor used was Y-27632.

1.6: Selecting a Targeted Genetic Modification in a Rat Embryonic Stem Cell.
1. Passaged cells for 24-48 hrs prior to electroporation.
2. Changed media to RVG2i+ROCKi (10 μM Y-27632) 24 hr. prior to electroporation
3. Changed media 30' prior to trypsinization.
4. Aliquoted DNA to be electroporated.
5. Allowed DNA warm at RT for >10 min.
6. Heated DNA for 5' @ 62° C. Place DNA on ice.
7. Trypsinized cells:
   a. Collected floating colonies. Washed plate to collect as many floaters as possible.
   b. Pelleted colonies: 3' @ 750 rpm.
   c. Washed pellet 1× with 5-10 ml PBS and re-spin/pellet
   d. Aspirated supernatant; add 500λ trypsin, 0.05%+1% chicken serum.
      i. Did not pool more than 110 cm plate of colonies per tube. If there are too many colonies packed into the bottom of the tube during trypsinization they will clump and most of the cells will be lost.
   e. 4' @ 37°. Pipetted colonies several times to minimize clumping
   f. Repeated 1-2 X: 4' @ 37°.
   g. Stopped trypsin with 500λ RVG2i+ 10% FBS.
8. Pelleted cells: 5' @ 1200 rpm.
9. Resuspended cells in 10 ml PBS. Count two 20λ aliquots to determine total cell number.
10. Pelleted cells (5'/1200 rpm); calculate total cell number and total resuspension volume to achieve correct cell concentration (target #/75 μl EP buffer).
11. Resuspend in a minimal volume of EP buffer; measured total volume and adjusted to target volume with EP buffer.
12. Added 75λ cells to 50×DNA; transfer the 125λ cells/DNA solution to one well of a BTX 48-well cuvette.
    a. Filled the empty wells in the same column with 125λ EP buffer.
13. Pulsed the cuvette once in the BTX electroporator:
    a. Settings: 400V; 100 μF (settings may vary)
14. Placed cuvette on ice for 15' to recover.
15. Removed cells into 5 ml RVG2i+ 10 μM ROCKi.
16. Added to 15 cm plate with 20 ml RVG2i+ 10 μM ROCKi. Plate had 2×neoR MEFs (or other MEFs depending on project).
17. Incubated @ 37°. Began selection 48 hrs later.
18. G418 selection protocol was as follows:
    a. Day 2 ($2^{nd}$ day after EP): incubated cells in 2i media+G418, 75 μg/ml.
    b. Day 3: incubated cells in 2i media without G418
    c. Day 4: incubated cells in 2i media+G418, 75 μg/ml.
    d. Day 5: incubated cells in 2i media without G418
    e. Day 6: incubated cells in 2i media+G418, 75 μg/ml.
    f. Day 7: incubated cells in 2i media without G418
    g. Day 8: incubated cells in 2i media+G418, 75 μg/ml.
    h. Day 9: incubated cells in 2i media without G418
    i. Day 10: incubated cells in 2i media+G418, 75 μg/ml.
    j. Day 11: incubated cells in 2i media without G418
    k. Day 12: picked colonies to expand for screening. Each colony was dissociated in 0.05% trypsin+1% chicken serum for 10 minutes and then plated into 1 well of a 96-well feeder plate.
19. Expanded colonies for 3 days in 2i media.
20. Passaged clones 1:1 to new 96-well feeder plates.
21. Expanded clones for 3 days in 2i media.
22. For each clone, dissociated colonies in trypsin. Froze ⅔ of each clone and store at −80°; plated the remaining ⅓ onto laminin plates (96-well plates coated with 10 μg/ml laminin).
23. When the laminin plates were confluent, passed off to the screening lab for genotyping of the clones.

1.7. Molecular Signature of the Rat Embryonic Stem Cells

The genes listed in Table 8 were expressed at 20-fold lower in rat ES cells than the corresponding genes in mouse ES cells. The genes listed in Table 9 were expressed at levels 20-fold higher in rat ES cells than the corresponding genes in mouse ES cells.

The microarray data in Tables 8 and 9 were generated as follows. Rat ES cells (ACI.G2 and DA.2B) and mouse ES cells (F1H4) were cultured in 2i media for 3 passages until confluent. F1H4 cells were cultured on gelatin-coated plates in the absence of feeders. F1H4 mouse ES cells were derived from 12956/SvEvTac and C57BL/6NTac heterozygous embryos (see, e.g., U.S. Pat. No. 7,294,754 and Poueymirou, W. T., Auerbach, W., Frendewey, D., Hickey, J. F., Escaravage, J. M., Esau, L., Dore, A. T., Stevens, S., Adams, N. C., Dominguez, M. G., Gale, N. W., Yancopoulos, G. D., DeChiara, T. M., Valenzuela, D. M. (2007), incorporated by reference herein in its entirety).

The following protocol was used for sample prep: The 1.5 mL Eppendorf tubes were labeled with the Sample ID. Cells grown on a plate were rinsed in 37° C. Phosphate-Buffered Saline (PBS). PBS was removed and 300 ul of Trizol® was added. A scraper was used to break the cells in Trizol® (Life Technology). The lysed cells were collected in Trizol® in a 1.5 mL Eppendorf tube. For cells grown on suspension, the cells were rinsed in 37° C. PBS and collected in a 1.5 mL tube. The cells were spun down; PBS was removed; and 300 ul of Trizol® was added to the cells. The cell membranes were broken by pipetting. Samples were sorted for FACS with 10 to $10^5$ cells, the volume was concentrated to less than 100 uL. 4 volumes of RNA Lysis buffer were added and mixed by pipetting. For sample, 320 uL RNA Lysis buffer was added to 80 uL sample. Samples were stored at −20° C.

RNA-Seq was used to measure the expression level of mouse and rat genes. Sequencing reads were mapped to mouse and rat reference genome by Tophat, and RPKM (fragments per kilobase of exon per million fragments mapped) were calculated for mouse and rat genes. Homology genes based on gene symbol were selected, and then used t-test to compare the expression level of each gene between mouse and rat. miR-32 was in the top 10 highest expressed in rat ESCs but was not expressed in mouse ES cells. Although no comparative data exist from miR-632, based on the level of its expression compared to other genes expressed in rat ESCs and their known function in embryonic development, miR-632 was selected as a marker for rat ES cells.

TABLE 8

The genes listed were expressed at levels 20-fold lower in rat ES cells than the corresponding genes in mouse ES cells.

| ID | Symbol | Entrez Gene Name | Location | Type(s) |
| --- | --- | --- | --- | --- |
| Abcb1b | Abcb1b | ATP-binding cassette, sub-family B (MDR/TAP), member 1B | Plasma Membrane | transporter |
| Acta2 | ACTA2 | actin, alpha 2, smooth muscle, aorta | Cytoplasm | other |
| Actg2 | ACTG2 | actin, gamma 2, smooth muscle, enteric | Cytoplasm | other |
| Aebp1 | AEBP1 | AE binding protein 1 | Nucleus | peptidase |
| Angptl2 | ANGPTL2 | angiopoietin-like 2 | Extracellular Space | other |
| Ankrd1 | ANKRD1 | ankyrin repeat domain 1 (cardiac muscle) | Cytoplasm | transcription regulator |
| Anxa1 | ANXA1 | annexin A1 | Plasma Membrane | other |
| Anxa6 | ANXA6 | annexin A6 | Plasma Membrane | other |
| Anxa8 | ANXA8L2 | annexin A8-like 2 | Plasma Membrane | other |
| Arhgef25 | ARHGEF25 | Rho guanine nucleotide exchange factor (GEF) 25 | Cytoplasm | other |
| Axl | AXL | AXL receptor tyrosine kinase | Plasma Membrane | kinase |
| Basp1 | BASP1 | brain abundant, membrane attached signal protein 1 | Nucleus | transcription regulator |
| Bgn | BGN | biglycan | Extracellular Space | other |
| Bst2 | BST2 | bone marrow stromal cell antigen 2 | Plasma Membrane | other |
| Btf3 | BTF3 | basic transcription factor 3 | Nucleus | transcription regulator |
| Btg2 | BTG2 | BTG family, member 2 | Nucleus | transcription regulator |
| Capsl | CAPSL | calcyphosine-like | Other | other |
| Cav1 | CAV1 | caveolin 1, caveolae protein, 22 kDa | Plasma Membrane | transmembrane receptor |
| Ccdc80 | CCDC80 | coiled-coil domain containing 80 | Nucleus | other |
| Ccnd2 | CCND2 | cyclin D2 | Nucleus | other |
| Cd248 | CD248 | CD248 molecule, endosialin | Plasma Membrane | other |
| Cd44 | CD44 | CD44 molecule (Indian blood group) | Plasma Membrane | enzyme |
| Cd97 | CD97 | CD97 molecule | Plasma Membrane | G-protein coupled receptor |
| Cdc42ep5 | CDC42EP5 | CDC42 effector protein (Rho GTPase binding) 5 | Cytoplasm | other |
| Cdh11 | CDH11 | cadherin 11, type 2, OB-cadherin (osteoblast) | Plasma Membrane | other |
| Cdkn2a | CDKN2A | cyclin-dependent kinase inhibitor 2A | Nucleus | transcription regulator |
| Cdo1 | CDO1 | cysteine dioxygenase type 1 | Cytoplasm | enzyme |

TABLE 8-continued

The genes listed were expressed at levels 20-fold lower in rat
ES cells than the corresponding genes in mouse ES cells.

| ID | Symbol | Entrez Gene Name | Location | Type(s) |
|---|---|---|---|---|
| Clip3 | CLIP3 | CAP-GLY domain containing linker protein 3 | Cytoplasm | other |
| Cln5 | CLN5 | ceroid-lipofuscinosis, neuronal 5 | Cytoplasm | other |
| Cnn1 | CNN1 | calponin 1, basic, smooth muscle | Cytoplasm | other |
| Col1a1 | COL1A1 | collagen, type I, alpha 1 | Extracellular Space | other |
| Col1a2 | COL1A2 | collagen, type I, alpha 2 | Extracellular Space | other |
| Col3a1 | COL3A1 | collagen, type III, alpha 1 | Extracellular Space | other |
| Col5a2 | COL5A2 | collagen, type V, alpha 2 | Extracellular Space | other |
| Col6a2 | COL6A2 | collagen, type VI, alpha 2 | Extracellular Space | other |
| Cryab | CRYAB | crystallin, alpha B | Nucleus | other |
| Csf1 | CSF1 | colony stimulating factor 1 (macrophage) | Extracellular Space | cytokine |
| Cth | CTH | cystathionase (cystathionine gamma-lyase) | Cytoplasm | enzyme |
| Cthrc1 | CTHRC1 | collagen triple helix repeat containing 1 | Extracellular Space | other |
| Ctsc | CTSC | cathepsin C | Cytoplasm | peptidase |
| Cyr61 | CYR61 | cysteine-rich, angiogenic inducer, 61 | Extracellular Space | other |
| Ddx58 | DDX58 | DEAD (Asp-Glu-Ala-Asp) box polypeptide 58 | Cytoplasm | enzyme |
| Dkk3 | DKK3 | dickkopf WNT signaling pathway inhibitor 3 | Extracellular Space | cytokine |
| Dmc1 | DMC1 | DNA meiotic recombinase 1 | Nucleus | enzyme |
| Dpysl3 | DPYSL3 | dihydropyrimidinase-like 3 | Cytoplasm | enzyme |
| Dse | DSE | dermatan sulfate epimerase | Cytoplasm | enzyme |
| Dusp1 | DUSP1 | dual specificity phosphatase 1 | Nucleus | phosphatase |
| Dusp27 | DUSP27 | dual specificity phosphatase 27 (putative) | Other | phosphatase |
| Dusp9 | DUSP9 | dual specificity phosphatase 9 | Nucleus | phosphatase |
| Ece2 | ECE2 | endothelin converting enzyme 2 | Plasma Membrane | peptidase |
| Ecm1 | ECM1 | extracellular matrix protein 1 | Extracellular Space | transporter |
| Egr1 | EGR1 | early growth response 1 | Nucleus | transcription regulator |
| Emp1 | EMP1 | epithelial membrane protein 1 | Plasma Membrane | other |
| Emp3 | EMP3 | epithelial membrane protein 3 | Plasma Membrane | other |
| Ephx2 | EPHX2 | epoxide hydrolase 2, cytoplasmic | Cytoplasm | enzyme |
| F3 | F3 | coagulation factor III (thromboplastin, tissue factor) | Plasma Membrane | transmembrane receptor |
| Fau | FAU | Finkel-Biskis-Reilly murine sarcoma virus (FBR-MuSV) ubiquitously expressed | Cytoplasm | other |
| Fbn1 | FBN1 | fibrillin 1 | Extracellular Space | other |
| Fbxo15 | FBXO15 | F-box protein 15 | Other | transcription regulator |
| Fhl2 | FHL2 | four and a half LIM domains 2 | Nucleus | transcription regulator |
| Flnc | FLNC | filamin C, gamma | Cytoplasm | other |
| Fos | FOS | FBJ murine osteosarcoma viral oncogene homolog | Nucleus | transcription regulator |

TABLE 8-continued

The genes listed were expressed at levels 20-fold lower in rat
ES cells than the corresponding genes in mouse ES cells.

| ID | Symbol | Entrez Gene Name | Location | Type(s) |
|---|---|---|---|---|
| Fundc2 | FUNDC2 | FUN14 domain containing 2 | Cytoplasm | other |
| Gjb3 | GJB3 | gap junction protein, beta 3, 31 kDa | Plasma Membrane | transporter |
| Gpa33 | GPA33 | glycoprotein A33 (transmembrane) | Plasma Membrane | other |
| Gpbp1l1 | GPBP1L1 | GC-rich promoter binding protein 1-like 1 | Other | other |
| Gpc3 | GPC3 | glypican 3 | Plasma Membrane | other |
| Grb10 | GRB10 | growth factor receptor-bound protein 10 | Cytoplasm | other |
| Gstm1 | GSTM5 | glutathione S-transferase mu 5 | Cytoplasm | enzyme |
| Hap1 | HAP1 | huntingtin-associated protein 1 | Cytoplasm | other |
| Hist1h2bc | HIST2H2BE (includes others) | histone cluster 2, H2be | Nucleus | other |
| Hmga2 | HMGA2 | high mobility group AT-hook 2 | Nucleus | enzyme |
| Hmgn3 | Hmgn3 | high mobility group nucleosomal binding domain 3 | Nucleus | other |
| Hormad1 | HORMAD1 | HORMA domain containing 1 | Nucleus | other |
| Hsd17b14 | HSD17B14 | hydroxysteroid (17-beta) dehydrogenase 14 | Cytoplasm | enzyme |
| Hspb1 | HSPB1 | heat shock 27 kDa protein 1 | Cytoplasm | other |
| Hspb8 | HSPB8 | heat shock 22 kDa protein 8 | Cytoplasm | kinase |
| Htra1 | HTRA1 | HtrA serine peptidase 1 | Extracellular Space | peptidase |
| Ifi204 | Ifi204 (includes others) | interferon activated gene 204 | Nucleus | transcription regulator |
| Ifi44 | IFI44 | interferon-induced protein 44 | Cytoplasm | other |
| Ifit1 | IFIT1B | interferon-induced protein with tetratricopeptide repeats 1B | Cytoplasm | other |
| Ifitm3 | IFITM2 | interferon induced transmembrane protein 2 | Cytoplasm | other |
| Igf2 | IGF2 | insulin-like growth factor 2 (somatomedin A) | Extracellular Space | growth factor |
| Igfbp7 | IGFBP7 | insulin-like growth factor binding protein 7 | Extracellular Space | transporter |
| Il1rl1 | IL1RL1 | interleukin 1 receptor-like 1 | Plasma Membrane | transmembrane receptor |
| Inhba | INHBA | inhibin, beta A | Extracellular Space | growth factor |
| Inhbb | INHBB | inhibin, beta B | Extracellular Space | growth factor |
| Irf7 | IRF7 | interferon regulatory factor 7 | Nucleus | transcription regulator |
| Isg15 | ISG15 | ISG15 ubiquitin-like modifier | Extracellular Space | other |
| Itga5 | ITGA5 | integrin, alpha 5 (fibronectin receptor, alpha polypeptide) | Plasma Membrane | transmembrane receptor |
| Jun | JUN | jun proto-oncogene | Nucleus | transcription regulator |
| Junb | JUNB | jun B proto-oncogene | Nucleus | transcription regulator |
| Lgals3bp | LGALS3BP | lectin, galactoside-binding, soluble, 3 binding protein | Plasma Membrane | transmembrane receptor |
| Lgals9 | LGALS9 | lectin, galactoside-binding, soluble, 9 | Extracellular Space | other |
| Lmna | LMNA | lamin A/C | Nucleus | other |
| Lox | LOX | lysyl oxidase | Extracellular Space | enzyme |
| Loxl2 | LOXL2 | lysyl oxidase-like 2 | Extracellular Space | enzyme |

TABLE 8-continued

The genes listed were expressed at levels 20-fold lower in rat ES cells than the corresponding genes in mouse ES cells.

| ID | Symbol | Entrez Gene Name | Location | Type(s) |
|---|---|---|---|---|
| Loxl3 | LOXL3 | lysyl oxidase-like 3 | Extracellular Space | enzyme |
| Lrp1 | LRP1 | low density lipoprotein receptor-related protein 1 | Plasma Membrane | transmembrane receptor |
| Mageb16 | MAGEB16 | melanoma antigen family B, 16 | Other | other |
| Mcam | MCAM | melanoma cell adhesion molecule | Plasma Membrane | other |
| Mgp | MGP | matrix Gla protein | Extracellular Space | other |
| Mmp2 | MMP2 | matrix metallopeptidase 2 (gelatinase A, 72 kDa gelatinase, 72 kDa type IV collagenase) | Extracellular Space | peptidase |
| Mxra8 | MXRA8 | matrix-remodelling associated 8 | Other | other |
| Myl9 | MYL9 | myosin, light chain 9, regulatory | Cytoplasm | other |
| Mylpf | MYLPF | myosin light chain, phosphorylatable, fast skeletal muscle | Cytoplasm | other |
| Nab2 | NAB2 | NGFI-A binding protein 2 (EGR1 binding protein 2) | Nucleus | transcription regulator |
| Ndufb4 | NDUFB4 | NADH dehydrogenase (ubiquinone) 1 beta subcomplex, 4, 15 kDa | Cytoplasm | transporter |
| Npm1 | NPM1 | nucleophosmin (nucleolar phosphoprotein B23, numatrin) | Nucleus | transcription regulator |
| Nr0b1 | NR0B1 | nuclear receptor subfamily 0, group B, member 1 | Nucleus | ligand-dependent nuclear receptor |
| Nr4a1 | NR4A1 | nuclear receptor subfamily 4, group A, member 1 | Nucleus | ligand-dependent nuclear receptor |
| Nrp2 | NRP2 | neuropilin 2 | Plasma Membrane | kinase |
| Oas1a | OAS1 | 2'-5'-oligoadenylate synthetase 1, 40/46 kDa | Cytoplasm | enzyme |
| Oasl2 | Oasl2 | 2'-5' oligoadenylate synthetase-like 2 | Other | enzyme |
| P4ha2 | P4HA2 | prolyl 4-hydroxylase, alpha polypeptide II | Cytoplasm | enzyme |
| Parp3 | PARP3 | poly (ADP-ribose) polymerase family, member 3 | Nucleus | enzyme |
| Pcolce | PCOLCE | procollagen C-endopeptidase enhancer | Extracellular Space | other |
| Pcyt1b | PCYT1B | phosphate cytidylyltransferase 1, choline, beta | Cytoplasm | enzyme |
| Pdgfc | PDGFC | platelet derived growth factor C | Extracellular Space | growth factor |
| Phlda1 | PHLDA1 | pleckstrin homology-like domain, family A, member 1 | Cytoplasm | other |
| Phlda2 | PHLDA2 | pleckstrin homology-like domain, family A, member 2 | Cytoplasm | other |
| Pla2g1b | PLA2G1B | phospholipase A2, group IB (pancreas) | Extracellular Space | enzyme |
| Pla2g4a | PLA2G4A | phospholipase A2, group IVA (cytosolic, calcium-dependent) | Cytoplasm | enzyme |
| Porcn | PORCN | porcupine homolog (Drosophila) | Cytoplasm | other |
| Postn | POSTN | periostin, osteoblast specific factor | Extracellular Space | other |
| Prrx1 | PRRX1 | paired related homeobox 1 | Nucleus | transcription regulator |
| Prss23 | PRSS23 | protease, serine, 23 | Extracellular Space | peptidase |

TABLE 8-continued

The genes listed were expressed at levels 20-fold lower in rat
ES cells than the corresponding genes in mouse ES cells.

| ID | Symbol | Entrez Gene Name | Location | Type(s) |
|---|---|---|---|---|
| Psmb8 | PSMB8 | proteasome (prosome, macropain) subunit, beta type, 8 | Cytoplasm | peptidase |
| Ptgs2 | PTGS2 | prostaglandin-endoperoxide synthase 2 (prostaglandin G/H synthase and cyclooxygenase) | Cytoplasm | enzyme |
| Ptn | PTN | pleiotrophin | Extracellular Space | growth factor |
| Ptrf | PTRF | polymerase I and transcript release factor | Nucleus | transcription regulator |
| Rarg | RARG | retinoic acid receptor, gamma | Nucleus | ligand-dependent nuclear receptor |
| Rgs16 | RGS16 | regulator of G-protein signaling 16 | Cytoplasm | other |
| Rn45s | Rn45s | 45S pre-ribosomal RNA | Other | other |
| Rpl10a | RPL10A | ribosomal protein L10a | Other | other |
| Rpl31 | RPL31 | ribosomal protein L31 | Other | other |
| Rpl37a | RPL37A | ribosomal protein L37a | Cytoplasm | other |
| Rps10 | RPS10-NUDT3 | RPS10-NUDT3 readthrough | Cytoplasm | other |
| Rps14 | RPS14 | ribosomal protein S14 | Cytoplasm | translation regulator |
| Rps20 | Rps20 | ribosomal protein S20 | Cytoplasm | other |
| Rps26 | RPS26 | ribosomal protein S26 | Cytoplasm | other |
| Rps9 | RPS9 | ribosomal protein S9 | Cytoplasm | translation regulator |
| S100a4 | S100A4 | S100 calcium binding protein A4 | Cytoplasm | other |
| S100a6 | S100A6 | S100 calcium binding protein A6 | Cytoplasm | transporter |
| Schip1 | SCHIP1 | schwannomin interacting protein 1 | Cytoplasm | other |
| Sdc2 | SDC2 | syndecan 2 | Plasma Membrane | other |
| Serpine1 | SERPINE1 | serpin peptidase inhibitor, clade E (nexin, plasminogen activator inhibitor type 1), member 1 | Extracellular Space | other |
| Serpine2 | SERPINE2 | serpin peptidase inhibitor, clade E (nexin, plasminogen activator inhibitor type 1), member 2 | Extracellular Space | other |
| Serpinf1 | SERPINF1 | serpin peptidase inhibitor, clade F (alpha-2 antiplasmin, pigment epithelium derived factor), member 1 | Extracellular Space | other |
| Sh3gl2 | SH3GL2 | SH3-domain GRB2-like 2 | Plasma Membrane | enzyme |
| Slc19a2 | SLC19A2 | solute carrier family 19 (thiamine transporter), member 2 | Plasma Membrane | transporter |
| Slc25a5 | SLC25A5 | solute carrier family 25 (mitochondrial carrier; adenine nucleotide translocator), member 5 | Cytoplasm | transporter |
| Slc29a1 | SLC29A1 | solute carrier family 29 (equilibrative nucleoside transporter), member 1 | Plasma Membrane | transporter |
| Slc35f2 | SLC35F2 | solute carrier family 35, member F2 | Other | other |
| Snrpn | SNRPN | small nuclear ribonucleoprotein polypeptide N | Nucleus | other |
| Snx22 | SNX22 | sorting nexin 22 | Other | transporter |
| Sparc | SPARC | secreted protein, acidic, cysteine-rich (osteonectin) | Extracellular Space | other |
| Spp1 | SPP1 | secreted phosphoprotein 1 | Extracellular Space | cytokine |
| Sult4a1 | SULT4A1 | sulfotransferase family 4A, member 1 | Cytoplasm | enzyme |

TABLE 8-continued

The genes listed were expressed at levels 20-fold lower in rat ES cells than the corresponding genes in mouse ES cells.

| ID | Symbol | Entrez Gene Name | Location | Type(s) |
|---|---|---|---|---|
| Tagln | TAGLN | transgelin | Cytoplasm | other |
| Tcea3 | TCEA3 | transcription elongation factor A (SII), 3 | Nucleus | transcription regulator |
| Tgfb3 | TGFB3 | transforming growth factor, beta 3 | Extracellular Space | growth factor |
| Thbs1 | THBS1 | thrombospondin 1 | Extracellular Space | other |
| Thbs2 | THBS2 | thrombospondin 2 | Extracellular Space | other |
| Tm4sf1 | TM4SF1 | transmembrane 4 L six family member 1 | Plasma Membrane | other |
| Tmbim1 | TMBIM1 | transmembrane BAX inhibitor motif containing 1 | Cytoplasm | other |
| Tmem176b | TMEM176B | transmembrane protein 176B | Other | other |
| Tnc | TNC | tenascin C | Extracellular Space | other |
| Tpd52l1 | TPD52L1 | tumor protein D52-like 1 | Cytoplasm | other |
| Tpm2 | TPM2 | tropomyosin 2 (beta) | Cytoplasm | other |
| Usp18 | USP18 | ubiquitin specific peptidase 18 | Cytoplasm | peptidase |
| Vim | VIM | vimentin | Cytoplasm | other |
| Wfdc2 | WFDC2 | WAP four-disulfide core domain 2 | Extracellular Space | other |
| Wisp2 | WISP2 | WNT1 inducible signaling pathway protein 2 | Extracellular Space | growth factor |
| Ybx1 | YBX1 | Y box binding protein 1 | Nucleus | transcription regulator |

TABLE 9

The genes listed were expressed at levels 20-fold higher in rat ES cells than the corresponding genes in mouse ES cells.

| ID | Symbol | Entrez Gene Name | Location | Type(s) |
|---|---|---|---|---|
| Ajap1 | Ajap1 | adherens junction associated protein 1 | Other | other |
| Amd1 | AMD1 | adenosylmethionine decarboxylase 1 | Cytoplasm | enzyme |
| Ankrd2 | ANKRD2 | ankyrin repeat domain 2 (stretch responsive muscle) | Nucleus | transcription regulator |
| Arhgef9 | ARHGEF9 | Cdc42 guanine nucleotide exchange factor (GEF) 9 | Cytoplasm | other |
| Atp5h | Atp5h | ATP synthase, H+ transporting, mitochondrial F0 complex, subunit d | Cytoplasm | enzyme |
| Btg3 | BTG3 | BTG family, member 3 | Nucleus | other |
| Car6 | CA6 | carbonic anhydrase VI | Extracellular Space | enzyme |
| Camk4 | CAMK4 | calcium/calmodulin-dependent protein kinase IV | Nucleus | kinase |
| Capn12 | CAPN12 | calpain 12 | Other | peptidase |
| Cct6b | CCT6B | chaperonin containing TCP1, subunit 6B (zeta 2) | Cytoplasm | transporter |
| Cdx2 | CDX2 | caudal type homeobox 2 | Nucleus | transcription regulator |
| Cldn5 | CLDN5 | claudin 5 | Plasma Membrane | other |
| Clec3a | CLEC3A | C-type lectin domain family 3, member A | Other | other |
| Clic6 | CLIC6 | chloride intracellular channel 6 | Plasma Membrane | ion channel |
| Dhrsx | DHRSX | dehydrogenase/reductase (SDR family) X-linked | Other | enzyme |
| Dpysl2 | DPYSL2 | dihydropyrimidinase-like 2 | Cytoplasm | enzyme |
| Dusp26 | DUSP26 | dual specificity phosphatase 26 (putative) | Cytoplasm | enzyme |
| Eci3 | Eci3 | enoyl-Coenzyme A delta isomerase 3 | Other | enzyme |

TABLE 9-continued

The genes listed were expressed at levels 20-fold higher in rat ES cells than the corresponding genes in mouse ES cells.

| ID | Symbol | Entrez Gene Name | Location | Type(s) |
|---|---|---|---|---|
| Eef2k | EEF2K | eukaryotic elongation factor-2 kinase | Cytoplasm | kinase |
| Efna1 | EFNA1 | ephrin-A1 | Plasma Membrane | other |
| Epha4 | EPHA4 | EPH receptor A4 | Plasma Membrane | kinase |
| Fank1 | FANK1 | fibronectin type III and ankyrin repeat domains 1 | Nucleus | transcription regulator |
| Fhit | FHIT | fragile histidine triad | Cytoplasm | enzyme |
| Filip1 | FILIP1 | filamin A interacting protein 1 | Cytoplasm | other |
| Fmod | FMOD | fibromodulin | Extracellular Space | other |
| Foxe1 | FOXE1 | forkhead box E1 (thyroid transcription factor 2) | Nucleus | transcription regulator |
| Fry | FRY | furry homolog (*Drosophila*) | Extracellular Space | other |
| Gjb5 | GJB5 | gap junction protein, beta 5, 31.1 kDa | Plasma Membrane | transporter |
| Gpx2 | GPX2 | glutathione peroxidase 2 (gastrointestinal) | Cytoplasm | enzyme |
| Grxcr2 | GRXCR2 | glutaredoxin, cysteine rich 2 | Other | other |
| Hecw2 | HECW2 | HECT, C2 and WW domain containing E3 ubiquitin protein ligase 2 | Extracellular Space | enzyme |
| Hey2 | HEY2 | hairy/enhancer-of-split related with YRPW motif 2 | Nucleus | transcription regulator |
| Icos | Icos | inducible T-cell co-stimulator | Plasma Membrane | other |
| Ifitm1 | IFITM1 | interferon induced transmembrane protein 1 | Plasma Membrane | transmembrane receptor |
| Il1f8 | IL1F8 (IL36B) | Interleukin-1 family member (Interleukin 36 beta) | Extracellular space | cytokine |
| Il28ra | IL-28RA | Interleukin 28 receptor, alpha | Plasma membrane | Cytokine receptor |
| Igfbpl1 | IGFBPL1 | insulin-like growth factor binding protein-like 1 | Other | other |
| Ipcef1 | IPCEF1 | interaction protein for cytohesin exchange factors 1 | Cytoplasm | enzyme |
| Lctl | Lctl | lactase-like | Cytoplasm | other |
| Ldhd | LDHD | lactate dehydrogenase D | Cytoplasm | enzyme |
| Lef1 | LEF1 | lymphoid enhancer-binding factor 1 | Nucleus | transcription regulator |
| Lefty1 | LEFTY1 | left-right determination factor 1 | Extracellular Space | growth factor |
| Lifr | LIFR | leukemia inhibitory factor receptor alpha | Plasma Membrane | transmembrane receptor |
| Lpar2 | LPAR2 | lysophosphatidic acid receptor 2 | Plasma Membrane | G-protein coupled receptor |
| Mog | MOG | myelin oligodendrocyte glycoprotein | Extracellular Space | other |
| Morn5 | MORN5 | MORN repeat containing 5 | Other | other |
| Pigz | NCBP2 | nuclear cap binding protein subunit 2, 20 kDa | Nucleus | other |
| Nptxr | NPTXR | neuronal pentraxin receptor | Plasma Membrane | transmembrane receptor |
| Ntm | NTM | neurotrimin | Plasma Membrane | other |
| Nutf2 | NUTF2 | nuclear transport factor 2 | Nucleus | transporter |
| Ocln | OCLN | occludin | Plasma Membrane | enzyme |
| Olr1 | OLR1 | oxidized low density lipoprotein (lectin-like) receptor 1 | Plasma Membrane | transmembrane receptor |
| Pabpc4 | PABPC4 | poly(A) binding protein, cytoplasmic 4 (inducible form) | Cytoplasm | translation regulator |
| Pde11a | PDE11A | phosphodiesterase 11A | Cytoplasm | enzyme |
| Pdyn | PDYN | prodynorphin | Extracellular Space | transporter |
| Per3 | PER3 | period circadian clock 3 | Nucleus | other |
| Pllp | PLLP | plasmolipin | Plasma Membrane | transporter |

TABLE 9-continued

The genes listed were expressed at levels 20-fold higher in rat ES cells than the corresponding genes in mouse ES cells.

| ID | Symbol | Entrez Gene Name | Location | Type(s) |
|---|---|---|---|---|
| Ppp1r14c | PPP1R14C | protein phosphatase 1, regulatory (inhibitor) subunit 14C | Cytoplasm | other |
| Pramel6 | Pramel6 | preferentially expressed antigen in melanoma like 6 | Other | other |
| Ptpn18 | PTPN18 | protein tyrosine phosphatase, non-receptor type 18 (brain-derived) | Nucleus | phosphatase |
| Pycr1 | PYCR1 | pyrroline-5-carboxylate reductase 1 | Cytoplasm | enzyme |
| Rab26 | RAB26 | RAB26, member RAS oncogene family | Plasma Membrane | enzyme |
| Ramp2 | RAMP2 | receptor (G protein-coupled) activity modifying protein 2 | Plasma Membrane | transporter |
| Rbm24 | RBM24 | RNA binding motif protein 24 | Other | other |
| Rhag | RHAG | Rh-associated glycoprotein | Plasma Membrane | peptidase |
| Rpl3 | RPL3 | ribosomal protein L3 | Cytoplasm | other |
| Sall3 | SALL3 | sal-like 3 (*Drosophila*) | Nucleus | other |
| Satb1 | SATB1 | SATB homeobox 1 | Nucleus | transcription regulator |
| Scg2 | SCG2 | secretogranin II | Extracellular Space | cytokine |
| Slc15a1 | SLC15A1 | solute carrier family 15 (oligopeptide transporter), member 1 | Plasma Membrane | transporter |
| Slc1a1 | SLC1A1 | solute carrier family 1 (neuronal/epithelial high affinity glutamate transporter, system Xag), member 1 | Plasma Membrane | transporter |
| Slc24a5 | Slc24a5 | solute carrier family 24 (sodium/potassium/calcium exchanger), member 5 | Other | other |
| Slc37a2 | SLC37A2 | solute carrier family 37 (glucose-6-phosphate transporter), member 2 | Other | transporter |
| 40424 | SNTB1 | syntrophin, beta 1 (dystrophin-associated protein A1 59 kDa, basic component 1) | Plasma Membrane | other |
| St6galnac3 | ST6GALNAC3 | ST6 (alpha-N-acetyl-neuraminyl-2,3-beta-galactosyl-1,3)-N-acetylgalactosaminide alpha-2,6-sialyltransferase 3 | Cytoplasm | enzyme |
| Tex12 | TEX12 | testis expressed 12 | Nucleus | other |
| Tex15 | TEX15 | testis expressed 15 | Extracellular Space | other |
| Tfap2a | TFAP2A | transcription factor AP-2 alpha (activating enhancer binding protein 2 alpha) | Nucleus | transcription regulator |
| Tmc1 | TMC1 | transmembrane channel-like 1 | Plasma Membrane | other |
| Tmem130 | TMEM130 | transmembrane protein 130 | Other | other |
| Tmem30b | TMEM30B | transmembrane protein 30B | Other | other |
| Tomm20 | TOMM20 | translocase of outer mitochondrial membrane 20 homolog (yeast) | Cytoplasm | transporter |
| Tox3 | TOX3 | TOX high mobility group box family member 3 | Other | other |
| Ttc25 | TTC25 | tetratricopeptide repeat domain 25 | Cytoplasm | other |
| Tymp | TYMP | thymidine phosphorylase | Extracellular Space | growth factor |
| Ubb | Ubb | ubiquitin B | Cytoplasm | other |
| Vamp7 | VAMP7 | vesicle-associated membrane protein 7 | Cytoplasm | transporter |
| Wfdc12 | Wfdc12 | WAP four-disulfide core domain 12 | Extracellular Space | other |
| Wfdc15a | Wfdc15a | WAP four-disulfide core domain 15A | Other | other |
| Wfdc6a | Wfdc6a | WAP four-disulfide core domain 6A | Other | other |

TABLE 10

A subset of genes from Table 9, which are expressed at levels 20-fold higher in rat ES cells than the corresponding genes in mouse ES cells.

| ID | Entrez Gene Name |
|---|---|
| Ajap1 | Adherens Junctions Associate Protein |
| Cldn5 | Claudin 5 |
| Arhgef9 | Cdc42 guanine nucleotide exchange factor 9 |
| Camk4 | Calcium/calmodulin-dependent protein kinase IV |
| Efna1 | ephrin-A1 |
| Epha4 | EPH receptor A4 |
| Gjb5 | gap junction protein beta 5 |
| Igfbpl1 | Insulin-like growth factor binding protein-like 1 |
| Il1f8 | Interleukin 36 beta |
| Il28ra | Interleukin 28 receptor, alpha |
| Lefty1 | left-right determination factor 1 |
| Lifr | Leukemia inhibitory factor receptor alpha |
| Lpar2 | Lysophosphatidic acid receptor 2 |
| Ntm | Neuronal pentraxin receptor |
| Ptpn18 | Protein tyrosine phosphatase non-receptor type 18 |
| Cdx2 | Caudal type homeobox 2 |
| Fank1 | Fibronectin type III and ankyrin repeat domains 1 |
| Foxe1 | Forkhead box E1 (thyroid transcription factor 2) |
| Hey2 | Hairy/enhancer-of-split related with YRPW motif 2 |
| Lef1 | Lymphoid enhancer-binding factor 1 |
| Sall3 | Sal-like 3 (*Drosophila*) |
| Satb1 | SATB homeobox 1 |

An additional molecular signature employing the pluripotency markers/genes for the rat ES cells has also been developed. Table 11 provides a gene list and their expression ranks from the RNA profiling data. mRNA was isolated from rat ES cells and the expression levels of various markers were compared relative to each other. The term "rank" means the comparative expression levels of individual genes: the higher the rank (1 is highest), the higher the expression. For example, Oct4's rank of 13 means that, of all the genes assayed, it was expressed higher than all but 12 genes. Background in this experiment was any expression value below 30; 6107 genes had expression values of 30 or higher.

TABLE 11

Rat ES cell molecular signature employing various pluripotency, mesodermal, endodermal, neural and trophectoderm markers/genes.

| Pluri-potency | Pluri-potency Rank | Meso-dermal | Meso-dermal Rank | Endo-dermal | Endo-dermal Rank | Neural | Neural Rank | Trophec-toderm | Trophec-toderm Rank |
|---|---|---|---|---|---|---|---|---|---|
| c-Myc | 8248 | Brachyury | 7542 | Gata6 | 11195 | Nestin | 7761 | Cdx2 | 739 |
| Dnmt3L | 127 | Flk1 | Not tested | Sox17 | 11418 | Pax6 | 13570 | | |
| Dppa2 | Not tested | Nodal | 3050 | Hhex1 | 4571 | Sox2 | 681 | | |
| Dppa5 | Not tested | Bmp4 | 3072 | Nodal | 3050 | | | | |
| Ecat1 | 9714 | Bmpr2 | 6382 | Ext1 | 6091 | | | | |
| Eras | 2541 | | | Sox7 | 10284 | | | | |
| Err-beta | 1368 | | | | | | | | |
| Fbxo15 | 1369 | | | | | | | | |
| Fgf4 | 3440 | | | | | | | | |
| Fthl17 | Not tested | | | | | | | | |
| Gdf3 | 2771 | | | Rank > 6107 = bkg expression | | | | | |
| Klf4 | 836 | | | | | | | | |
| Lef1 | 1313 | | | | | | | | |
| LIF receptor | 724 | | | | | | | | |
| Lin28 | 828 | | | | | | | | |
| Nanog | 774 | | | | | | | | |
| Oct4 | 13 | | | | | | | | |
| Rexo1 | 6119 | | | | | | | | |
| Sox15 | 4524 | | | | | | | | |
| Sox2 | 681 | | | | | | | | |
| SSEA1 | Not tested | | | | | | | | |
| SSEA4 | Not tested | | | | | | | | |
| Stella | Not tested | | | | | | | | |
| Tel1 | Not tested | | | | | | | | |
| Utf1 | 1501 | | | | | | | | |

Example 2. Inactivation of Genomic Loci in Rats 2.1. Inactivation of Endogenous Genomic Loci Using an Endonuclease Agent In order to introduce a mutant allele at an endogenous rat genomic locus, the rat ES cells described herein are electroporated with expression vectors (or mRNA) that express ZFNs 1 and 2 (or TALENs 1 and 2). These proteins bind their target sequences on opposite strands, separated by about 6 bp to about 40 bp. A double-stranded break is formed within the target locus, which the cell attempts to repair by Non-Homologous End-Joining (NHEJ). In many cases, NHEJ results in creation of a deletion, which often disrupts the function of the gene (most often by producing a frameshift mutation). In order to identify a positive clone comprising a mutant allele, the electroporated cells are plated at low density, because no drug selection is done. Colonies are picked and assayed at the target site to see if a mutation was produced (e.g., using a modification of allele (MOA) assay described above). The selected ES cells comprising the mutant allele are then introduced into a host rat embryo, for example, a pre-morula stage or blastocyst stage rat embryo, and implanted in the uterus of a surrogate mother to generate a founder rat (F0 rat). Subsequently, the founder rat is bred to a wild-type rat to create F1 progeny heterozygous for the mutant allele. Mating of the heterozygous F1 rat can produce progeny homozygous for the mutant allele.

Figure 15:
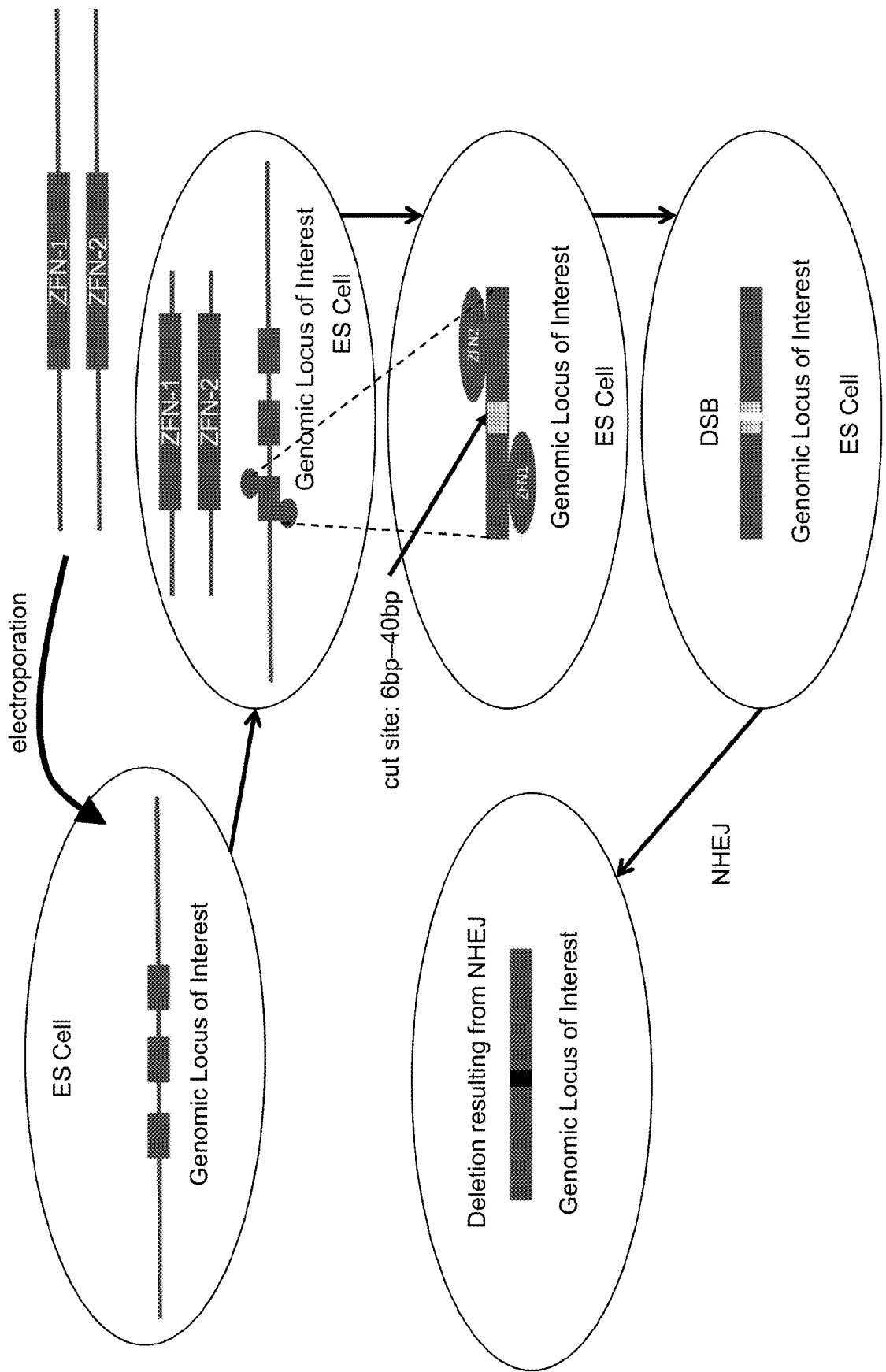
FIG. 15 illustrates the mechanism by which genome-editing endonucleases (e.g., ZFNs and TALENs) introduce a double strand break (DSB) in a target genomic sequence and activate non-homologous end-joining (NHEJ) in an ES cell.

2.2.: Rat ESC Targeting for the Inactivation of the Rat Apolipoprotein E (ApoE) Gene Using Zinc Finger Nucleases Zinc finger nucleases use sequence specific modular DNA binding domains to direct endonuclease activity to unique target sequence in the genome. ZFNs are engineered as a pair of monomers. Each monomer contains nonspecific cleavage domain from FokI endonuclease fused to 3 or more zinc finger DNA-binding domains. Each zinc finger binds a 3 bp subsite and specificity is achieved by the combined target sites of both monomers. ZFNs produce double-stranded breaks (DSBs) in DNA, and mutations (insertions or deletions) frequently occur during non-homologous end joining (NHEJ). FIG. 15 illustrates the mechanism by which genome-editing endonucleases such as ZFNs and TALENs introduce double strand breaks in a target genomic sequence and activate NHEJ in a cell. DSBs also stimulate homology-directed repair (HDR) by homologous recombination if a donor sequence is provided with ZFN.

Such ZFNs were employed in combination with the various methods and compositions described herein to improve targeting efficiency. The rat Apolipoprotein E (ApoE) locus was targeted as described in Example 3.2(a)(i), except expression vectors that express ZFNs 1 and 2 were also introduced into the rat ES cells. See FIG. 11, which provides a schematic of the ApoE targeting event in combination with rTZFN1P and rTZFN2P. The targeting efficiency was determined as discussed below in Example 5 and results are shown in Table 12. To screen for heterozygous targeting, homozygous targeting, and "mixed" doubles (e.g., compound heterozygous targeting), specific primers and probes were used to determine genotype. Surprisingly, the targeting efficiency went up 8-10 fold.

TABLE 12

Rat ApoE ZFNs: Improved Targeting Efficiency.

| DNA | Colonies | Screened | Heterozygous Targeted | Homozygous Targeted | "Mixed" Doubles | Cut/ Untargeted |
|---|---|---|---|---|---|---|
| vector | 330 | 184 | 15 (8.2%) | 0 | 0 | N/A |
| vector + ZFN 1 | 560 | 192 | 132 (68.8%) | 6 (3.1%) | 18 (9.4%) | 17 (8.9%) |
| vector + ZFN 2 | 410 | 192 | 136 (70.8%) | 2 (1.0%) | 6 (3.1%) | 18 (9.4%) |

Figure 14:
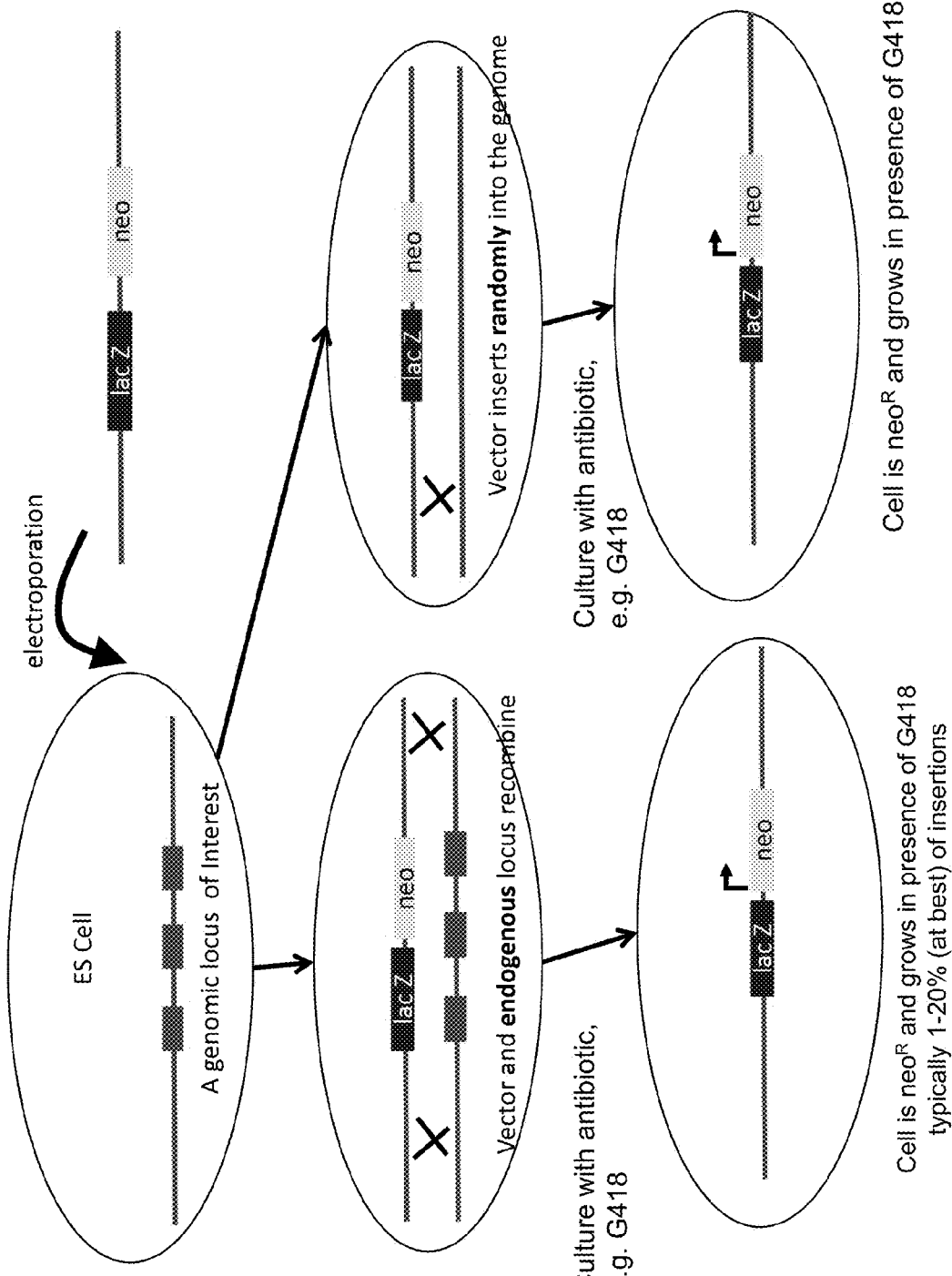
FIG. 14 illustrates a homologous or non-homologous recombination event that occurs inside a rat ES cell following an electroporation of a targeting vector comprising a selection cassette (lacZ-neo cassette).
Figure 16:
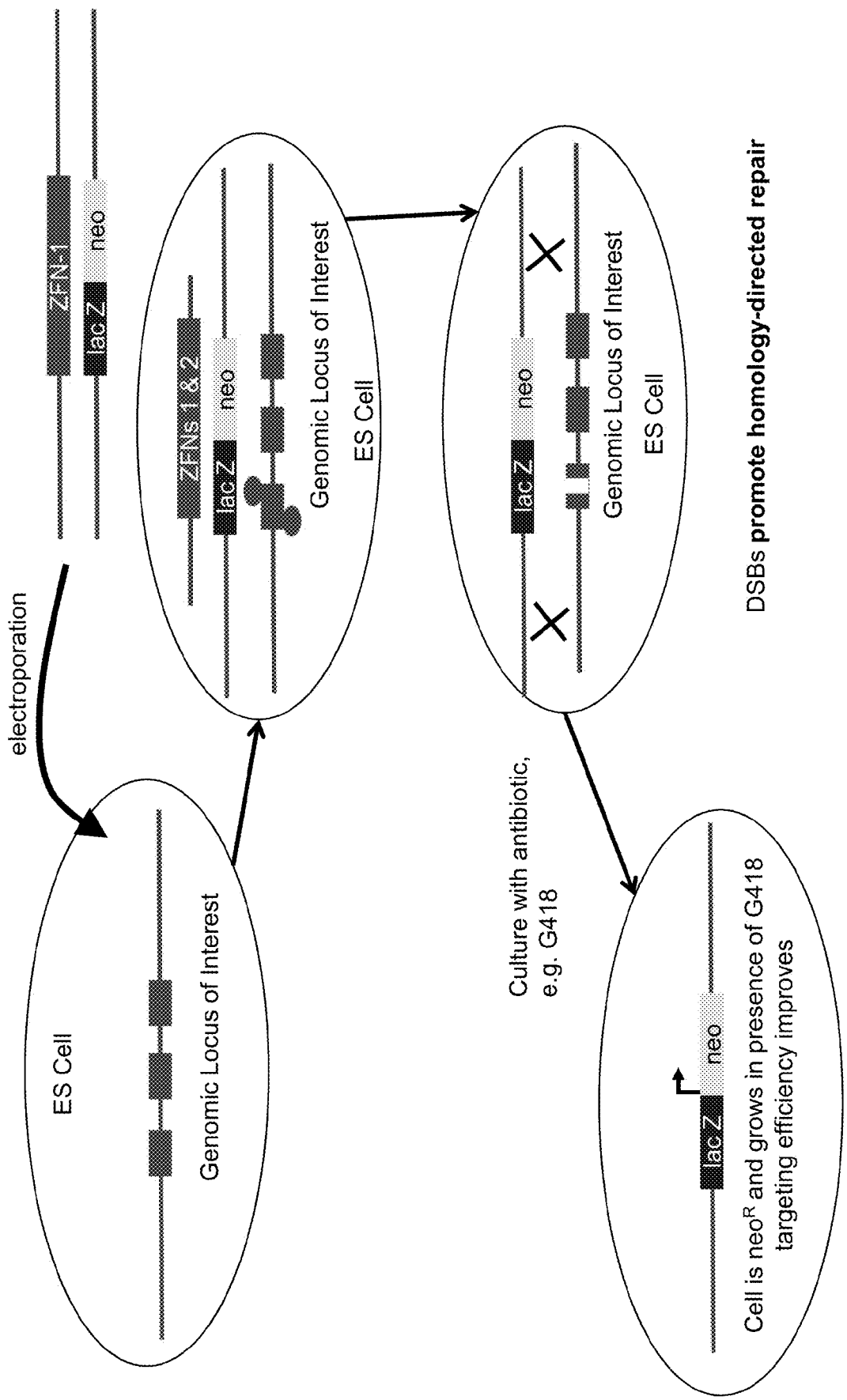
FIG. 16 illustrates a gene targeting technique that utilizes ZFN/TALENs to improve the efficiency of homologous recombination of a targeting vector. DSB represents double strand break.

A plasmid targeting vector was built with a self-deleting drug selection cassette and a lacZ gene as a reporter gene (see FIG. 14 for an illustration of the homologous and non-homologous recombination events that can occur upon electroporation of a targeting vector comprising a selection cassette). Good targeting efficiency was achieved and high % chimeras were produced. Zinc finger nucleases (ZFNs) were also tested in combination with targeting vectors to examine its effect on improving targeting efficiency (see FIG. 16 for an illustration of the gene targeting technique utilizing ZFNs or TALENs to improve the efficiency of homologous recombination of a targeting vector). The targeting vector was co-expressed with the expression vectors for 2 ZFN pairs that cut the ApoE locus. The rat ESC clones electroporated with both the targeting vector and a set of the ZFNs showed a targeting efficiency of 8-10 fold higher than that of rat ESC clones electroporated with a targeting vector alone. Moreover, bi-allelic homozygous targeting in about 2% of our clones was detected. High % chimeras from two of these targeted clones were obtained.

Figure 17:
FIG. 17 shows ApoE-ZFN-AB5 chimeras produced by chimera production and germline transmission of the modified rat ApoE locus. The targeted modification was assisted by zinc finger nucleases.

The ApoE-targeted (with ZFN assistance) rat ESC clones were microinjected into SD blastocysts, which were then transferred to pseudopregnant SD recipient females, using standard techniques. Chimeras were identified by coat color (see FIG. 17, showing ApoE-ZFN-AB5 chimeras (i.e., ApoE$^{-/-}$ chimeras); male F0 chimeras were bred to SD females. Germline F1 pups were genotyped for the presence of the targeted ApoE allele (Table 13). High % chimeras were obtained from two of these targeted clones.

TABLE 13

Microinjection Results.

| Clone | Pups | Chimeras (% of chimera) |
|---|---|---|
| ApoE-ZFN1-AB5 (homozygous targeted) | 12 | 4 (90, 90, 80, 80) |
| ApoE-ZFN1-AE5 (homozygous targeted) | 6 | 3 (90, 80, 70) |

An ApoE knockout rat provides a means to study various types of disorders and diseases. In humans, Apolipoprotein is found in chylomicron, HDL, LDL and VLDL. ApoE is essential for the normal catabolism of triglyceride-rich lipoprotein constituents. Defects in APOE result in numerous disease states including, for example, familial hypercholesterolemia, hyperlipidemia, betalipoproteinemia, familial dysbetalipoproteinemia, type III hyperlipoproteinemia (HLP III), risk of coronary artery disease. One isoform (ApoE4) is associated with late-onset familial and sporadic Alzheimer's disease, possibly with MS as well.

In mice, ApoE is primarily found in HDL; transports cholesterol, as in humans. ApoE-deficient mice (2 independent KOs) have 5 times normal plasma cholesterol; developed foam cell-rich depositions in their proximal aortas by age 3 months (comparable to human syndrome).

ApoE knockouts in rats offer an animal model to study endothelial function, including, but not limited to, plaque formation, transcriptional changes (RNA-Seq), ex vivo function. Moreover, larger size of rats would facilitate all these assays and potentially improve the quality of the RNA-Seq data.

Figure 18:
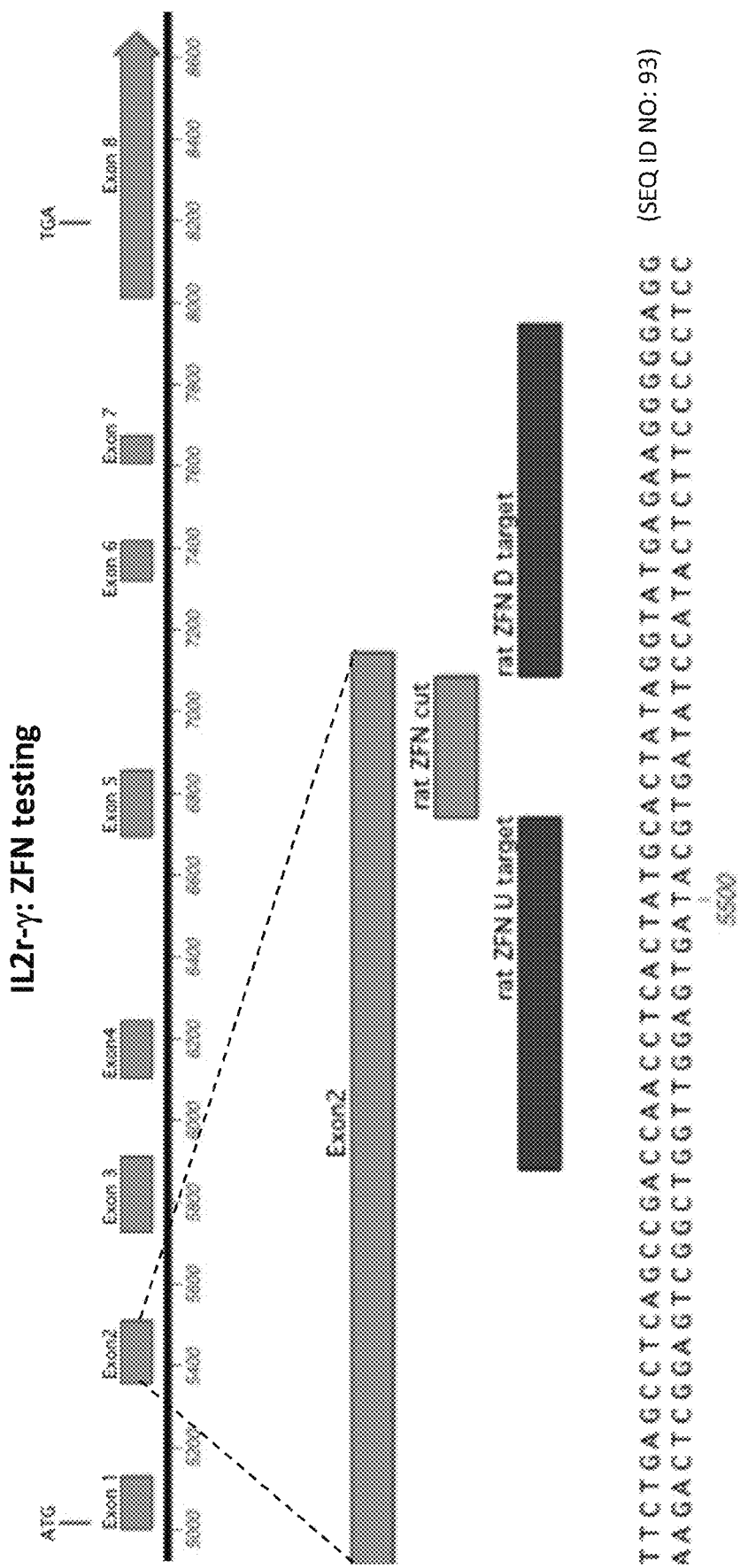
FIG. 18 provides a schematic of the IL2r-γ targeting event in combination with zinc finger nucleases that target ZFN U and ZFN D. The region of the rat IL2r-γ locus targeted by ZFN U and ZFN D is shown (SEQ ID NO: 93). ZFN cut sites are noted in the figure.

2.3. Inactivation of the Rat Interleukin-2 Receptor Gamma (IL2r-γ) Locus Using Zinc Finger Nucleases The rat Interleukin-2 receptor gamma (IL2r-γ or Il2rg) locus was targeted as described in Example 3.3(a), except that expression vectors that express ZFN U (ZFN upstream) and ZFN D (ZFN downstream) were also introduced into the rat ES cells. FIG. 18 provides a schematic of the IL2r-γ targeting event in combination with ZFN U and ZFN D. The sequence of the IL2r-γ locus which these zinc fingers bind is denoted in FIG. 18 within SEQ ID NO: 93. The targeting efficiency was determined as discussed below in Example 3.3(a) and the results are shown in Table 14. Briefly, homozygously targeted clones were confirmed by PCR. For the ZFN1 pair: 173 mutant clones out of 192 screened (90%) and for the ZFN2 pair: 162 clones out of 192 (84%) screened.

TABLE 14

Targeting of Rat IL2r-γ Locus.

| Plate | Colonies screened | Targeted | Efficiency |
|---|---|---|---|
| 7/18: Vector alone | 96 | 4 | 4.2% |
| 7/18: Vector + ZFN | 96 | 3 | 3.1% |

The IL2r-γ-targeted (with ZFN assistance) rat ESC clones were microinjected into SD blastocysts, which were then transferred to pseudopregnant SD recipient females, using standard techniques. Chimeras were identified by coat color; male F0 chimeras were bred to SD females. Germline F1 pups were genotyped for the presence of the targeted IL2r-γ allele.

2.4. Inactivation of the Rat Interleukin-2 Receptor Gamma (IL2r-γ) Using CRISPR/Cas9

Figure 19:
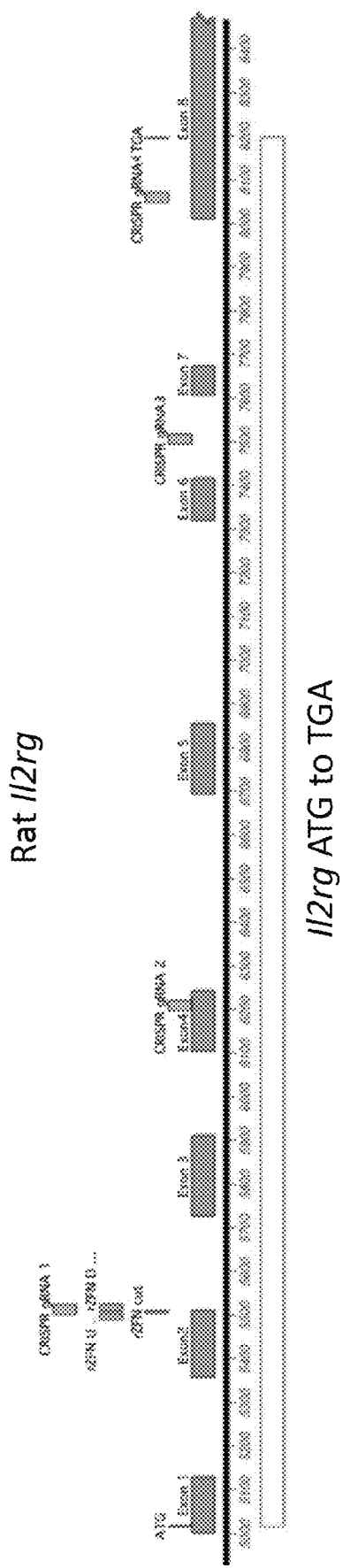
FIG. 19 provides a schematic of the IL2r-γ targeting event in combination with zinc finger nucleases that target ZFN U and ZFN D or in combination with gRNAs (gRNA1, gRNA2, gRNA3, gRNA4). The regions of the rat IL2r-γ locus targeted by ZFN U and ZFN D or gRNAs1-4 are shown, and ZFN cut sites are noted.

The rat IL2r-γ locus was targeted as described in Example 3.3(a), except that the CRISPR/Cas9 system was also introduced into the rat ES cells to aid in targeting efficiency. SBI: System Biosciences Cas9 "SmartNuclease" all-in-one vectors were employed and Cas9 expression was driven by CAG, EF1a, PGK, or CMV promoter. Custom gRNA was ligated into a vector and expressed by H1 promoter. 4 gRNAs against Il2rg were designed. The regions of the rat IL2r-γ locus targeted by gRNAs1-4 are shown in FIG. 19. To screen for targeting (e.g., heterozygous targeting, homozygous targeting, and compound heterozygous targeting), specific primers and probes were used to determine genotype. Targeting results when employing the various guide RNAs is shown in Table 15. "Strong" and "weak" refer to the strength of the evidence based on screening that the colony has a targeted modification.

TABLE 15

Targeting of Rat Il2rg Locus with Guide RNAs.

| Construct(s) | DNA (ug) | Colonies | Candidates (Potentially Targeted) |
|---|---|---|---|
| Il2rg plasmid vector | 6 ug | 30 | 3 weak |
| plasmid + SBI gRNA1 | 6 ug/40 ug | 22 | 1 strong, 1 weak |
| plasmid + SBI gRNA2 | 6 ug/40 ug | 45 | 2 strong, 1 weak |
| plasmid + SBI gRNA3 | 6 ug/40 ug | 66 | 1 strong, 2 weak |
| plasmid + SBI gRNA4 | 6 ug/40 ug | 59 | 0 |

2.5. Inactivation of the Mouse Hypoxanthine Guanine Phosphoribosyl Transferase (Hprt) Gene Using CRISPR/Cas9

The mouse Hprt locus was targeted in mouse ES cells using LTVECs alone or in combination with CRISPR/Cas9. The 32.9 kb complete Hprt coding sequence was targeted for deletion and replacement with the pCAGG-Puro puromycin resistance selection cassette, which also expressed eGFP. The deletion end points were the start and stop codons. The guide RNA sequence used was 5'-GACCCGCAGU-CCCAGCGUCG-3' (SEQ ID NO: 84), which targeted exon 1 of the mouse Hprt gene. The predicted target site cleavage position was 22 base pairs from the 5' end of the deletion. The Cas9/gRNA on-target cleavage efficiency observed in the ES cells was >93%. A summary is shown in Table 16. Use of CRISPR/Cas9 to assist in targeting of the complete 32.9 kb Hprt locus resulted in a five-fold enhancement of targeting over use of LTVEC alone.

TABLE 16

Summary of CRISPR-Assisted Deletion of Hprt Gene
Summary of CRISPR-Assisted Deletion of the Hprt Gene

| | | | | Targeting Efficiency (%) | | |
|---|---|---|---|---|---|---|
| Target Gene | Deletion (kb) | 5'Homology Arm (kb) | 3'Homology Arm (kb) | LTVEC Alone | LTVEC + CRISPR/Cas9 | Fold Enhancement |
| Hprt | 32.9 | 88 | 66 | 5.0 | 25.4 | 5.1 |

Example 3. Targeted Modification of Rat Genomic Loci 3.1 Rat ESC Targeting: The Rat Rosa26 Locus.

The rat Rosa26 locus lies between the Setd5 and Thumpd3 genes as in mouse, with the same spacing. The rat Rosa26 locus (FIG. 12, Panel B) differs from the mouse Rosa26 locus (FIG. 12, Panel A). The mouse Rosa26 transcripts consist of 2 or 3 exons. The rat locus contains a 2nd exon 1 (Ex1b) in addition to the homologous exon to mouse exon1 (Ex1a). No 3rd exon has been identified in rat. Targeting of a rat Rosa26 allele is depicted in FIG. 12C, where homology arms of 5 kb each were cloned by PCR using genomic DNA from DA rat ESC. The targeted allele contains a SA (splicing acceptor)-lacZ-hUb-neo cassette replacing a 117 bp deletion in the rat Rosa26 intron.

Targeting efficiency at the rat Rosa26 locus was determined (Table 17). Linearized vector was electroporated into DA or ACI rat ESCs, and transfected colonies were cultured in 2i media+G418, using standard techniques. Individual colonies were picked and screened using a Loss of Allele (LOA) assay (Valenzuela, D. et al. (2003) High-throughput engineering of the mouse genome coupled with high-resolution expression analysis, *Nature Biotech.* 21:652-660, incorporated herein by reference).

TABLE 17 rat Rosa26 Targeting Efficiency

| Cell line | Colonies picked | Reconfirmed positives | Targeting efficiency (%) |
|---|---|---|---|
| DA.2B | 192 | 4 | 2.1 |
| ACI.G1 | 96 | 4 | 4.2 |

Chimera Production and Germline Transmission Using Rosa26-Targeted Rat ESC Clones.

Reconfirmed Rosa26-targeted rat ESC clones were microinjected into SD blastocysts, which were then transferred to pseudopregnant SD recipient females, using standard techniques. Chimeras were identified by coat color; male F0 chimeras were bred to SD females. Germline (agouti) F1 pups were genotyped for the presence of the targeted Rosa26 allele; nine of 22 agouti pups genotyped as heterozygous at the Rosa26 locus (Table 18).

TABLE 18

Germline Transmission Using Targeted Rosa26 rESC

| Cell line | R26 clones injected | Clones producing Chimeras | Germline Transmitting Clones | Total Pups | rESC-derived Pups | ESC-derived pups (%) |
|---|---|---|---|---|---|---|
| DA.2B | 4 | 3 | 2 | AH7: 64 AE3: 112 | AH7: 41 AE3: 6 | AH7: 63 AE3: 3 |
| ACI.G1 | 4 | 4 | 1 | DE9: 39 | DE9: 4 | 10 |

Figure 13E:
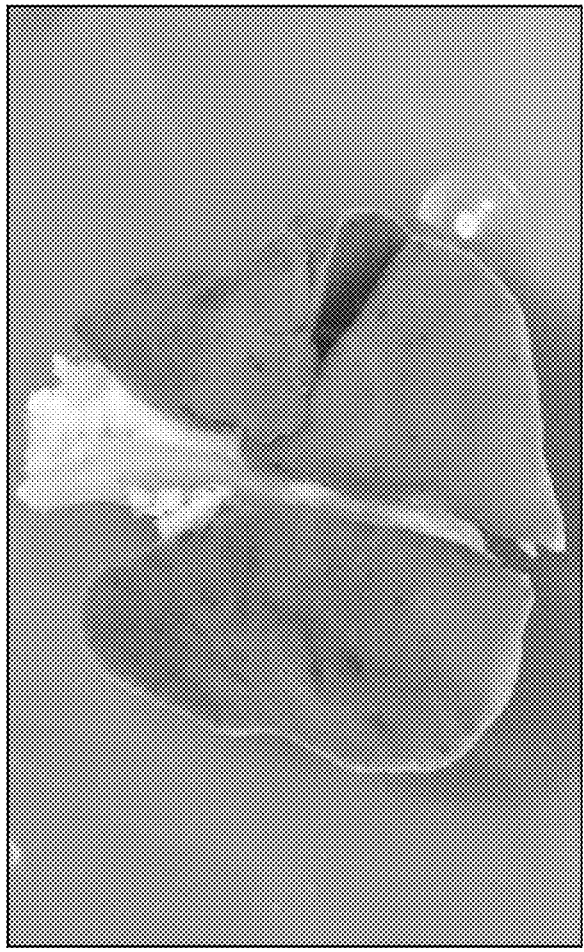
FIG. 13E depicts a control lung of a 14-week-old wild type rat, which was treated with X-gal. The control lung showed a low level of background staining for LacZ.
Figure 13F:
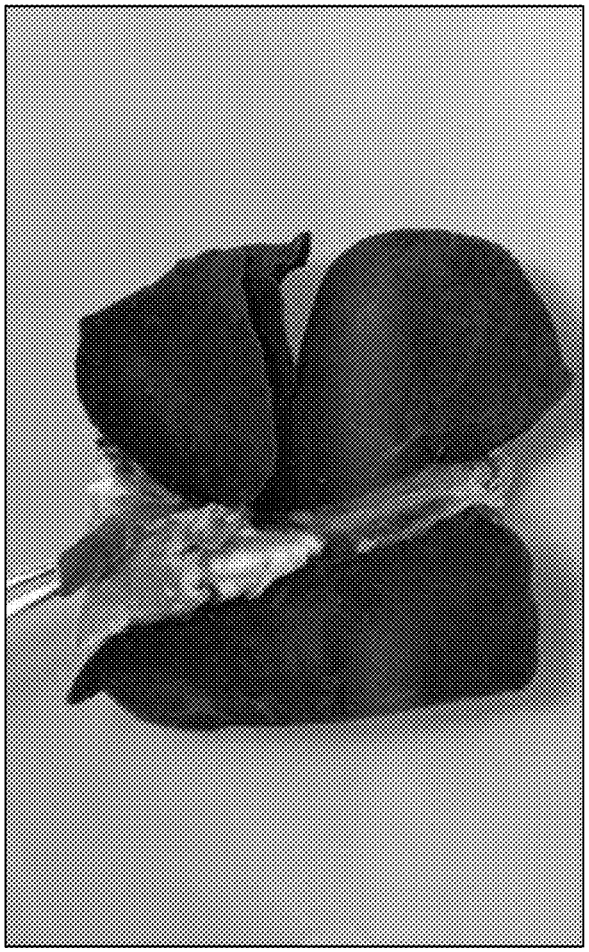
FIG. 13F depicts LacZ expression in the lung of a 14-week-old rRosa26 heterozygote rat. The lacZ reporter was expressed ubiquitously throughout the lung of the rRosa26 heterozygote.
Figure 13H:
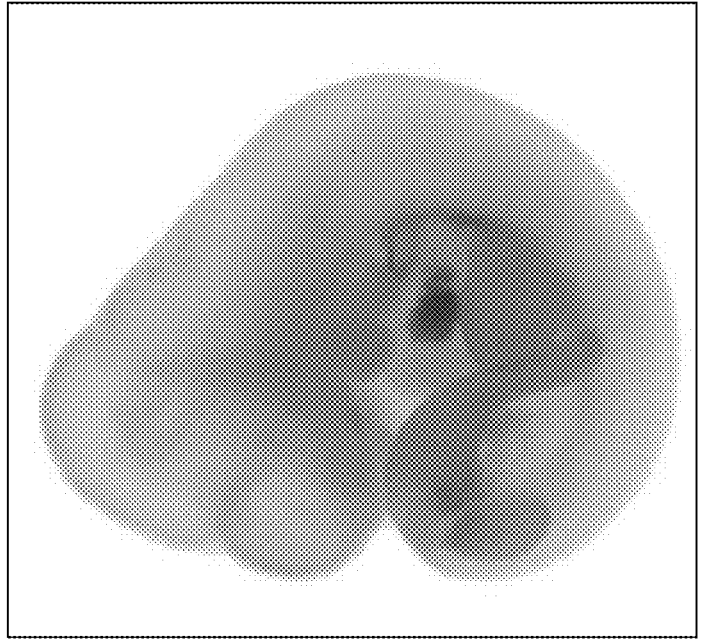
FIG. 13A depicts a control brain of a 14-week-old wild type rat, which was stained with X-gal. The control brain showed a low level of background staining for LacZ (dorsal view).
FIG. 13B depicts LacZ expression in the brain of an rRosa26 heterozygous rat (14-week old). The lacZ reporter was expressed ubiquitously throughout the brain of the rRosa26 heterozygote.
FIG. 13C depicts a control heart and thymus (inset) of a 14-week-old wild type rat, which were treated with X-gal. The control heart and thymus showed a low level of background staining for LacZ.
FIG. 13D depicts LacZ expression in the heart and thymus (inset) of a 14-week-old rRosa26 heterozygous rat. The lacZ reporter was expressed ubiquitously throughout the heart and thymus of the rROSA26 heterozygote.
FIGS. 13G and H depict LacZ expression in E12.5 rat embryos. In contrast to the wild-type control embryo (H), which shows a low level of background LacZ staining, the rRosa26 heterozygous embryo exhibited ubiquitous expression of the LacZ reporter throughout the embryo.
FIGS. 13I and J depict LacZ expression in E14.5 rat embryos. In contrast to the wild-type control embryo (J), which shows a low level of background LacZ staining, the rRosa26 heterozygous rat embryo exhibited ubiquitous expression of the LacZ reporter throughout the embryo.
Figure 13G:
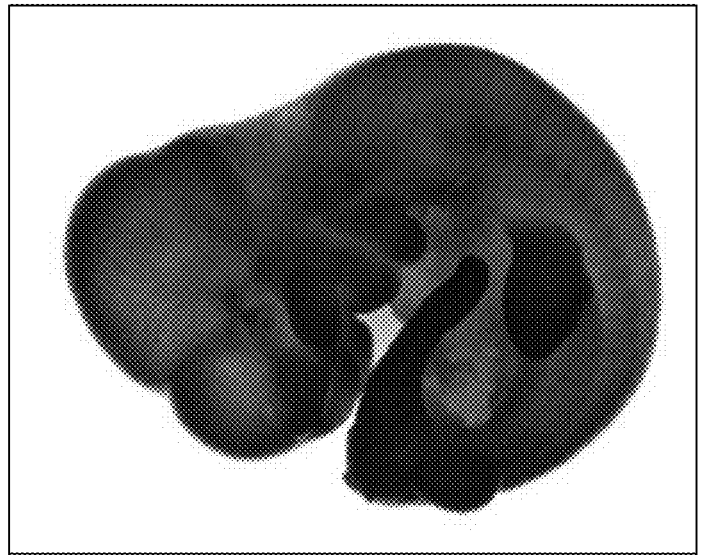
Figure 13J:
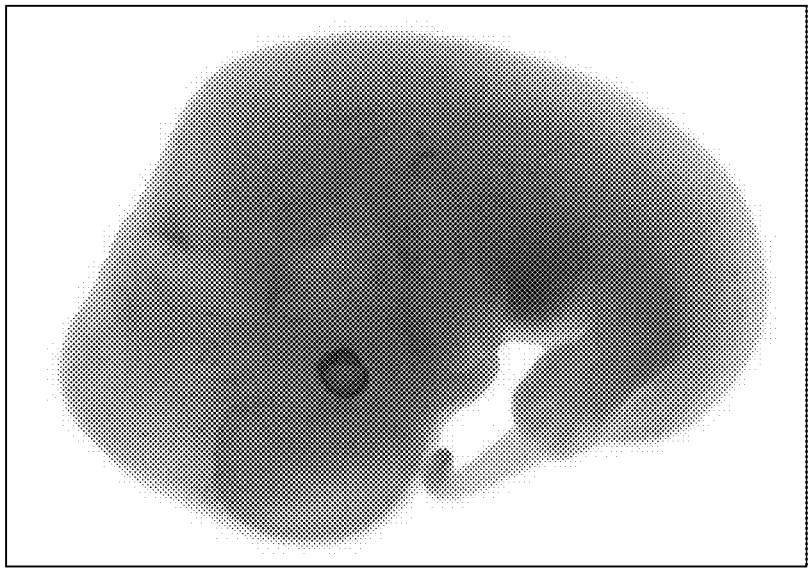
Figure 13I:
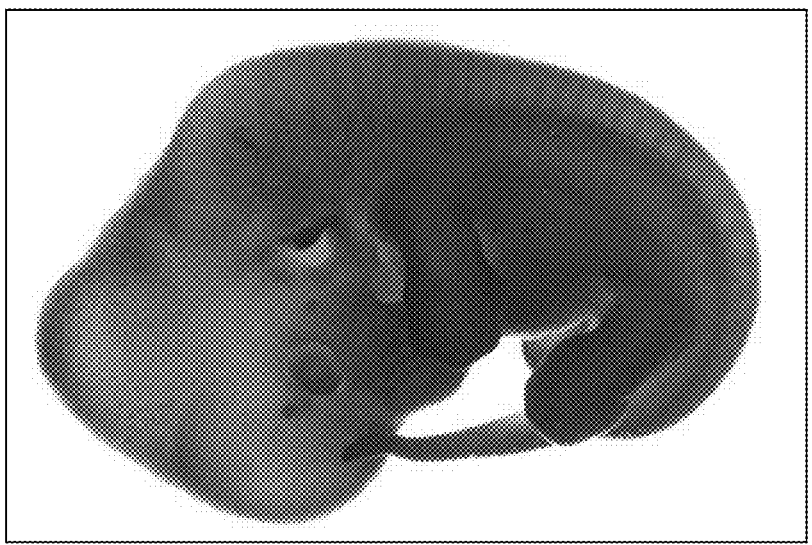

To confirm that the genetically modified allele at the Rosa26 locus was transmitted through the germline, lacZ expression was confirmed by X-gal staining in heterozygous Rosa26-targeted rats. X-gal staining of the brain, heart and thymus, and a lung from a 14-week-old heterozygous Rosa26-targeted rat showed expression of lacZ (FIGS. 13B, D, and F, respectively), whereas age-matched wild type controls showed a low level of background X-gal staining (FIGS. 13A, C, and E, respectively). X-gal staining in E12.5 and E 14.5 heterozygous Rosa26-targeted rat embryos showed ubiquitous expression of lacZ (FIGS. 13G and I, respectively), whereas control rat embryos showed low levels of background X-gal staining (FIGS. 13H and J, respectively).

3.2.(a)(i). Targeting of the Rat Apolipoprotein E (ApoE) Locus.

Figure 20:
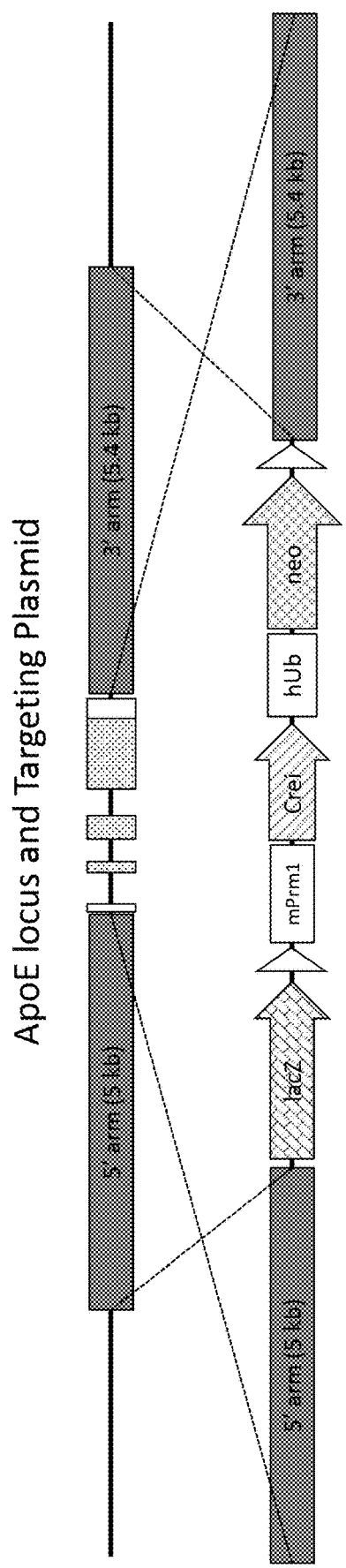
FIG. 20 provides a schematic of the rat ApoE locus and a targeting plasmid. The upper schematic shows the genomic structure of the rat ApoE locus and the genomic regions corresponding to the 5' and 3' homology arms (5 kb and 5.4 kb respectively; dark grey boxes). Exon 1 of the ApoE gene is non-coding and is shown as an open box closest to the 5' homology arm. The three introns of the ApoE gene are denoted as lines. Exons 2 and 3 comprise coding regions and are shown as stippled grey boxes. Exon 4 contains both coding and non-coding sequences as denoted by the stippled grey shading and the open box. The lower panel shows the targeting plasmid. The 5' and 3' homology arms (5 kb and 5.4 kb, respectively) are denoted by the dark grey boxes. The targeting vector comprises a reporter gene (lacZ) and a self-deleting cassette flanked by loxP sites (open arrows). The self-deleting cassette comprises a mouse Prm1 promoter operably linked to the Crei gene and a drug selection cassette comprising a human ubiquitin promoter operably linked to a neomycin resistance gene.

The rat Apolipoprotein E (ApoE) locus was targeted to disrupt ApoE function. Targeting of the ApoE locus was done using a targeting vector comprising a lacZ-hUb-neo cassette flanked with a 5' and 3' homology arms homologous to the ApoE locus. FIG. 20 depicts a genetically modified rat ApoE locus that has been disrupted by a 1.8 kb deletion and the insertion of a lacZ-hUb-neo cassette, which further includes a self-deleting Cre cassette comprising a Crei gene driven by a protamine promoter. The electroporation conditions were as follows: 6 ug DNA; $2.05 \times 10^6$ cells; 400V; 200 uF: 342 V, 593 usec; plate on 15 cm 2× dense neoR MEFs in 2i+ 10 uM ROCKi.

Targeting efficiency at the ApoE locus was determined and is shown in Table 19. Linearized vector was electroporated into DA.2B rat ESCs derived from the DA strain, and transfected colonies were cultured using standard techniques. Individual colonies were picked and screened using a Loss of Allele (LOA) assay.

TABLE 19 rat ApoE Targeting Efficiency

| Cell line | Vector | Colonies picked | Targeted | Targeting efficiency (%) |
|---|---|---|---|---|
| DA.2B | ApoE-mSDC | 192 | 7 | 3.7 |
| DA.2B | ApoE-mSDC | 192 | 15 | 7.8 |

Chimera production and germline transmission using ApoE-targeted rat ESC clones was performed. ApoE-targeted rat ESC clones were microinjected into SD blastocysts, which were then transferred to pseudopregnant SD recipient females, using standard techniques. Chimeras were identified by coat color; male F0 chimeras were bred to SD females. Germline transmission was achieved. F1 pups were genotyped for the presence of the targeted ApoE allele (Table 20).

TABLE 20

Microinjection Results

| Exp | Clone | Pups | Chimeras (% of chimera) |
|---|---|---|---|
| 1 | ApoE-AF5 | 4 | 3 (90, 90, 90) |
| 2 | ApoE-BC4 | 5 | 0 |

LacZ expression driven by the endogenous ApoE promoter was confirmed by X-gal staining in 12-week-old ApoE$^{+/-}$ female rats in the brain, blood vessels, and liver (FIGS. 43-45, respectively). FIGS. 43-45 show an expression pattern for lacZ that mirrors the expression pattern of endogenous ApoE. Age-matched wild type controls showed a low level of background X-gal staining.

The phenotypes of ApoE-deleted rats were further studied. Longitudinal serum chemistry studies were performed to measure cholesterol, LDL, HDL, and triglyceride levels at three-week intervals. FIG. 46A-D show serum cholesterol, LDL, HDL, and triglyceride levels in homozygous targeted, heterozygous targeted, and wild type rats at 6 weeks, 9 weeks, 12 weeks, and 15 weeks of age. Eye bleeds were performed on an age-matched cohort consisting of 2 wild type, 7 heterozygous, and 8 homozygous rats. No significant differences were seen between males and females. Homozygous ApoE-deleted rats showed elevated cholesterol and LDL levels and decreased HDL levels. Unlike ApoE$^{-/-}$ mice, no significant increase in triglycerides was observed in ApoE-deleted rats.

Additional phenotypic analysis that is performed includes histology/ex vivo imaging for aortic arch plaque formation, in vivo imaging for aortic arch plaque formation, and transcriptional changes (Whole Transcriptome Shotgun Sequencing (RNA-Seq)) for aortic arch endothelium. The timing of these assays depends on the timeline of plaque formation. Plaques are detectable in ApoE$^{-/-}$ mice at 24 weeks.

Additional targeting data for ApoE is also provided in Table 22.

3.2.(a)(h). Targeting ApoE in Rats with a Targeting Vector

FIG. 20 provides a schematic of the rat ApoE locus and a targeting plasmid. The upper schematic of FIG. 20 shows the genomic structure of the rat ApoE locus and the genomic regions corresponding to 5' and 3' homology arms (5 kb and 5.4 kb, respectively; dark grey boxes). Exon 1 of ApoE is non-coding and is shown as an open box closest to the 5' homology arm. The 3 introns of ApoE are denoted as lines and exons 2 and 3 comprise coding regions and are shown as stippled grey boxes. Exon 4 contains both coding and non-coding sequences as denoted by the stippled grey shading and the open box.

The lower schematic in FIG. 20 is the targeting vector. The 5' and 3' homology arms (5 kb and 5.4 kb respectively) are denoted by the dark grey boxes. The targeting vector comprises a reporter gene (lacZ) and a self-deleting cassette flanked by loxP sites (open arrows). The self-deleting cassette comprises the Crei gene operably linked to a mouse Prm1 promoter and a selection cassette comprising a neomycin resistance gene operably linked to a human ubiquitin promoter.

The Crei gene comprises two exons encoding a Cre recombinase, which are separated by an intron (Crei) to prevent its expression in a prokaryotic cell. See, for example, U.S. Pat. No. 8,697,851 and U.S. Application Publication 2013-0312129, which describe the self-deleting cassette in detail and are hereby incorporated by reference in their entirety. By employing the Prm1 promoter, the self-deleting cassette can be deleted specifically in male germ cells of F0 rats. The targeting vector was electroporated into the rat ES cells obtained in Example 1 and the cells were plated on 15 cm 2× dense neomycin-resistant MEFs in 2i+ 10 uM ROCKi. The transformed rat ES cells were cultured, selected, and maintained as described in Example 1.

As shown in Table 44, 384 colonies were screened and 23 targeted clones were obtained. The targeting efficiency was 5.99%. 3 clones were injected into blastocysts as described herein in Example 1. 3 clones producing chimeras were obtained and 1 of the clones transmitted the targeted modification through the germline.

3.2.(a)(iii). Targeting ApoE in Rats with a Targeting Vector in Combination with Zinc Finger Nucleases The targeting vector employed in Example 3.2(a)(ii) was used in combination with zinc finger nucleases to target the rat ApoE locus. Table 21 provides a summary of the genomic organization of the rat ApoE locus. The positions shown in the Table 21 were taken from build 5.0 of the Reference Sequence of the rat genome (ENSMBL). ApoE is on chromosome 1 on the (–) strand.

TABLE 21

Summary of the rat ApoE locus and the positions of the zinc finger nuclease binding sites and cutting sites.

| Feature | Start | End | length | Notes |
|---|---|---|---|---|
| Exon 1 | 81881110 | 81881182 | 73 | 5' non-coding |
| Exon 2 | 81880269 | 81880332 | 64 | contains ATG |
| ATG | 81880309 | 81880311 | 3 | start codon |
| Exon 3 | 81879607 | 81879775 | 169 | |
| ZFN1a binding site | 81879707 | 81879693 | 15 | CAGGCCCTGAAC CGC (SEQ ID NO: 10) |
| ZFN1 cutting site | 81879692 | 81879687 | 6 | TTCTGG (SEQ ID NO: 11) |
| ZFN1b binding site | 81879686 | 81879671 | 16 | GATTACCTGCGCT GGG (SEQ ID NO: 12) |
| Intron 3-4 | 81879776 | 81879207 | 400 | |
| ZF21a binding site | 81879591 | 81879577 | 15 | TTCACCCTCCGC ACC (SEQ ID NO: 13) |
| ZFN2 cutting site | 81879576 | 81879570 | 7 | TGCTGAG (SEQ ID NO: 14) |
| ZF21b binding site | 81879569 | 81879552 | 18 | TATCCA-GATCCAGGG GTT (SEQ ID NO: 15) |
| Exon 4 | 81878371 | 81879208 | 838 | contains TGA |
| TGA | 81878482 | 81878484 | 3 | |
| ApoE deletion | 81878482 | 81880311 | 1830 | |

Figure 11:
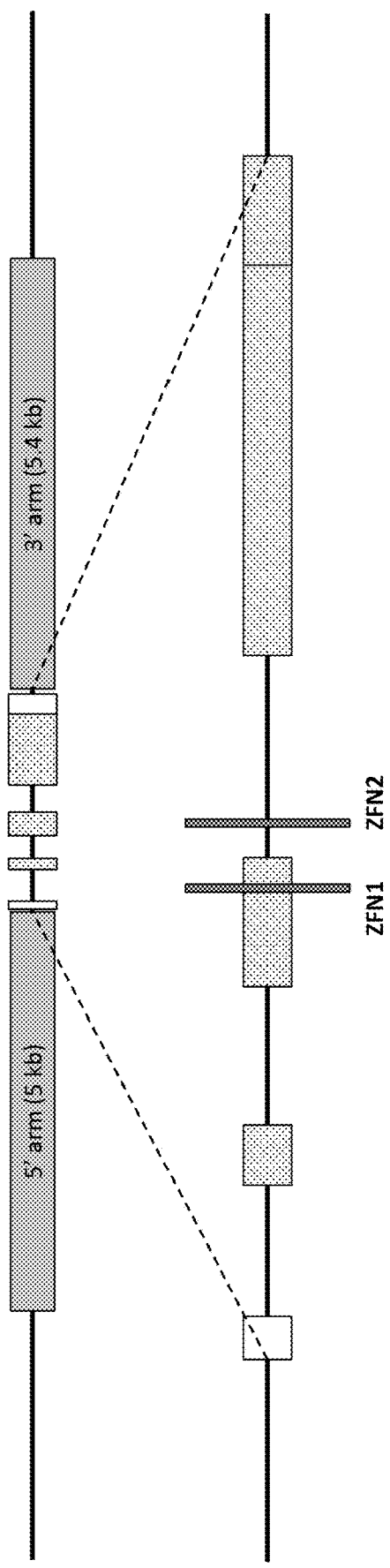
FIG. 11 provides a schematic of the rat ApoE locus and denotes with grey bars the cutting site for zinc finger nucleases (ZFN1 and ZFN2). The genomic regions corresponding to the 5' and 3' homology arms (5 kb and 5.4 kb, respectively) are denoted by the dark grey boxes. Exon 1 of the ApoE gene is non-coding and is shown as an open box closest to the 5' homology arm. The three introns of the ApoE gene are denoted as lines. Exons 2 and 3 comprise coding regions and are shown as stippled grey boxes. Exon 4 contains both coding and non-coding sequences as denoted by the stippled grey shading and the open box.

FIG. 11 provides a schematic of the rat ApoE locus and denotes with grey bars the cutting site for ZFN1 and ZFN2. The cutting site for ZFN1 is in exon 3 and the cutting site for ZNF2 is in intron 3. The exact position of the both ZFN sites is set forth in Table 21. The genomic regions corresponding to the 5' and 3' homology arms (5 kb and 5.4 kb, respectively) are denoted by the dark grey boxes. Exon 1 of ApoE is non-coding and is shown as an open box closest to the 5' homology arm. The three introns of the ApoE gene are denoted as lines and exons 2 and 3 comprise coding regions and are shown as stippled grey boxes. Exon 4 contains both coding and non-coding sequences as denoted by the stippled grey shading and the open box.

Figure 21A:
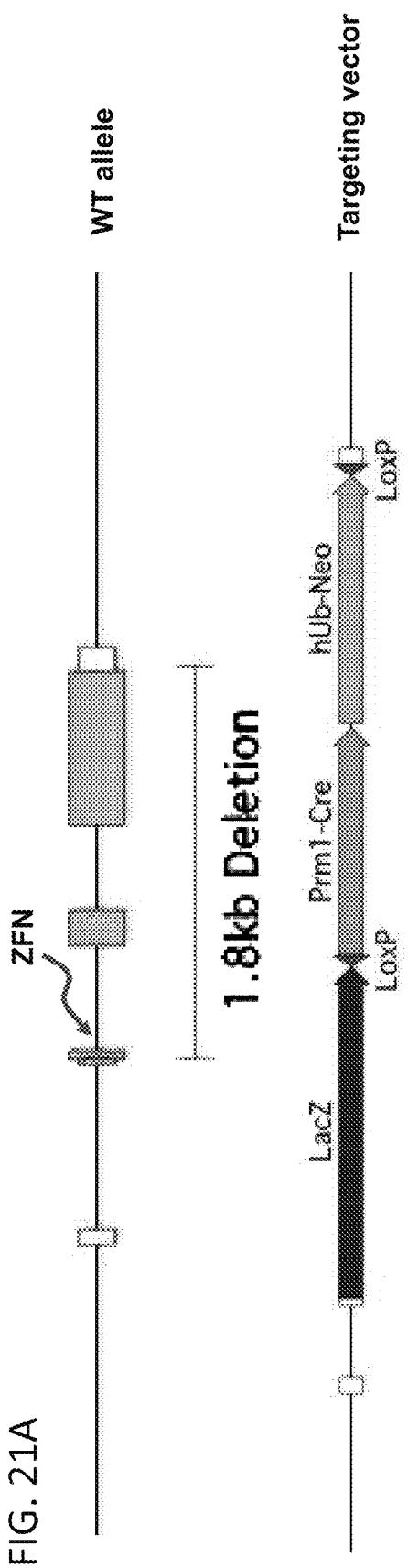
FIGS. 21A and B depict targeting of the rat ApoE locus.
Figure 21B:
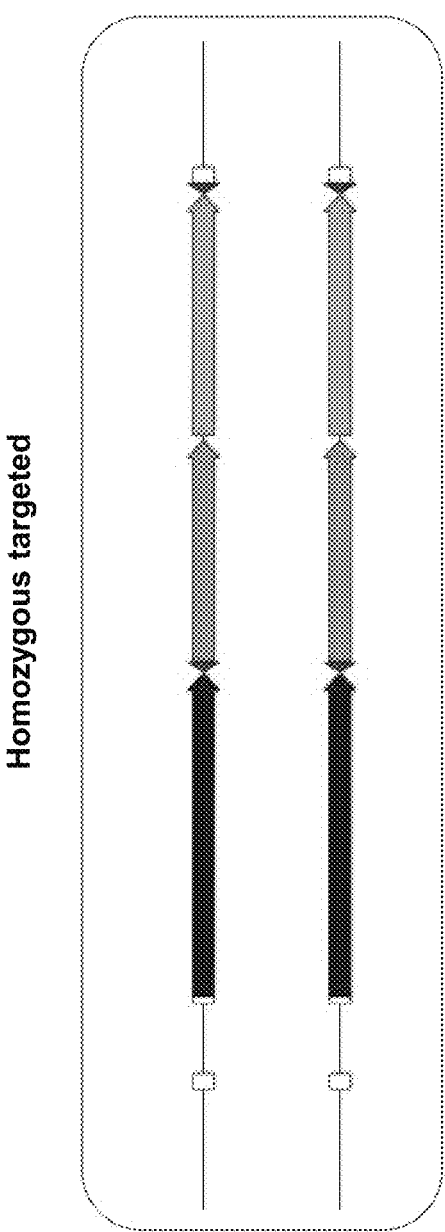
FIG. 21B depicts a homozygous targeted ApoE locus.

The employed targeting vector was the same as that in Example 3.2(a)(ii) and shown in FIG. 20, and FIG. 21A provides a schematic for targeting the ApoE locus in rat ES cells using zinc-finger nucleases and the targeting vector depicted in FIG. 20. The ZFNs were introduced as two expression plasmids, one for each half of the ZFN pair. 20 ug of the plasmid for ZFN1 and 20 ug of the plasmid for ZFN2 was used. ZFNs were purchased from Sigma. The expression of each ZFN was driven by the CMV promoter.

The targeting vector were electroporated into the rat ES cells obtained in Example 1 and the cells were plated on 15 cm 2× dense neoR MEFs in 2i+ 10 uM ROCKi. The transformed rat ES cells were cultured, selected and maintained as described in Example 1.

As shown in Table 22 and Table 44, 384 colonies were screened and 290 targeted clones were obtained. The targeting efficiency was 75.52%. 2 clones were injected into blastocysts as described herein in Example 1. Two clones producing chimeras were obtained and one of the clones transmitted the targeted modification through the germline.

Moreover, employing ZFN1 and ZFN2 produced 8 biallelic targeted clones with an efficiency of 2.08%.

TABLE 22

Targeting of ApoE Locus.

| DNA | Heterozygous Targeted | Homozygous Targeted | Microinjected | Chimeras (% Chimerism) | Breeding |
|---|---|---|---|---|---|
| vector alone | 15/192 (8%) | 0 | | | |
| vector + ZFN pair 1 | 156/192 (81%) | 6/192 (3%) | 2 clones | 7 (70-90%) | |
| vector + ZFN pair 2 | 134/192 (70%) | 2/192 (1%) | | | |

3.2.(b)(i). Targeted Modification of the Rat Apolipoprotein E (ApoE) Locus Using a Large Targeting Vector (LTC).

Figure 22:
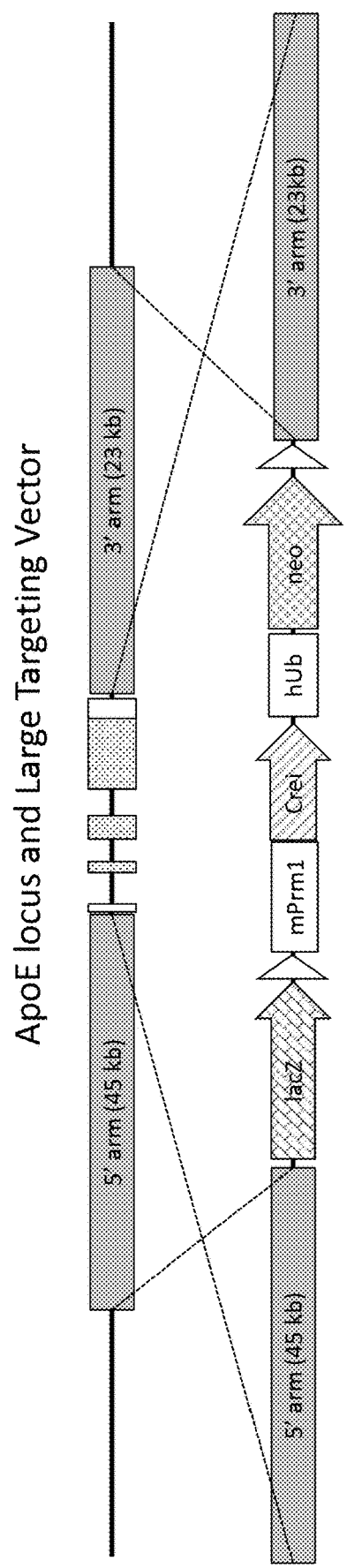
FIG. 22 provides a schematic of the rat ApoE locus and a large targeting vector (LTVEC). The upper panel shows the genomic organization of the rat ApoE locus and the genomic regions corresponding to the 5' and 3' homology arms (45 kb and 23 kb, respectively; the dark grey boxes). Exon 1 of ApoE is non-coding and is shown as an open box closest to the 5' homology arm. The three introns of the ApoE gene are denoted as lines and exons 2 and 3 comprise coding regions and are shown as stippled grey boxes. Exon 4 contains both coding and non-coding sequences as denoted by the stippled grey shading and the open box. The lower panel shows the LTVEC for modifying the rat ApoE locus. The 5' and 3' homology arms (45 kb and 23 kb, respectively) are denoted by the dark grey boxes. The LTVEC comprises a reporter gene (lacZ) and a self-deleting cassette flanked by loxP sites (open arrows), which comprises a mouse Prm1 promoter operably linked to the Crei gene and a drug selection cassette comprising a human ubiquitin promoter operably linked to a neomycin resistance gene.

Targeting of the ApoE locus is done using a large targeting vector (LTVEC) comprising a lacZ-mouse Prm1-Crei cassette flanked with a 5' homology arm to the ApoE locus of about 45 kb and a 3' homology arm to the ApoE locus of about 23 Kb. FIG. 22 depicts the rat ApoE locus in which the ApoE locus has been disrupted by a 1.83 kb deletion and the insertion of the lacZ gene and a self-deleting cassette comprising mPrm1-Crei cassette and a hUb-neo selection cassette. Methods employed in example 3.2(a)(i) can be used to introduce this vector into rat ES cells.

Example 3.2.(b)(h). Targeting of the Rat ApoE Locus with a Large Targeting Vector (LTVEC)

FIG. 22 provides a schematic of the rat ApoE locus and a large targeting vector (LTVEC). The upper schematic of FIG. 22 shows the genomic organization of the rat ApoE locus and the genomic regions corresponding to the 5' and 3' homology arms (45 kb and 23 kb, respectively; dark grey boxes). Exon 1 of ApoE is non-coding and is shown as an open box closest to the 5' homology arm. The 3 introns of ApoE are denoted as lines and exons 2 and 3 comprise coding regions and are shown as stippled grey boxes. Exon 4 contains both coding and non-coding sequences as denoted by the stippled grey shading and the open box.

The lower schematic in FIG. 22 is the LTVEC. The 5' and 3' homology arms (45 kb and 23 kb, respectively) are denoted by the dark grey boxes. The targeting vector comprises a reporter gene (lacZ) and a self-deleting cassette flanked by loxP sites (open arrows), which comprises the Crei gene operably linked to a mouse Prm1 promoter and a drug selection cassette comprising a neomycin resistance gene operably linked to a human ubiquitin promoter. The Crei comprises two exons encoding the Cre recombinase which are separated by an intron (Crei) to prevent its expression in a prokaryotic cell. See, for example, U.S. Pat. No. 8,697,851 and U.S. Application Publication 2013-0312129, which describes the self-deleting cassette in detail and is hereby incorporated by reference in their entirety. By employing a mouse Prm1 promoter, the self-deleting cassette can be deleted specifically in male germ cells of F0 rat.

The LTVEC was electroporated into the rat ES cells obtained in Example 1 and the cells were plated on 15 cm 2× dense neoR MEFs in 2i+ 10 uM ROCKi. The transformed rat ES cells were cultured, selected, and maintained as described in Example 1.

As shown in Table 44, 288 colonies were screened and 8 targeted clones were obtained. The targeting efficiency was 2.78%. 3 clones were injected into a host embryo at a blastocyst stage as described herein in Example 2 to produce chimeric rats (F0). Moreover, one biallelic targeted clone was produced providing a biallelic efficiency of 0.35%.

3.2.(b)(iii). Targeting ApoE in Rats with a Large Targeting Vector (LTVEC) in Combination with Zinc Finger Nucleases The LTVEC employed in Example 3.2.(b)(ii) was used in combination with zinc finger nucleases to target the rat ApoE locus. Table 21 provides a summary of the genomic organization of the rat ApoE locus and the positions shown were taken from build 5.0 of the Reference Sequence of the rat genome (ENSMBL).

Figure 23:
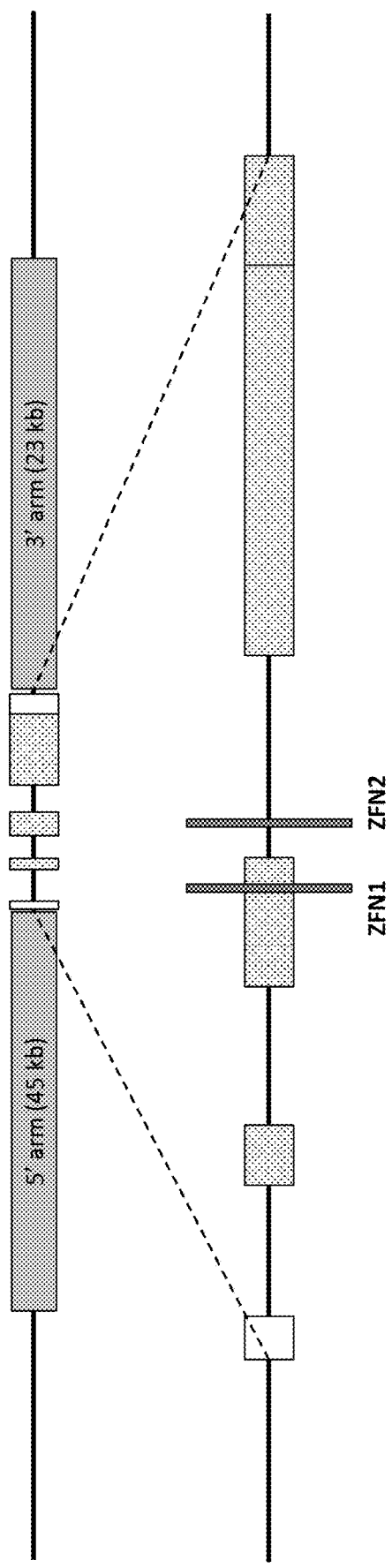
FIG. 23 provides a schematic of the rat ApoE locus and denotes with grey bars the cutting sites for zinc finger nucleases (ZFN1 and ZFN2) used together with the large targeting vector (LTVEC) to enhance homologous recombination between the targeting vector and the target cognate chromosomal region.

FIG. 23 provides a schematic of the rat ApoE locus and denotes with grey bars the cutting site for ZFN1 and ZFN2. The cutting site for ZFN1 is in t exon 3 and the cutting site for ZNF2 is in intron 3. The exact position of the both ZFN sites is set forth in Table 21. The 5' and 3' homology arms (45 kb and 23 kb, respectively) are denoted by the dark grey boxes. Exon 1 of the ApoE gene is non-coding and is shown as an open box closest to the 5' homology arm. The three introns of the ApoE gene are denoted as lines. Exons 2 and 3 comprise coding regions and are shown as stippled grey boxes. Exon 4 contains both coding and non-coding sequences as denoted by the stippled grey shading and the open box.

The LTVEC employed was the same as that in Example 3.2(b)(ii) and shown in FIG. 22. The ZFNs were introduced as two expression plasmids, one for each half of the ZFN pair. 20 ug of the plasmid for ZFN 1 and 20 ug of the plasmid for ZFN2 was used. ZFNs were purchased from Sigma. The expression of each ZFN was driven by the CMV promoter.

The targeting vector was electroporated into the rat ES cells obtained in Example 1 and the cells were plated on 15 cm 2× dense neoR MEFs in 2i+ 10 uM ROCKi. The transformed rat ES cells were cultured, selected, and maintained as described in Example 1.

As shown in Table 44, 288 colonies were screened and 16 targeted clones were obtained. The targeting efficiency was 5.56%. One clone was injected into blastocysts as described herein in Example 2.

Moreover, the employment of ZFN1 and ZFN2 produced one biallelic targeted clone, with an efficiency of 0.35%.

3.2. (b)(iv). Targeting ApoE in Rats with a Large Targeting Vector (LTVEC) in Combination with CRISPR/Cas9

Figure 47:
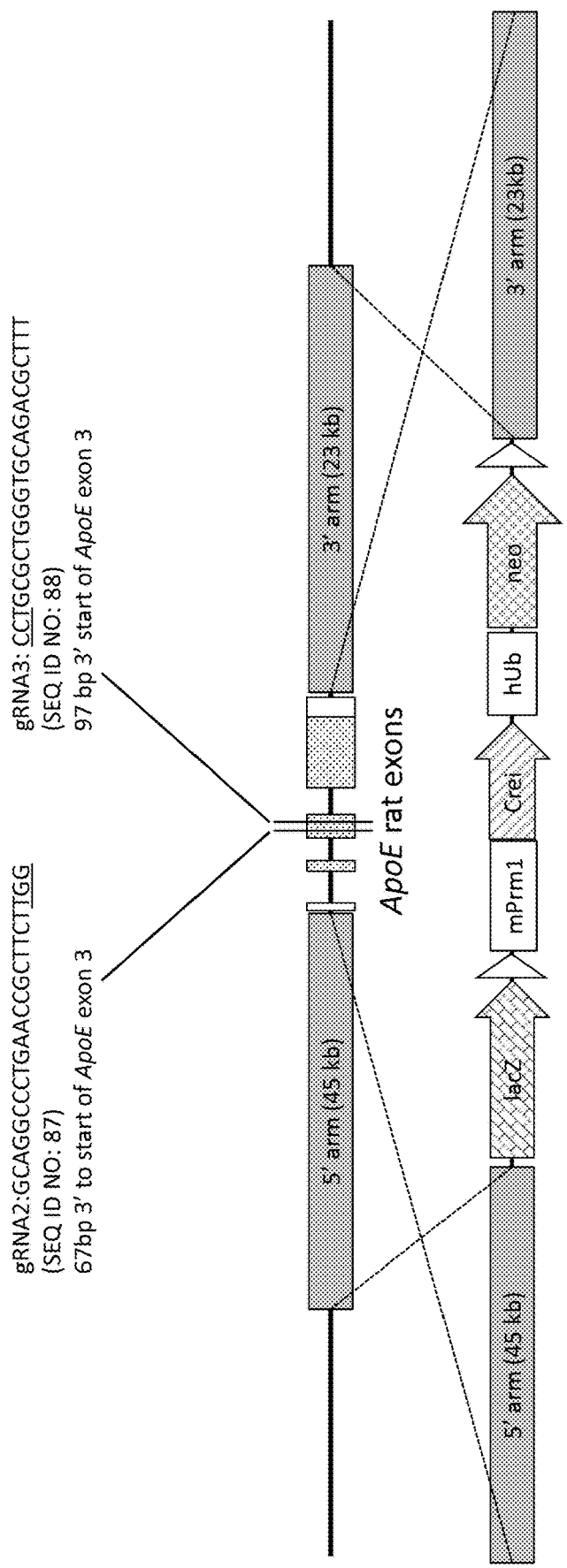
FIG. 47 shows a schematic of the rat ApoE locus (upper panel) and a large targeting vector (LTVEC) that targets the rat ApoE locus (lower panel). The upper panel shows the genomic organization of the rat ApoE locus and the genomic regions corresponding to the 5' and 3' homology arms (45 kb and 23 kb, respectively; the dark grey boxes). Exon 1 of ApoE is non-coding and is shown as an open box closest to the 5' homology arm. The three introns of the ApoE gene are denoted as lines and exons 2 and 3 comprise coding regions and are shown as stippled grey boxes. Exon 4 contains both coding and non-coding sequences as denoted by the stippled grey shading and the open box. Target sites for ApoE gRNA2 (SEQ ID NO: 87) and gRNA3 (SEQ ID NO: 88) are indicated. The lower panel shows the LTVEC for modifying the rat ApoE locus. The 5' and 3' homology arms (45 kb and 23 kb, respectively) are denoted by the dark grey boxes. The LTVEC comprises a reporter gene (lacZ) and a self-deleting cassette flanked by loxP sites (open arrows), which comprises a mouse Prm1 promoter operably linked to the Crei gene and a drug selection cassette comprising a human ubiquitin promoter operably linked to a neomycin resistance gene.

The LTVEC employed in Example 3.2.(b)(ii) was used in combination with CRISPR/Cas9 to target the rat ApoE locus. Table 23 shows a comparison of the results of experiments in which the ApoE LTVEC was used alone to target the rat ApoE locus or was used in combination with a CRISPR/Cas9 nuclease to target the rat ApoE locus. In each experiment, electroporated cells were plated at a high density and subjected to drug selection to find colonies that were drug-resistant. Drug-resistant colonies were picked and screened for the targeted modification using the modification of allele (MOA) assay as described herein. Specifically, $4 \times 10^6$ cells were electroporated with 2 ug of ApoE LTVEC at a voltage of 400V, a capacitance of 100 uF, and a resistance of 0. In the latter experiment, 6 ug of Cas9 expression plasmid and 3 ug of ApoE gRNA2 or 3 ug of ApoE gRNA3 were also electroporated. Selection was done using 75 ug/mL of G418. ApoE gRNA2 has a sequence of GCAGGCCCTGAACCGCTTCTTGG (SEQ ID NO: 87) and targets a region 67 bp 3' of the start of rat ApoE exon 3. ApoE gRNA3 has a sequence of CCTGCGCTGGGTGCAGACGCTTT (SEQ ID NO: 88) and targets a region 97 bp 3' of the start of rat ApoE exon 3 (see FIG. 47). As shown in Table 23, when Cas9 and either of the gRNAs were introduced into the cells together with the ApoE LTVEC, targeting efficiency increased (from 43% to 53% or 47%). Biallelic targeting was observed in five colonies targeted with the ApoE LTVEC in combination with ApoE gRNA2 or 3, but no biallelic targeting was observed with ApoE LTVEC alone.

TABLE 23

Comparison of Rag2 LTVEC Targeting with and without CRISPR/Cas9

| Vector | Cas9 | gRNA | Colonies Screened | Targeted Clones | Biallelic Targeted | Targeting Efficiency |
|---|---|---|---|---|---|---|
| ApoE LTVEC | NO | NO | 75 | 32 | 0 | 43% |
| ApoE LTVEC | Yes | ApoE gRNA2 | 80 | 42 | 1 | 53% |
| ApoE LTVEC | Yes | ApoE gRNA3 | 89 | 42 | 4 | 47% |

3.3(a). Targeting of the Rat Interleukin-2 Receptor Gamma (IL2r-γ) Locus

The rat Interleukin-2 receptor gamma (IL2r-γ or Il2rg) locus was targeted to disrupt IL2r-γ function. IL2r-γ plays an important role for signaling by IL-2, IL-4, IL-7, IL-9, IL-15, IL-21 and mutations in IL2r-γ are associated with severe defects in T, B and NK cell development.

Figure 24:
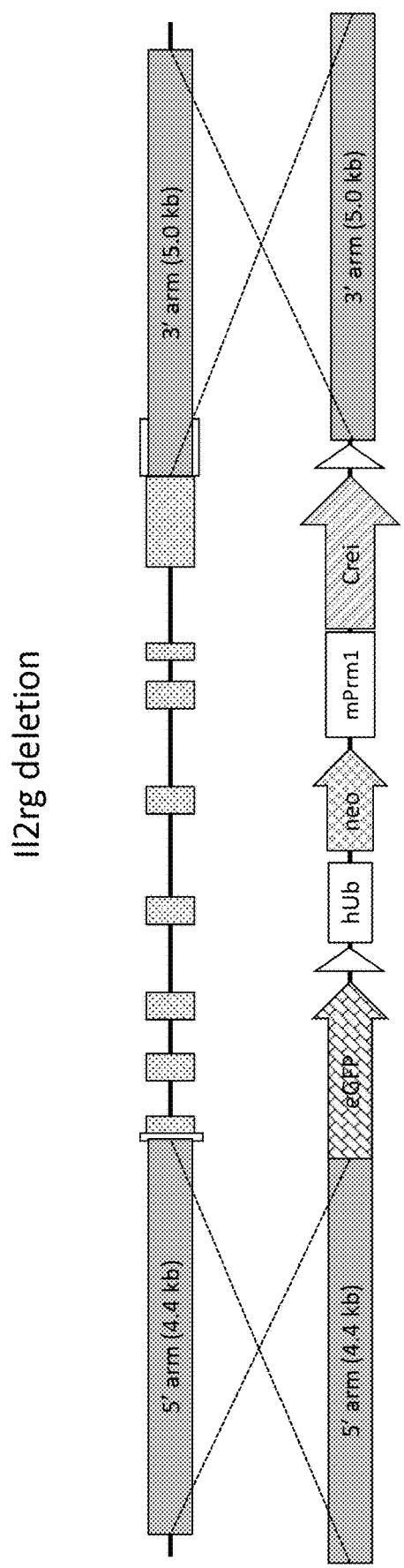
FIG. 24 depicts the rat IL2r-γ locus that has been disrupted by a 3.2 kb deletion and the insertion of a reporter gene (eGFP) and a self-deleting cassette comprising a drug selection cassette (hUb-neo) and the Crei gene operably linked to a mouse Prm1 promoter.
Figure 25:
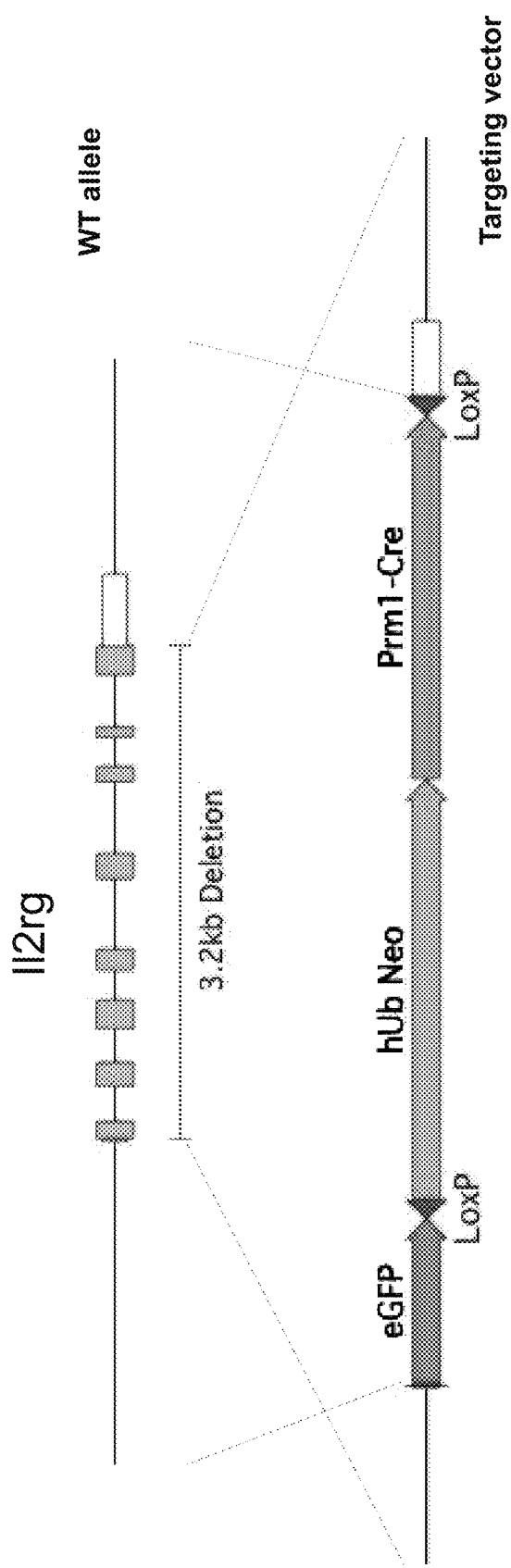
FIG. 25 provides another depiction of the rat IL2r-γ locus that has been disrupted by a 3.2 kb deletion and the insertion of a reporter gene (eGFP) and a self-deleting cassette comprising the Crei gene operably linked to a mouse Prm1 promoter and a drug selection cassette (hUb-Neo).

Targeting of the IL2r-γ locus was done using a targeting vector comprising an eGFP-hUb-neo cassette flanked with a 5' and 3' homology arms homologous to the IL2r-γ locus, as depicted in FIG. 24. FIG. 25 depicts the genomic structure of the rat IL2r-γ locus in which the IL2r-γ locus has been disrupted by a 3.2 kb deletion. The targeted IL2r-γ locus also comprised an eGFP gene and a self-deleting cassette containing Crei operably linked to a mouse Protamine1 promoter and a drug selection cassette comprising a hUb promoter operably linked to a neomycin resistance gene.

Targeting efficiency at the IL2r-γ locus was determined and shown in Table 24. Linearized vector was electroporated into DA.2B rat ESCs, and transfected colonies were cultured using standard techniques. Individual colonies were picked and screened using a Loss of Allele (LOA) assay.

TABLE 24 rat IL2r-γ Targeting Efficiency

| Cell line | Vector | Colonies picked | Targeted | Targeting efficiency (%) | Chimeras (% Chimerism) |
|---|---|---|---|---|---|
| DA.2B | Il2rg-floxed neo | 136 | 1 | 0.7 | 5 (70-90%) |
| DA.2B | Il2rg-mSDC | 96 | 4 | 4.2 | |

Chimera production and germline transmission using IL2r-γ-targeted rat ESC clones was performed. IL2r-γ-targeted rat ESC clones were microinjected into SD blastocysts, which were then transferred to pseudopregnant SD recipient females, using standard techniques. Chimeras were identified by coat color; male F0 chimeras were bred to SD females. Germline F1 pups were genotyped for the presence of the targeted IL2r-γ allele (Table 25). In another microinjection experiment with clone Il2rg-CG12, germline transmission was also confirmed by coat colors and genotyping.

TABLE 25

Microinjection Results

| Exp | Clone | pups | Chimeras (% of chimera) |
|---|---|---|---|
| 1 | Il2rg-AA1 | 5 | 2 (90, 70) |
| 2 | Il2rg-AA1 | 10 | 3 (90, 90, 80) |
| 3 | Il2rg-CG12 | 11 | 7 (95, 90, 90, 90, 80, 80, 80) |

Figure 30:
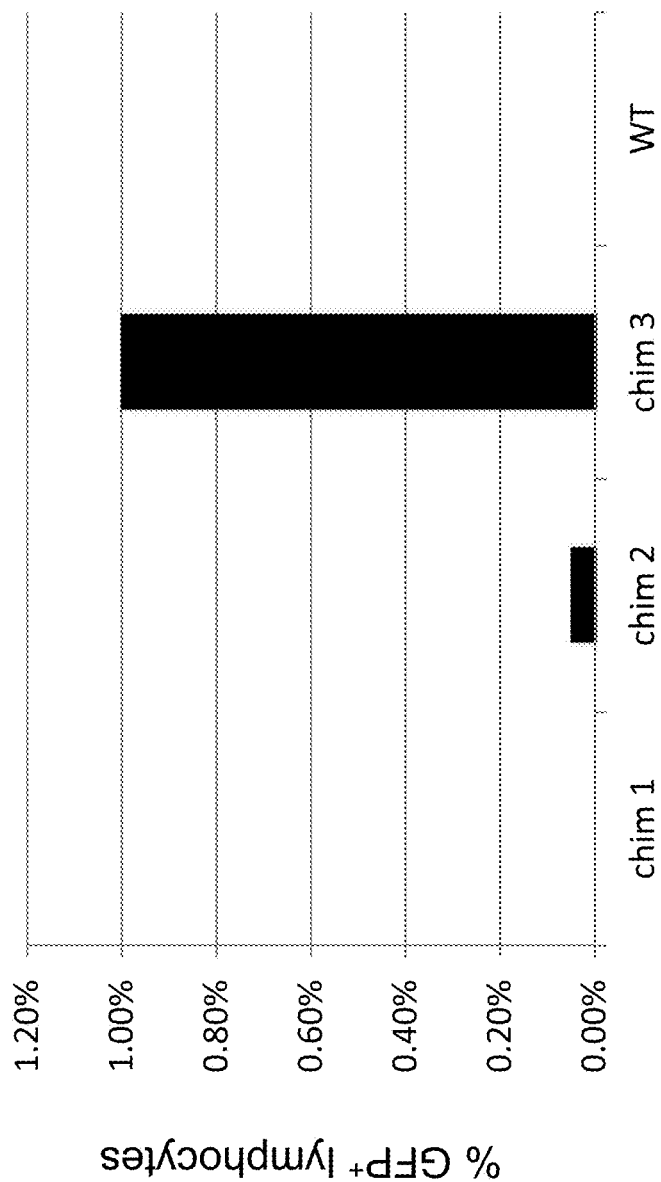
FIG. 30 shows that GFP-positive lymphocytes were detected in peripheral blood in 2 of the 3 Il2rg−/y chimeras.

The phenotype of Il2rg$^{-/Y}$ chimera #3 was further studied. The peripheral blood mononuclear cells (PBMCs) were stained with antibodies that recognize antigens in several lymphoid lineages. GFP-positive PBMCs were detected from 2 of the chimeras, as shown in FIG. 30. Moreover, the GFP+ cells were negative for the T-cell marker CD3 (FIG. 29A), and were mostly negative for the B-cell marker B220 and the NK cell marker CD161a (FIGS. 29B and C, respectively). PBMCs from a wild type rat were used as negative controls for GFP expression. See FIG. 29D-F. The small double-positive populations are consistent with the published Il2rg knockout phenotype in mice. These data were obtained from a chimeric rat, which contains IL2 receptor gamma-positive cells, and this may complicate the analysis of the phenotype. Flow cytometry analysis can also be performed on cell populations from bone marrow and spleen to reveal corresponding decreases in the number of lymphocytes. See Mashimo et al. (2010) PLoS One 5(1):e8870.

3.3(b): Targeted Modification of the Rat Interleukin-2 Receptor Gamma (IL2r-γ) Locus The rat Interleukin-2 receptor gamma (IL2r-γ) locus was targeted to disrupt the IL2r-γ function in rats. FIG. 25 shows the genomic structure of the rat Il2rg locus (upper panel of FIG. 25) and the targeting vector introduced into the locus (lower panel of FIG. 25). eGFP was chosen as a reporter so that the immunophenotype of the genetically modified rats could be examined using FACS. The self-deleting cassette (hUb-Neo; Prm1-Cre) was used to delete the drug section cassette and the Cre gene specifically in male germ cells of the F0 rat. Additionally, the targeting vector was designed to delete the entire coding region (about 3.2 kb) of the rat Il2rg gene.

The size of the deletion in rat ESCs was confirmed by PCR using primers specific to the rat Il2rg locus. Upon microinjection of the targeted clones into host embryos at a blastocyst stage, high percentage chimeras were obtained. Those chimeras have been set up for breeding. To determine if the targeting worked as expected, the peripheral blood from the chimeras were collected prior to breeding, and the phenotype of the immune cells in the peripheral blood was analyzed via FACS. As shown in FIG. 30, GFP-positive cells were detected in the peripheral blood in 2 of the 3 chimeras examined, and the chimeric rats contained less than 1% of T cells, less than 1% of B cells, and less than 1% of NK-cells, which are positive for GFP (i.e., Il2rg KO cells) (FIG. 29A-C).

3.4(a)(i). Targeting the Rag2 Locus in Rats with a Large Targeting Vector (LTVEC)

Table 26 provides a summary of the genomic organization of the rat Rag2 locus and the positions shown were taken from build 5.0 of the Reference Sequence of the rat genome (ENSMBL). Rag2 is on chromosome 3 on the (+) strand.

TABLE 26

Genomic organization summary of the rat Rag2 locus.

| Feature | Start | End | Length | Notes |
|---|---|---|---|---|
| Exon 1 | 97,851,317 | 97,851,448 | 132 | |
| Exon 2 | 97,854,635 | 97,854,693 | 59 | |
| Exon 3 | 97,858,260 | 97,859,615 | 1,356 | contains entire coding sequence |
| ATG | 97,856,286 | 97,856,288 | 3 | start codon |
| TGA | 97,857,867 | 97,857,869 | 3 | stop codon |
| Rag2 deletion | 97,856,289 | 97,859,784 | 3,496 | |

Figure 26:
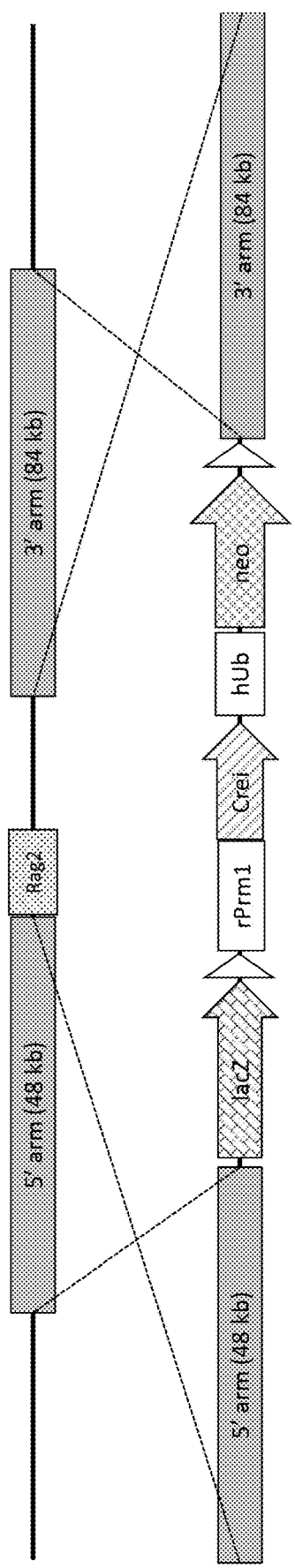
FIG. 26 provides a schematic of the rat Rag2 locus and a large targeting vector (LTVEC) for modifying the rat Rag2 locus. The upper panel shows the genomic organization of the rat Rag2 locus and the cognate genomic regions corresponding to the 5' and 3' homology arms (48 kb and 84 kb, respectively; dark grey boxes). Rag2 comprises single exon denoted by the stippled grey shading. The lower panel is the LTVEC. The 5' and 3' homology arms (48 kb and 84 kb, respectively) are denoted by the dark grey boxes. The LTVEC comprises a reporter gene (lacZ) and a self-deleting cassette flanked by loxP sites (open arrows) that contains a rat Prm1 promoter operably linked to the Crei gene and a drug selection cassette containing a human ubiquitin promoter operably linked to a neomycin resistance gene.

FIG. 26 provides a schematic of the rat Rag2 locus and a large targeting vector (LTVEC). The LTVEC is 140 kb and targets an approximately 5.7 kb portion of the rat Rag2 locus for deletion. The upper schematic of FIG. 26 shows the genomic organization of the rat ApoE locus and the genomic regions corresponding to the 5' and 3' homology arms (48 kb and 84 kb, respectively; dark grey boxes). Rag2 comprises a single exon denoted by the stippled grey shading.

The lower schematic in FIG. 26 is the LTVEC. The 5' and 3' homology arms (48 kb and 84 kb, respectively) are denoted by the dark grey boxes. The LTVEC comprises a reporter gene (lacZ) and a self-deleting cassette flanked by loxP sites (open arrows). The self-deleting cassette comprises a mouse Prm1 promoter operably linked to the Crei gene and a drug selection cassette comprising a human ubiquitin promoter operably linked to a neomycin resistance gene. Another version of the LTVEC was generated in which the neomycin resistance gene was replaced with a hygromycin resistance gene to enable retargeting of Il2rg-targeted rat ES cells. The Crei comprises two exons encoding the Cre recombinase that are separated by an intron (Crei) to prevent its expression in a prokaryotic cell. See, for example, U.S. Pat. No. 8,697,851 and U.S. Application Publication 2013-0312129, which describe the self-deleting cassette in detail and are hereby incorporated by reference in their entirety. By employing a mouse Prm1 promoter, the self-deleting cassette can be deleted specifically in male germ cells of F0 rats.

The LTVEC was electroporated into the rat ES cells obtained in Example 1 and the cells were plated on 15 cm 2× dense neoR MEFs in 2i+ 10 uM ROCKi. The transformed rat ES cells were cultured and maintained as described in Example 1.

Colonies are screened as described elsewhere herein and targeted clones are obtained. The targeted clones are then injected into a host embryo as described elsewhere herein to produce an F0 rat.

3.4(a)(ii). Targeting the Rag2 Locus in Rats with a Large Targeting Vector (LTVEC) and CRISPR/Cas9

Figure 48:
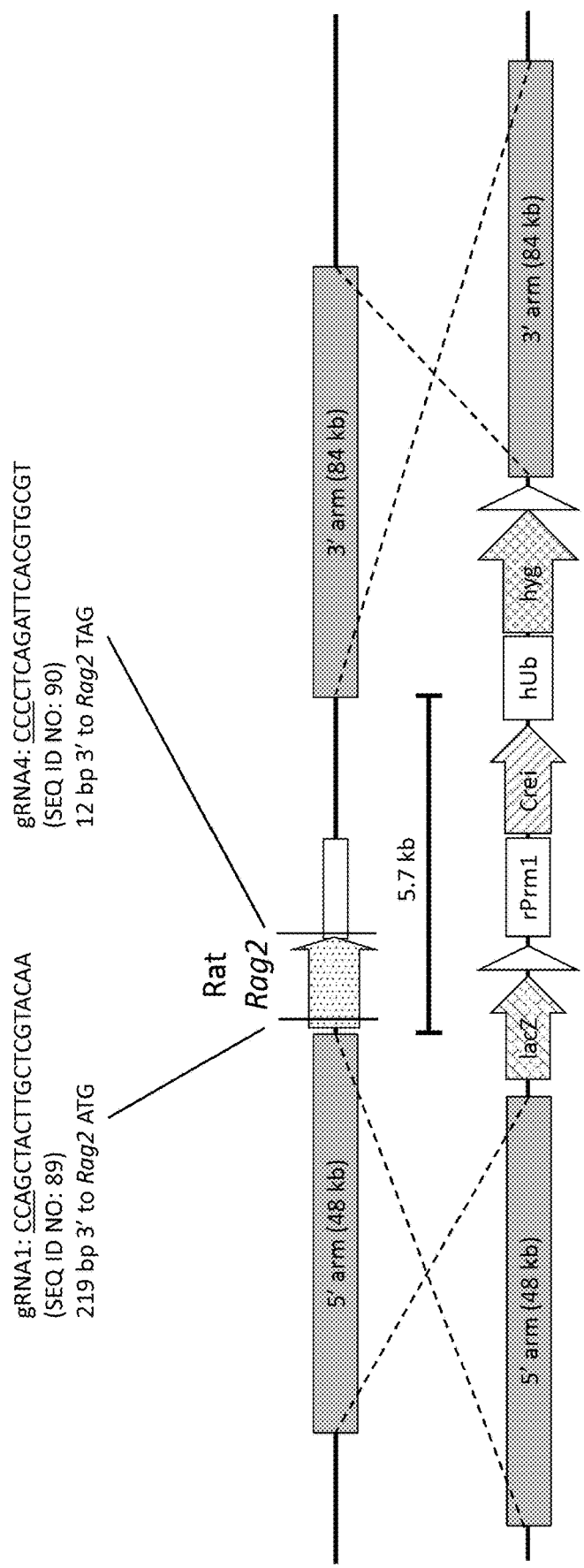
FIG. 48 shows a schematic of the rat Rag2 locus (upper panel) and a large targeting vector (LTVEC) that targets the rat Rag2 locus (lower panel). The upper panel shows the genomic organization of the rat Rag2 locus and the cognate genomic regions corresponding to the 5' and 3' homology arms (48 kb and 84 kb, respectively; dark grey boxes). Rag2 comprises a single exon denoted by the stippled grey shading. Target sites for Rag2 gRNA1 (SEQ ID NO: 89) and gRNA4 (SEQ ID NO: 90) are indicated. The lower panel is the LTVEC. The 5' and 3' homology arms (48 kb and 84 kb, respectively) are denoted by the dark grey boxes. The LTVEC comprises a reporter gene (lacZ) and a self-deleting cassette flanked by loxP sites (open arrows) that contains a rat Prm1 promoter operably linked to the Crei gene and a drug selection cassette containing a human ubiquitin promoter operably linked to a hygromycin resistance gene.

Table 27 shows a comparison of the results of experiments in which a version of the Rag2 LTVEC having a hygromycin resistance gene (see FIG. 48) was used alone to target the rat Rag2 locus or was used in combination with a CRISPR/Cas9 nuclease to target the rat Rag2 locus. In each experiment, electroporated cells were plated at a high density and subjected to drug selection to find colonies that were drug-resistant. Drug-resistant colonies were picked and screened for the targeted modification using the modification of allele (MOA) assay as described herein. Specifically, 4×10$^6$ cells were electroporated with 2 ug of Rag2 LTVEC at a voltage of 400V, a capacitance of 100 uF, and a resistance of 0. In the latter experiment, 6 ug of Cas9 expression plasmid and 3 ug of Rag2 gRNA1 or 3 ug of Rag2 gRNA4 were also electroporated. Selection was done using 75 ug/mL of G418. Rag2 gRNA1 has a sequence of CCAGCTACTTGCTCGTACAA (SEQ ID NO: 89) and targets a region 219 bp 3' of the rat Rag2 start codon (ATG). Rag2 gRNA4 has a sequence of CCCCTCAGATTCACGTGCGT (SEQ ID NO: 90) and targets a region 12 bp 3' of the rat Rag2 stop codon (TAG) (see FIG. 48). As shown in Table 27, when Cas9 and either of the gRNAs were introduced into the cells together with the Rag2 LTVEC, targeting efficiency increased (from 0 to 10% or 38%). Biallelic targeting was observed in one colony.

TABLE 27

Comparison of Rag2 LTVEC Targeting with and without CRISPR/Cas9

| Vector | Cas9 | gRNA | Colonies Screened | Targeted Clones | Biallelic Targeted | Targeting Efficiency |
|---|---|---|---|---|---|---|
| Rag2 LTVEC | NO | NO | 36 | 0 | 0 | 0 |
| Rag2 LTVEC | Yes | Rag2 gRNA1 | 23 | 5 | 1 | 22% |
| Rag2 LTVEC | Yes | Rag2 gRNA4 | 16 | 1 | 0 | 6% |

3.4.(b)(i). Targeting the Rag1 and the Rag2 Locus in Rats

Figure 27:
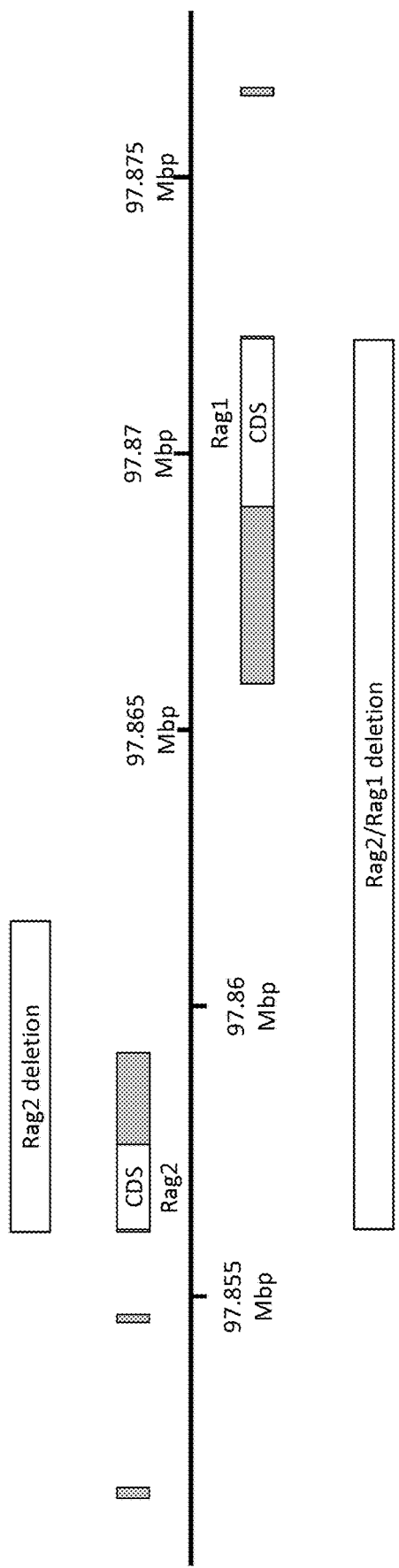
FIG. 27 provides the genomic structure of the rat Rag1lRag2 locus and the genomic regions deleted by either Rag2 targeting (Rag2 deletion) or Rag2/Rag1 double targeting (Rag2/Rag1 deletion).

FIG. 27 provides the genomic structure of the rat Rag1/Rag2 locus. CDS denotes the coding sequence and grey boxes represent exons. Rag2 is on the "plus" strand with transcription to the right. Rag1 is on the "minus" strand with transcription to the left. Mbp=million base pairs.

Table 28 provides a summary of the genomic organization of the rat Rag2 and Rag1 locus and the positions shown were taken from build 5.0 of the Reference Sequence of the rat genome (ENSMBL). Rag1 is on chromosome 3 on the (−) strand.

TABLE 28

Genomic organization summary of the rat Rag1 locus.

| Feature | Start | End | Length | Notes |
|---|---|---|---|---|
| Exon 1 | 97,877,145 | 97,877,066 | 80 | |
| Exon 2 | 97,872,503 | 97,866,047 | 6,457 | contains entire coding sequence |
| ATG | 97,872,489 | 97,872,487 | 3 | start codon |
| TAA | 97,869,369 | 97,869,367 | 3 | stop codon |
| Rag1-2 deletion | 97,856,289 | 97,872,486 | 16,198 | |

Figure 28:
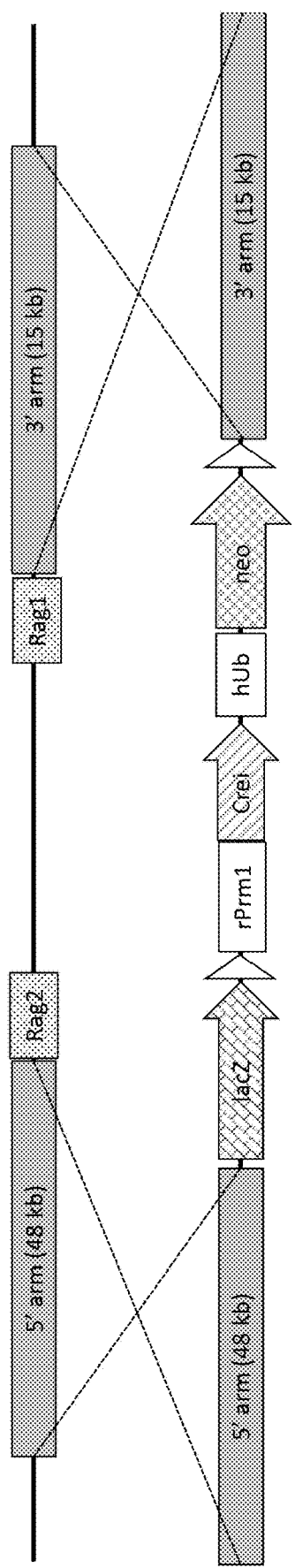
FIG. 28 provides a schematic of the rat Rag2 and Rag1 loci and a large targeting vector (LTVEC) used for modifying the loci. The upper panel shows the genomic organization of the Rag1 and Rag2 loci and the cognate genomic regions corresponding to the 5' and 3' homology arms (48 kb and 15 kb, respectively; dark grey boxes). Rag2 and Rag1 each comprise a single exon denoted by the stippled grey shading. The lower panel is the LTVEC. The 5' and 3' homology arms (48 kb and 15 kb, respectively) are denoted by the dark grey boxes. The LTVEC comprises a reporter gene (lacZ) and a self-deleting cassette flanked by loxP sites (open arrows), which comprises a rat Prm1 promoter operably linked to the Crei gene and a drug selection cassette comprising a human ubiquitin promoter operably linked to a neomycin resistance gene.

FIG. 28 provides a schematic of the rat Rag2 and Rag1 locus and a large targeting vector (LTVEC). The LTVEC is about 70 kb and targets an approximately 16.6 kb rat genomic locus comprising the Rag1 and Rag2 loci for deletion. The upper schematic of FIG. 28 shows the genomic organization of the Rag1 and Rag2 loci and the genomic regions corresponding to the 5' and 3' homology arms (48 kb and 15 kb, respectively; dark grey boxes). Rag2 and Rag1 each comprises a single exon denoted by the stippled grey shading. The lower schematic in FIG. 28 is the LTVEC. The 5' and 3' homology arms (48 kb and 15 kb, respectively) are denoted by the dark grey boxes. The LTVEC comprises a reporter gene (lacZ) and a self-deleting cassette flanked by loxP sites (open arrows). The self-deleting cassette comprises a rat Prm1 promoter operably linked to the Crei gene and a drug selection cassette comprising a human ubiquitin promoter operably linked to a neomycin resistance gene. Another version of the LTVEC was generated in which the neomycin resistance gene was replaced with a hygromycin resistance gene to enable retargeting of Il2rg-targeted rat ES cells. The Crei comprises two exons encoding the Cre recombinase are separated by an intron (Crei) to prevent its expression in a prokaryotic cell. See, for example, U.S. Pat. No. 8,697,851 and U.S. Application Publication 2013-0312129, which describe the self-deleting cassette in detail and is hereby incorporated by reference in their entirety. By employing a rat Prm1 promoter that drives expression of Crei specifically in male germ cells, the self-deleting cassette can be deleted from the male germ cells of F0 rats.

The LTVEC was electroporated into the rat ES cells obtained in Example 1 and the cells were plated on 15 cm 2× dense neoR MEFs in 2i+ 10 uM ROCKi. The transformed rat ES cells were cultured and maintained as described in Example 1.

Colonies are screened as described elsewhere herein and targeted clones are obtained. The targeted clones are then injected into a host embryo as described elsewhere herein to produce an F0 rat.

Figure 50:
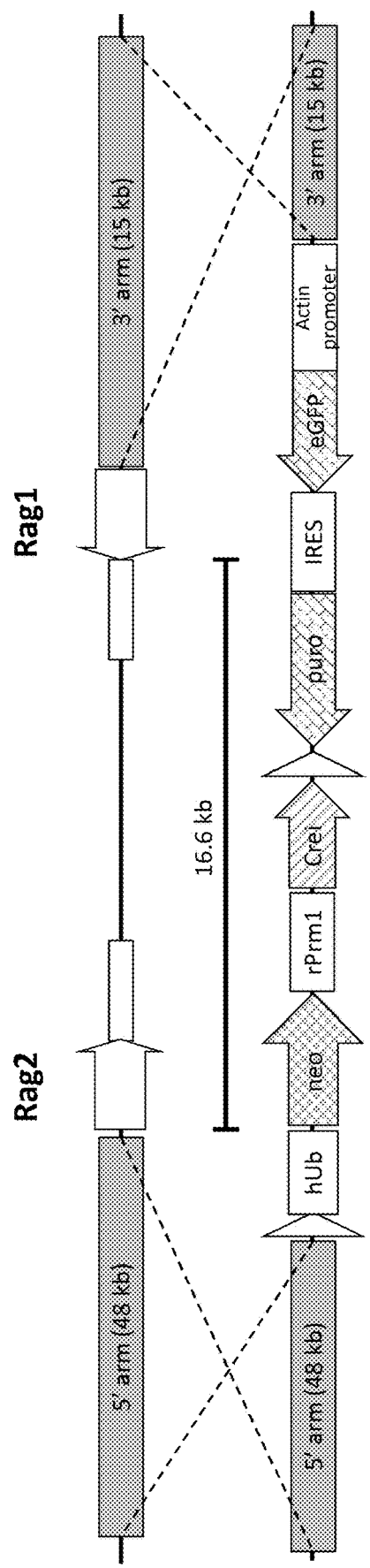
FIG. 50 shows a schematic of the rat Rag2 and Rag1 loci and a large targeting vector (LTVEC) used for modifying the loci in Il2rg-targeted rat ES cells (clone Il2rg-CG12). The upper panel shows the genomic organization of the Rag1 and Rag2 loci and the cognate genomic regions corresponding to the 5' and 3' homology arms (48 kb and 15 kb, respectively.

3.4.(b)(h). Retargeting the Rag1 and the Rag2 Locus in Rats ES Cells in which the Il2rg Locus has Already been Targeted An LTVEC as in FIG. 50 was prepared to target the Rag1 and Rag2 loci for deletion. The total length of the LTVEC was 72 kb. The LTVEC was electroporated into rat ES cells that had already been targeted for deletion of the Il2rg locus as in Example 3.3. Specifically, the rat ES cells were from clone Il2rg-CG12, for which germline transmission was confirmed in Example 3.3(a). The transformed rat ES cells were cultured and maintained as described in Example 1. Double targeted clones were screened as described elsewhere herein, and targeted clones were obtained. Il2rg-CG12 cells were retargeted at an efficiency of 85%, and Il2rg mutations were still present in the targeted clones. Electroporation was carried out as described elsewhere herein, and antibiotic selection was carried out using 1.5 ug/ml of puromycin. The targeted clones will then be injected into a host embryo as described elsewhere herein to produce an F0 rat. Retargeting is advantageous because it is faster than interbreeding Rag1/Rag2-targeted rats with Il2rg-targeted rats.

Example 4. Humanization 4.1. Humanization of Rat Genomic Loci

Humanization of rat genomic loci is carried out employing the rat ES cells described herein, which are capable of sustaining their pluripotency following one or more electroporations in vitro, and are capable of transmitting the targeted genetic modifications to subsequent generations. In addition, in order to circumvent the limitations of plasmids in accommodating a large genomic DNA fragment, and to overcome the low efficiency of introducing a targeted genetic modification into an endogenous locus in rat ES cells, one or more targeted genetic modifications are carried out in bacteria, e.g., E. coli, by utilizing bacterial homologous recombination (BHR) and employing a large targeting vector (LTVEC). The LTVEC described herein, for example, includes a large fragment of an endogenous rat genomic sequence with one or more modifications or comprises an exogenous nucleic acid (e.g., a homologous or orthologous human nucleic acid) flanked with rat homology arms complementary to specific genomic regions.

4.2. Humanization of Rat Immunoglobulin Loci

Humanization of an endogenous rat immunoglobulin heavy chain locus is carried out by removing one or more endogenous rat immunoglobulin heavy chain nucleic acid sequences (e.g., one or more endogenous $V_H$ gene segments, one or more human D gene segments, and one or more human $J_H$ gene segments); and introducing into the modified immunoglobulin locus a targeting vector, e.g., a large targeting vector (LTVEC) comprising: (i) one or more unrearranged human variable region nucleic acid sequences (e.g., one or more human $V_H$ gene segments, one or more human D gene segments, and one or more human $J_H$ gene segments), or one or more rearranged human variable region nucleic acid sequences (e.g., one or more human rearranged V-D-J gene segments); (ii) a selection cassette (e.g., neomycin resistance gene flanked with loxP sites); and (iii) 5' and 3' rat homology arms.

Briefly, one or more endogenous rat immunoglobulin heavy chain variable region gene segments (i.e., one or more $V_H$ gene segments, one or more human D gene segments, and one or more human $J_H$ gene segments) in a rat BAC clone are removed or inactivated by targeting the endogenous rat immunoglobulin heavy chain locus with a selection cassette flanked by rat homology arms. More specifically, a targeting vector is constructed to contain a selection cassette (e.g., a neomycin resistance gene flanked with loxP sites) flanked with 5' and 3' rat homology arms that are complementary to target rat genomic sequences (e.g., upstream and downstream rat genomic DNA sequences encompassing one or more rat $V_H$ gene segments, one or more human D gene segments, and one or more human $J_H$ gene segments).

Next, bacterial cells containing a large rat genomic DNA fragment encompassing a rat immunoglobulin heavy chain locus are selected and introduced with a plasmid (e.g., pABG) encoding a recombinase operably linked to a transiently inducible promoter. The targeting vector constructed above is then introduced into the recombination-competent bacterial cells. Following electroporation, the bacterial cells are treated with an inducer (e.g., arabinoside) to initiate homologous recombination between the targeting vector and the target rat genomic sequence in the BAC clone. Transformed cells are plated at a high density and subjected to drug selection to find colonies that are drug-resistant. Drug-resistant colonies are picked and screened for the targeted modification.

In order to facilitate identification of the targeted genetic modification, a high-throughput quantitative assay, namely, modification of allele (MOA) assay, is employed, which allows a large-scale screening of a modified allele(s) in a parental chromosome following a genetic modification. The MOA assay can be carried out via various analytical techniques, including, but not limited to, a quantitative PCR, e.g., a real-time PCR (qPCR). For example, the real-time PCR comprises a first primer set that recognizes the target locus and a second primer set that recognizes a non-targeted reference locus. In addition, the primer set can comprise a fluorescent probe that recognizes the amplified sequence. Alternatively, the quantitative assay can be carried out via a variety of analytical techniques, including, but not limited to, fluorescence-mediated in situ hybridization (FISH), comparative genomic hybridization, isothermic DNA amplification, quantitative hybridization to an immobilized probe(s), Invader Probes®, MMP Assays®, TaqMan® Molecular Beacon, and Eclipse™ probe technology. (See, for example, US2005/0144655, incorporated by reference herein in its entirety).

The bacterial cells comprising the modified rat BAC clone, i.e., a BAC clone containing a rat genomic DNA sequence wherein one or more endogenous heavy chain variable region gene segments ($V_H$, D, and/or $J_H$ gene segments) have been deleted or inactivated, are then electroporated with a large targeting vector (LTVEC) comprising: (i) one or more unrearranged human variable region nucleic acid sequences (e.g., one or more unrearranged human $V_H$ gene segments, one or more human D gene segments, and one or more human $J_H$ gene segments), or one or more rearranged human variable region nucleic acid sequences (e.g., one or more rearranged human V-D-J gene segments).

Initiation of homologous recombination in the bacterial cells and the selection of positive clones are performed as described above. The unrearranged or rearranged human immunoglobulin heavy chain variable region nucleic acid sequences, when targeted into the endogenous immunoglobulin heavy chain locus, become operably linked to an endogenous rat immunoglobulin heavy chain constant region nucleic acid sequence. Alternatively, endogenous rat heavy chain constant region locus can be inactivated, for example, by deleting one or more rat heavy chain constant region gene segments ($C_H$) from the endogenous heavy chain constant region locus, and can be replaced with a human heavy chain constant region nucleic acid sequence.

Likewise, humanization of an endogenous rat immunoglobulin κ or λ light chain locus is carried out by removing one or more endogenous rat immunoglobulin κ and/or λ light chain variable region nucleic acid sequences (e.g., one or more endogenous rat $V_\kappa$ gene segments and one or more endogenous rat $J_\kappa$ gene segments); and targeting the modified immunoglobulin light chain locus with a targeting vector, e.g., a large targeting vector (LTVEC), comprising: (i) one or more unrearranged human immunoglobulin light chain variable region nucleic acid sequences (e.g., one or more human $V_\kappa$ gene segments and one or more human $J_\kappa$ gene segments), or one or more rearranged human variable region nucleic acid sequences (e.g., one or more human rearranged $V_\kappa$-$J_\kappa$ gene segments); (ii) a selection cassette (e.g., neomycin resistance gene flanked with loxP sites); and (iii) 5' and 3' rat homology arms.

The unrearranged or rearranged human immunoglobulin light chain variable region nucleic acid sequences, when targeted into the endogenous immunoglobulin light chain locus, become operably linked to the endogenous rat immunoglobulin light chain constant region nucleic acid sequence.

The LTVEC so produced in the bacterial cells comprises, for example, an insert nucleic acid that contains a humanized rat immunoglobulin heavy chain or light chain locus in which one or more endogenous rat heavy or light chain variable region gene segments have been replaced with one or more human heavy or light chain variable region gene segments; and rat homologous arms (e.g., ranging from 5 kb to 150 kb) complementary to specific genomic target sequences. The LTVEC comprising the genetic modification described above is then linearized and electroporated into the rat ES cells. Electroporated rat ES cells are plated at a high density to select drug-resistant ES cells comprising the targeting vector. The drug selection process removes the majority of the plated cells (~99%), leaving behind individual colonies, each of which is a clone derived from a single cell. Of the remaining cells, most cells (~80-100%) contain the targeting vector integrated at a random location in the genome. Therefore, the colonies are picked and genotyped individually in order to identify rat ES cells comprising the targeting vector at the correct genomic location (e.g., using the modification of allele (MOA) assay described above).

In order to increase the efficiency of the targeted genetic modification, the rat ES cells are electroporated with expression vectors (or mRNA) that express ZFNs 1 and 2 (or TALENs 1 and 2) together with the LTVEC. The targeting vector's homology arms lie outside the ZFN target site, therefore, the targeting vector is not cleaved by the ZFNs. The double strand break produced by the ZFNs stimulates homology-directed repair (HDR), which otherwise accounts for a very small percentage of repairs occurred normally in mammalian cells (compared to non-homologous end-joining; NHEJ).

Alternatively, expression vectors containing a type II CRISPR-associated nuclease (e.g., Cas9), a guide RNA (including CRISPR-RNA (cr-RNA) and trans-activating CRISPR RNA (tracrRNA)), as described herein, can be introduced into the bacterial cells together with the LTVEC to increase the efficiency of homologous recombination at the target genomic locus. Electroporated cells are plated at a high density and subjected to drug selection to find colonies that are drug-resistant. Drug-resistant colonies are picked and screened for the targeted modification using the modification of allele (MOA) assay as described herein. Following these procedures, improvement in the targeting efficiency can be achieved. For example, the amount of improvement can be small (e.g., improve from 10% to 15%) or large (e.g., improve from 10% to 80%).

The selected rat ES cells comprising the targeted genetic modification are then introduced into a host rat embryo, for example, a pre-morula stage or blastocyst stage rat embryo, and implanted in the uterus of a surrogate mother to generate a founder rat (F0 rat). Subsequently, the founder rat is bred to a wild-type rat to create F1 progeny heterozygous for the genetic modification. Mating of the heterozygous F1 rat can produce progeny homozygous for the genetic modification.

4.3(a). Replacing Rat IL2rg with Human IL2 Receptor Gamma

Table 29 provides a summary of the genomic organization of the rat Interleukin 2 receptor gamma locus and the positions shown were taken from build 5.0 of the Reference Sequence of the rat genome (ENSMBL). Il2rg is on chromosome X on the (−) strand.

TABLE 29

Summary of the genomic organization of the rat Il2rg locus

| Feature | Start | End | length | Notes |
|---|---|---|---|---|
| Exon 1 | 72,021,388 | 72,021,516 | 129 | contains ATG |
| ATG | 72,017,500 | 72,017,502 | 3 | start codon |
| Exon 2 | 72,021,007 | 72,021,160 | 154 | |
| ZFN1a binding site | 72,021,014 | 72,021,028 | 15 | CAGGCCCTGAAC CGC (SEQ ID NO: 17) |
| ZFN1 cutting site | | 72,021,013 | 6 | TTCTGG (SEQ ID NO: 18) |
| ZFN1b binding site | 72,020,993 | 72,021,007 | 15 | GATTACCTGCGC TGGG (SEQ ID NO: 20) |
| Exon 3 | 72,020,606 | 72,020,790 | 185 | |
| Exon 4 | 72,020,274 | 72,020,413 | 140 | |
| Exon 5 | 72,019,662 | 72,019,824 | 163 | |
| Exon 6 | 72,019,101 | 72,019,197 | 97 | |
| Exon 7 | 72,018,844 | 72,018,910 | 67 | |
| Exon 8 | 72,017,856 | 72,018,506 | 651 | contains TGA |
| TGA | 72,018,321 | 72,018,323 | 3 | stop codon |
| Il2rg deletion | 72,018,323 | 72,021,502 | 3,180 | |

The lower schematic in FIG. 25 is the targeting vector for the Il2rg 3.2 kb deletion. The targeting vector comprises a reporter gene (eGFP) operably linked to the endogenous promoter and a self-deleting cassette flanked by loxP sites (open arrows). The self-deleting cassette comprises the Crei gene operably linked to a mouse Prm1 promoter and a selection cassette comprising a neomycin resistance gene operably linked to a human ubiquitin promoter.

The Crei gene comprises two exons encoding a Cre recombinase, which are separated by an intron (Crei) to prevent its expression in a prokaryotic cell. See, for example, U.S. Pat. No. 8,697,851 and U.S. Application Publication 2013-0312129, which describe the self-deleting cassette in detail and are hereby incorporated by reference in their entirety. By employing the mouse Prm1 promoter the Cre expression cassette and the drug selection cassette can be deleted specifically in male germ cells of F0 rats. The targeting vector was electroporated into the rat ES cells obtained in Example 1 and the cells were plated on 15 cm 2× dense neomycin-resistant MEFs in 2i+ 10 uM ROCKi. The transformed rat ES cells were cultured, selected, and maintained as described in Example 1.

Figure 31:
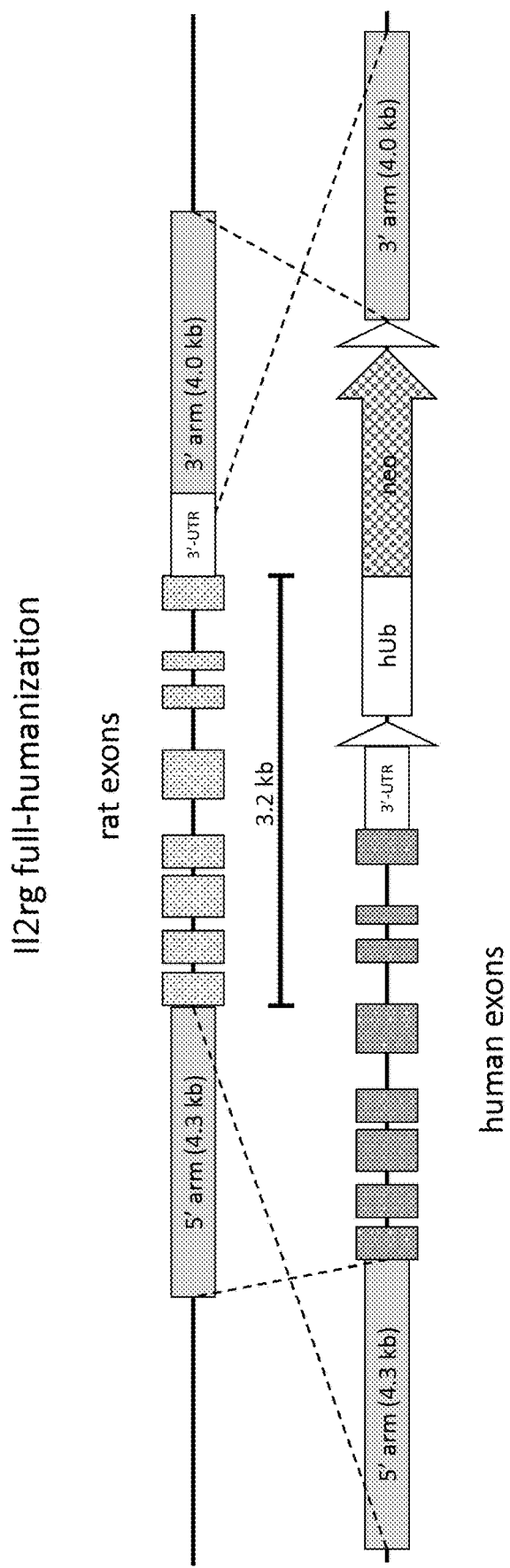
FIG. 31 provides a schematic of the rat Il2rg locus and a targeting plasmid for the full humanization of the rat Il2rg locus. The upper panel shows the genomic organization of the rat Il2rg locus and the cognate genomic regions corresponding to the 5' and 3' homology arms (4.3 kb and 4.0 kb, respectively; grey boxes). The lower panel is the targeting plasmid. The 5' and 3' homology arms (4.3 kb and 4.0 kb, respectively) are denoted by the grey boxes. The targeting plasmid comprises the human IL-2rg genomic region and a deletion cassette flanked by loxP sites (open arrows) that contains a drug selection cassette containing a human ubiquitin promoter operably linked to a neomycin resistance gene.

A plasmid targeting vector was constructed to replace the full-length rat interleukin 2 receptor gamma coding region with the full-length human interleukin 2 receptor gamma coding region as shown in FIG. 31. The targeting vector was electroporated into the rat ES cells obtained in Example 1, and the cells were plated on 15 cm 2× dense neomycin-resistant MEFs in 2i+ 10 uM ROCKi. Specifically, $4 \times 10^6$ cells were electroporated with 2 ug of Il2rg full-length humanization vector at a voltage of 400V, a capacitance of 100 uF, and a resistance of 0. Selection was done using 75 ug/mL of G418. The transformed rat ES cells were cultured, selected, and maintained as described in Example 1.

As shown in Table 44, 168 colonies were screened and 6 targeted clones were obtained. The targeting efficiency was 3.57%. One clone was injected into blastocysts as described in Example 1, and one clone producing chimeras was obtained.

Clones were injected into blastocysts as described herein in Example 1. Clones producing F0 chimeric rats were obtained. The blastocysts were transferred to pseudopregnant recipient females using standard techniques, and chimeric F0 rats were obtained. F0 rats that transmit the targeted modification through the germline are obtained.

4.3(b)(i). Replacing Rat IL2rg Ecto-Domain with Human IL2rg Ecto-Domain

The full-length humanization of IL 2 receptor gamma is useful because rats having this modified locus will produce human Il2rg; and this would allow for the detection of human Il2rg in rats with antibodies specific to human Il2rg.

Figure 33:
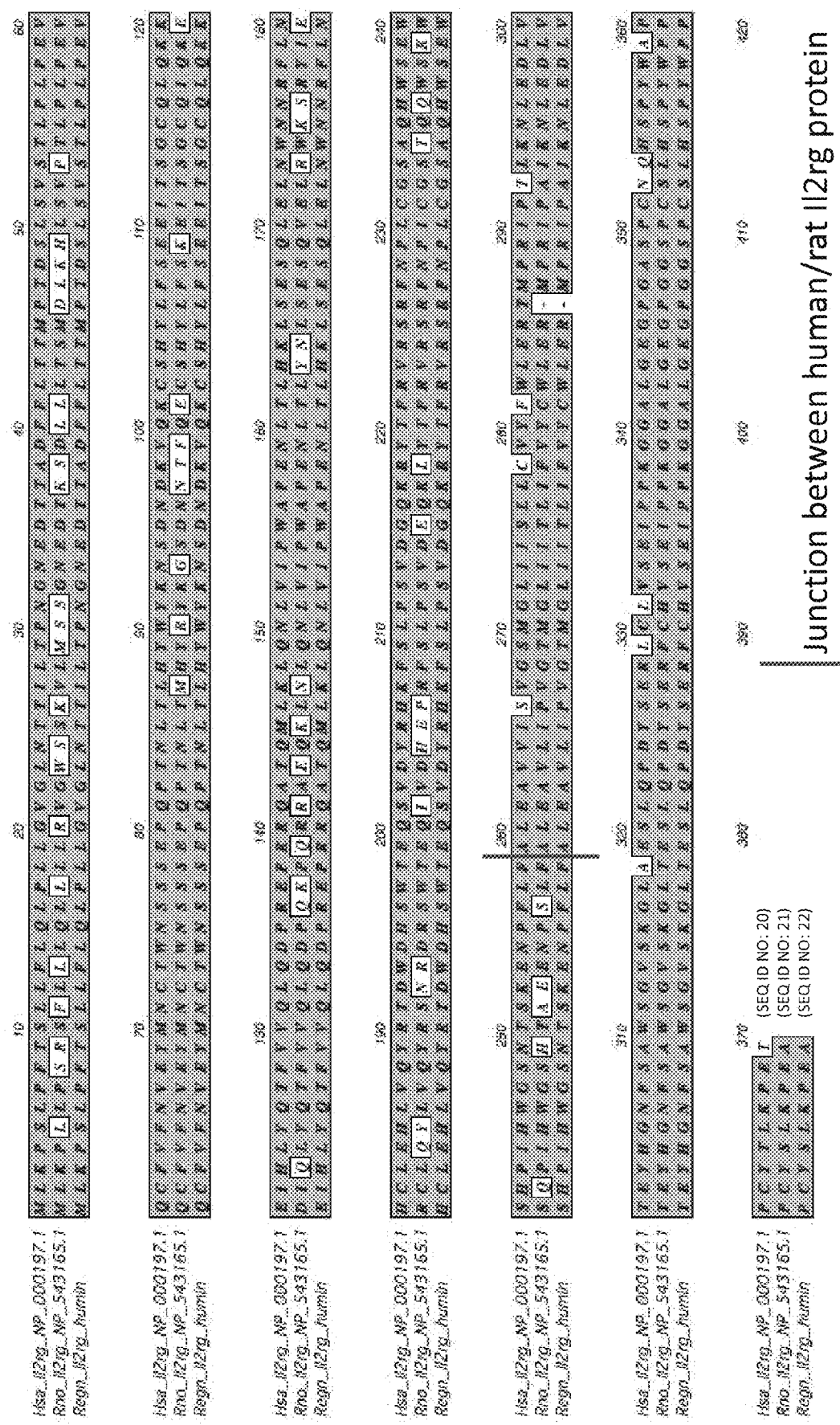
FIG. 33 provides a sequence alignment of the human IL-2rg protein (SEQ ID NO: 20; NP 000197.1); the rat IL-2rg protein (SEQ ID NO: 21; NP_543165.1); and the chimeric IL-2rg protein (SEQ ID NO: 22) comprising the human ecto-domain of IL-2rg fused to the remainder of the rat IL-2rg protein. The junction between the human and rat IL-2rg is noted by the vertical line.

The ecto-humanization (i.e., replacing the rat ecto-domain of Il2rg with the human ecto-domain of Il2rg) will result in an Il2rg polypeptide that will bind the human ligands for Il2rg, but because the cytoplasmic domain is still rat, it ecto-humanized form of Il2rg will also interact with the rat signaling machinery. FIG. 33 provides a sequence alignment of the human IL-2rg protein (SEQ ID NO: 20; NP_000197.1); the rat IL-2rg protein (SEQ ID NO: 21; NP_543165.1); and the chimeric IL-2rg protein (SEQ ID NO: 22) comprising the human ecto-domain of IL-2rg fused to the remainder of the rat IL-2rg protein. The junction between the human and rat IL-2rg is noted by the vertical line.

Table 30 provides a summary of the genomic organization of the rat Interleukin 2 receptor gamma locus and the positions shown were taken from build 5.0 of the Reference Sequence of the rat genome (ENSMBL). Il2rg is on chromosome X on the (−) strand. Further noted is the position of the ecto-domain of Il2rg.

TABLE 30

Summary of the genomic organization of the rat Il2rg locus

| Feature | Start | End | Length | Notes |
|---|---|---|---|---|
| Exon 1 | 71,111,444 | 71,111,543 | 100 | contains ATG |
| ATG | 71,111,537 | 71,111,539 | 3 | start codon |
| Exon2 | 71,110,897 | 71,111,050 | 154 | |
| Exon3 | 71,110,504 | 71,110,688 | 185 | |
| Exon4 | 71,110,156 | 71,110,295 | 140 | |

TABLE 30-continued

Summary of the genomic organization of the rat Il2rg locus

| Feature | Start | End | Length | Notes |
|---|---|---|---|---|
| Exon5 | 71,109,228 | 71,109,390 | 163 | |
| Exon6 | 71,108,599 | 71,108,645 | 47 | contains transmembrane domain |
| Exon7 | 71,108,277 | 71,108,346 | 70 | |
| Exon8 | 71,107,404 | 71,107,921 | 518 | contains TGA |
| TGA | 71,108,736 | 71,108,738 | 3 | stop codon |
| full-length humanization: | 71,107,404 | 71,111,539 | 4,136 | (ATG to TGA plus 3' poly-A) |
| ecto-humanization | 71,108,679 | 71,111,539 | 2,861 | (ATG to beginning of transmembrane domain) |

Figure 32:
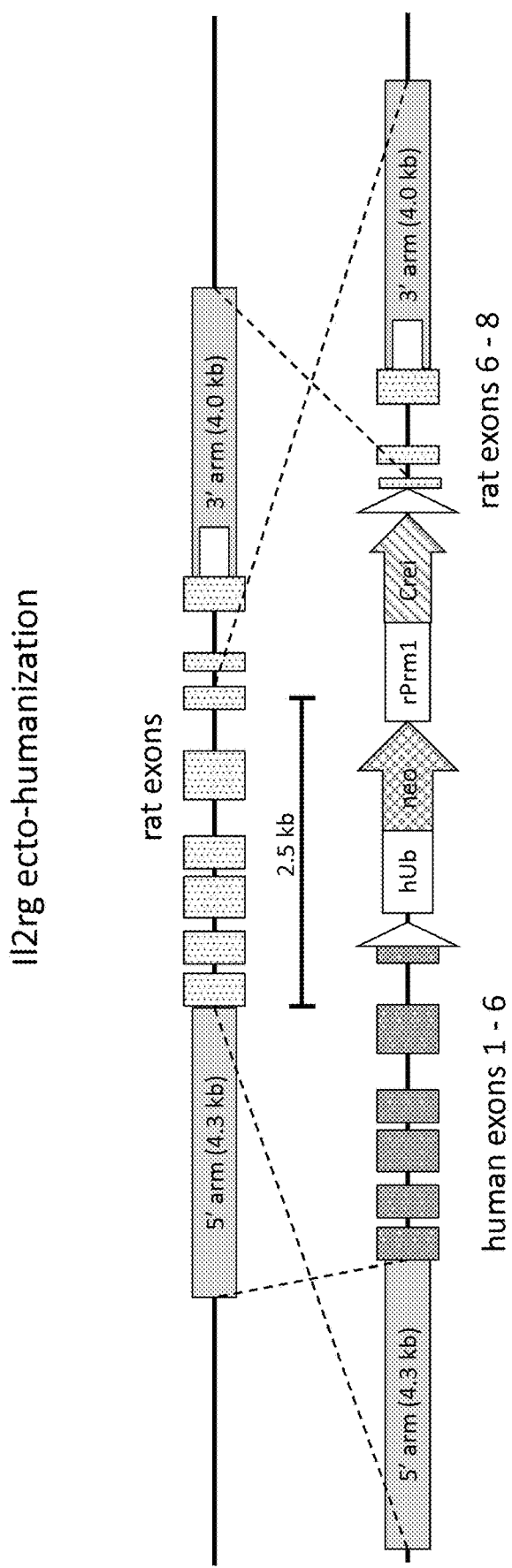
FIG. 32 provides a schematic of the rat Il2rg locus and a targeting plasmid for the ecto-domain humanization of the rat Il2rg locus. The upper panel shows the genomic organization of the rat Il2rg locus and the cognate genomic regions corresponding to the 5' and 3' homology arms (4.3 kb and 4.0 kb, respectively; grey boxes). The lower panel is the targeting plasmid. The 5' and 3' homology arms (4.3 kb and 4.0 kb, respectively) are denoted by the grey boxes. The targeting plasmid comprises the human ecto-domain of the IL-2Rg genomic region and a self-deleting cassette flanked by loxP sites (open arrows) that contains a rat Prm1 promoter operably linked to the Crei gene and a drug selection cassette containing a human ubiquitin promoter operably linked to a neomycin resistance gene.

A plasmid targeting vector was constructed to replace the rat ecto-domain of the interleukin 2 receptor gamma coding region with the human ecto domain as shown in FIG. 32. The targeting vector was electroporated into the rat ES cells obtained in Example 1 and the cells were plated on 15 cm 2× dense neomycin-resistant MEFs in 2i+10 uM ROCKi. The transformed rat ES cells were cultured, selected, and maintained as described in Example 1.

As shown in Table 44, 192 colonies were screened and 13 targeted clones were obtained. The targeting efficiency was 6.77%.

Two clones were injected into blastocysts as described herein in Example 1, and two clones producing chimeras were obtained. Clones producing F0 rats were obtained. F0 rats that transmit the targeted modification through the germline are obtained.

4.3(b)(ii). Replacing Rat IL2rg Ecto-Domain with Human IL2rg Ecto-Domain Using Plasmid in Combination with CRISPR/Cas9

Figure 49:
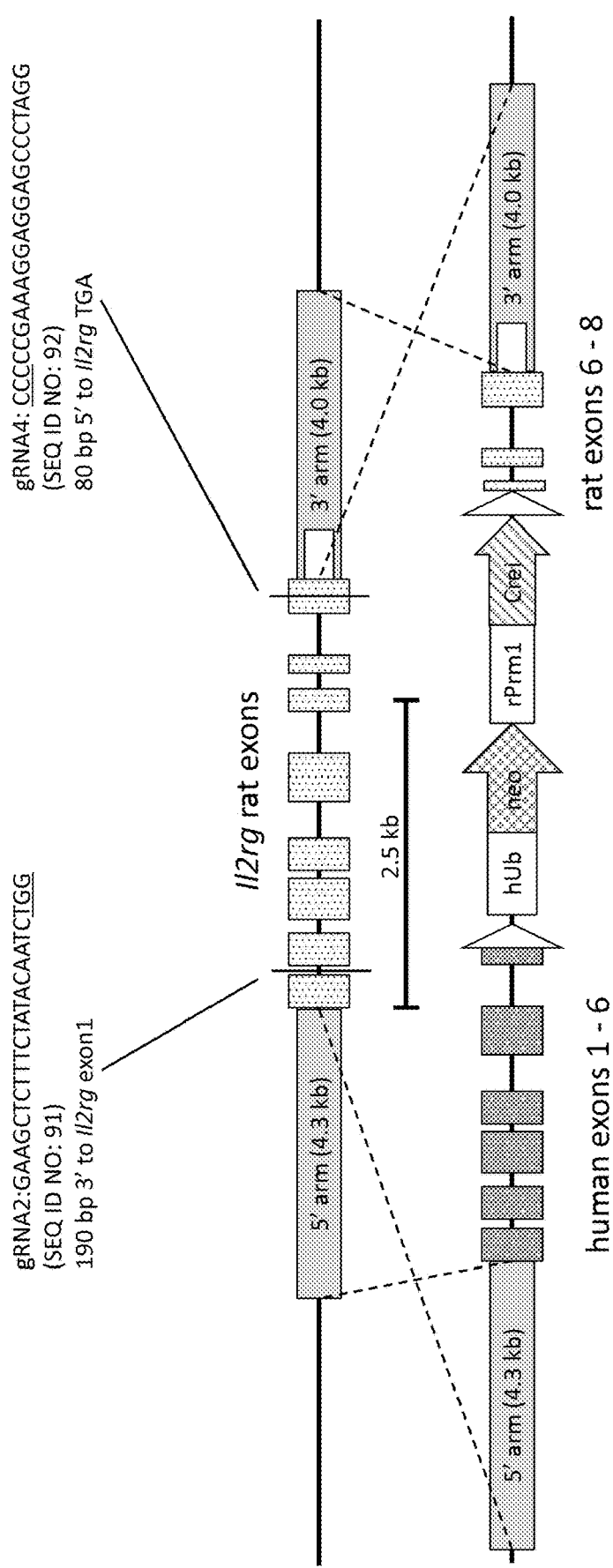
FIG. 49 shows a schematic of the rat Il2rg locus (upper panel) and a targeting plasmid for ectodomain humanization of the rat Il2rg locus (lower panel). The upper panel shows the genomic organization of the rat Il2rg locus and the cognate genomic regions corresponding to the 5' and 3' homology arms (4.3 kb and 4.0 kb, respectively; grey boxes). Target sites for Il2rg gRNA2 (SEQ ID NO: 91) and gRNA4 (SEQ ID NO: 92) are indicated. The lower panel is the targeting plasmid. The 5' and 3' homology arms (4.3 kb and 4.0 kb, respectively) are denoted by the grey boxes. The targeting plasmid comprises the human ecto-domain of the IL-2Rg genomic region and a self-deleting cassette flanked by loxP sites (open arrows) that contains a rat Prm1 promoter operably linked to the Crei gene and a drug selection cassette containing a human ubiquitin promoter operably linked to a neomycin resistance gene.

Table 31 shows a comparison of the results of experiments in which a version of the Il2rg ecto-domain humanization vector shown in FIG. 32 was used alone to target the rat Il2rg locus or was used in combination with a CRISPR/Cas9 nuclease to target the rat Il2rg locus. In each experiment, electroporated cells were plated at a high density and subjected to drug selection to find colonies that were drug-resistant. Drug-resistant colonies were picked and screened for the targeted modification using the modification of allele (MOA) assay as described herein. Specifically, 4×10⁶ cells were electroporated with 2 ug of Il2rg ecto-domain humanization vector at a voltage of 400V, a capacitance of 100 uF, and a resistance of 0. In the latter experiment, 6 ug of Cas9 expression plasmid and 3 ug of Il2rg gRNA2 or 3 ug of Il2rg gRNA4 were also electroporated. Selection was done using 75 ug/mL of G418. Il2rg gRNA2 has a sequence of GAAGCTCTTTCTATACAATCTGG (SEQ ID NO: 91) and targets a region 190 bp 3' of the rat Il2rg exon 1. Il2rg gRNA4 has a sequence of CCCCCGAAAGGAG-GAGCCCTAGG (SEQ ID NO: 92) and targets a region 80 bp 5' of the rat Il2rg stop codon (TGA) (see FIG. 49).

TABLE 31

Comparison of Il2rg Ecto-Domain Humanization Vector Targeting with and without CRISPR/Cas9

| Vector | Cas9 | gRNA | Colonies Screened | Targeted Clones | Targeting Efficiency |
|---|---|---|---|---|---|
| Il2rg plasmid vector | NO | NO | 77 | 46 | 60% |
| Il2rg plasmid vector | Yes | Il2rg gRNA2 | 84 | 54 | 64% |
| Il2rg plasmid vector | Yes | Il2rg gRNA4 | 88 | 50 | 57% |

4.4(a). Enhanced Targeting by CRISPR/Cas9 Endonucleases of Large Non-Human Animal Gene Deletions with Simultaneous Human Gene Replacements Newly developed drugs for human disease conditions, such as fully human antibodies, are often highly specific for their targets in human cells and tissues and do not recognize the homologous targets in rodents. This high level of selectivity makes it impossible to test the efficacy and mechanism of action of the drugs in rodents prior to their first use in humans.

A very effective solution to this problem is to create a genetically modified mouse or rat in which the human gene encoding the drug target replaces the rodent homolog. One way to create such a humanized allele in a rodent is to first delete the rodent gene in an embryonic stem (ES) cell and then, in a second gene modification event, to insert the human gene precisely at the deleted locus. The ES cells are then injected into a rodent embryo and implanted in the uterus of a surrogate mother rodent, which subsequently gives birth to genetically modified pups that carry the humanized allele.

A more efficient method of creating the humanized gene modification is to use a large targeting vector (LTVEC) that directs the simultaneous deletion of the rodent gene and replacement with its human counterpart. By employing VELOCIGENE® genetic engineering methods, such single-step humanizations can be achieved with relatively high efficiency when the rodent gene deletion and human gene insertion are smaller than about 20 kilobase pairs (kb). Larger single-step humanizations entailing deletions and replacements of greater than 100 kb are possible with LTVECs and genetic engineering methods such as VELOCIGENE® genetic engineering methods, but because of reduced targeting efficiencies sometimes encountered with very large modifications, success often requires the screening or hundreds to thousands of ES cell clones to find one that carries the desired gene modification.

To improve the efficiency of large humanizations we have developed methods that combine LTVEC gene targeting with clustered regularly interspaced short palindromic repeat RNA-guided Cas9 endonucleases (CRISPR/Cas9). CRISPR/Cas9 nucleases are ribonucleoprotein enzymes comprised of a bacterial Cas9 DNA endonuclease bound to a CRISPR RNA that guides Cas9 to cleave at a specific DNA sequence by Watson-Crick base pairing between the guide RNA and one strand of the target DNA. Because of the simplicity of the targeting mechanism, it is easy to design CRISPR/Cas9 endonucleases that direct a double strand break at nearly any genomic locus. Double strand breaks induce cellular genomic repair by the non-homologous end joining (NHEJ) pathways, which are error prone and often result in deletions or insertions at the site of the double strand break. An alternative mechanism of repairing the double strand break is homology-directed repair (HDR) in which an endogenous or exogenous piece of DNA that shares sequence identity or similarity with the broken site seamlessly repairs the broken ends by the action of the cellular homologous recombination machinery. HDR can result in a perfect repair that restores the original sequence at the broken site, or it can be used to direct a designed modification, such as a deletion, insertion, or replacement of the sequence at the site of the double strand break. CRISPR/Cas9 nucleases can greatly enhance the rate of engineered HDR events by directing precise double strand cleavages at the sites of the intended gene modifications.

To effect a precise, single-step deletion of all or part of a rodent gene and simultaneous replacement with all or part of its human homolog, we introduced by electroporation into rodent ES cells three nucleic acid molecules: (1) an LTVEC; (2) a plasmid or mRNA encoding a Cas9 endonuclease; and (3) a plasmid encoding a CRISPR single guide RNA (sgRNA) or the sgRNA itself. The LTVEC comprised all or part of a human gene that encodes the gene product (protein or RNA) flanked by homology arms of rodent DNA designed to direct an HR event that deletes the rodent gene and inserts the human gene. The humanizing LTVEC also carried a drug selection cassette that directs the expression of an enzyme (e.g., neomycin phosphotransferase) that imparts resistance to an antibiotic drug (for example, G418). ES cells that took up the LTVEC and incorporated it into their genomes were able to grow and form colonies on a Petri dish in a growth medium containing the antibiotic drug. Because we introduced 500 to 1,000 times more CRISPR/Cas9-encoding nucleic molecules than LTVEC molecules, most of the LTVEC-containing drug resistant colonies also contained, at least transiently, the CRISPR/Cas9 components. We picked drug resistant colonies and screened them by the loss-of-allele method (Valenzuela, D. et al. (2003) High-throughput engineering of the mouse genome coupled with high-resolution expression analysis, Nature Biotech. 21:652-660; Frendewey, D. et al. (2010) The loss-of-allele assay for ES cell screening and mouse genotyping, Methods Enzymol. 476:295-307; incorporated herein by reference in their entireties) to identify clones that had the correctly targeted humanized allele.

Figure 34:
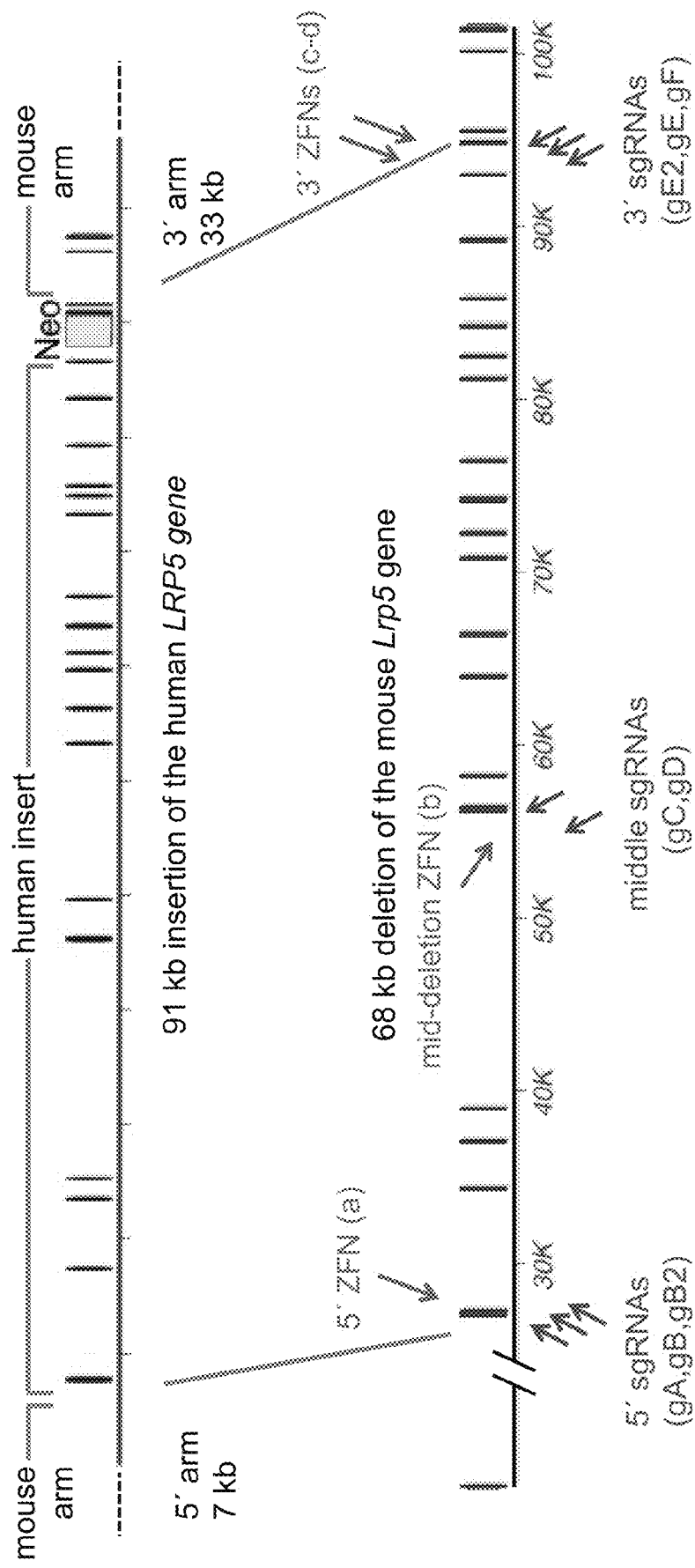
FIG. 34 provides a schematic of CRISPR/Cas9-assisted humanization of the mouse Lrp5 gene; the LTVEC is shown the top panel and the mouse Lrp5 locus is shown in the bottom panel. The region humanized is the ectodomain. The arrows indicate target sites for each gRNA (gA, gB, gB2, gC, gD, gE2, gE, gF) and ZFN (a-d).

In one particular experiment the LTVEC was designed to create a 68 kb deletion of the mouse Lrp5 (low-density lipoprotein receptor-related protein 5) gene and a simultaneous replacement with a 91 kb fragment of the homologous human LRP5 gene (FIG. 34). The LTVEC comprised the 91-kb fragment of the human LRP5 gene flanked by homology arms containing 7 kb and 33 kb of genomic DNA derived from parts of the mouse Lrp5 locus that flank the 68 kb sequence of the mouse Lrp5 gene intended for deletion. In separate experiments, we combined the Lrp5 humanizing LTVEC with a plasmid encoding Cas9 and a second plasmid encoding one of eight sgRNAs (gA, gB, gB2, gC, gD, gE2, gE, gF) designed to create double strand breaks within the region of the mouse Lrp5 gene that was targeted for deletion. The sgRNAs were designed to avoid recognition of any sequence in the inserted portion of the human LRP5 gene.

The results of the CRISPR/Cas9-assisted humanization of the Lrp5 gene are shown in Table 32. When the LTVEC alone was introduced into ES cells, we found that 1.0% of the screened drug resistant clones carried a correctly targeted mono-allelic heterozygous humanized allele. In contrast, combining the LTVEC with Cas9 endonucleases guided by seven of the eight tested sgRNAs (sgRNA-5'A, sgRNA-5'B, sgRNA-5'B2, sgRNA-C, sgRNA-D, sgRNA-3'E2, and sgRNA-3'F; sequences provided in Table 33) produced correctly targeted monoallelic heterozygous mutations at efficiencies that ranged from 2.1 to 7.3%, representing a 2- to 9-fold enhancement of single-step humanized gene targeting compared with the unaided LTVEC. For Cas9-guided cleavage by sgRNA-5'B2, in addition to monoallelic targeting, we detected biallelic homozygous humanization at a frequency of 1%. The homozygous Lrp5 humanized ES cells can be converted by the VELOCIMOUSE® genetic engineering method (Poueymirou, W. T. et al. (2007) F0 generation mice fully derived from gene-targeted embryonic stem cells allowing immediate phenotypic analyses, Nature Biotech. 25:91-99, incorporated herein by reference in its entirety) directly into completely ES cell-derived mice ready for phenotypic and drug efficacy studies.

TABLE 32

Screening Results for CRISPR/Cas9-Assisted Humanization of the Lrp5 Gene.

| Experiment | Clones Screened | CRISPR Activity (%) | Monoallelic Heterozygous Mutation Frequency (%) | Biallelic Compound Heterozygous Mutation Frequency (%) | Biallelic Homozygous Mutation Frequency (%) |
|---|---|---|---|---|---|
| LTVEC alone | 96 | N/A | 1.0 (1/96) | 0 | 0 |
| LTVEC + Cas9 + sgRNA-5'A | 96 | 75.6 | 7.3 (7/96) | 0 | 0 |
| LTVEC + Cas9 + sgRNA-5'B | 96 | 79.5 | 4.2 (4/96) | 0 | 0 |
| LTVEC + Cas9 + sgRNA-5'B2 | 96 | 60.5 | 6.2 (6/96) | 0 | 1.0 (1/96) |
| LTVEC + Cas9 + sgRNA-C | 96 | no assay | 4.2 (4/96) | 0 | 0 |
| LTVEC + Cas9 + sgRNA-D | 96 | no assay | 7.3 (7/96) | 0 | 0 |

TABLE 32-continued

Screening Results for CRISPR/Cas9-Assisted Humanization of the Lrp5 Gene.

| Experiment | Clones Screened | CRISPR Activity (%) | Monoallelic Heterozygous Mutation Frequency (%) | Biallelic Compound Heterozygous Mutation Frequency (%) | Biallelic Homozygous Mutation Frequency (%) |
|---|---|---|---|---|---|
| LTVEC + Cas9 + sgRNA-3'E2 | 96 | 84.5 | 2.1 (2/96) | 0 | 0 |
| LTVEC + Cas9 + sgRNA-3'E | 96 | 52.4 | 0 | 0 | 0 |
| LTVEC + Cas9 + sgRNA-3'F | 96 | 79.8 | 6.2 (6/96) | 0 | 0 |

TABLE 33

Sequences of the Guide Portions of Six sgRNAs Targeting the Mouse Lrp5 Gene.

| SGrna | Approximate Distance from Deletion Endpoint (bp) | Guide Sequence (5' to 3') |
|---|---|---|
| sgRNA-5'A | 50 | GGGAACCCACAGCATACTCC (SEQ ID NO: 24) |
| sgRNA-5'B | 500 | GAATCATGCACGGCTACCCC (SEQ ID NO: 25) |
| sgRNA-5'B2 | 1000 | TGCTCCTATGGGGAGGCGCG (SEQ ID NO: 26) |
| sgRNA-C | 29900/38430 | ACTGAGATCAATGACCCCGA (SEQ ID NO: 85) |
| sgRNA-D | 29950/38380 | GGGTCGCCCGGAACCTCTAC (SEQ ID NO: 86) |
| sgRNA-3'E2 | 1000 | CTTGGATAACATTGATACCC (SEQ ID NO: 27) |
| sgRNA-3'E | 500 | GGGGCAGAGCCCTTATATCA (SEQ ID NO: 28) |
| sgRNA-3'F | 50 | TCGCTCACATTAATCCCTAG (SEQ ID NO: 29) |

The enhanced targeting of the large Lrp5 humanization by CRISPR/Cas9 endonucleases is remarkable when compared with equivalent experiments performed with zinc finger nucleases (ZFNs). We obtained four ZFNs designed to make double strand breaks at sites within the region of the mouse Lrp5 gene targeted for deletion (FIG. 34). One ZFN targeted a sequence near the 5' end of the deletion (a), one targeted a sequence in the middle of the deletion (b), and two targeted sequences near the 3' end of the deletion (c, d). In separate experiments, we combined the Lrp5 humanizing LTVEC with a plasmid encoding one of the four ZFNs (a-d) designed to create double strand breaks within the region of the mouse Lrp5 gene that were targeted for deletion. We determined that all of the ZFNs were active and able to induce NHEJ mutations in the Lrp5 gene (data not shown), but when combined with the LTVEC, none enhanced HDR-mediated gene targeting compared with the LTVEC alone.

Figure 35A:
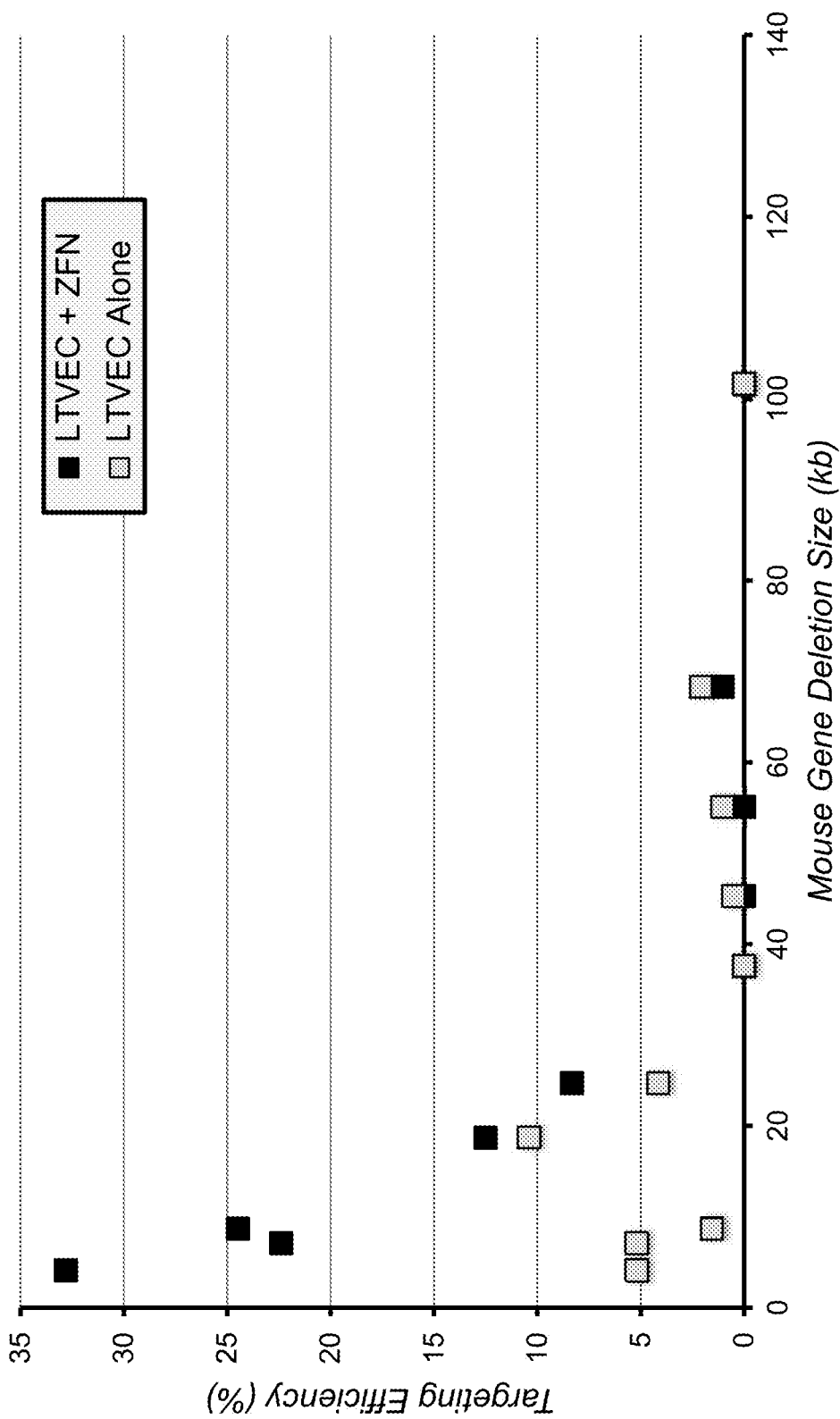
FIG. 35A-B depict the percent targeting efficiency of LTVECs targeting genes of increasing size for deletion (FIG. 35A) and the percent targeting efficiency of LTVECs with human gene insertions of increasing size (FIG. 35B). The LTVECs were used alone (gray squares or triangles) or in combination with ZFNs (black squares or triangles).
Figure 35B:
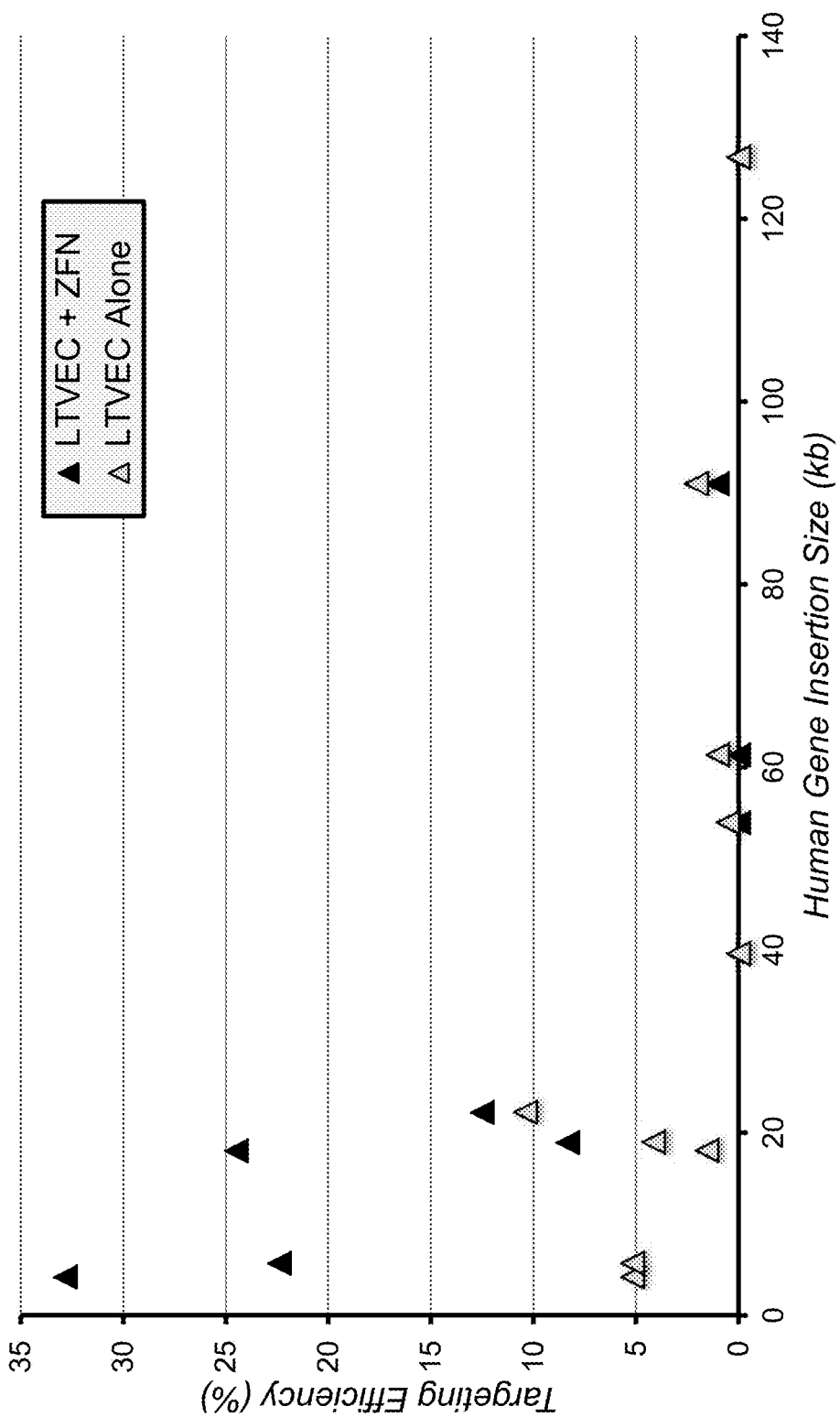

The enhanced targeting efficiency of the large Lrp5 humanization by CRISPR/Cas9 endonucleases is also remarkable when compared with a series of ZFN-assisted humanization experiments. In these experiments, a series of ZFN-assisted humanizations were performed in which the mouse target gene deletions and the human gene insertions were generally of increasing size (Table 34; FIG. 35). FIG. 35A depicts the percent targeting efficiency of LTVECs targeting genes of increasing size for deletion. The LTVECs were used alone (gray squares) or in combination with ZFNs (black squares). FIG. 35B depicts the percent targeting efficiency of LTVECs with human gene insertions of increasing size. Again, the LTVECs were used alone (gray triangles) or in combination with ZFNs (black triangles). As shown in Table 34 and FIG. 35, the ability of ZFN-mediated DNA cleavage to enhance LTVEC targeting efficiency disappeared when the size of the mouse target gene deletion was greater than 24.7 kb and when the size of the human gene insertion was greater than 22.2 kb (Table 34; FIG. 35A). In contrast, CRISPR/Cas9 was capable of enhancing LTVEC targeting efficiency of the Lrp5 gene, which involved a mouse gene deletion of 68.3 kb and a human gene insertion of 91.0 kb (Table 32; FIG. 34). This indicates that CRISPR/Cas9 endonucleases are able to enhance LTVEC targeting efficiency in situations where other nucleases (e.g., zinc finger nucleases) cannot.

TABLE 34

Summary of ZFN-Assisted Humanizations.

| Target Gene | Mouse Gene Deletion (kb) | Human Gene Insertion (kb) | 5'Homology Arm (kb) | 3'Homology Arm (kb) | ZFN Cleavage Efficiency (%) | Targeting Efficiency (%) | | Fold Enhancement |
|---|---|---|---|---|---|---|---|---|
| | | | | | | LTVEC Alone | LTVEC + ZFN | |
| Fcer1a | 4.1 | 4.2 | 10.9 | 76.8 | 22.9 | 5.20 | 32.81 | 6.3 |
| Tlr4 | 7.1 | 5.7 | 67.6 | 85.5 | 12.5 | 5.20 | 22.39 | 4.3 |
| Prlr | 8.7 | 18.0 | 49.6 | 112.9 | 30.7 | 1.56 | 24.48 | 15.7 |
| Notch4 | 18.7 | 22.2 | 50.1 | 34.9 | 27.1 | 10.41 | 12.50 | 1.2 |
| Accn2 | 24.7 | 18.9 | 57.8 | 60.1 | 20.8 | 4.17 | 8.33 | 2.0 |
| Adamts5 | 37.6 | 39.6 | 83.3 | 61.5 | 4.2 | 0.00 | 0.00 | n.a. |

TABLE 34-continued

Summary of ZFN-Assisted Humanizations.

Figure 36:
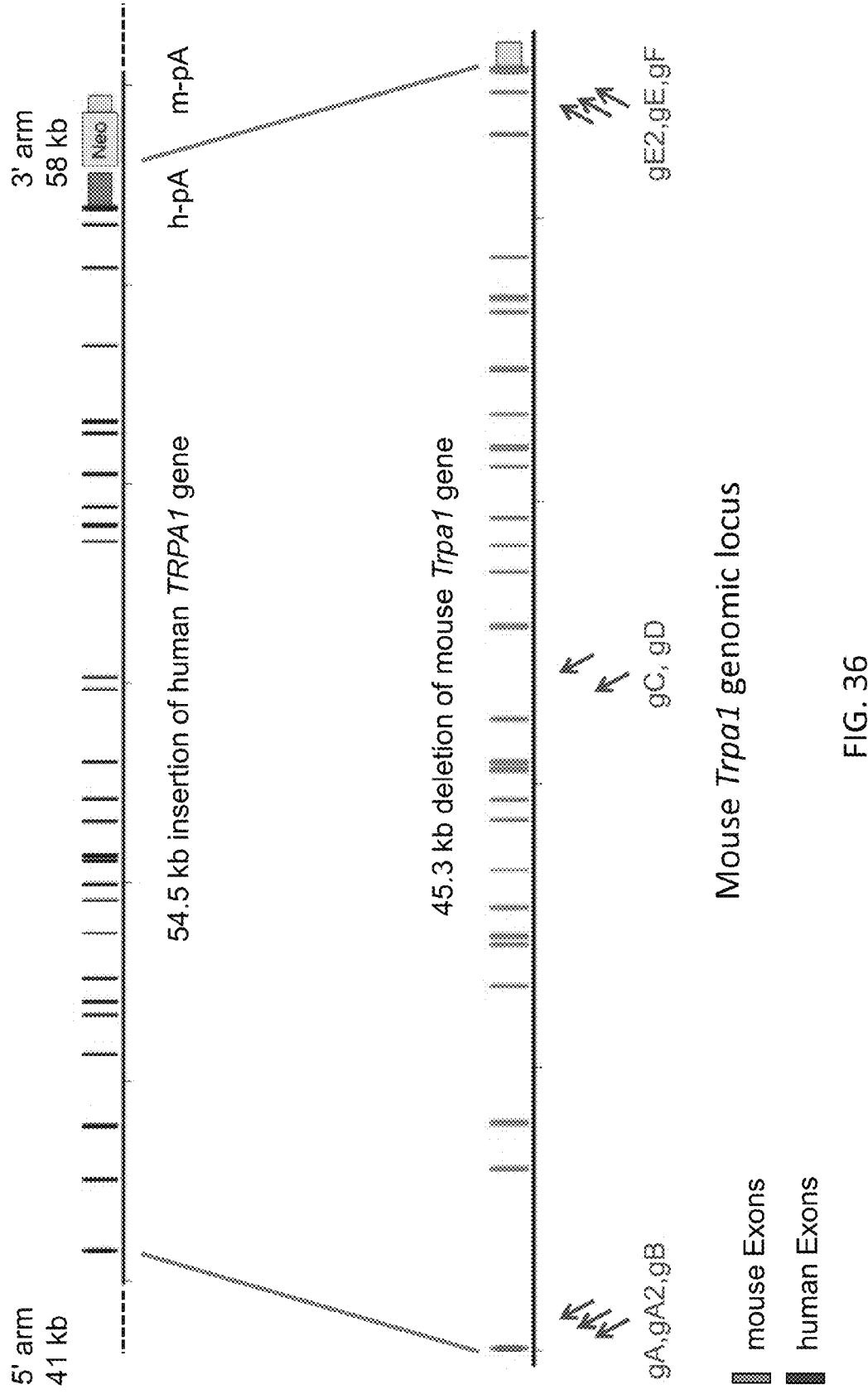
FIG. 36 provides a schematic of CRISPR/Cas9-assisted humanization of the entire coding region of the mouse Trpa1 gene; the LTVEC is shown the top panel and the mouse Trpa1 locus is shown in the bottom panel. The arrows indicate target sites for each gRNA (gA, gA2, gB, gC, gD, gE2, gE, gF).

| Target Gene | Mouse Gene Deletion (kb) | Human Gene Insertion (kb) | 5'Homology Arm (kb) | 3'Homology Arm (kb) | ZFN Cleavage Efficiency (%) | Targeting Efficiency (%) LTVEC Alone | Targeting Efficiency (%) LTVEC + ZFN | Fold Enhancement |
|---|---|---|---|---|---|---|---|---|
| Trpa1 | 45.3 | 53.9 | 41.3 | 57.8 | 8.8 | 0.52 | 0.00 | 0 |
| Folh1 | 55.1 | 61.3 | 18.4 | 114.7 | 8.8 | 1.04 | 0.00 | 0 |
| Lrp5 | 68.3 | 91.0 | 6.9 | 33.4 | 35.9 | 2.08 | 1.04 | (0.5) |
| Erbb4 | 101.6 | 126.7 | 47.8 | 26.0 | n.d. | 0.00 | 0.00 | n.a. | n.d. = not determined
n.a. = not applicable
( ) = targeting efficiency lower with ZFN than without Comparable experiments were performed for humanization of other mouse genes. In one experiment, the LTVEC was designed to create a 45 kb deletion of the mouse Trpa1 (transient receptor potential cation channel subfamily A member 1) gene and a simultaneous replacement with a 55 kb fragment of the homologous human TRPA1 gene (FIG. 36). The LTVEC comprised the 55 kb fragment of the human TRPA1 gene flanked by homology arms containing 41 kb and 58 kb of genomic DNA derived from parts of the mouse Trpa1 locus that flank the 45 kb sequence of the mouse Trpa1 gene intended for deletion. In separate experiments, we combined the Trpa1 humanizing LTVEC with a plasmid encoding Cas9 and a second plasmid encoding one of eight sgRNAs (gA, gA2, gB, gC, gD, gE, gE2, and gF) designed to create double strand breaks within the region of the mouse Trpa1 gene that was targeted for deletion. The sgRNAs were designed to avoid recognition of any sequence in the inserted portion of the human TRPA1 gene.

The results of the CRISPR/Cas9-assisted humanization of the Trpa1 gene are shown in Table 35. When the LTVEC alone was introduced into ES cells, we found that 1.0% of the screened drug resistant clones carried a correctly targeted monoallelic heterozygous humanized allele. In contrast, combining the LTVEC with Cas9 endonuclease guided by six of eight tested sgRNAs (A, A2, B, C, D, and F; sequences provided in Table 43) produced correctly targeted monoallelic heterozygous mutations or biallelic compound heterozygous or homozygous mutations at efficiencies that ranged from 1.0 to 3.1%. For Cas9-guided cleavage by gRNA A and gRNA F, we detected compound heterozygous mutations at a frequency of 1.0%.

Figure 37:
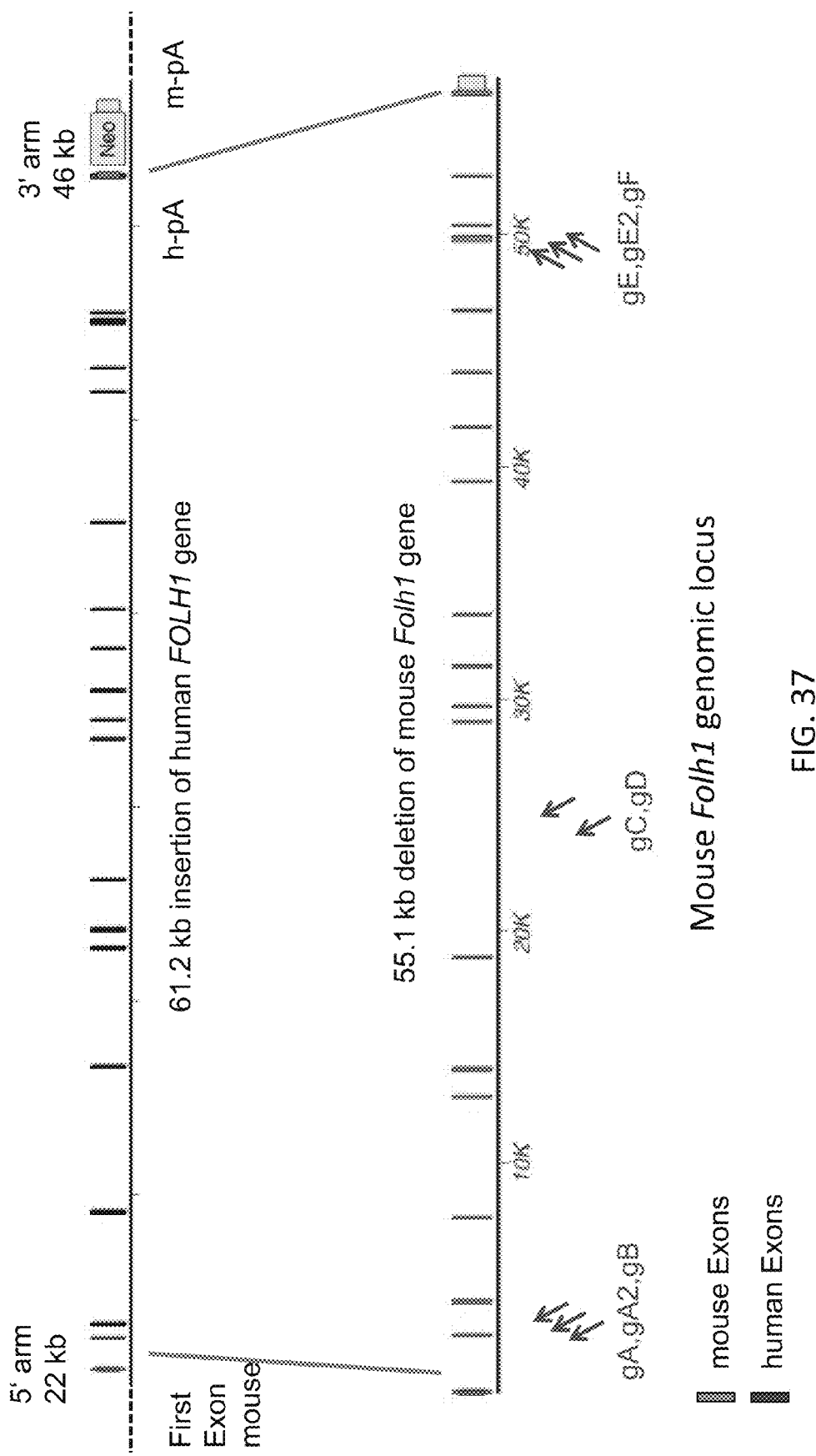
FIG. 37 provides a schematic of CRISPR/Cas9-assisted humanization of the ectodomain (exon 2 to stop codon) of the mouse Folh1 gene; the LTVEC is shown the top panel and the mouse Folh1 locus is shown in the bottom panel. The arrows indicate target sites for each gRNA (gA, gA2, gB, gC, gD, gE, gE2, gF).

In another experiment, the LTVEC was designed to create a 55 kb deletion of the mouse Folh1 (glutamate carboxypeptidase 2) gene and a simultaneous replacement with a 61 kb fragment of the homologous human FOLH1 gene (FIG. 37). The LTVEC comprised the 61 kb fragment of the human FOLH1 gene flanked by homology arms containing 22 kb and 46 kb of genomic DNA derived from parts of the mouse Folh1 locus that flank the 55 kb sequence of the mouse Folh1 gene intended for deletion. In separate experiments, we combined the Folh1 humanizing LTVEC with a plasmid encoding Cas9 and a second plasmid encoding one of six sgRNAs (gA, gA2, gC, gD, gE, and gE2) designed to create double strand breaks within the region of the mouse Folh1 gene that was targeted for deletion. The sgRNAs were designed to avoid recognition of any sequence in the inserted portion of the human FOLH1 gene.

The results of the CRISPR/Cas9-assisted humanization of the Folh1 gene are shown in Table 36. When the LTVEC alone was introduced into ES cells, we found that none of the 96 screened drug resistant clones carried a correctly targeted monoallelic heterozygous humanized allele. In contrast, combining the LTVEC with Cas9 endonuclease guided by three of six tested sgRNAs (A, D, and E2; sequences provided in Table 43) produced correctly targeted monoallelic heterozygous mutations at efficiencies that ranged from 1.0 to 3.1%.

TABLE 35

Screening Results for CRISPR/Cas9-Assisted Humanization of the Trpa1 Gene.

| sgRNA Position | Approximate Distance from Deletion Endpoint (bp) | gRNA | CRISPR Activity (%) | Clones Screened | Heterozygous Targeted | Compound Heterozygous | Homozygous Targeted |
|---|---|---|---|---|---|---|---|
| 5' | 100 | gRNA A | 30.9 | 96 | 0 | 1 | 0 |
| 5' | 500 | gRNA A2 | no assay | 96 | 2 | 0 | 0 |
| 5' | 1000 | gRNA B | 42.8 | 96 | 3 | 0 | 0 |
| middle | 25600/19740 | gRNA C | no assay | 96 | 1 | 0 | 0 |
| middle | 26970/18370 | gRNA D | no assay | 96 | 2 | 0 | 0 |
| 3' | 1000 | gRNA E2 | no assay | 96 | 0 | 0 | 0 |
| 3' | 500 | gRNA E | 22.6 | 96 | 0 | 0 | 0 |
| 3' | 100 | gRNA F | 28.6 | 96 | 1 | 1 | 0 |
| N/A | N/A | none | N/A | 96 | 1 | 0 | 0 |

TABLE 36

Screening Results for CRISPR/Cas9-Assisted Humanization of the Folh1 Gene.

| sgRNA Position | Approximate Distance from Deletion Endpoint (bp) | gRNA | CRISPR Activity (%) | Clones Screened | Heterozygous Targeted | Compound Heterozygous | Homozygous Targeted |
|---|---|---|---|---|---|---|---|
| 5' | 100 | gRNA A | 45.2 | 96 | 2 | 0 | 0 |
| 5' | 500 | gRNA A2 | 61.9 | 96 | 0 | 0 | 0 |
| middle | 30300/24800 | gRNA C | 7.1 | 96 | 0 | 0 | 0 |
| middle | 31290/23810 | gRNA D | 39.2 | 96 | 1 | 0 | 0 |
| 3' | 500 | gRNA E2 | no assay | 96 | 1 | 0 | 0 |
| 3' | 100 | gRNA E | 1.2 | 96 | 0 | 0 | 0 |
| N/A | N/A | none | N/A | 96 | 0 | 0 | 0 |

Figure 38:
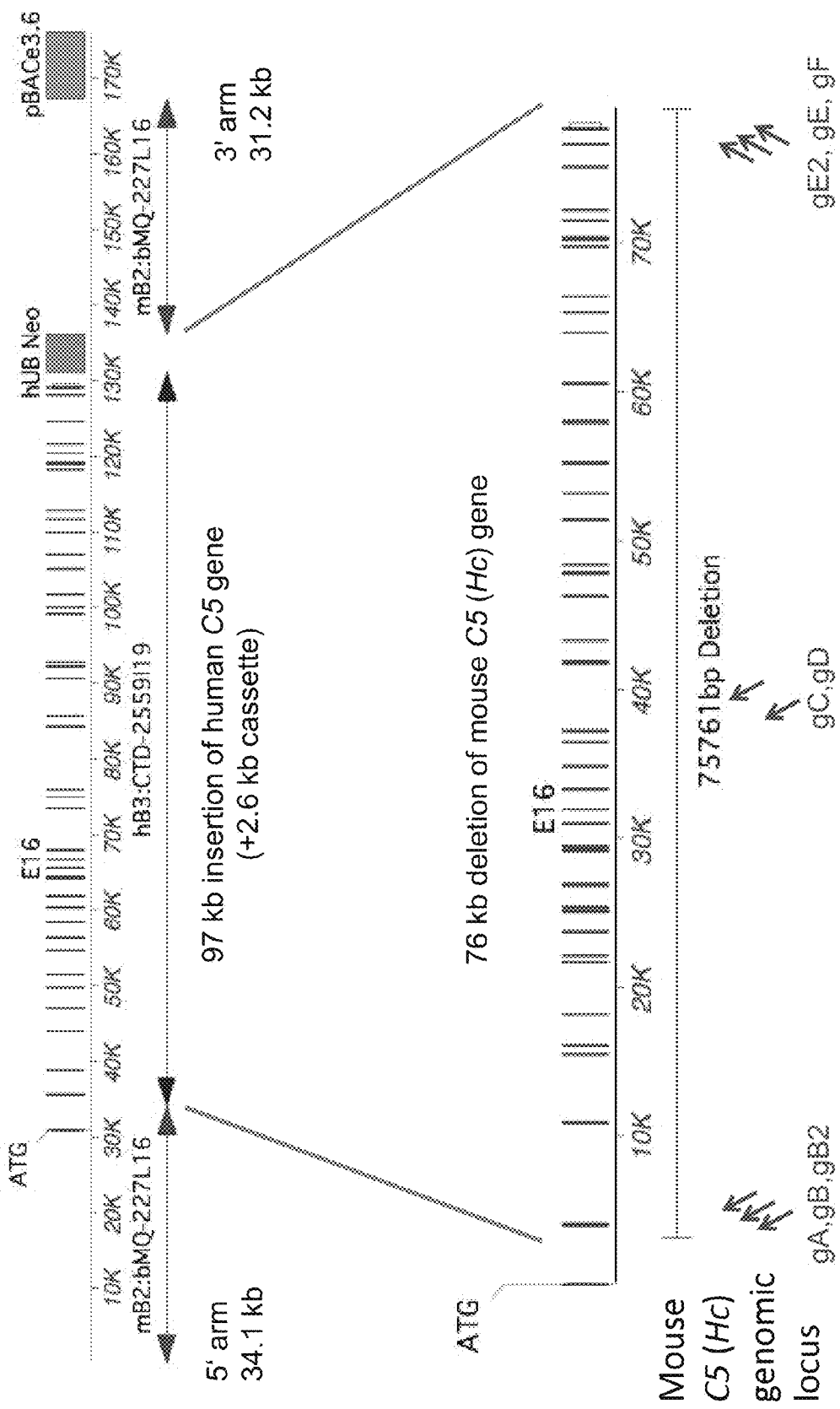
FIG. 38 provides a schematic of CRISPR/Cas9-assisted humanization of the region from exon 2 to the stop codon of the mouse C5 (Hc) gene; the LTVEC is shown the top panel and the mouse C5 (Hc) locus is shown in the bottom panel. The arrows indicate target sites for each gRNA (gA, gB, gB2, gC, gD, gE2, gE, gF).

In another experiment, the LTVEC was designed to create a 76 kb deletion of the mouse gene for complement component 5 (C5 or Hc) and a simultaneous replacement with a 97 kb fragment of the homologous human C5 gene (FIG. 38). The LTVEC comprised the 97 kb fragment of the human C5 gene flanked by homology arms containing 34.1 kb and 31.2 kb of genomic DNA derived from parts of the mouse C5 (Hc) locus that flank the 76 kb sequence of the mouse C5 (Hc) gene intended for deletion. In separate experiments, we combined the C5 (Hc) humanizing LTVEC with a plasmid encoding Cas9 and a second plasmid encoding one of six sgRNAs (gA, gB, gC, gD, gE, and gE2) designed to create double strand breaks within the region of the mouse C5 (Hc) gene that was targeted for deletion. The sgRNAs were designed to avoid recognition of any sequence in the inserted portion of the human C5 gene.

The results of the CRISPR/Cas9-assisted humanization of the C5 (Hc) gene are shown in Table 37. When the LTVEC alone was introduced into ES cells, we found that 1.0% of the screened drug resistant clones carried a correctly targeted monoallelic heterozygous humanized allele. In contrast, combining the LTVEC with Cas9 endonuclease guided by all six tested sgRNAs (A, B, C, D, E, and E2; sequences provided in Table 43) produced correctly targeted monoallelic heterozygous mutations or biallelic compound heterozygous or homozygous mutations at efficiencies that ranged from 4.2 to 16.7%. For Cas9-guided cleavage by gRNAs A and E, we detected compound heterozygous mutations at frequencies of 5.2% and 4.2%, respectively.

Figure 39:
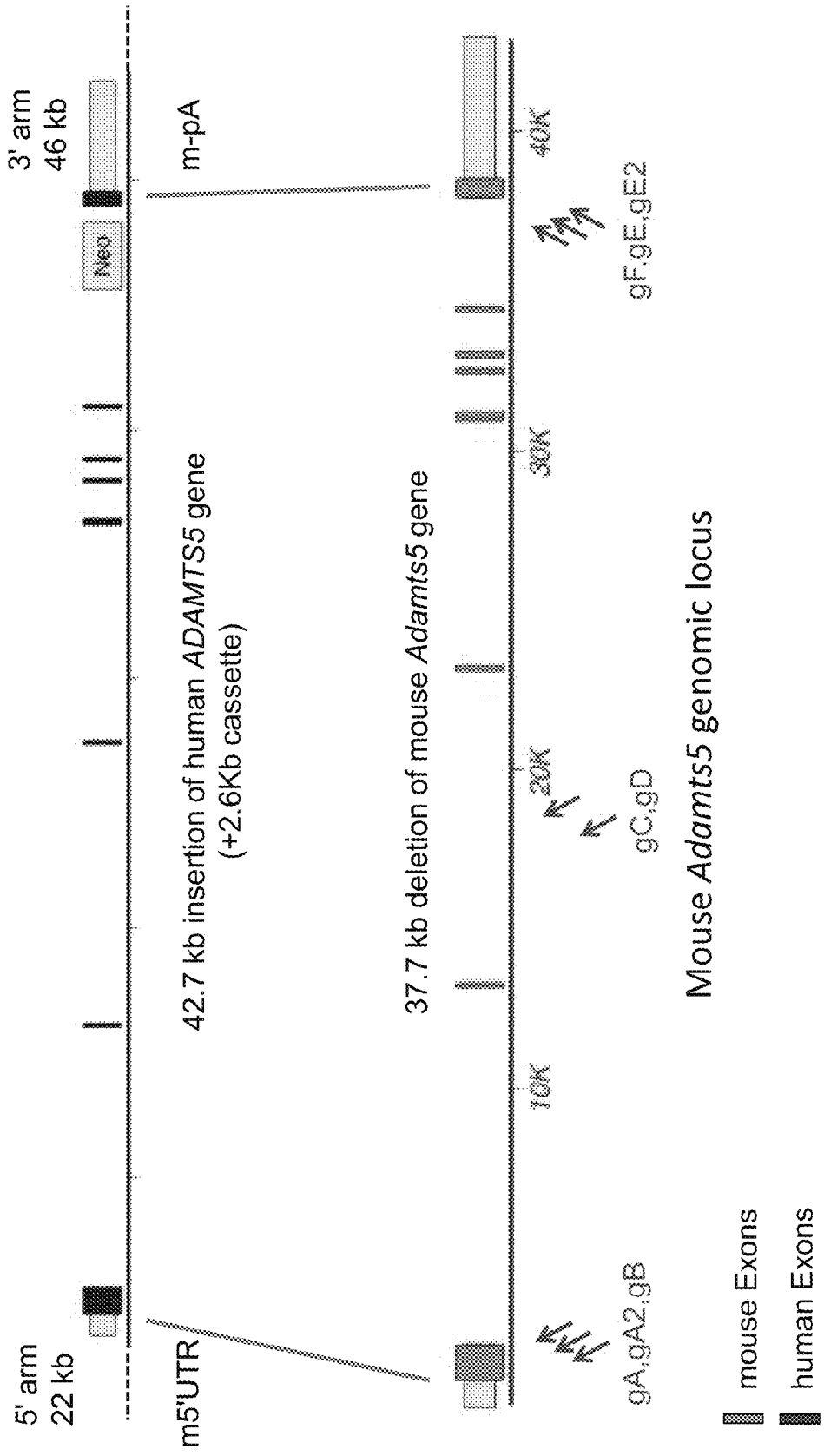
FIG. 39 provides a schematic of CRISPR/Cas9-assisted humanization of the entire coding region of the mouse Adamts5 gene; the LTVEC is shown the top panel and the mouse Adamts5 locus is shown in the bottom panel. The arrows indicate target sites for each gRNA (gA, gA2, gB, gC, gD, gE2, gE, gF).

In another experiment, the LTVEC was designed to create a 38 kb deletion of the mouse Adamts5 (a disintegrin and metalloproteinase with thrombospondin motifs 5) gene and a simultaneous replacement with a 43 kb fragment of the homologous human ADAMTS5 gene (FIG. 39). The LTVEC comprised the 43 kb fragment of the human ADAMTS5 gene flanked by homology arms containing 22 kb and 46 kb of genomic DNA derived from parts of the mouse Adamts5 locus that flank the 38 kb sequence of the mouse Adamts5 gene intended for deletion. In separate experiments, we combined the Adamts5 humanizing LTVEC with a plasmid encoding Cas9 and a second plasmid encoding one of eight sgRNAs (gA, gA2, gB, gC, gD, gE, gE2, and gF) designed to create double strand breaks within the region of the mouse Adamts5 gene that was targeted for deletion. The sgRNAs were designed to avoid recognition of any sequence in the inserted portion of the human ADAMTS5 gene.

The results of the CRISPR/Cas9-assisted humanization of the Adamts5 gene are shown in Table 38. When the LTVEC alone was introduced into ES cells, we found that none of the 96 screened drug resistant clones carried a correctly targeted monoallelic heterozygous humanized allele. In contrast, combining the LTVEC with Cas9 endonuclease guided by two of eight tested sgRNAs (B and F; sequences provided in Table 43) produced correctly targeted monoallelic heterozygous mutations or biallelic compound heterozygous mutations at an efficiency of 1.0%. For Cas9-guided cleavage by gRNA E2, we detected compound heterozygous mutations at a frequency of 1.0%.

TABLE 37

Screening Results for CRISPR/Cas9-Assisted Humanization of the C5 (Hc) Gene.

| sgRNA Position | Approximate Distance from Deletion Endpoint (bp) | gRNA | CRISPR Activity (%) | Clones Screened | Heterozygous Targeted | Compound Heterozygous | Homozygous Targeted |
|---|---|---|---|---|---|---|---|
| 5' | 100 | gRNA A | 64.3 | 96 | 11 | 5 | 0 |
| 5' | 500 | gRNA B | 72.6 | 96 | 14 | 0 | 0 |
| middle | 38200/37500 | gRNA C | 47.6 | 96 | 11 | 0 | 0 |
| middle | 43500/32200 | gRNA D | 47.6 | 96 | 7 | 0 | 0 |
| 3' | 500 | gRNA E | 25.0 | 96 | 0 | 4 | 0 |
| 3' | 100 | gRNA E2 | 27.4 | 96 | 6 | 0 | 0 |
| N/A | N/A | none | N/A | 96 | 1 | 0 | 0 |

TABLE 38

Screening Results for CRISPR/Cas9-Assisted Humanization of the Adamts5 Gene.

| sgRNA Position | Approximate Distance from Deletion Endpoint (bp) | gRNA | CRISPR Activity (%) | Clones Screened | Heterozygous Targeted | Compound Heterozygous | Homozygous Targeted |
|---|---|---|---|---|---|---|---|
| 5' | 100 | gRNA A | 85.7 | 96 | 0 | 0 | 0 |
| 5' | 500 | gRNA A2 | 54.8 | 96 | 0 | 0 | 0 |
| 5' | 1000 | gRNA B | 66.7 | 96 | 1 | 0 | 0 |
| middle | 18700/18950 | gRNA C | 9.5 | 96 | 0 | 0 | 0 |
| middle | 18800/18850 | gRNA D | 4.8 | 96 | 0 | 0 | 0 |
| 3' | 1000 | gRNA F | 36.9 | 96 | 0 | 1 | 0 |
| 3' | 500 | gRNA E | 54.8 | 96 | 0 | 0 | 0 |
| 3' | 100 | gRNA E2 | 54.8 | 96 | 0 | 0 | 0 |
| N/A | N/A | none | N/A | 96 | 0 | 0 | 0 |

Figure 40:
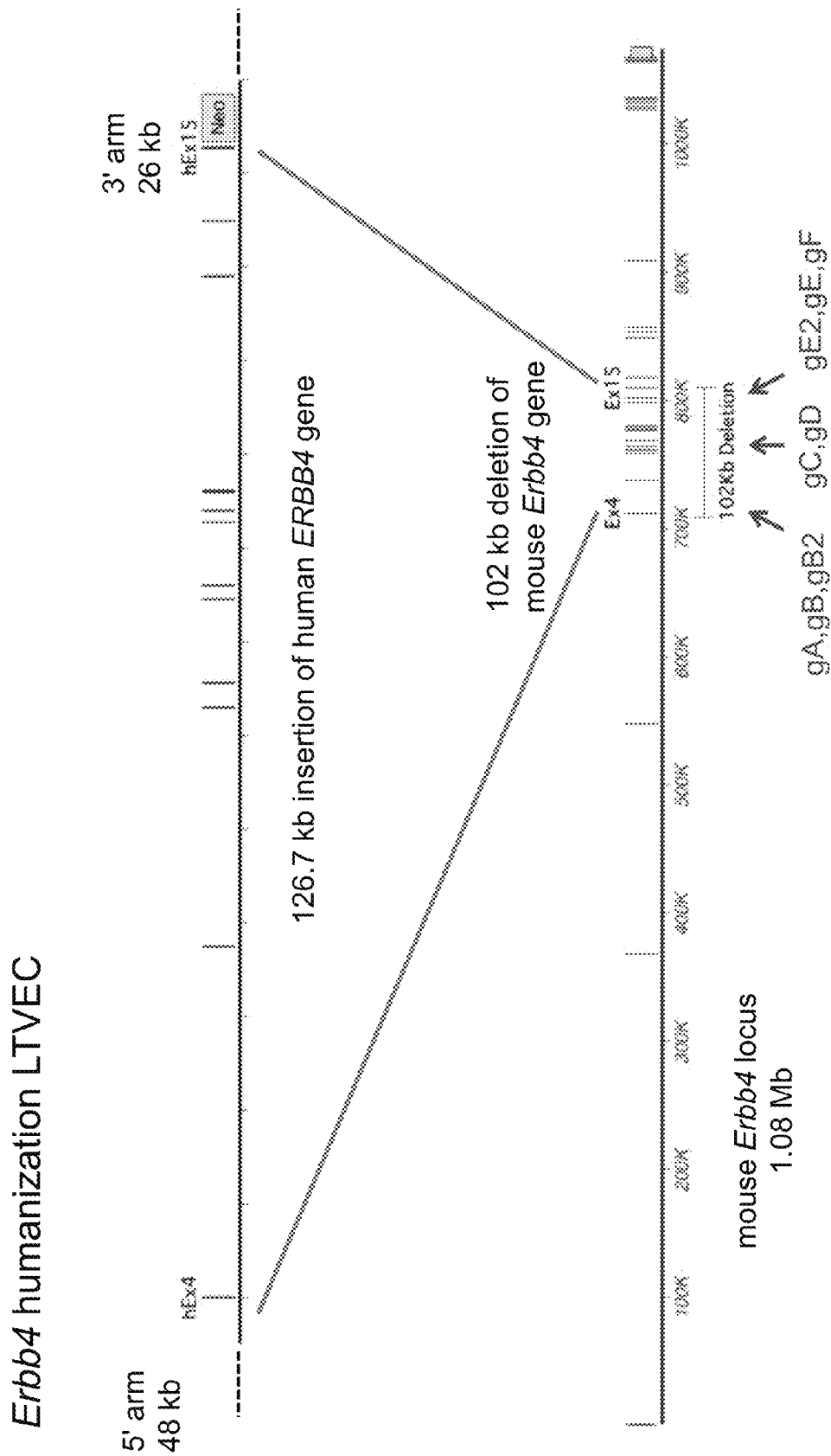
FIG. 40 provides a schematic of CRISPR/Cas9-assisted humanization of exons 4-15 of the mouse Erbb4 gene; the LTVEC is shown the top panel and the mouse Erbb4 locus is shown in the bottom panel. The arrows indicate target sites for each gRNA (gA, gB, gB2, gC, gD, gE2, gE, gF).

In another experiment, the LTVEC was designed to create a 102 kb deletion of the mouse Erbb4 (receptor tyrosine-protein kinase erbB-4) gene and a simultaneous replacement with a 127 kb fragment of the homologous human ERBB4 gene (FIG. 40). The LTVEC comprised the 127 kb fragment of the human ERBB4 gene flanked by homology arms containing 48 kb and 26 kb of genomic DNA derived from parts of the mouse Erbb4 locus that flank the 102 kb sequence of the mouse Erbb4 gene intended for deletion. In separate experiments, we combined the Erbb4 humanizing LTVEC with a plasmid encoding Cas9 and a second plasmid encoding one of eight sgRNAs (gA, gB, gB2, gC, gD, gE, gE2, and gF) designed to create double strand breaks within the region of the mouse Erbb4 gene that was targeted for deletion. The sgRNAs were designed to avoid recognition of any sequence in the inserted portion of the human ERBB4 gene.

The results of the CRISPR/Cas9-assisted humanization of the Erbb4 gene are shown in Table 39. When the LTVEC alone was introduced into ES cells, we found that none of the 96 screened drug resistant clones carried a correctly targeted monoallelic heterozygous humanized allele. In contrast, combining the LTVEC with Cas9 endonuclease guided by one of eight tested sgRNAs (D; sequence provided in Table 43) produced correctly targeted monoallelic heterozygous mutations or biallelic compound heterozygous mutations at an efficiency of 1.0%. For Cas9-guided cleavage by gRNA D, we detected compound heterozygous mutations at a frequency of 1%.

Figure 41:
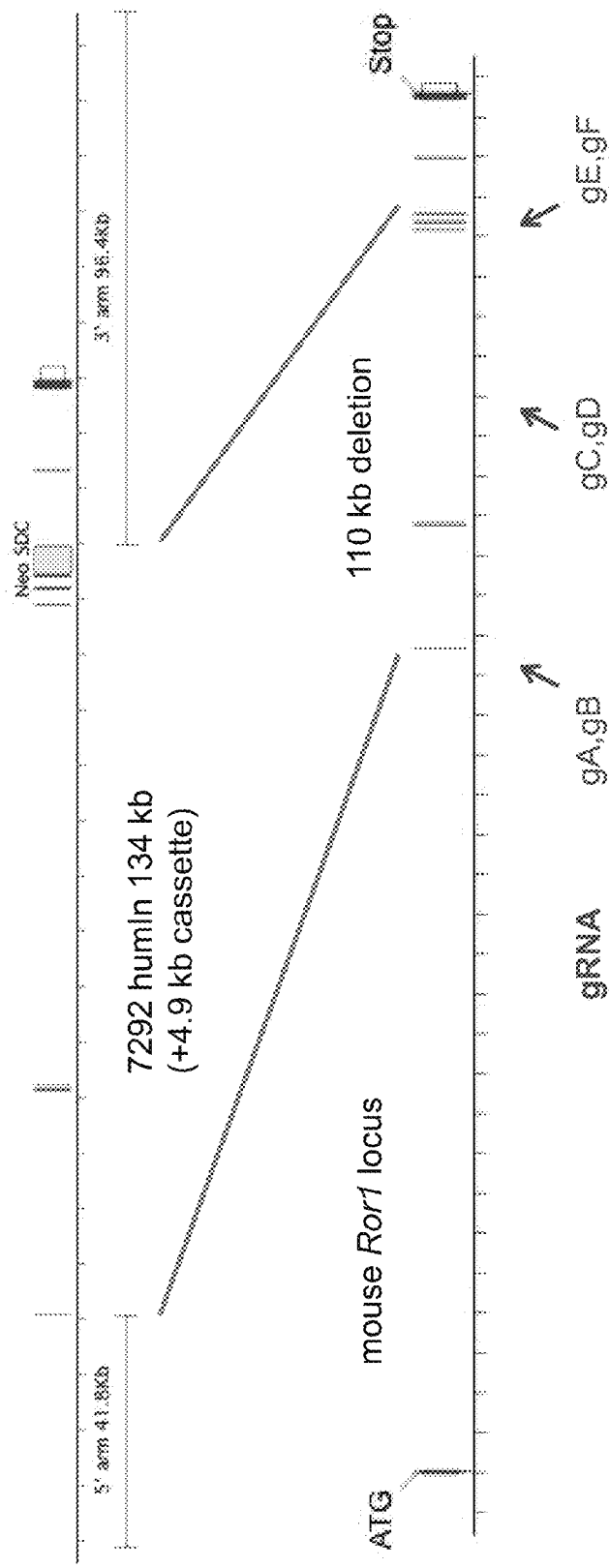
FIG. 41 provides a schematic of CRISPR/Cas9-assisted humanization of exons 2-7 of the mouse Ror1 gene; the LTVEC is shown the top panel and the mouse Ror1 locus is shown in the bottom panel. The arrows indicate target sites for each gRNA (gA, gB, gC, gD, gE, gF).

In another experiment, the LTVEC was designed to create a 110 kb deletion of the mouse Ror1 (tyrosine-protein kinase transmembrane receptor ROR1) gene and a simultaneous replacement with a 134 kb fragment of the homologous human ROR1 gene (FIG. 41). The LTVEC comprised the 134 kb fragment of the human ROR1 gene flanked by homology arms containing 41.8 kb and 96.4 kb of genomic DNA derived from parts of the mouse Ror1 locus that flank the 110 kb sequence of the mouse Ror1 gene intended for deletion. In separate experiments, we combined the Ror1 humanizing LTVEC with a plasmid encoding Cas9 and a second plasmid encoding one of six sgRNAs (gA, gB, gC, gD, gE, and gF) designed to create double strand breaks within the region of the mouse Ror1 gene that was targeted for deletion. The sgRNAs were designed to avoid recognition of any sequence in the inserted portion of the human ROR1 gene.

The results of the CRISPR/Cas9-assisted humanization of the Ror1 gene are shown in Table 40. When the LTVEC alone was introduced into ES cells, we found that none of the 96 screened drug resistant clones carried a correctly targeted monoallelic heterozygous humanized allele. In contrast, combining the LTVEC with Cas9 endonuclease guided by two of six tested sgRNAs (D and F; sequences provided in Table 43) produced correctly targeted monoallelic heterozygous or biallelic mutations at efficiencies of 1.0%. For Cas9-guided cleavage by gRNA F, we also detected compound heterozygous mutations at a frequency of 1%.

TABLE 39

Screening Results for CRISPR/Cas9-Assisted Humanization of the Erbb4 Gene.

| sgRNA Position | Approximate Distance from Deletion Endpoint (bp) | gRNA | CRISPR Activity (%) | Clones Screened | Heterozygous Targeted | Compound Heterozygous | Homozygous Targeted |
|---|---|---|---|---|---|---|---|
| 5' | 100 | gRNA A | 25.0 | 96 | 0 | 0 | 0 |
| 5' | 500 | gRNA B | no assay | 96 | 0 | 0 | 0 |
| 5' | 1000 | gRNA B2 | 47.6 | 96 | 0 | 0 | 0 |
| middle | 50200/51350 | gRNA C | 20.2 | 96 | 0 | 0 | 0 |
| middle | 50230/51320 | gRNA D | 42.8 | 96 | 0 | 1 | 0 |
| 3' | 1000 | gRNA F | 15.5 | 96 | 0 | 0 | 0 |
| 3' | 500 | gRNA E | 89.2 | 96 | 0 | 0 | 0 |
| 3' | 100 | gRNA E2 | 14.3 | 96 | 0 | 0 | 0 |
| N/A | N/A | none | N/A | 96 | 0 | 0 | 0 |

TABLE 40

Screening Results for CRISPR/Cas9-Assisted Humanization of the Ror1 Gene.

| sgRNA Position | Approximate Distance from Deletion Endpoint (bp) | gRNA | CRISPR Activity (%) | Clones Screened | Heterozygous Targeted | Compound Heterozygous | Homozygous Targeted |
|---|---|---|---|---|---|---|---|
| 5' | 200 | gRNA A | no assay | 96 | 0 | 0 | 0 |
| 5' | 1000 | gRNA B | no assay | 96 | 0 | 0 | 0 |
| middle | 54300/55500 | gRNA D | no assay | 96 | 1 | 0 | 0 |
| middle | 54500/55300 | gRNA C | no assay | 96 | 0 | 0 | 0 |
| 3' | 1000 | gRNA E | no assay | 96 | 0 | 0 | 0 |
| 3' | 200 | gRNA F | no assay | 96 | 0 | 1 | 0 |
| N/A | N/A | none | N/A | 96 | 0 | 0 | 0 |

Figure 42:
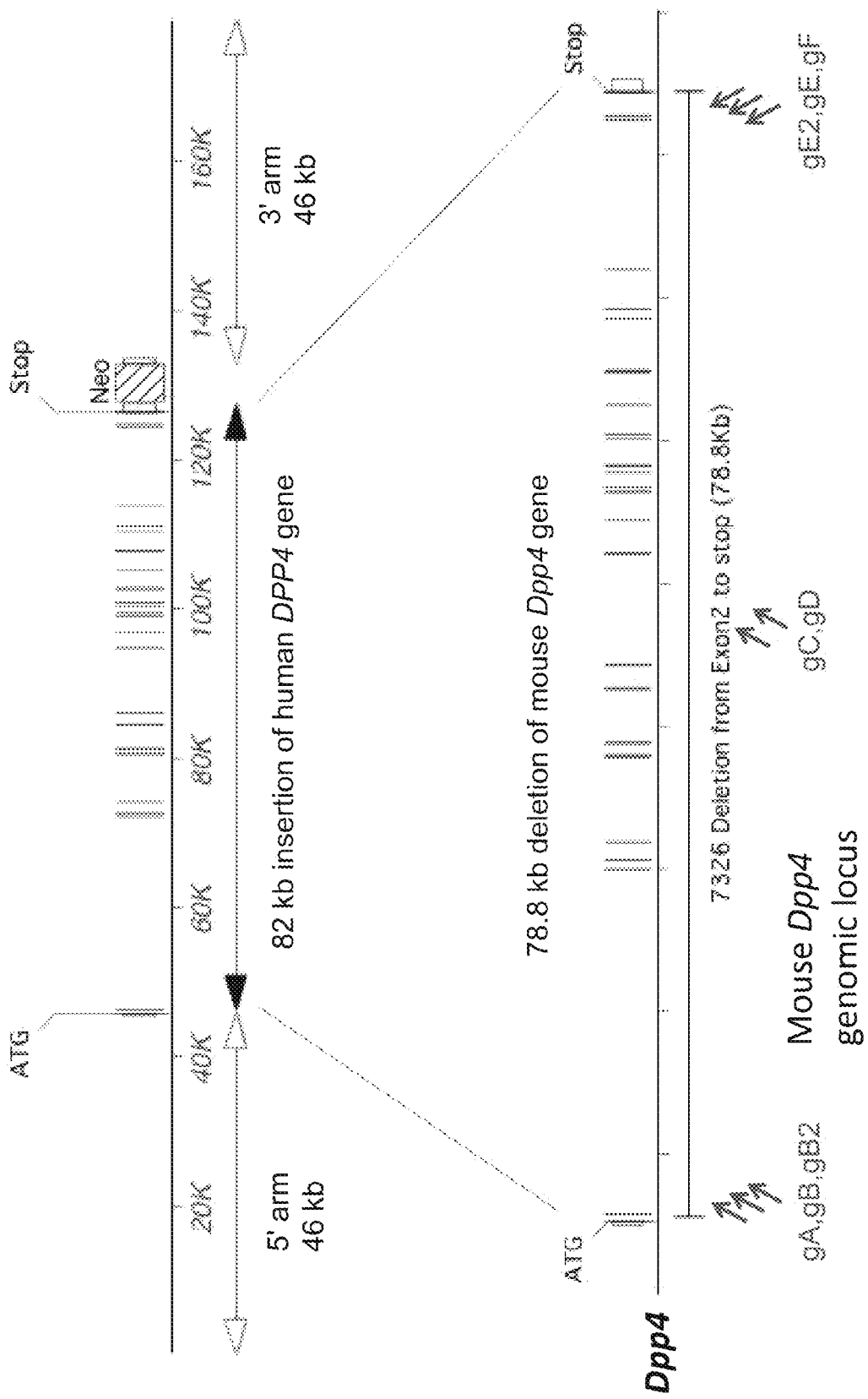
FIG. 42 provides a schematic of CRISPR/Cas9-assisted humanization of the region from exon 2 to the stop codon of the mouse Dpp4 gene; the LTVEC is shown the top panel and the mouse Dpp4 locus is shown in the bottom panel. The arrows indicate target sites for each gRNA (gA, gB, gB2, gC, gD, gE2, gE, gF).
Figure 43C:
FIG. 43A-F show 12-week-old female rat brains stained with X-gal.
Figure 43B:
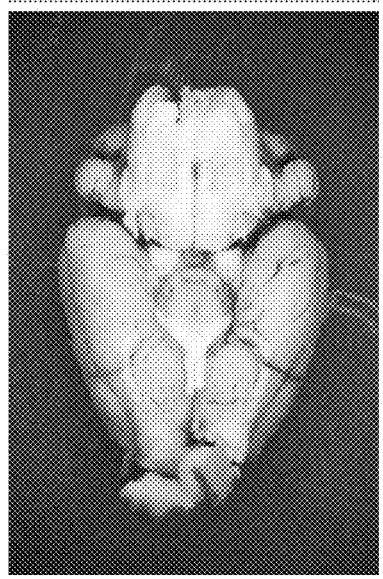
Figure 43A:
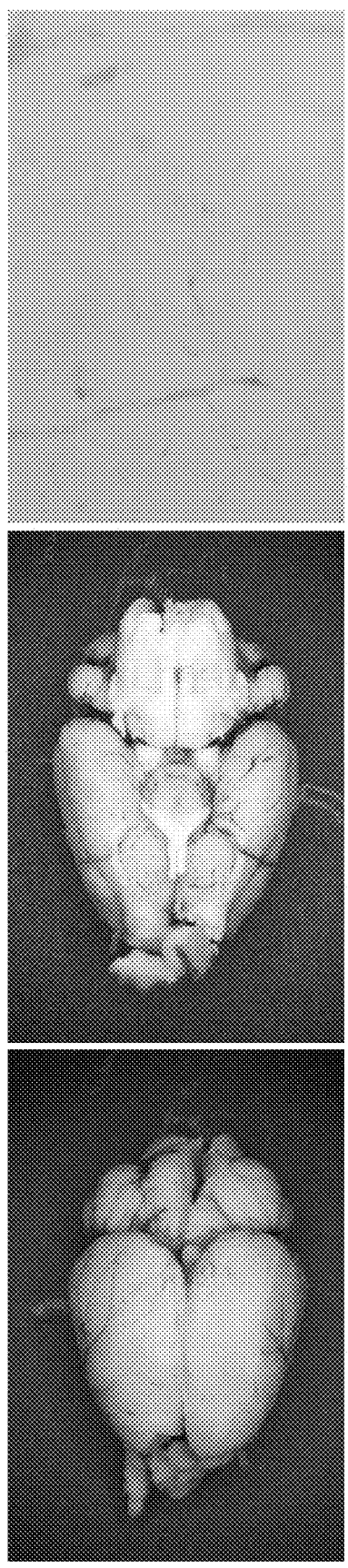
Figure 43F:
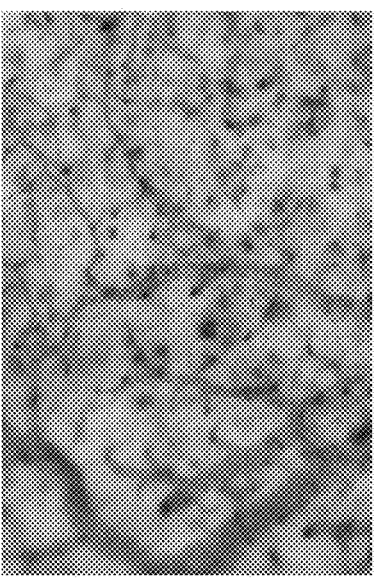
Figure 43E:
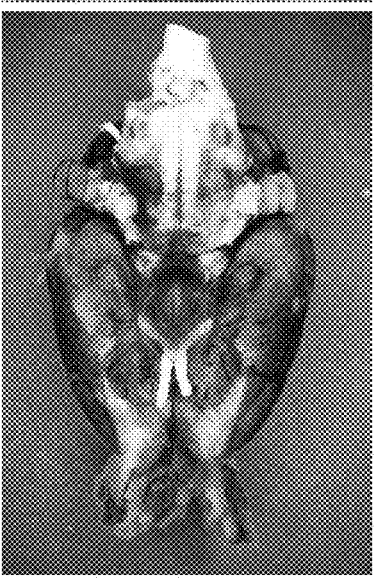
Figure 43D:
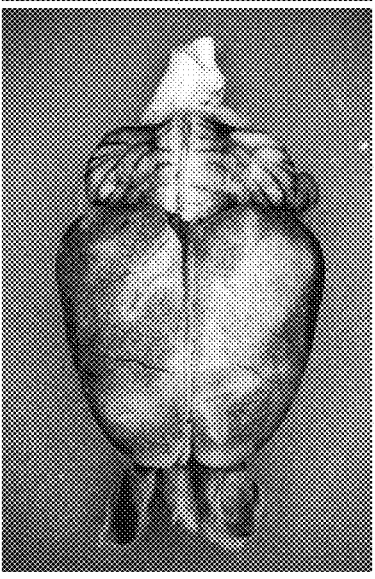
Figure 44B:
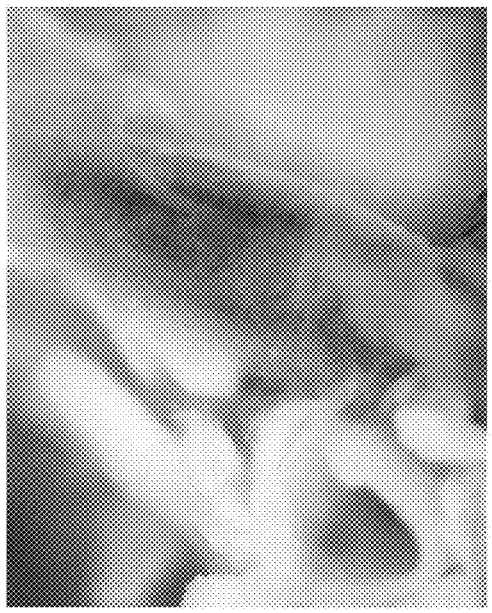
FIG. 44A-D show 12-week-old female rat hearts (A and C) and corresponding close-ups of blood vessels (B and D) stained with X-gal.
Figure 44A:
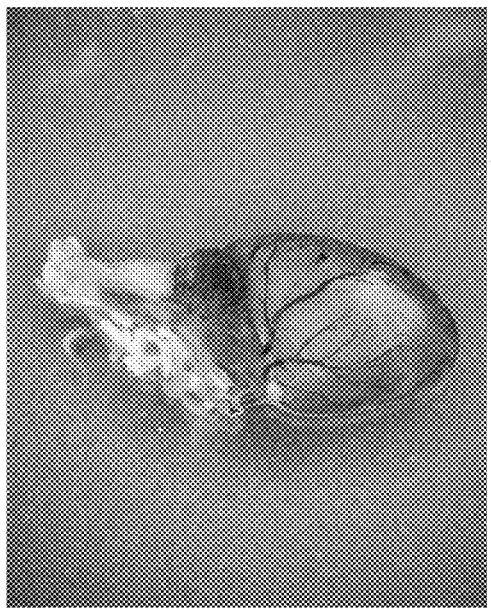
Figure 44D:
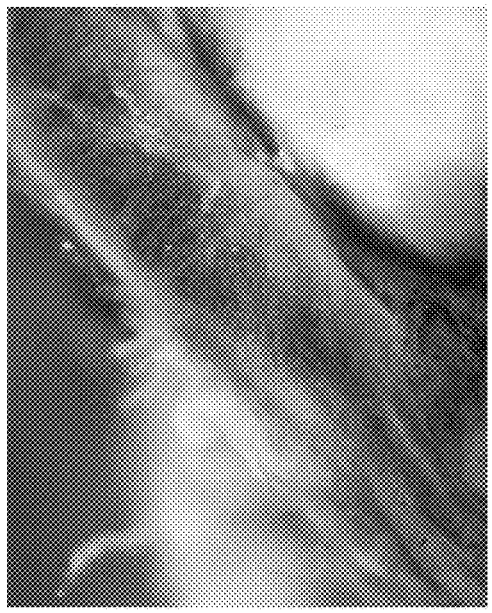
Figure 44C:
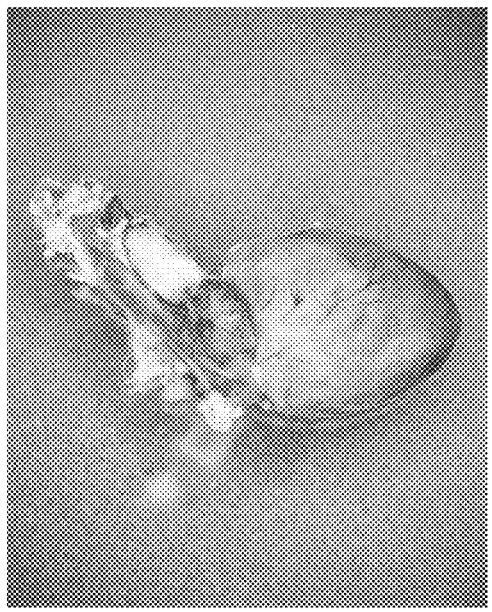
Figure 45B:
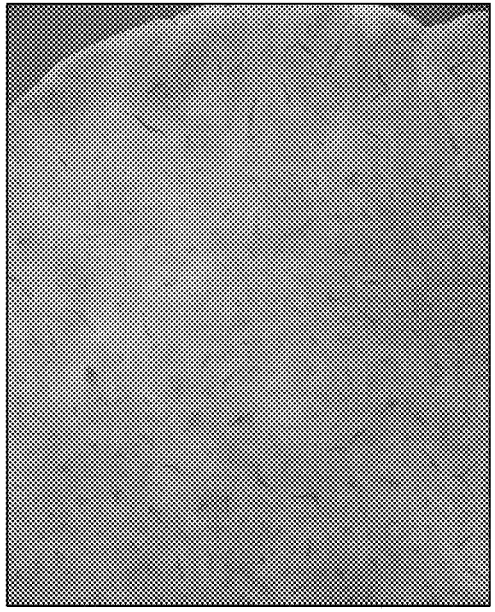
FIG. 45A-D show 12-week-old female rat livers stained with X-gal.
Figure 45D:
Figure 45A:
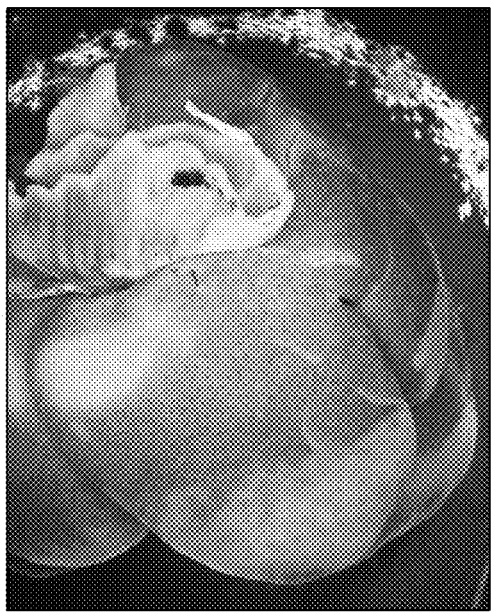
Figure 45C:
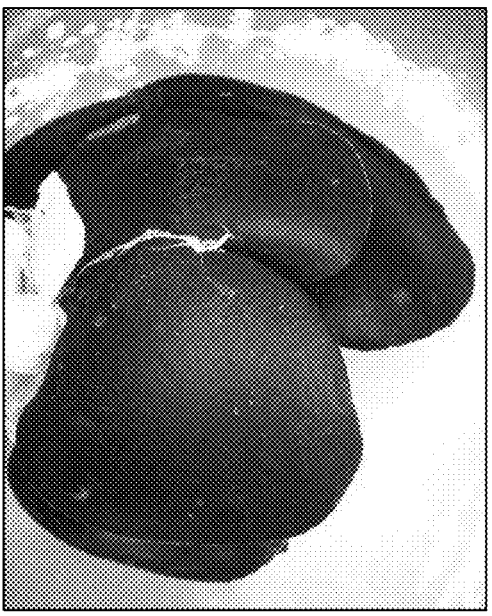
Figure 46A:
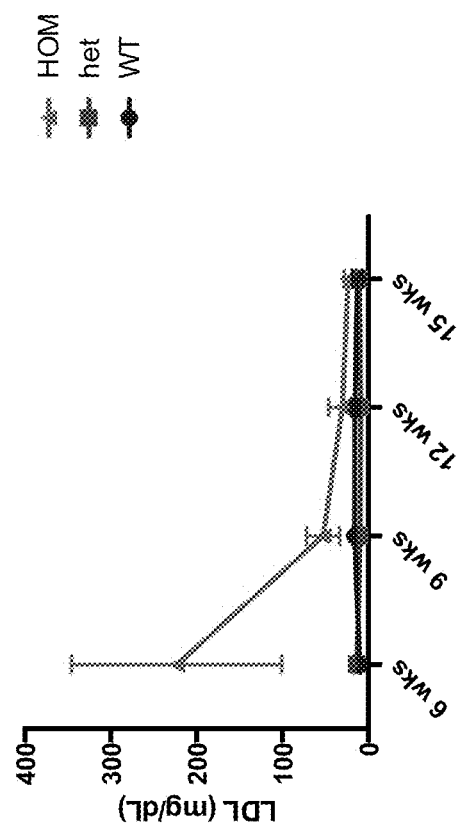
FIG. 46A-D show detection of cholesterol (FIG. 46A), LDL (FIG. 46B), HDL (FIG. 46C), and triglyceride levels (FIG. 46D) in homozygous ApoE-targeted rats, heterozygous ApoE-targeted rats, and wild type rats at 6 weeks, 9 weeks, 12 weeks, and 15 weeks.
Figure 46C:
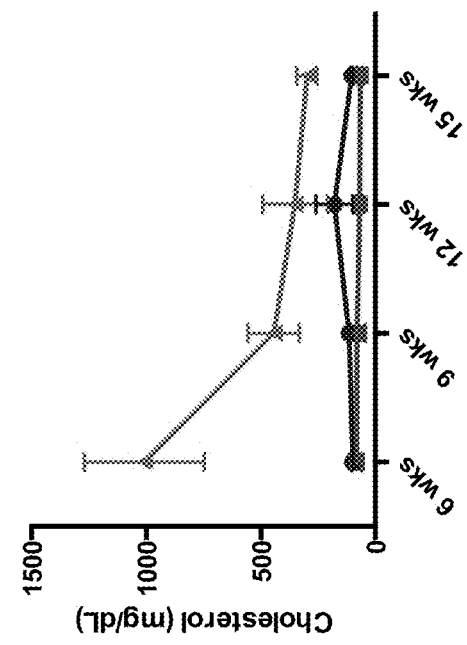
Figure 46B:
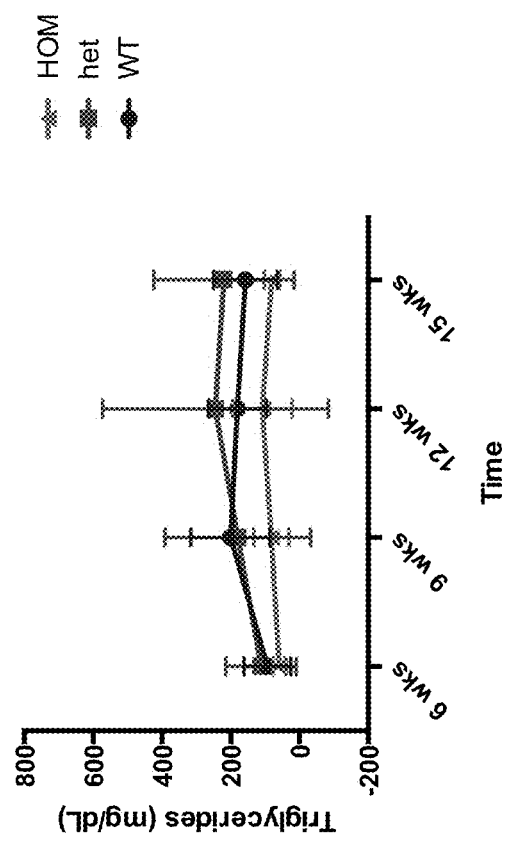
Figure 46D:
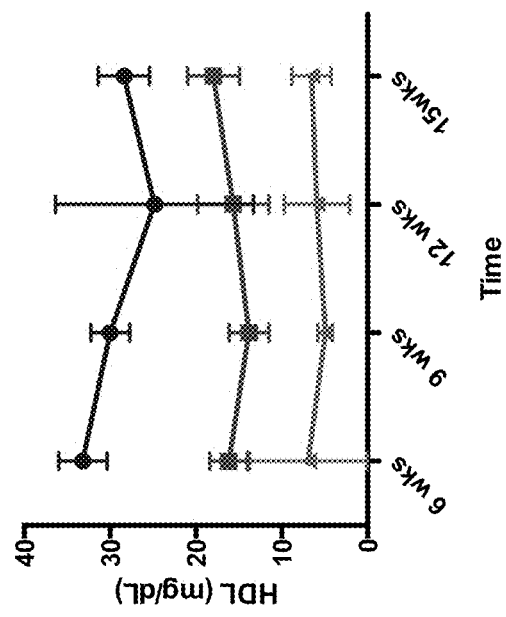

In another experiment, the LTVEC was designed to create a 79 kb deletion of the mouse Dpp4 (dipeptidyl peptidase 4) gene and a simultaneous replacement with an 82 kb fragment of the homologous human DPP4 gene (FIG. 42). The LTVEC comprised the 82 kb fragment of the human DPP4 gene flanked by 5' and 3' homology arms, each containing 46 kb of genomic DNA derived from parts of the mouse Dpp4 locus that flank the 79 kb sequence of the mouse Dpp4 gene intended for deletion. In separate experiments, we combined the Dpp4 humanizing LTVEC with a plasmid encoding Cas9 and a second plasmid encoding one of eight sgRNAs (gA, gB, gB2, gC, gD, gE, gE2, and gF) designed to create double strand breaks within the region of the mouse Dpp4 gene that was targeted for deletion. The sgRNAs were designed to avoid recognition of any sequence in the inserted portion of the human DPP4 gene.

The results of the CRISPR/Cas9-assisted humanization of the Dpp4 gene are shown in Table 41. When the LTVEC alone was introduced into ES cells, we found that 2.1% of the screened drug resistant clones carried a correctly targeted monoallelic heterozygous humanized allele. In contrast, combining the LTVEC with Cas9 endonuclease guided by any one of eight tested sgRNAs (A, B, B2, C, D, E, E2, and F; sequences provided in Table 43) produced correctly targeted monoallelic heterozygous mutations at efficiencies that ranged from 2.1 to 7.3%.

TABLE 41

Screening Results for CRISPR/Cas9-Assisted Humanization of the Dpp4 Gene.

| sgRNA Position | Approximate Distance from Deletion Endpoint (bp) | gRNA | CRISPR Activity (%) | Clones Screened | Heterozygous Targeted | Compound Heterozygous | Homozygous Targeted |
|---|---|---|---|---|---|---|---|
| 5' | 50 | gRNA A | no assay | 96 | 7 | 0 | 0 |
| 5' | 400 | gRNA B | no assay | 96 | 2 | 0 | 0 |
| 5' | 900 | gRNA B2 | no assay | 96 | 5 | 0 | 0 |
| middle | 38800/40200 | gRNA C | no assay | 96 | 3 | 0 | 0 |
| middle | 40800/38100 | gRNA D | no assay | 96 | 3 | 0 | 0 |
| 3' | 900 | gRNA E2 | no assay | 96 | 2 | 0 | 0 |
| 3' | 500 | gRNA E | no assay | 96 | 6 | 0 | 0 |
| 3' | 200 | gRNA F | no assay | 96 | 5 | 0 | 0 |
| N/A | N/A | none | N/A | 96 | 2 | 0 | 0 |

A table summarizing the results for CRISPR/Cas9-assisted humanization of the various mouse genes is provided in Table 42. The first row indicates the gene locus being targeted. The second row indicates the deletion size (Del) of the endogenous mouse locus and the insertion size (Ins) of the corresponding human locus. The remaining rows show the number of colonies (out of 96) for each condition that had correctly targeted monoallelic heterozygous mutations, biallelic compound heterozygous mutations, or biallelic homozygous mutations. "No gRNA" represents LTVEC alone, whereas the other rows represent LTVEC plus corresponding gRNAs (indicated by relative position within the deletion locus).

TABLE 42

Summary of CRISPR/Cas9-Assisted Humanization of Mouse Genes.

| | Lrp5 | Trpa1 | Folh1 | C5 (Hc) | Adamts5 | Erbb4 | Ror1 | Dpp4 |
|---|---|---|---|---|---|---|---|---|
| Del/Ins (kb) | 68/91 | 45/55 | 55/61 | 76/97 | 38/43 | 102/127 | 110/134 | 79/82 |

TABLE 42-continued

Summary of CRISPR/Cas9-Assisted Humanization of Mouse Genes.

|         | Lrp5 | Trpa1 | Folh1 | C5 (Hc) | Adamts5 | Erbb4 | Ror1 | Dpp4 |
|---------|------|-------|-------|---------|---------|-------|------|------|
| Most 5' | 7    | 1     | 2     | 16      | 0       | 0     | 0    | 7    |
| 5'      | 4    | 2     | 0     | 14      | 0       | 0     | 0    | 2    |
| 5'      | 7    | 3     | N/A   | N/A     | 1       | 0     | N/A  | 5    |
| Middle  | 4    | 1     | 0     | 11      | 0       | 0     | 1    | 3    |
| Middle  | 7    | 2     | 1     | 7       | 0       | 1     | 0    | 3    |
| 3'      | 2    | 0     | N/A   | N/A     | 1       | 0     | N/A  | 2    |
| 3'      | 0    | 0     | 1     | 4       | 0       | 0     | 0    | 6    |
| Most 3' | 6    | 2     | 0     | 6       | 0       | 0     | 1    | 5    |
| No gRNA | 1    | 1     | 0     | 1       | 0       | 0     | 0    | 2    |

TABLE 43

Guide RNA Sequences Used for CRISPR/Cas9-Assisted Humanization of Mouse Genes.

| gRNA | Guide Sequence (5' to 3') | SEQ ID NO |
|------|---------------------------|-----------|
| Trpa1 gRNA A | GTACTGGGGAATCGGTGGTC | 30 |
| Trpa1 gRNA A2 | CACGCACTCCAAATTTATCC | 31 |
| Trpa1 gRNA B | CTAAGTGTGTATCAGTACAT | 32 |
| Trpa1 gRNA C | TGCCCTGCACAATAAGCGCA | 33 |
| Trpa1 gRNA D | ACTCATTGAAACGTTATGGC | 34 |
| Trpa1 gRNA E2 | AGTAAGGGTGGATTAAATTC | 35 |
| Trpa1 gRNA E | GCCATCTAGATTCATGTAAC | 36 |
| Trpa1 gRNA F | GACTAGAAATGTTCTGCACC | 37 |
| Folh1 gRNA A | TGAACCAATTGTGTAGCCTT | 38 |
| Folh1 gRNA A2 | AATAGTGGTAAAGCACCATG | 39 |
| Folh1 gRNA B | GTGTGCTAAGGATCGAAGTC | 40 |
| Folh1 gRNA C | CACCGAGATGCTTGGGTATT | 41 |
| Folh1 gRNA D | TGTAACCGCCCTGAATGACC | 42 |
| Folh1 gRNA E | AAAAGGGCATCATAAATCCC | 43 |
| Folh1 gRNA E2 | TCAAAAATAGTCATACACCT | 44 |
| Folh1 gRNA F | GGTCTCTAGTACATTGTAGA | 45 |
| C5 (He) gRNA A | ATCACAAACCAGTTAACCGG | 46 |
| C5 (He) gRNA B | TTTCAGACGAGCCGACCCGG | 47 |
| C5 (He) gRNA B2 | CTGTCAACAGTGCCGCGTTT | 48 |
| C5 (He) gRNA C | TGTGTGTCATAGCGATGTCG | 49 |
| C5 (He) gRNA D | AACAGGTACCCTATCCTCAC | 50 |
| C5 (He) gRNA E2 | TCGTGGTTGCATGCGCACTG | 51 |
| C5 (He) gRNA E | GGCCCGGACCTAGTCTCTCT | 52 |
| C5 (He) gRNA F | AGTCTGTAAAGTTAGCAGTC | 53 |
| Adamts5 gRNA A | GGTGGTGGTGCTGACGGACA | 54 |
| Adamts5 gRNA A2 | TATGAGATCAACACTCGCTA | 55 |
| Adamts5 gRNA B | CCAAGGACTTCCCCACGTTA | 56 |
| Adamts5 gRNA C | TGCTTCCCTTATGCAAGATT | 57 |
| Adamts5 gRNA D | TTAGGTACCCTATTTGAATA | 58 |
| Adamts5 gRNA E2 | TGCAGTGGGTGACAGGTCCA | 59 |
| Adamts5 gRNA E | AGGGTTATACTGACGTTGTG | 60 |
| Adamts5 gRNA F | TGTCTTTCAAGGAGGGCTAC | 61 |
| Erhh4 gRNA A | TGATGTGCAGTCAGACAAAG | 62 |
| Erhh4 gRNA B | TGCACTATGGTTGACTATGA | 63 |
| Erhh4 gRNA B2 | GGAATATTCTAATAGGAAGT | 64 |
| Erhh4 gRNA C | AAGTGCTGTACCATTCTAGC | 65 |
| Erhh4 gRNA D | TAATCAATAGACAACCTCGT | 66 |
| Erhh4 gRNA E2 | TCATTCCTAATGGTATTATA | 67 |
| Erhh4 gRNA E | AGGGTACATAGATGGCATCG | 68 |
| Erhh4 gRNA F | CTCTTTAACAATTACCACTT | 69 |
| Ror1 gRNA A | TGTGGGCCTTTGCTGATCAC | 70 |
| Ror1 gRNA B | AATCTATGATCCTATGGCCT | 71 |
| Ror1 gRNA D | TGCCAATAGCAGTGACTTGA | 72 |
| Ror1 gRNA C | GGGAAGAATGGGCTATTGTC | 73 |
| Ror1 gRNA E | GGTTGTTTGTGCTGATGACG | 74 |
| Ror1 gRNA F | CCGTCCTAGGCCTTCTACGT | 75 |
| Dpp4 gRNA A | ACTAGTAGACCTGAGGGGTT | 76 |
| Dpp4 gRNA B | GCTCCAGTGTTTAGGCCTTG | 77 |
| Dpp4 gRNA B2 | GGCAAGCTGAAAACGCATGC | 78 |
| Dpp4 gRNA C | GTAGATCGCTTTCCACTACC | 79 |
| Dpp4 gRNA D | GAACTCCACTGCTCGTGAGC | 80 |
| Dpp4 gRNA E2 | ATAGGTGGGCACTATTGAAG | 81 |
| Dpp4 gRNA E | ATGGGAAGGTTTATACCAGC | 82 |
| Dpp4 gRNA F | CGGTGTAAAAACAACGGGAA | 83 |

Example 5. Summary of Targeted Modification of Rat Genomic Loci

Table 44. Summary of rat targeting with various vector types and nuclease agents discussed in Examples 3 and 4.

TABLE 44

| Example # | Locus | Vector | Colonies screened | Targeted Clones | Targeting efficiency | Biallelic targeted | Biallelic efficiency | Clones Injected | Clones producing chimeras | Clones transmitting through germline | Notes |
|---|---|---|---|---|---|---|---|---|---|---|---|
| 3.2(a)(ii) | ApoE | plasmid | 384 | 23 | 5.99% | 0 | 0 | 3 | 3 | 1 | |
| 3.2(a)(iii) | ApoE + ZFN | plasmid | 384 | 290 | 75.52% | 8 | 2.08% | 2 | 2 | 1 | These 2 clones are biallelic targeted |
| 3.3(a) | Il2rg | plasmid | 232 | 5 | 2.16% | N/A | N/A | 6 | 5 | 1 | |
| 3.2(b)(ii) | ApoE LTVEC | LTVEC | 288 | 8 | 2.78% | 1 | 0.35% | 3 | 1 | 0 | |
| 3.2(b)(iii) | ApoE LTVEC + ZFN | LTVEC | 288 | 16 | 5.56% | 1 | 0.35% | 1 | N/A | 0 | This clone is biallelic targeted |
| 3.2(b)(iv) | ApoE LTVEC | LTVEC | 75 | 32 | 42.67% | 0 | 0 | | | | |
| 3.2(b)(iv) | ApoE LTVEC + CRISPR/Cas9 | LTVEC | 169 | 84 | 50% | 5 | 3% | 0 | 0 | 0 | |
| 4.3(a) | Il2rg Humanization 1 | plasmid | 168 | 6 | 3.57% | N/A | N/A | 1 | 1 | 0 | replaces entire rat Il2rg with human Il2rg |
| 4.3(b)(i) | Il2rg Humanization 2 | plasmid | 192 | 13 | 6.77% | N/A | N/A | 2 | 2 | 0 | replaces rat Il2rg ecto-domain with human Il2rg ecto-domain |
| 4.3(b)(ii) | Il2rg Humanization 2 | plasmid | 77 | 46 | 59.74% | | | | | | |
| 4.3(b)(ii) | Il2rg Humanization 2 + CRISPR/Cas9 | plasmid | 172 | 104 | 60.47% | N/A | N/A | 0 | 0 | 0 | replaces rat Il2rg ecto-domain with human Il2rg ecto-domain |
| 3.4(a)(i) | Rag2 | LTVEC | 270 | 0 | 0 | 0 | 0 | 0 | 0 | 0 | Predicted 5.7 KB deletion |
| 3.4(a)(ii) | Rag2 LTVEC | LTVEC | 36 | 0 | 0 | 0 | 0 | | | | |
| 3.4(a)(ii) | Rag2 LTVEC + CRISPR/Cas9 | LTVEC | 39 | 6 | 15.38% | 1 | 2.5% | 1 | 1 | 0 | |
| 3.4(b)(i) | Rag1-2 | LTVEC | 256 | 1 | 0.39% | 0 | 0 | 1 | 1 | 0 | Predicted 16.2 kb deletion |
| 3.4(b)(ii) | Rag1-2 | LTVEC | 94 | 80 | 85% | 0 | 0 | 0 | 0 | 0 | Rag1-2 LTVEC was electroporated into Il2rg-CG12 mutant clone (retargeting) |

Table 45 shows a summary of the targeting of rat ES cells with either plasmids or LTVECs in combination with CRISPR/Cas9. Two gRNAs were tested separately for each targeted locus: Rag2, ApoE, and Il2rg. The cleavage efficiency of CRISPR/Cas9 was >20% at all three loci. Increased targeting efficiency and increased biallelic targeting was observed when CRISPR/Cas9 was used in combination with the targeting plasmids and LTVECs.

TABLE 45

Summary of Rat ES Cell Targeting with Plasmids or LTVECs in Combination with CRISPR/Cas9

| Condition | Targeting efficiency | Biallelic Targeting |
| --- | --- | --- |
| Rag2 (LTVEC) | 0 | 0 |
| Rag2 (LTVEC + CRISPR) | 6-22% | 0-4% |
| ApoE (LTVEC) | 43% | 0 |
| ApoE (LTVEC + CRISPR) | 47-53% | 1-4% |
| Il2rg Humanization (plasmid vector) | 60% | N/A (X-linked) |
| Il2rg Humanization (plasmid + CRISPR) | 57-64% | N/A (X-linked) |

Table 46 shows a summary of germline transmission data for targeted modification of rat genomic loci. Germline transmission was confirmed for ApoE-targeted rats and Il2rg-targeted rats. The rat ES cells were XY (male) and were heterozygous targeted. Therefore, when the targeted ES cells contribute to the germline, approximately 50% of the sperm derived from the ES cells will carry the mutant allele and will produce heterozygous F1 pups.

TABLE 46

Germline Transmission Data for Targeted Modification of Rat Genomic Loci

| Targeted Gene | Clones Microinjected | Clones Producing Chimeras | Clones Achieving Germline Transmission | Germline Pups/Total Pups | Heterozygous F1 Pups* | Heterozygous Pups in Which Neo Cassette Was Deleted |
| --- | --- | --- | --- | --- | --- | --- |
| ApoE | 3 | 3 | 1 | 7/79 (9%) | 4 | 4 |
| Il2rg | 5 | 5 | 1 | 11/257 (5%) | 5 | 5 |

Example 6. Generating, Maintaining, and Targeting Human Induced Pluripotent Stem Cells 6.1. Generation of Human iPS Cells This example describes the generation of human iPS cells from non-pluripotent human cells. PiggyBac (System Biosciences) vectors (PB-600A_CAGGS Bst XI (0.64 µg/µL) and PB-200 (0.99 µg/µL) comprising the genes that encode four reprogramming factors (hOct4, hSox2, hKLF-4, hMYC) operably linked to a CM7 promoter were introduced into neonatal human foreskin fibroblasts using RED and BLUE GeneIn™ transfection reagents (GlobalStem). The transfected cells were incubated on NuFF1 feeder cells in E7 medium to allow for incorporation of the vectors and expression of the reprogramming factors. E7 medium comprised DMEM/F-12, NaHCO$_3$, L-ascorbic acid, insulin, transferrin, selenium, and FGF-2.

Puromycin selection began 10 days after transfection using 2 µg/mL puromycin in E7 medium. At day 21, colonies were selected and cultured in mTeSR™ medium, which comprised DMEM/F-12, NaHCO$_3$, L-ascorbic acid, insulin, transferrin, selenium, FGF-2, TGFβ1, glutathione, L-glutamine, defined lipids, thiamine, trace elements B and C, β-mercaptoethanol, bovine serum albumin, pipecolic acid, lithium chloride, and GABA. At days 29 to 57, cells were propagated and passaged in mTeSR™ medium until reaching ~50% confluent in 6 well plates. At days 65 to 73, propagation and passage continued using mTeSR™ medium and Gentle Cell Dissociation Reagent (Stem Cell Technologies). At day 76, medium was changed to low osmolality VG2i medium for further propagation, passage, and maintenance of the cells comprising naïve or naïve-looking hiPSCs.

6.2. LTVEC Targeting in Human iPS Cells

This example describes the use of LTVEC targeting in human iPS cells. As shown in FIG. 51, we introduced by electroporation into human iPS cells propagated in VG2i medium the following nucleic acid molecules: (1) an LTVEC (0.67 µg); (2) a plasmid encoding a Cas9 endonuclease (5 µg); and (3) a plasmid encoding a CRISPR single guide RNA (gRNA) (10 µg). In one set of samples, the Cas9 and gRNA were excluded. Specifically, 3×10$^6$ cells were electroporated at a voltage of 700V, a capacitance of 25 uF, and a resistance of 400 ohms. The LTVEC comprised a 16.7 kb nucleic acid comprising mouse Adam6a and Adam6b genes flanked by homology arms containing 34 kb and 105 kb of genomic DNA derived from genomic regions that flank the 4.1 kb sequence of the human ADAM6 locus intended for deletion. The LTVEC also carried a drug selection cassette that directs the expression of an enzyme that imparts resistance to an antibiotic drug (hygromycin). The human ADAM6 gRNA used had the following sequence: GTATAGCCCTGTTACACATT (SEQ ID NO: 94).

Cells that took up the LTVEC and incorporated it into their genomes were able to grow and form colonies on a GELTREX™-coated tissue culture dish in a growth medium containing the antibiotic drug. Because we introduced 500 to 1,000 times more CRISPR/Cas9-encoding nucleic molecules than LTVEC molecules, most of the LTVEC-containing drug resistant colonies also contained, at least transiently, the CRISPR/Cas9 components. We picked drug resistant colonies and screened them by the loss-of-allele method (Valenzuela et al. (2003) Nat. Biotech. 21:652-660; Frendewey et al. (2010) Methods Enzymol. 476:295-307; incorporated herein by reference in their entireties) to identify clones that had the correctly targeted allele.

The results of the CRISPR/Cas9-assisted LTVEC targeting of the ADAM6 locus are shown in Table 47.

TABLE 47

CRISPR/Cas9-assisted LTVEC targeting

| | Targeting Efficiency |
| --- | --- |
| LTVEC Only | 3.1% |
| LTVEC + CRISPR | 7.3% |

When the LTVEC alone was introduced into human iPS cells, a targeting efficiency of 3.1% was observed. In contrast, combining the LTVEC with Cas9 guided by the ADAM6 gRNA resulted in a targeting efficiency of 7.3%.

6.3. Effect of Low Osmolality Medium on Human iPS Cell Morphology

This example describes the effect of salt concentration, ionic strength, and/or osmolality on the pluripotency state of human iPS cells in culture. Human iPS cells were cultured on a MATRIGEL™ or GELTREX™ substrate in a medium described in Table 48 or in mTeSR™-hLIF medium.

TABLE 48

Medium for iPS cell culture.

| Component | Amount (v/v) |
|---|---|
| Base Medium | 24.75 |
| F-12 Medium | 24.75 |
| N2 ® Supplement | 0.5 |
| Neurobasal ® Medium | 49 |
| B-27 ® Supplement | 1 |
| Penicillin/Streptomycin | 1 |
| L-Glutamine (200 mM) | 1 |
| 2-Mercaptoethanol (55 mM) | 0.1836 |
| hLIF (1 × 10$^4$ units/mL) | 0.001 |
| CHIR99021 (10 mM) | 0.03 |
| PD0325901 (10 mM) | 0.005 |

When the base medium used was DMEM, this medium was referred to as 2i medium. When the base medium used was VG-DMEM, this low osmolality medium was referred to as VG2i medium. The osmolality of VG2i medium (233 mOsm/kg) is lower than the osmolality of traditional 2i medium (261 mOsm/kg).

As shown in FIG. 52, human iPS cells cultured on MATRIGEL™ in 2i medium for a period of 8 days (FIG. 52A) or 12 days (FIG. 52B) displayed a morphology characteristic of iPS cells in a primed state, particularly growth in an epithelial monolayer and the appearance of apico-basal polarity.

mTeSR-hLIF medium and VG2i medium were further evaluated for their effects on the morphology and pluripotency state of human iPS cells. In this study, human iPS cells were cultured on MATRIGEL™ or NuFF feeder cells in mTeSR™-hLIF medium (FIGS. 53A and 53C) or in VG2i medium (FIGS. 53B and 53D) for a period of 6 days. When cultured in mTeSR™-hLIF medium on MATRIGEL™ or NuFF feeder cells, human iPS cells displayed a morphology characteristic of a primed pluripotency state, particularly growth in an epithelial monolayer and the appearance of apico-basal polarity. Some cells cultured in mTeSR™-hLIF medium began to display a morphology characterized by three-dimensional clumping. By contrast, when cultured in VG2i medium on MATRIGEL™ or NuFF feeder cells, the human iPS cells displayed a morphology characteristic of a naïve pluripotency state, particularly growth in round, dome-shaped colonies and a lack of apico-basal polarity.

6.4. Effect of Low Osmolality Medium on the Expression of Pluripotency Markers in Human iPS Cells This example describes the effect of salt concentration, ionic strength, and/or osmolality on the expression of pluripotency markers in human iPS cells that have been reprogrammed from a primed state to a naïve state. Following 24 days of culture in VG2i medium on a MATRIGEL™ substrate, reprogrammed naïve human iPS cells were stained for the expression of alkaline phosphatase or NANOG. It was observed that the reprogrammed cells strongly expressed both alkaline phosphatase (FIG. 54A) and NANOG (FIGS. 54B and 54C), which are indicative of a naïve pluripotency state.

6.5. Effect of Low Osmolality Medium on Enzymatic Dissociation and Subculture of Human iPS Cells In this example, human iPS cells that were reprogrammed to a naïve state using low osmolality VG2i medium were enzymatically dissociated using trypsin to create a single cell suspension (FIG. 55A). The cell suspension was passaged onto new GELTREX™-coated plates for subculture in VG2i medium. It was observed after 1 day (FIG. 55B) and 4 days (FIG. 55C) that the subcultured cells continued to display a morphology characteristic of cells in a naïve pluripotency state. Particularly, the cells grew as rounded dome-shaped colonies and did not exhibit an apico-basal polarity. It was notable that enzymatic dissociation could be performed in the absence of a ROCK inhibitor, which is typically necessary to prevent activation of pro-apoptotic pathways. This suggests that pro-apoptotic pathways are not as strongly activated during enzymatic dissociation and subculture in naïve human iPS cells cultured under the conditions identified herein.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. Unless otherwise apparent from the context of any embodiment, aspect, step or feature of the invention can be used in combination with any other. Reference to a range includes any integers within the range, any subrange within the range. Reference to multiple ranges includes composites of such ranges.

We claim:

1. An in vitro method for modifying a genome at a genomic locus of interest in a mouse embryonic stem (ES) cell, comprising contacting the genome with:
   (a) a Clustered Regularly Interspaced Short Palindromic Repeats (CRISPR)-associated 9 (Cas9) endonuclease;
   (b) a CRISPR RNA (crRNA) that hybridizes to a CRISPR target sequence at the genomic locus of interest;
   (c) a trans-activating CRISPR RNA (tracrRNA); and
   (d) a large targeting vector (LTVEC) comprising an insert nucleic acid that is at least 20 kb in size flanked by:
      (i) a 5' homology arm that is homologous to a 5' target sequence at the genomic locus of interest; and
      (ii) a 3' homology arm that is homologous to a 3' target sequence at the genomic locus of interest,
      wherein the 5' homology arm is at least 5 kb and/or the 3' homology arm is at least 5 kb, and
   wherein following the contacting, the genome of the mouse ES cell is modified to comprise a targeted genetic modification comprising insertion of the insert nucleic acid at the genomic locus of interest, wherein the insertion is at least 20 kb.

2. The method of claim 1, wherein the method comprises introducing into the mouse ES cell:
   (a) the Cas9 endonuclease, wherein the Cas9 endonuclease is introduced in the form of a protein, a messenger RNA (mRNA) encoding the Cas9 endonuclease, or a DNA encoding the Cas9 endonuclease;
   (b) the crRNA, wherein the crRNA is introduced in the form of an RNA or a DNA encoding the crRNA;
   (c) the tracrRNA, wherein the tracrRNA is introduced in the form of an RNA or a DNA encoding the tracrRNA; and
   (d) the LTVEC.

3. The method of claim 2, wherein the crRNA and the tracrRNA are introduced as a single nucleic acid molecule comprising the crRNA and the tracrRNA.

4. The method of claim 2, wherein the method comprises introducing into the mouse ES cell:
   (a) the crRNA, the tracrRNA, and the Cas9 endonuclease;
   (b) the crRNA, the tracrRNA, and the mRNA encoding the Cas9 endonuclease; or
   (c) the DNA encoding the crRNA, the DNA encoding the tracrRNA, and the DNA encoding the Cas9 endonuclease.

5. The method of claim 4, wherein the Cas9 endonuclease, the crRNA, and the tracrRNA are introduced as a protein-RNA complex.

6. The method of claim 4, wherein the method comprises introducing into the mouse ES cell the DNA encoding the crRNA, the DNA encoding the tracrRNA, and the DNA encoding the Cas9 endonuclease, and wherein:
   (I) (a) the DNA encoding the Cas9 endonuclease is in a first expression construct comprising a first promoter operably linked to a first nucleic acid encoding the Cas9 endonuclease;
   (b) the DNA encoding the crRNA is in a second expression construct comprising a second promoter operably linked to a second nucleic acid encoding the crRNA; and (c) the DNA encoding the tracrRNA is in a third expression construct comprising a third promoter operably linked to a third nucleic acid encoding the tracrRNA;

wherein the first, second, and third promoters are active in the mouse ES cell, and wherein the first, second, and third expression constructs are on a single nucleic acid molecule or on multiple nucleic acid molecules; or (II) (a) the DNA encoding the Cas9 endonuclease is in a first expression construct comprising a first promoter operably linked to a first nucleic acid encoding the Cas9 endonuclease; and (b) the DNA encoding the crRNA and the DNA encoding the tracrRNA are in a second expression construct comprising a second promoter operably linked to a second nucleic acid encoding the crRNA and the tracrRNA;

wherein the first and second promoters are active in the mouse ES cell, and wherein the first and second expression constructs are on a single nucleic acid molecule or on separate nucleic acid molecules.

7. The method of claim 1, wherein the insert nucleic acid is at least 50 kb in size.

8. The method of claim 7, wherein the insert nucleic acid is at least 100 kb in size.

9. The method of claim 1, wherein the insertion is at least 50 kb in size.

10. The method of claim 9, wherein the insertion is at least 100 kb in size.

11. The method of claim 1, wherein the crRNA and the tracrRNA are fused together in the form of a single guide RNA (sgRNA).

12. The method of claim 1, wherein the crRNA and the tracrRNA are separate molecules.

13. The method of claim 1, wherein the targeted genetic modification comprises simultaneous deletion of an endogenous nucleic acid sequence at the genomic locus of interest and insertion of the insert nucleic acid at the genomic locus of interest.

14. The method of claim 13, wherein the deletion is at least 20 kb, and the insert nucleic acid is at least 20 kb, at least 50 kb, or at least 100 kb.

15. The method of claim 13, wherein the deleted endogenous nucleic acid sequence is from 30 kb to 110 kb, and the insert nucleic acid is from 40 kb to 140 kb.

16. The method of claim 1, wherein the targeted genetic modification is a biallelic modification.

17. The method of claim 16, wherein:
(a) the biallelic genetic modification comprises deletion of an endogenous nucleic acid sequence and insertion of the insert nucleic acid at the genomic locus of interest in two homologous chromosomes; or
(b) the modified mouse ES cell is compound heterozygous or hemizygous at the genomic locus of interest.

18. The method of claim 17, wherein the targeted genetic modification at the genomic locus of interest in one chromosome comprises deletion of an endogenous nucleic acid sequence and insertion of the insert nucleic acid.

19. The method of claim 18, wherein the targeted genetic modification comprises: (1) deletion of an endogenous nucleic acid sequence at the genomic locus of interest in first and second homologous chromosomes; and (2) insertion of the insert nucleic acid into the genomic locus of interest in the first homologous chromosome and disruption of the genomic locus of interest in the second homologous chromosome.

20. The method of claim 1, wherein the CRISPR target sequence is immediately flanked by a Protospacer Adjacent Motif (PAM) sequence.

21. The method of claim 1, wherein the targeted genetic modification comprises:
(I) replacement of an endogenous nucleic acid sequence with a homologous nucleic acid sequence or an orthologous nucleic acid sequence;
(II) deletion of an endogenous nucleic acid sequence;
(III) insertion of an exogenous nucleic acid sequence;
(IV) insertion of an exogenous nucleic acid sequence comprising a homologous nucleic acid sequence or an orthologous nucleic acid sequence;
(V) insertion of a selectable marker; or
(VI) a combination thereof.

22. The method of claim 21, wherein the targeted genetic modification comprises insertion of one or more human antibody heavy chain variable domains, one or more human kappa light chain variable domains, or one or more human lambda light chain variable domains.

23. The method of claim 1, wherein the crRNA is designed to avoid recognition of any sequence in the insert nucleic acid.

24. The method of claim 1, wherein the targeted genetic modification comprises a deletion of a region of the genomic locus of interest, and the CRISPR target sequence is within the region of the genomic locus of interest targeted for deletion.

25. The method of claim 24, wherein the CRISPR target sequence is within the 5' end of the region of the genomic locus of interest targeted for deletion or the 3' end of the region of the genomic locus of interest targeted for deletion.

26. The method of claim 25, wherein the CRISPR target sequence is 50 to 1000 base pairs from the 5' deletion endpoint or the 3' deletion endpoint.

27. The method of claim 1, wherein the CRISPR target sequence is located in an intron, an exon, a promoter, an enhancer, a regulatory region, or any non-protein coding region.

28. The method of claim 1, wherein the CRISPR target sequence is located within a coding region of a gene or within a regulatory region that influences expression of the gene.

29. The method of claim 1, wherein the crRNA and the tracrRNA are part of a guide RNA that comprises SEQ ID NO: 2, 3, 4, 5, 6, 7, or 8.

30. The method of claim 1, wherein the LTVEC is at least 40 kb.

31. The method of claim 1, wherein the insert nucleic acid is from 40 kb to 140 kb.

32. The method of claim 1, wherein the sum total of the 5' and the 3' homology arms of the LTVEC is from 10 kb to 150 kb.

33. The method of claim 1, wherein the targeted genetic modification comprises:
(a) replacement of an endogenous nucleic acid sequence with a homologous nucleic acid sequence or an orthologous nucleic acid sequence;
(b) deletion of an endogenous nucleic acid sequence;
(c) deletion of an endogenous nucleic acid sequence, wherein the deletion ranges from at least 20 kb to 3 Mb;
(d) insertion of an exogenous nucleic acid sequence;
(e) insertion of an exogenous nucleic acid sequence ranging from at least 20 kb to 400 kb;

(f) insertion of an exogenous nucleic acid sequence comprising a homologous or an orthologous nucleic acid sequence;
(g) insertion of a chimeric nucleic acid sequence comprising a human and a non-human nucleic acid sequence;
(h) insertion of a conditional allele flanked by site-specific recombinase target sequences;
(i) insertion of a selectable marker or a reporter gene operably linked to a promoter active in the mouse ES cell; or
(j) a combination thereof.

34. The method of claim 1, wherein the targeted genetic modification comprises deletion of a region of the genomic locus of interest, wherein the deletion is at least 10 kb.

35. The method of claim 34, wherein the region of the genomic locus of interest deleted is from 30 kb to 110 kb.

36. The method of claim 1, wherein the targeted genetic modification comprises deletion of a region of the genomic locus of interest wherein the deletion is at least 30 kb and insertion of the insert nucleic acid at the genomic locus of interest wherein the insertion is at least 30 kb.

37. The method of claim 1, wherein the genomic locus of interest is endogenous to the mouse ES cell.

38. The method of claim 1, wherein the genomic locus of interest comprises a heterologous or exogenous segment of DNA that was integrated into the genome of the mouse ES cell.

39. The method of claim 1, wherein the genomic locus of interest is an immunoglobulin locus.

40. The method of claim 39, wherein the immunoglobulin locus encodes:
(a) a mouse immunoglobulin heavy chain variable region amino acid sequence; or
(b) a mouse immunoglobulin light chain variable region amino acid sequence.

41. The method of claim 40, wherein the immunoglobulin locus comprises:
(a) an unrearranged mouse lambda and/or kappa light chain variable region nucleic acid sequence; or
(b) a rearranged mouse lambda and/or kappa light chain variable region nucleic acid sequence.

42. The method of claim 39, wherein the targeted genetic modification results in a humanized genomic locus comprising: (a) an insertion of a homologous human nucleic acid sequence or an orthologous human nucleic acid sequence; (b) a replacement of an endogenous nucleic acid sequence with a homologous human nucleic acid sequence or an orthologous human nucleic acid sequence; or (c) a combination thereof.

43. The method of claim 39, wherein the targeted genetic modification comprises a replacement of an endogenous mouse nucleic acid sequence with a homologous human nucleic acid sequence or an orthologous human nucleic acid sequence.

44. The method of claim 43, wherein the targeted genetic modification comprises deletion of a region of the genomic locus of interest wherein the deletion is at least 20 kb and insertion of the insert nucleic acid at the genomic locus of interest wherein the insertion is at least 20 kb.

45. The method of claim 44, wherein the deleted region is from 30 kb to 110 kb, and the insert nucleic acid is from 40 kb to 140 kb.

46. The method of claim 1, wherein the genomic locus of interest is a T cell receptor locus.

47. The method of claim 46, wherein the T cell receptor locus is a T cell receptor alpha locus.

48. The method of claim 46, wherein the targeted genetic modification results in a humanized genomic locus comprising: (a) an insertion of a homologous or orthologous human nucleic acid sequence; (b) a replacement of an endogenous nucleic acid sequence with a homologous or orthologous nucleic acid sequence; or (c) a combination thereof.

49. The method of claim 46, wherein the targeted genetic modification comprises a replacement of an endogenous mouse nucleic acid sequence with a homologous human nucleic acid sequence or an orthologous human nucleic acid sequence.

50. The method of claim 49, wherein the targeted genetic modification comprises deletion of a region of the genomic locus of interest wherein the deletion is at least 20 kb and insertion of the insert nucleic acid at the genomic locus of interest wherein the insertion is at least 20 kb.

51. The method of claim 50, wherein the deleted region is from 30 kb to 110 kb, and the insert nucleic acid is from 40 kb to 140 kb.

52. The method of claim 1, wherein the insert nucleic acid comprises a genomic nucleic acid sequence that encodes a human immunoglobulin heavy chain variable region amino acid sequence.

53. The method of claim 52, wherein the insert nucleic acid comprises:
(a) one or more functional human $V_H$ gene segments comprising $V_H1$-2, $V_H1$-3, $V_H1$-8, $V_H1$-18, $V_H1$-24, $V_H1$-45, $V_H1$-46, $V_H1$-58, $V_H1$-69, $V_H2$-5, $V_H2$-26, $V_H2$-70, $V_H3$-7, $V_H3$-9, $V_H$ 3-11, $V_H3$-13, $V_H3$-15, $V_H3$-16, $V_H3$-20, $V_H3$-21, $V_H3$-23, $V_H3$-30, $V_H3$-30-3, $V_H3$-30-5, $V_H3$-33, $V_H3$-35, $V_H3$-38, $V_H3$-43, $V_H3$-48, $V_H3$-49, $V_H3$-53, $V_H3$-64, $V_H3$-66, $V_H3$-72, $V_H3$-73, $V_H3$-74, $V_H4$-4, $V_H4$-28, $V_H4$-30-1, $V_H4$-30-2, $V_H4$-30-4, $V_H4$-31, $V_H4$-34, $V_H4$-39, $V_H4$-59, $V_H4$-61, $V_H5$-51, $V_H6$-1, $V_H7$-4-1, $V_H7$-81, or a combination thereof;
(b) one or more functional human D gene segments comprising D1-1, D1-7, D1-14, D1-20, D1-26, D2-2, D2-8, D2-15, D2-21, D3-3, D3-9, D3-10, D3-16, D3-22, D4-4, D4-11, D4-17, D4-23, D5-12, D5-5, D5-18, D5-24, D6-6, D6-13, D6-19, D6-25, D7-27, or a combination thereof; or
(c) one or more functional JH gene segments comprising $J_H1$, $J_H2$, $J_H3$, $J_H4$, $J_H5$, $J_H6$, or a combination thereof.

54. The method of claim 1, wherein the insert nucleic acid comprises a genomic nucleic acid sequence that encodes a human immunoglobulin light chain variable region amino acid sequence.

55. The method of claim 54, wherein the insert nucleic acid comprises:
(a) one or more human Vκ gene segments comprising Vκ4-1, Vκ5-2, Vκ7-3, Vκ2-4, Vκ1-5, Vκ1-6, Vκ3-7, Vκ1-8, Vκ1-9, Vκ2-10, Vκ3-11, Vκ1-12, Vκ1-13, Vκ2-14, Vκ3-15, Vκ1-16, Vκ1-17, Vκ2-18, Vκ2-19, Vκ3-20, Vκ6-21, Vκ1-22, Vκ1-23, Vκ2-24, Vκ3-25, Vκ2-26, Vκ1-27, Vκ2-28, Vκ2-29, Vκ2-30, Vκ3-31, Vκ1-32, Vκ1-33, Vκ3-34, Vκ1-35, Vκ2-36, Vκ1-37, Vκ2-38, Vκ1-39, Vκ2-40, or a combination thereof;
(b) one or more human $V_\lambda$ gene segments comprising $V_\lambda3$-1, $V_\lambda4$-3, $V_\lambda2$-8, $V_\lambda3$-9, $V_\lambda3$-10, $V_\lambda2$-11, $V_\lambda3$-12, $V_\lambda2$-14, $V_\lambda3$-16, $V_\lambda2$-18, $V_\lambda3$-19, $V_\lambda3$-21, $V_\lambda3$-22, $V_\lambda2$-23, $V_\lambda3$-25, $V_\lambda3$-27, or a combination thereof; or
(c) one or more human Jκ gene segments comprising Jκ1, Jκ2, Jκ3, Jκ4, Jκ5, or a combination thereof.

56. The method of claim 1, wherein the insert nucleic acid comprises a polynucleotide encoding at least a region of a human T cell receptor.

57. The method of claim 56, wherein the T cell receptor is a T cell receptor alpha.

58. The method of claim 1, wherein the genomic locus of interest comprises an Il2rg locus, an ApoE locus, a Rag1 locus, a Rag2 locus, both the Rag1 and the Rag2 loci, an Adamts5 locus, a Trpal locus, a Folhl locus, an Erbb4 locus, a Lrp5 locus, a C5(Hc) locus, a Ror 1 locus, or a Dpp4 locus.

59. The method of claim 58, wherein the targeted genetic modification comprises a replacement of an endogenous mouse nucleic acid sequence with a homologous human nucleic acid sequence or an orthologous human nucleic acid sequence.

60. The method of claim 59, wherein the targeted genetic modification comprises deletion of a region of the genomic locus of interest wherein the deletion is at least 20 kb and insertion of the insert nucleic acid at the genomic locus of interest wherein the insertion is at least 20 kb.

61. The method of claim 60, wherein the deleted region is from 30 kb to 110 kb, and the insert nucleic acid is from 40 kb to 140 kb.

62. The method of claim 1, wherein the insert nucleic acid comprises at least one disease allele.

63. The method of claim 62, wherein the insert nucleic acid comprises at least one human disease allele of a human gene.

64. The method of claim 63, wherein the targeted genetic modification comprises a replacement of an endogenous mouse nucleic acid sequence with a homologous human nucleic acid sequence or an orthologous human nucleic acid sequence.

65. The method of claim 64, wherein the targeted genetic modification comprises deletion of a region of the genomic locus of interest wherein the deletion is at least 20 kb and insertion of the insert nucleic acid at the genomic locus of interest wherein the insertion is at least 20 kb.

66. The method of claim 65, wherein the deleted region is from 30 kb to 110 kb, and the insert nucleic acid is from 40 kb to 140 kb.

67. The method of claim 1, wherein the LTVEC is from 20 kb to 250 kb in length,
wherein the sum total of the 5' and 3' homology arms is from 20 kb to 200 kb in length, and
wherein the targeted genetic modification comprises deletion of a region of the genomic locus of interest wherein the deletion is from 30 kb to 110 kb and insertion of the insert nucleic acid at the genomic locus of interest wherein the insertion is from 40 kb to 140 kb, and
wherein the guide RNA is designed to create a double strand break within a region of the genomic locus of interest targeted for deletion.

68. The method of claim 1, wherein the Cas9 endonuclease comprises a nuclear localization signal.

69. The method of claim 1, wherein the sum total of the 5' and the 3' homology arms of the LTVEC is at least 10 kb.

70. The method of claim 1, wherein the CRISPR target sequence is a native sequence that is endogenous to the cell.

71. The method of claim 1, wherein the sum total of the 5' and the 3' homology arms of the LTVEC is at least 10 kb, and
wherein the CRISPR target sequence is a native sequence that is endogenous to the cell.

72. The method of claim 1, wherein the CRISPR target sequence is immediately adjacent to the 5' target sequence or the 3' target sequence.

73. The method of claim 1, wherein the CRISPR target sequence is a native sequence that is endogenous to the cell, and wherein the sum total of the 5' and the 3' homology arms of the LTVEC is from 10 kb to 150 kb.

* * * * *

SEQUENCE LISTING

```
<160> NUMBER OF SEQ ID NOS: 94

<210> SEQ ID NO 1
<211> LENGTH: 23
<212> TYPE: DNA
<213> ORGANISM: Artificial Sequence
<220> FEATURE:
<223> OTHER INFORMATION: a genomic target sequence that is linked to a
      guide RNA (gRNA)
<220> FEATURE:
<221> NAME/KEY: misc_feature
<222> LOCATION: 2, 3, 4, 5, 6, 7, 8, 9, 10, 11, 12, 13, 14, 15, 16, 17,
      18, 19, 20, 21
<223> OTHER INFORMATION: n = A,T,C or G
```

```
<400> SEQUENCE: 1
gnnnnnnnnn nnnnnnnnnn ngg                                           23

<210> SEQ ID NO 2
<211> LENGTH: 80
<212> TYPE: RNA
<213> ORGANISM: Artificial Sequence
<220> FEATURE:
<223> OTHER INFORMATION: a guide RNA (gRNA)

<400> SEQUENCE: 2
guuuuagagc uagaaauagc aaguuaaaau aaggcuaguc cguuaucaac uugaaaaagu    60
ggcaccgagu cggugcuuuu                                               80

<210> SEQ ID NO 3
<211> LENGTH: 42
<212> TYPE: RNA
<213> ORGANISM: Artificial Sequence
<220> FEATURE:
<223> OTHER INFORMATION: a guide RNA (gRNA)

<400> SEQUENCE: 3
guuuuagagc uagaaauagc aaguuaaaau aaggcuaguc cg                      42

<210> SEQ ID NO 4
<211> LENGTH: 30
<212> TYPE: RNA
<213> ORGANISM: Artificial Sequence
<220> FEATURE:
<223> OTHER INFORMATION: a crRNA

<400> SEQUENCE: 4
guuuuagagc uagaaauagc aaguuaaaau                                    30

<210> SEQ ID NO 5
<211> LENGTH: 33
<212> TYPE: RNA
<213> ORGANISM: Artificial Sequence
<220> FEATURE:
<223> OTHER INFORMATION: a crRNA

<400> SEQUENCE: 5
guuuuagagc uagaaauagc aaguuaaaau aag                                33

<210> SEQ ID NO 6
<211> LENGTH: 26
<212> TYPE: RNA
<213> ORGANISM: Artificial Sequence
<220> FEATURE:
<223> OTHER INFORMATION: a crRNA

<400> SEQUENCE: 6
gaguccgagc agaagaagaa guuuua                                        26

<210> SEQ ID NO 7
<211> LENGTH: 12
<212> TYPE: RNA
<213> ORGANISM: Artificial Sequence
<220> FEATURE:
<223> OTHER INFORMATION: a tracrRNA

<400> SEQUENCE: 7
aaggcuaguc cg                                                       12
```

```
<210> SEQ ID NO 8
<211> LENGTH: 50
<212> TYPE: RNA
<213> ORGANISM: Artificial Sequence
<220> FEATURE:
<223> OTHER INFORMATION: a tracrRNA

<400> SEQUENCE: 8
aaggcuaguc cguuaucaac uugaaaaagu ggcaccgagu cggugcuuuu            50

<210> SEQ ID NO 9
<211> LENGTH: 203
<212> TYPE: PRT
<213> ORGANISM: Mus Musculus

<400> SEQUENCE: 9
```

Met Lys Val Leu Ala Ala Gly Ile Val Pro Leu Leu Leu Val Leu
1               5                   10                  15

His Trp Lys His Gly Ala Gly Ser Pro Leu Pro Ile Thr Pro Val Asn
            20                  25                  30

Ala Thr Cys Ala Ile Arg His Pro Cys His Gly Asn Leu Met Asn Gln
        35                  40                  45

Ile Lys Asn Gln Leu Ala Gln Leu Asn Gly Ser Ala Asn Ala Leu Phe
    50                  55                  60

Ile Ser Tyr Tyr Thr Ala Gln Gly Glu Pro Phe Pro Asn Asn Val Glu
65                  70                  75                  80

Lys Leu Cys Ala Pro Asn Met Thr Asp Phe Pro Ser Phe His Gly Asn
                85                  90                  95

Gly Thr Glu Lys Thr Lys Leu Val Glu Leu Tyr Arg Met Val Ala Tyr
            100                 105                 110

Leu Ser Ala Ser Leu Thr Asn Ile Thr Arg Asp Gln Lys Val Leu Asn
        115                 120                 125

Pro Thr Ala Val Ser Leu Gln Val Lys Leu Asn Ala Thr Ile Asp Val
    130                 135                 140

Met Arg Gly Leu Leu Ser Asn Val Leu Cys Arg Leu Cys Asn Lys Tyr
145                 150                 155                 160

Arg Val Gly His Val Asp Val Pro Val Pro Asp His Ser Asp Lys
                165                 170                 175

Glu Ala Phe Gln Arg Lys Lys Leu Gly Cys Gln Leu Leu Gly Thr Tyr
            180                 185                 190

Lys Gln Val Ile Ser Val Val Val Gln Ala Phe
            195                 200

```
<210> SEQ ID NO 10
<211> LENGTH: 15
<212> TYPE: DNA
<213> ORGANISM: Artificial Sequence
<220> FEATURE:
<223> OTHER INFORMATION: ZFN1a binding site

<400> SEQUENCE: 10
caggccctga accgc                                                  15

<210> SEQ ID NO 11
<211> LENGTH: 6
<212> TYPE: DNA
<213> ORGANISM: Artificial Sequence
<220> FEATURE:
<223> OTHER INFORMATION: ZFN1 cutting site
```

```
<400> SEQUENCE: 11 ttctgg                                                                       6

<210> SEQ ID NO 12
<211> LENGTH: 16
<212> TYPE: DNA
<213> ORGANISM: Artificial Sequence
<220> FEATURE:
<223> OTHER INFORMATION: ZFN1b binding site

<400> SEQUENCE: 12
gattacctgc gctggg                                                           16

<210> SEQ ID NO 13
<211> LENGTH: 15
<212> TYPE: DNA
<213> ORGANISM: Artificial Sequence
<220> FEATURE:
<223> OTHER INFORMATION: ZF21a binding site

<400> SEQUENCE: 13
ttcaccctcc gcacc                                                            15

<210> SEQ ID NO 14
<211> LENGTH: 7
<212> TYPE: DNA
<213> ORGANISM: Artificial Sequence
<220> FEATURE:
<223> OTHER INFORMATION: ZFN2 cutting site

<400> SEQUENCE: 14 tgctgag                                                                      7

<210> SEQ ID NO 15
<211> LENGTH: 18
<212> TYPE: DNA
<213> ORGANISM: Artificial Sequence
<220> FEATURE:
<223> OTHER INFORMATION: ZF21b binding site

<400> SEQUENCE: 15
tatccagatc caggggtt                                                         18

<210> SEQ ID NO 16
<211> LENGTH: 9
<212> TYPE: PRT
<213> ORGANISM: Artificial Sequence
<220> FEATURE:
<223> OTHER INFORMATION: conserved domain of a family of homing
      nucleases

<400> SEQUENCE: 16

Leu Ala Gly Leu Ile Asp Ala Asp Gly
1               5

<210> SEQ ID NO 17
<211> LENGTH: 15
<212> TYPE: DNA
<213> ORGANISM: Artificial Sequence
<220> FEATURE:
<223> OTHER INFORMATION: ZFN1a binding site

<400> SEQUENCE: 17
caggccctga accgc                                                            15
```

-continued

<210> SEQ ID NO 18
<211> LENGTH: 6
<212> TYPE: DNA
<213> ORGANISM: Artificial Sequence
<220> FEATURE:
<223> OTHER INFORMATION: ZFN1 cutting site

<400> SEQUENCE: 18 ttctgg                                                                    6

<210> SEQ ID NO 19
<211> LENGTH: 16
<212> TYPE: DNA
<213> ORGANISM: Artificial Sequence
<220> FEATURE:
<223> OTHER INFORMATION: ZFN1b binding site

<400> SEQUENCE: 19
gattacctgc gctggg                                                        16

<210> SEQ ID NO 20
<211> LENGTH: 369
<212> TYPE: PRT
<213> ORGANISM: Homo sapiens

<400> SEQUENCE: 20

Met Leu Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
    50                  55                  60

Phe Asn Val Glu Tyr Met Asn Cys Thr Trp Asn Ser Ser Ser Glu Pro
65                  70                  75                  80

Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
        115                 120                 125

Val Val Gln Leu Gln Asp Pro Arg Glu Pro Arg Arg Gln Ala Thr Gln
    130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
            180                 185                 190

Trp Asp His Ser Trp Thr Glu Gln Ser Val Asp Tyr Arg His Lys Phe
        195                 200                 205

Ser Leu Pro Ser Val Asp Gly Gln Lys Arg Tyr Thr Phe Arg Val Arg
    210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Pro Phe
                245                 250                 255

```
Leu Phe Ala Leu Glu Ala Val Val Ile Ser Val Gly Ser Met Gly Leu
                260                 265                 270

Ile Ile Ser Leu Leu Cys Val Tyr Phe Trp Leu Glu Arg Thr Met Pro
            275                 280                 285

Arg Ile Pro Thr Leu Lys Asn Leu Glu Asp Leu Val Thr Glu Tyr His
        290                 295                 300

Gly Asn Phe Ser Ala Trp Ser Gly Val Ser Lys Gly Leu Ala Glu Ser
305                 310                 315                 320

Leu Gln Pro Asp Tyr Ser Glu Arg Leu Cys Leu Val Ser Glu Ile Pro
                325                 330                 335

Pro Lys Gly Gly Ala Leu Gly Glu Gly Pro Gly Ala Ser Pro Cys Asn
                340                 345                 350

Gln His Ser Pro Tyr Trp Ala Pro Pro Cys Tyr Thr Leu Lys Pro Glu
            355                 360                 365

Thr

<210> SEQ ID NO 21
<211> LENGTH: 368
<212> TYPE: PRT
<213> ORGANISM: Rattus norvegicus

<400> SEQUENCE: 21

Met Leu Lys Pro Leu Pro Ser Arg Ser Phe Leu Leu Gln Leu
1               5                   10                  15

Leu Leu Leu Arg Val Gly Trp Ser Ser Lys Val Leu Met Ser Ser Gly
            20                  25                  30

Asn Glu Asp Thr Lys Ser Asp Leu Leu Thr Ser Met Asp Leu Lys
                35                  40                  45

His Leu Ser Val Pro Thr Leu Pro Leu Pro Glu Val Gln Cys Phe Val
    50                  55                  60

Phe Asn Val Glu Tyr Met Asn Cys Thr Trp Asn Ser Ser Ser Glu Pro
65                  70                  75                  80

Gln Pro Thr Asn Leu Thr Met His Tyr Arg Tyr Lys Gly Ser Asp Asn
                85                  90                  95

Asn Thr Phe Gln Glu Cys Ser His Tyr Leu Phe Ser Lys Glu Ile Thr
                100                 105                 110

Ser Gly Cys Gln Ile Gln Lys Glu Asp Ile Gln Leu Tyr Gln Thr Phe
            115                 120                 125

Val Val Gln Leu Gln Asp Pro Gln Lys Pro Gln Arg Arg Ala Glu Gln
        130                 135                 140

Lys Leu Asn Leu Gln Asn Leu Val Ile Pro Trp Ala Pro Glu Asn Leu
145                 150                 155                 160

Thr Leu Tyr Asn Leu Ser Glu Ser Gln Val Glu Leu Arg Trp Lys Ser
                165                 170                 175

Arg Tyr Ile Glu Arg Cys Leu Gly Tyr Leu Val Gln Tyr Arg Ser Asn
            180                 185                 190

Arg Asp Arg Ser Trp Thr Glu Gln Ile Val Asp His Glu Pro Arg Phe
        195                 200                 205

Ser Leu Pro Ser Val Asp Glu Gln Lys Leu Tyr Thr Phe Arg Val Arg
    210                 215                 220

Ser Arg Phe Asn Pro Ile Cys Gly Ser Thr Gln Gln Trp Ser Lys Trp
225                 230                 235                 240

Ser Gln Pro Ile His Trp Gly Ser His Thr Ala Glu Glu Asn Pro Ser
                245                 250                 255
```

```
Leu Phe Ala Leu Glu Ala Val Leu Ile Pro Val Gly Thr Met Gly Leu
            260                 265                 270

Ile Ile Thr Leu Ile Phe Val Tyr Cys Trp Leu Glu Arg Met Pro Arg
        275                 280                 285

Ile Pro Ala Ile Lys Asn Leu Glu Asp Leu Val Thr Glu Tyr His Gly
    290                 295                 300

Asn Phe Ser Ala Trp Ser Gly Val Ser Lys Gly Leu Thr Glu Ser Leu
305                 310                 315                 320

Gln Pro Asp Tyr Ser Glu Arg Phe Cys His Val Ser Glu Ile Pro Pro
                325                 330                 335

Lys Gly Gly Ala Leu Gly Glu Gly Pro Gly Gly Ser Pro Cys Ser Leu
            340                 345                 350

His Ser Pro Tyr Trp Pro Pro Cys Tyr Ser Leu Lys Pro Glu Ala
            355                 360                 365

<210> SEQ ID NO 22
<211> LENGTH: 368
<212> TYPE: PRT
<213> ORGANISM: Artificial Sequence
<220> FEATURE:
<223> OTHER INFORMATION: chimeric IL-2 receptor gamma comprising the rat
      IL-2 receptor gamma protein having the ecto domain
      of IL-2 gamma receptor from human

<400> SEQUENCE: 22

Met Leu Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
    50                  55                  60

Phe Asn Val Glu Tyr Met Asn Cys Thr Trp Asn Ser Ser Ser Glu Pro
65                  70                  75                  80

Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
        115                 120                 125

Val Val Gln Leu Gln Asp Pro Arg Glu Pro Arg Arg Gln Ala Thr Gln
    130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
            180                 185                 190

Trp Asp His Ser Trp Thr Glu Gln Ser Val Asp Tyr Arg His Lys Phe
        195                 200                 205

Ser Leu Pro Ser Val Asp Gly Gln Lys Arg Tyr Thr Phe Arg Val Arg
    210                 215                 220

Ser Arg Phe Asn Pro Leu Cys Gly Ser Ala Gln His Trp Ser Glu Trp
225                 230                 235                 240
```

```
Ser His Pro Ile His Trp Gly Ser Asn Thr Ser Lys Glu Asn Pro Phe
            245                 250                 255

Leu Phe Ala Leu Glu Ala Val Leu Ile Pro Val Gly Thr Met Gly Leu
        260                 265                 270

Ile Ile Thr Leu Ile Phe Val Tyr Cys Trp Leu Glu Arg Met Pro Arg
        275                 280                 285

Ile Pro Ala Ile Lys Asn Leu Glu Asp Leu Val Thr Glu Tyr His Gly
        290                 295                 300

Asn Phe Ser Ala Trp Ser Gly Val Ser Lys Gly Leu Thr Glu Ser Leu
305                 310                 315                 320

Gln Pro Asp Tyr Ser Glu Arg Phe Cys His Val Ser Glu Ile Pro Pro
                325                 330                 335

Lys Gly Gly Ala Leu Gly Glu Gly Pro Gly Gly Ser Pro Cys Ser Leu
            340                 345                 350

His Ser Pro Tyr Trp Pro Pro Pro Cys Tyr Ser Leu Lys Pro Glu Ala
            355                 360                 365

<210> SEQ ID NO 23
<211> LENGTH: 23
<212> TYPE: DNA
<213> ORGANISM: Artificial Sequence
<220> FEATURE:
<223> OTHER INFORMATION: a genomic target sequence that is linked to a
      guide RNA (gRNA)
<220> FEATURE:
<221> NAME/KEY: misc_feature
<222> LOCATION: (2)...(21)
<223> OTHER INFORMATION: n= A, T, C or G
<220> FEATURE:
<221> NAME/KEY: misc_feature
<222> LOCATION: (0)...(0)
<223> OTHER INFORMATION: n can be from 1-20 nucleotides

<400> SEQUENCE: 23
gnnnnnnnnn nnnnnnnnnn ngg                                           23

<210> SEQ ID NO 24
<211> LENGTH: 20
<212> TYPE: DNA
<213> ORGANISM: Artificial Sequence
<220> FEATURE:
<223> OTHER INFORMATION: a guide sequence

<400> SEQUENCE: 24
gggaacccac agcatactcc                                               20

<210> SEQ ID NO 25
<211> LENGTH: 20
<212> TYPE: DNA
<213> ORGANISM: Artificial Sequence
<220> FEATURE:
<223> OTHER INFORMATION: a guide sequence

<400> SEQUENCE: 25
gaatcatgca cggctacccc                                               20

<210> SEQ ID NO 26
<211> LENGTH: 20
<212> TYPE: DNA
<213> ORGANISM: Artificial Sequence
<220> FEATURE:
<223> OTHER INFORMATION: a guide sequence
```

<400> SEQUENCE: 26
tgctcctatg gggaggcgcg            20

<210> SEQ ID NO 27
<211> LENGTH: 20
<212> TYPE: DNA
<213> ORGANISM: Artificial Sequence
<220> FEATURE:
<223> OTHER INFORMATION: a guide sequence

<400> SEQUENCE: 27
cttggataac attgataccc            20

<210> SEQ ID NO 28
<211> LENGTH: 20
<212> TYPE: DNA
<213> ORGANISM: Artificial Sequence
<220> FEATURE:
<223> OTHER INFORMATION: a guide sequence

<400> SEQUENCE: 28
ggggcagagc ccttatatca            20

<210> SEQ ID NO 29
<211> LENGTH: 20
<212> TYPE: DNA
<213> ORGANISM: Artificial Sequence
<220> FEATURE:
<223> OTHER INFORMATION: a guide sequence

<400> SEQUENCE: 29
tcgctcacat taatccctag            20

<210> SEQ ID NO 30
<211> LENGTH: 20
<212> TYPE: DNA
<213> ORGANISM: Artificial Sequence
<220> FEATURE:
<223> OTHER INFORMATION: a guide sequence

<400> SEQUENCE: 30
gtactgggga atcggtggtc            20

<210> SEQ ID NO 31
<211> LENGTH: 20
<212> TYPE: DNA
<213> ORGANISM: Artificial Sequence
<220> FEATURE:
<223> OTHER INFORMATION: a guide sequence

<400> SEQUENCE: 31
cacgcactcc aaatttatcc            20

<210> SEQ ID NO 32
<211> LENGTH: 20
<212> TYPE: DNA
<213> ORGANISM: Artificial Sequence
<220> FEATURE:
<223> OTHER INFORMATION: a guide sequence

<400> SEQUENCE: 32
ctaagtgtgt atcagtacat            20

```
<210> SEQ ID NO 33
<211> LENGTH: 20
<212> TYPE: DNA
<213> ORGANISM: Artificial Sequence
<220> FEATURE:
<223> OTHER INFORMATION: a guide sequence

<400> SEQUENCE: 33
tgccctgcac aataagcgca                                                   20

<210> SEQ ID NO 34
<211> LENGTH: 20
<212> TYPE: DNA
<213> ORGANISM: Artificial Sequence
<220> FEATURE:
<223> OTHER INFORMATION: a guide sequence

<400> SEQUENCE: 34
actcattgaa acgttatggc                                                   20

<210> SEQ ID NO 35
<211> LENGTH: 20
<212> TYPE: DNA
<213> ORGANISM: Artificial Sequence
<220> FEATURE:
<223> OTHER INFORMATION: a guide sequence

<400> SEQUENCE: 35
agtaagggtg gattaaattc                                                   20

<210> SEQ ID NO 36
<211> LENGTH: 20
<212> TYPE: DNA
<213> ORGANISM: Artificial Sequence
<220> FEATURE:
<223> OTHER INFORMATION: a guide sequence

<400> SEQUENCE: 36
gccatctaga ttcatgtaac                                                   20

<210> SEQ ID NO 37
<211> LENGTH: 20
<212> TYPE: DNA
<213> ORGANISM: Artificial Sequence
<220> FEATURE:
<223> OTHER INFORMATION: a guide sequence

<400> SEQUENCE: 37
gactagaaat gttctgcacc                                                   20

<210> SEQ ID NO 38
<211> LENGTH: 20
<212> TYPE: DNA
<213> ORGANISM: Artificial Sequence
<220> FEATURE:
<223> OTHER INFORMATION: a guide sequence

<400> SEQUENCE: 38
tgaaccaatt gtgtagcctt                                                   20

<210> SEQ ID NO 39
<211> LENGTH: 20
<212> TYPE: DNA
<213> ORGANISM: Artificial Sequence
<220> FEATURE:
<223> OTHER INFORMATION: a guide sequence
```

```
<400> SEQUENCE: 39
aatagtggta aagcaccatg                                               20

<210> SEQ ID NO 40
<211> LENGTH: 20
<212> TYPE: DNA
<213> ORGANISM: Artificial Sequence
<220> FEATURE:
<223> OTHER INFORMATION: a guide sequence

<400> SEQUENCE: 40
gtgtgctaag gatcgaagtc                                               20

<210> SEQ ID NO 41
<211> LENGTH: 20
<212> TYPE: DNA
<213> ORGANISM: Artificial Sequence
<220> FEATURE:
<223> OTHER INFORMATION: a guide sequence

<400> SEQUENCE: 41
caccgagatg cttgggtatt                                               20

<210> SEQ ID NO 42
<211> LENGTH: 20
<212> TYPE: DNA
<213> ORGANISM: Artificial Sequence
<220> FEATURE:
<223> OTHER INFORMATION: a guide sequence

<400> SEQUENCE: 42
tgtaaccgcc ctgaatgacc                                               20

<210> SEQ ID NO 43
<211> LENGTH: 20
<212> TYPE: DNA
<213> ORGANISM: Artificial Sequence
<220> FEATURE:
<223> OTHER INFORMATION: a guide sequence

<400> SEQUENCE: 43
aaaagggcat cataaatccc                                               20

<210> SEQ ID NO 44
<211> LENGTH: 20
<212> TYPE: DNA
<213> ORGANISM: Artificial Sequence
<220> FEATURE:
<223> OTHER INFORMATION: a guide sequence

<400> SEQUENCE: 44
tcaaaaatag tcatacacct                                               20

<210> SEQ ID NO 45
<211> LENGTH: 20
<212> TYPE: DNA
<213> ORGANISM: Artificial Sequence
<220> FEATURE:
<223> OTHER INFORMATION: a guide sequence

<400> SEQUENCE: 45
ggtctctagt acattgtaga                                               20
```

```
<210> SEQ ID NO 46
<211> LENGTH: 20
<212> TYPE: DNA
<213> ORGANISM: Artificial Sequence
<220> FEATURE:
<223> OTHER INFORMATION: a guide sequence

<400> SEQUENCE: 46
atcacaaacc agttaaccgg                                                    20

<210> SEQ ID NO 47
<211> LENGTH: 20
<212> TYPE: DNA
<213> ORGANISM: Artificial Sequence
<220> FEATURE:
<223> OTHER INFORMATION: a guide sequence

<400> SEQUENCE: 47
tttcagacga gccgacccgg                                                    20

<210> SEQ ID NO 48
<211> LENGTH: 20
<212> TYPE: DNA
<213> ORGANISM: Artificial Sequence
<220> FEATURE:
<223> OTHER INFORMATION: a guide sequence

<400> SEQUENCE: 48
ctgtcaacag tgccgcgttt                                                    20

<210> SEQ ID NO 49
<211> LENGTH: 20
<212> TYPE: DNA
<213> ORGANISM: Artificial Sequence
<220> FEATURE:
<223> OTHER INFORMATION: a guide sequence

<400> SEQUENCE: 49
tgtgtgtcat agcgatgtcg                                                    20

<210> SEQ ID NO 50
<211> LENGTH: 20
<212> TYPE: DNA
<213> ORGANISM: Artificial Sequence
<220> FEATURE:
<223> OTHER INFORMATION: a guide sequence

<400> SEQUENCE: 50
aacaggtacc ctatcctcac                                                    20

<210> SEQ ID NO 51
<211> LENGTH: 20
<212> TYPE: DNA
<213> ORGANISM: Artificial Sequence
<220> FEATURE:
<223> OTHER INFORMATION: a guide sequence

<400> SEQUENCE: 51
tcgtggttgc atgcgcactg                                                    20

<210> SEQ ID NO 52
<211> LENGTH: 20
<212> TYPE: DNA
<213> ORGANISM: Artificial Sequence
<220> FEATURE:
<223> OTHER INFORMATION: a guide sequence
```

```
<400> SEQUENCE: 52
ggcccggacc tagtctctct                                               20

<210> SEQ ID NO 53
<211> LENGTH: 20
<212> TYPE: DNA
<213> ORGANISM: Artificial Sequence
<220> FEATURE:
<223> OTHER INFORMATION: a guide sequence

<400> SEQUENCE: 53
agtctgtaaa gttagcagtc                                               20

<210> SEQ ID NO 54
<211> LENGTH: 20
<212> TYPE: DNA
<213> ORGANISM: Artificial Sequence
<220> FEATURE:
<223> OTHER INFORMATION: a guide sequence

<400> SEQUENCE: 54
ggtggtggtg ctgacggaca                                               20

<210> SEQ ID NO 55
<211> LENGTH: 20
<212> TYPE: DNA
<213> ORGANISM: Artificial Sequence
<220> FEATURE:
<223> OTHER INFORMATION: a guide sequence

<400> SEQUENCE: 55
tatgagatca acactcgcta                                               20

<210> SEQ ID NO 56
<211> LENGTH: 20
<212> TYPE: DNA
<213> ORGANISM: Artificial Sequence
<220> FEATURE:
<223> OTHER INFORMATION: a guide sequence

<400> SEQUENCE: 56
ccaaggactt ccccacgtta                                               20

<210> SEQ ID NO 57
<211> LENGTH: 20
<212> TYPE: DNA
<213> ORGANISM: Artificial Sequence
<220> FEATURE:
<223> OTHER INFORMATION: a guide sequence

<400> SEQUENCE: 57
tgcttccctt atgcaagatt                                               20

<210> SEQ ID NO 58
<211> LENGTH: 20
<212> TYPE: DNA
<213> ORGANISM: Artificial Sequence
<220> FEATURE:
<223> OTHER INFORMATION: a guide sequence

<400> SEQUENCE: 58
ttaggtaccc tatttgaata                                               20
```

-continued

```
<210> SEQ ID NO 59
<211> LENGTH: 20
<212> TYPE: DNA
<213> ORGANISM: Artificial Sequence
<220> FEATURE:
<223> OTHER INFORMATION: a guide sequence

<400> SEQUENCE: 59
tgcagtgggt gacaggtcca                                                 20

<210> SEQ ID NO 60
<211> LENGTH: 20
<212> TYPE: DNA
<213> ORGANISM: Artificial Sequence
<220> FEATURE:
<223> OTHER INFORMATION: a guide sequence

<400> SEQUENCE: 60
agggttatac tgacgttgtg                                                 20

<210> SEQ ID NO 61
<211> LENGTH: 20
<212> TYPE: DNA
<213> ORGANISM: Artificial Sequence
<220> FEATURE:
<223> OTHER INFORMATION: a guide sequence

<400> SEQUENCE: 61
tgtctttcaa ggagggctac                                                 20

<210> SEQ ID NO 62
<211> LENGTH: 20
<212> TYPE: DNA
<213> ORGANISM: Artificial Sequence
<220> FEATURE:
<223> OTHER INFORMATION: a guide sequence

<400> SEQUENCE: 62
tgatgtgcag tcagacaaag                                                 20

<210> SEQ ID NO 63
<211> LENGTH: 20
<212> TYPE: DNA
<213> ORGANISM: Artificial Sequence
<220> FEATURE:
<223> OTHER INFORMATION: a guide sequence

<400> SEQUENCE: 63
tgcactatgg ttgactatga                                                 20

<210> SEQ ID NO 64
<211> LENGTH: 20
<212> TYPE: DNA
<213> ORGANISM: Artificial Sequence
<220> FEATURE:
<223> OTHER INFORMATION: a guide sequence

<400> SEQUENCE: 64
ggaatattct aataggaagt                                                 20

<210> SEQ ID NO 65
<211> LENGTH: 20
<212> TYPE: DNA
<213> ORGANISM: Artificial Sequence
<220> FEATURE:
<223> OTHER INFORMATION: a guide sequence
```

<400> SEQUENCE: 65
aagtgctgta ccattctagc                                               20

<210> SEQ ID NO 66
<211> LENGTH: 20
<212> TYPE: DNA
<213> ORGANISM: Artificial Sequence
<220> FEATURE:
<223> OTHER INFORMATION: a guide sequence

<400> SEQUENCE: 66
taatcaatag acaacctcgt                                               20

<210> SEQ ID NO 67
<211> LENGTH: 20
<212> TYPE: DNA
<213> ORGANISM: Artificial Sequence
<220> FEATURE:
<223> OTHER INFORMATION: a guide sequence

<400> SEQUENCE: 67
tcattcctaa tggtattata                                               20

<210> SEQ ID NO 68
<211> LENGTH: 20
<212> TYPE: DNA
<213> ORGANISM: Artificial Sequence
<220> FEATURE:
<223> OTHER INFORMATION: a guide sequence

<400> SEQUENCE: 68
agggtacata gatggcatcg                                               20

<210> SEQ ID NO 69
<211> LENGTH: 20
<212> TYPE: DNA
<213> ORGANISM: Artificial Sequence
<220> FEATURE:
<223> OTHER INFORMATION: a guide sequence

<400> SEQUENCE: 69
ctctttaaca attaccactt                                               20

<210> SEQ ID NO 70
<211> LENGTH: 20
<212> TYPE: DNA
<213> ORGANISM: Artificial Sequence
<220> FEATURE:
<223> OTHER INFORMATION: a guide sequence

<400> SEQUENCE: 70
tgtgggcctt tgctgatcac                                               20

<210> SEQ ID NO 71
<211> LENGTH: 20
<212> TYPE: DNA
<213> ORGANISM: Artificial Sequence
<220> FEATURE:
<223> OTHER INFORMATION: a guide sequence

<400> SEQUENCE: 71
aatctatgat cctatggcct                                               20

```
<210> SEQ ID NO 72
<211> LENGTH: 20
<212> TYPE: DNA
<213> ORGANISM: Artificial Sequence
<220> FEATURE:
<223> OTHER INFORMATION: a guide sequence

<400> SEQUENCE: 72
tgccaatagc agtgacttga                                              20

<210> SEQ ID NO 73
<211> LENGTH: 20
<212> TYPE: DNA
<213> ORGANISM: Artificial Sequence
<220> FEATURE:
<223> OTHER INFORMATION: a guide sequence

<400> SEQUENCE: 73
gggaagaatg ggctattgtc                                              20

<210> SEQ ID NO 74
<211> LENGTH: 20
<212> TYPE: DNA
<213> ORGANISM: Artificial Sequence
<220> FEATURE:
<223> OTHER INFORMATION: a guide sequence

<400> SEQUENCE: 74
ggttgtttgt gctgatgacg                                              20

<210> SEQ ID NO 75
<211> LENGTH: 20
<212> TYPE: DNA
<213> ORGANISM: Artificial Sequence
<220> FEATURE:
<223> OTHER INFORMATION: a guide sequence

<400> SEQUENCE: 75
ccgtcctagg ccttctacgt                                              20

<210> SEQ ID NO 76
<211> LENGTH: 20
<212> TYPE: DNA
<213> ORGANISM: Artificial Sequence
<220> FEATURE:
<223> OTHER INFORMATION: a guide sequence

<400> SEQUENCE: 76
actagtagac ctgaggggtt                                              20

<210> SEQ ID NO 77
<211> LENGTH: 20
<212> TYPE: DNA
<213> ORGANISM: Artificial Sequence
<220> FEATURE:
<223> OTHER INFORMATION: a guide sequence

<400> SEQUENCE: 77
gctccagtgt ttaggccttg                                              20

<210> SEQ ID NO 78
<211> LENGTH: 20
<212> TYPE: DNA
<213> ORGANISM: Artificial Sequence
<220> FEATURE:
<223> OTHER INFORMATION: a guide sequence
```

<400> SEQUENCE: 78
ggcaagctga aaacgcatgc                                                    20

<210> SEQ ID NO 79
<211> LENGTH: 20
<212> TYPE: DNA
<213> ORGANISM: Artificial Sequence
<220> FEATURE:
<223> OTHER INFORMATION: a guide sequence

<400> SEQUENCE: 79
gtagatcgct ttccactacc                                                    20

<210> SEQ ID NO 80
<211> LENGTH: 20
<212> TYPE: DNA
<213> ORGANISM: Artificial Sequence
<220> FEATURE:
<223> OTHER INFORMATION: a guide sequence

<400> SEQUENCE: 80
gaactccact gctcgtgagc                                                    20

<210> SEQ ID NO 81
<211> LENGTH: 20
<212> TYPE: DNA
<213> ORGANISM: Artificial Sequence
<220> FEATURE:
<223> OTHER INFORMATION: a guide sequence

<400> SEQUENCE: 81
ataggtgggc actattgaag                                                    20

<210> SEQ ID NO 82
<211> LENGTH: 20
<212> TYPE: DNA
<213> ORGANISM: Artificial Sequence
<220> FEATURE:
<223> OTHER INFORMATION: a guide sequence

<400> SEQUENCE: 82
atgggaaggt ttataccagc                                                    20

<210> SEQ ID NO 83
<211> LENGTH: 20
<212> TYPE: DNA
<213> ORGANISM: Artificial Sequence
<220> FEATURE:
<223> OTHER INFORMATION: a guide sequence

<400> SEQUENCE: 83
cggtgtaaaa acaacgggaa                                                    20

<210> SEQ ID NO 84
<211> LENGTH: 20
<212> TYPE: RNA
<213> ORGANISM: Artificial Sequence
<220> FEATURE:
<223> OTHER INFORMATION: a guide sequence

<400> SEQUENCE: 84
gacccgcagu cccagcgucg                                                    20

-continued

```
<210> SEQ ID NO 85
<211> LENGTH: 20
<212> TYPE: DNA
<213> ORGANISM: Artificial Sequence
<220> FEATURE:
<223> OTHER INFORMATION: a guide sequence

<400> SEQUENCE: 85
actgagatca atgaccccga                                        20

<210> SEQ ID NO 86
<211> LENGTH: 20
<212> TYPE: DNA
<213> ORGANISM: Artificial Sequence
<220> FEATURE:
<223> OTHER INFORMATION: a guide sequence

<400> SEQUENCE: 86
gggtcgcccg gaacctctac                                        20

<210> SEQ ID NO 87
<211> LENGTH: 23
<212> TYPE: DNA
<213> ORGANISM: Artificial Sequence
<220> FEATURE:
<223> OTHER INFORMATION: a guide sequence

<400> SEQUENCE: 87
gcaggccctg aaccgcttct tgg                                    23

<210> SEQ ID NO 88
<211> LENGTH: 23
<212> TYPE: DNA
<213> ORGANISM: Artificial Sequence
<220> FEATURE:
<223> OTHER INFORMATION: a guide sequence

<400> SEQUENCE: 88
cctgcgctgg gtgcagacgc ttt                                    23

<210> SEQ ID NO 89
<211> LENGTH: 20
<212> TYPE: DNA
<213> ORGANISM: Artificial Sequence
<220> FEATURE:
<223> OTHER INFORMATION: a guide sequence

<400> SEQUENCE: 89
ccagctactt gctcgtacaa                                        20

<210> SEQ ID NO 90
<211> LENGTH: 20
<212> TYPE: DNA
<213> ORGANISM: Artificial Sequence
<220> FEATURE:
<223> OTHER INFORMATION: a guide sequence

<400> SEQUENCE: 90
cccctcagat tcacgtgcgt                                        20

<210> SEQ ID NO 91
<211> LENGTH: 23
<212> TYPE: DNA
<213> ORGANISM: Artificial Sequence
<220> FEATURE:
<223> OTHER INFORMATION: a guide sequence
```

-continued

```
<400> SEQUENCE: 91
gaagctcttt ctatacaatc tgg                                              23

<210> SEQ ID NO 92
<211> LENGTH: 23
<212> TYPE: DNA
<213> ORGANISM: Artificial Sequence
<220> FEATURE:
<223> OTHER INFORMATION: a guide sequence

<400> SEQUENCE: 92
cccccgaaag gaggagccct agg                                              23

<210> SEQ ID NO 93
<211> LENGTH: 56
<212> TYPE: DNA
<213> ORGANISM: Rattus norvegicus

<400> SEQUENCE: 93
ttctgagcct cagccgacca acctcactat gcactatagg tatgagaagg gggagg          56

<210> SEQ ID NO 94
<211> LENGTH: 20
<212> TYPE: DNA
<213> ORGANISM: aArtificial Sequence
<220> FEATURE:
<223> OTHER INFORMATION: a guide sequence

<400> SEQUENCE: 94
gtatagccct gttacacatt                                                  20
```